(12) United States Patent
Schulz

(10) Patent No.: US 8,895,300 B2
(45) Date of Patent: *Nov. 25, 2014

(54) SCALABLE PRIMATE PLURIPOTENT STEM CELL AGGREGATE SUSPENSION CULTURE AND DIFFERENTIATION THEREOF

(71) Applicant: ViaCyte, Inc., San Diego, CA (US)

(72) Inventor: Thomas C Schulz, Athens, GA (US)

(73) Assignee: Viacyte, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/672,688

(22) Filed: Nov. 8, 2012

(65) Prior Publication Data

US 2013/0115695 A1 May 9, 2013

Related U.S. Application Data

(63) Continuation-in-part of application No. 13/220,590, filed on Aug. 29, 2011, now Pat. No. 8,445,273, and a continuation-in-part of application No. 12/264,760, filed on Nov. 4, 2008, now Pat. No. 8,008,075.

(51) Int. Cl.
| | |
|---|---|
| C12N 5/00 | (2006.01) |
| C12N 5/02 | (2006.01) |
| C12N 5/071 | (2010.01) |
| C12N 5/07 | (2010.01) |
| C12N 5/10 | (2006.01) |
| C12N 5/0735 | (2010.01) |

(52) U.S. Cl.
CPC ........ *C12N 5/0606* (2013.01); *C12N 2501/415* (2013.01); *C12N 2506/02* (2013.01); *C12N 2509/00* (2013.01); *C12N 2501/41* (2013.01); *C12N 5/0676* (2013.01); *C12N 2501/105* (2013.01); *C12N 2501/16* (2013.01); *C12N 2501/195* (2013.01); *C12N 2501/117* (2013.01); *C12N 2501/115* (2013.01); *C12N 2501/15* (2013.01); *C12N 2501/11* (2013.01)
USPC ........... 435/363; 435/377; 435/383; 435/384; 435/366; 435/375

(58) Field of Classification Search
USPC ....................................................... 435/363
See application file for complete search history.

(56) References Cited

U.S. PATENT DOCUMENTS

| | | | |
|---|---|---|---|
| 7,442,548 | B2 | 10/2008 | Thomson |
| 7,695,963 | B2 | 4/2010 | Agulnick |
| 7,704,738 | B2 | 4/2010 | D'Amour |
| 7,803,619 | B2 | 9/2010 | Ezekial |
| 7,964,402 | B2 | 6/2011 | Terskikh |
| 8,008,075 | B2 | 8/2011 | Green |
| 2003/0203008 | A1 | 10/2003 | Gunasekaran |
| 2005/0233446 | A1 | 10/2005 | Parsons |
| 2006/0003446 | A1 | 1/2006 | Keller |
| 2006/0194321 | A1 | 8/2006 | Colman et al. |
| 2007/0015210 | A1 | 1/2007 | Ezekiel |
| 2007/0154984 | A1 | 7/2007 | D'Amour et al. |
| 2008/0102063 | A1 | 5/2008 | Moviglia |
| 2008/0206343 | A1 | 8/2008 | Edinger |
| 2009/0093372 | A1 | 4/2009 | Agulnick et al. |
| 2012/0034618 | A1 | 2/2012 | Terskikh et al. |
| 2012/0045830 | A1 | 2/2012 | Green |

FOREIGN PATENT DOCUMENTS

| | | |
|---|---|---|
| WO | 2007101130 | 9/2001 |
| WO | 2005005621 | 1/2005 |
| WO | 2006020919 | 2/2006 |
| WO | WO 2007002086 | 1/2007 |
| WO | WO 2008015682 | 2/2008 |
| WO | WO 2010053472 | 5/2010 |

OTHER PUBLICATIONS

Jaregui, 1997, Tissue Engineering, 3:17-25.*
Dang et al (2004, Stem Cells, 22:275-282.*
Amit et al., Feeder Layer- and Serum-Free Culture of Human Embryonic Stem Cells, Biology of Reproduction, 70, 837-845 (2004).
Bajpai et al., Efficient Propagation of Single Cells Accutase-Dissociated Human Embryonic Stem Cells, Molecular Reproduction and Development, Wiley InterScience, DOI 10.1002/mrd (2007).
Bettiol et al., Fetal Bovine Serum enables Cardiac Differentiation of Human Embryonic Stem Cells, Differentiation, 75:669-681, (2007).
Braam, Stefan et al., Inhibition of ROCK Improves Survival of Human Embryonic Stem Cell-Derived Cardiomyocytes After Dissociation, Annals of the New York Academy of Sciences, 1188 52-57, (2010).
CelliGen Plus, Stirred-Tank Bioreactor a Cell Culture Facility for Animal Cells Single System for Anchorage-Dependent and Suspension Cultures.
D'Amour et al, Production of Pancreatic Hormone-Expressing Endocrine Cells from Human Embryonic Stem Cells, Nature Biotechnology, vol. 24, No. 11, 1392-1401 (2006).
Edy, 1984, Adv. Esp. Med. Biol. 174:169.
Elliot, 1990, Bioprocess Tech. 10:207.
Gerami-Naini, et al., Trophoblast Differentiation Embryoid Bodies Derived from Human Embryonic Stem Cells, Endocrinology, 145(4):1517-1524, (2004).
Gerecht-Nir, et al., Bioreactor Cultivation Enhances the Efficiency of Human Embryoid Body (hEB) Formation and Differentiation, Nature Biotechnology, vol. 86, No. 5, 493-502, Jun. 5 2004.
Green, et al, Generation of anterior foregut endoderm from human embr-yonic and induced pluripotent stem cells, Nature Biotechnology, vol. 29., No. 3, 267-273, Mar. 2011.
Hong, et al., 1989, Growth Kinetics of Strawberry Cell Suspension Cultures in Shake Flask, Airlift, Stirred Jar, and Roller Bottle Bioreactors, Biotechnology Progress, vol. 5, No. 4, 137-143, Dec. 1989.
Koyanagi, et al. Inhibition of the Rho/ROCK Pathway Reduces Apoptosis During Transplantation of Embryonic Stem Cell-Derived Neural Precursors, Journal of Neuroscience Research, 86:270-280 (2008).
Krawetz, et al., Human embryonic stem cells: caught between a ROCK inhibitor and a hard place, BioEssays 31:336-343, (2009).
Kunitake et al. 1997, Fully-Automated Roller Bottle Handling System for Large Scale Culture of Mammalian Cells, Journal of Biotechnology, 52: 289-294, (1997).

(Continued)

*Primary Examiner* — Valarie Bertoglio
(74) *Attorney, Agent, or Firm* — The Law Office of Jane K. Babin, Professional Corporation; Jane K. Babin

(57) ABSTRACT

The present invention relates to methods for production of undifferentiated or differentiated embryonic stem cell aggregate suspension cultures from undifferentiated or differentiated embryonic stem cell single cell suspensions and methods of differentiation thereof.

22 Claims, 43 Drawing Sheets

(56) References Cited

OTHER PUBLICATIONS

Lim et al., Proteome Analysis of Conditioned Medium from Mouse Embryonic Fibroblast Feeder Layers which Support the Growth of Human Embryonic Stem Cells, Proteomics, 2: 1187-1203, (2002).

Ludwig et al., Derivation of Human Embryonic Stem Cells in Defined Conditions, Nature Biotechnology, vol. 24, No. 2, 185-187, Feb. 2006.

Niebruegge, et al., Cardiomyocyte Production in mass Suspension Culture: Embryonic Stem Cells as a Source for Great Amounts of Functional Cardiomyocytes, Tissue Engineering, Part A, vol. 14, No. 10, (2008).

NIH (Stem Cells: Scientific Progress and Future Research Directions, Department of Health and Human Services, Chapter 1, pp. 1-4, Jun. 2001.

Oh et al., Human Embryonic Stem Cells: Technological Challenges Towards Therapy, Clinical and Experimental Pharmacology and Physiology, 33:489-495, (2006).

Olivas et al., Use of the Pannell-Milstein Roller Bottle Apparatus to Produce High concentrations of the CSF-1, the Mouse Macrophage Growth Factor, Journal of Immunological Methods, vol. 1982, 73-79, (1995).

Palena, et al., The Human T-Box Mesodermal Transcription Factor Brachyury is a Candidate Target for T-Cell-Mediated Cancer Immunotherapy, Clinical Cancer Res., vol. 13:, No. 8, 2471-2478 (2007).

Pennell, et al., An Oscillating Bubble Chamber for Laboratory Scale Production of Monoclonal Antibodies as an Alternative to Ascitic Tumours, Journal of Immunological Methods, 146, 43-48, (1992).

Prowse et al.,, A Proteome Analysis of Conditioned Media from Human Neonatal Fibroblasts Used in the Maintenance of Human Embryonic Stem Cells, Proteomics, vol. 5, 978-989 (2005).

Robins, et al., Media and Extra Cellular Matrix Requirements for Large-Scale ESC Growth, Emerging Technology Platforms for Stem Cells, Edited by Uma Lakshmipathy, 251-274 (2009).

Schuldiner et al, Effects of Eight Growth Factors on the Differentiation of Cells Derived from Human Embryonic Stem Cells, PNAS, vol. 97, No. 21, 11307-11312, Oct. 10, 2000.

Singhvi et al., Assessment of virus Infection in Cultured Cells Using Metabolic Monitoring, Cytotechnology, vol. 22,79-85, (1996).

Tanaka et al., Rotating Drum Fermentor for Plant Cell Suspension Cultures, Biotechnology and Bioengineering, vol. 25, 2359-2370 (1983).

Tanaka, 1987, Process Biochem., August., 106.

Thomson, et al., Isolation of a Primate Embryonic Stem Cell Line, Proc. Natl. Acad. Sci., USA, vol. 92, 7844-7848, Aug. 1995.

Tsao, Optimization of a Roller Bottle Process for the Production of Recombinant Erythorpoietin, Annals New York Academy of Sciences, 665:127-136 (1992).

Valdimarsdottir et al., Functions of the TGFβ superfamily in human embryonic stem cells. APMIS, vol. 113, 773-89, (2005).

Watanabe, A ROCK Inhibitore Permits Survival of Dissociated Human Embryonic Stem Cells, Nature Biotechnology, vol. 25, No. 6, 681-686, Jun. 2007.

Xu et al. Feeder-Free Growth of Undifferentiated Human Embryonic Stem Cells, Nature Biotechnology, vol. 19, 971-974, (2001).

Xu et al., Basic Fibroblast Growth Factor Supports Undifferentiated Human Embryonic Stem Cell Growth Without Conditioned Medium, Stem Cells; vol. 23, 315-323, (2005).

Hunt, et al., "Bioprocess Development for the Expansion of Embryonic Stem Cells", In "Embryonic Stem Cells—Basic Biology to Bioengineering" Kallos ed. , InTech, Available from: http://www.intechopen.com/books/embryonic-stem-cells-basic-biology-to-bioengineering/bioprocess-development-for-the-expansion-of-embryonic-stem-cells, pp. 49-72 (2011).

European Patent Office, "European Search Report for EP 13191191140.6-1402", pp. 1-7 (Feb. 10, 2014).

Schulz, et al., "A Scalable System for Production of Functional Pancreatic Progenitors from Human Embryonic Stem Cells", PLOS 7:e37004 (1-17) (2012).

Lock, et al., "Expansion and Differentiation of Human Embryonic Stem Cells to Endoderm Progeny in a Microcarrier Stirred-Suspension Culture", Tissue Eng Part A 15:2051-62 (2009).

Zur Nieden, et al., "Embryonic stem cells remain highly pluripotent following long term expansion as aggregates in suspension bioreactors", J Biotech129:421-32 (2007).

Jiang, et al., "In vitro derivation of functional insulin-producing cells from human embryonic stem cells", Cell Research 17:333-44 (2007).

Kurosawa, "Methods for Inducing Embryoid Body Formation: In Vitro Differentiation System of Embryonic Stem Cells", J Biosci Bioeng 103:389-98 (2007).

Wang, et al., "Self-renewal of human embryonic stem cells requires insulin-like growth factor-1 receptor and ERBB2 receptor signaling", Blood 110:4110-4119 (2007).

Cormier, et al., "Expansion of undifferentiated murine embryonic stem cells as aggregates in suspension culture bioreactors.", Tissue Eng 12:3233-45. (2006).

Schroeder, et al., "Differentiation and Lineage Selection of Mouse Embryonic Stem Cells in a Stirred Bench Scale Bioreactor With Automated Process Control", Biotechnol Bioeng 92:920-33 (2005).

D'Amour, et al., "Efficient differentiation of human embryonic stem cells to definitive endoderm.", Nature Biotechnology. 23:1534-41. (2005).

Fok, et al., "Shear-Controlled Single-Step Mouse Embryonic Stem Cell Expansion and Embryoid Body-Based Differentiation", Stem Cells 23:1333-42 (2005).

Sen, "Effects of Hydrodynamics on Cultures of Mammalian Neural Stem Cell Aggregates in Suspension Bioreactors", Ind. Eng. Chem. Res. 40:5350-57 (2001).

\* cited by examiner

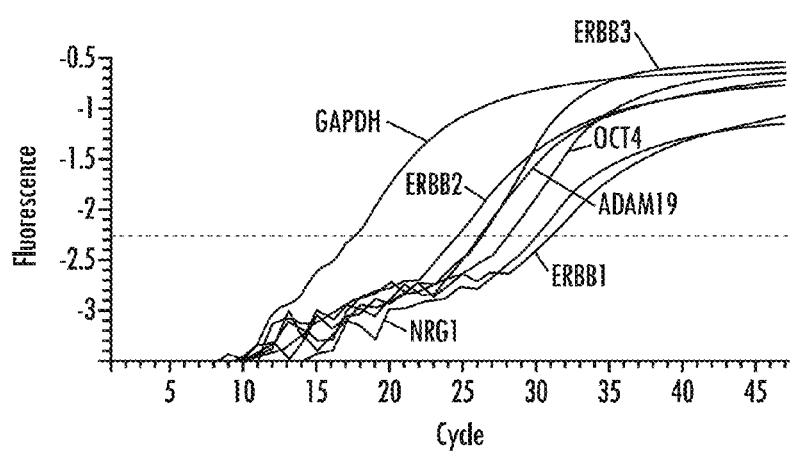
Fig. 1
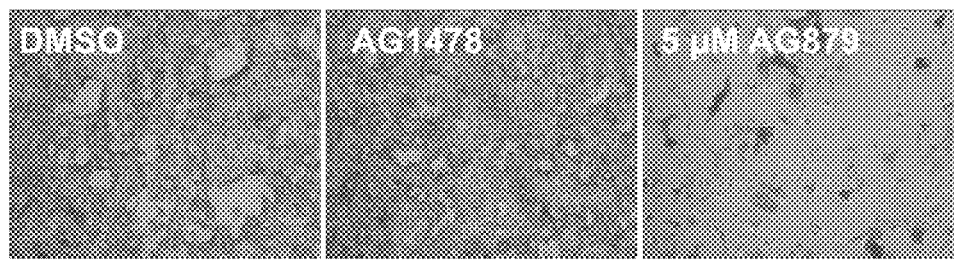
Fig. 2A   Fig. 2B   Fig. 2C

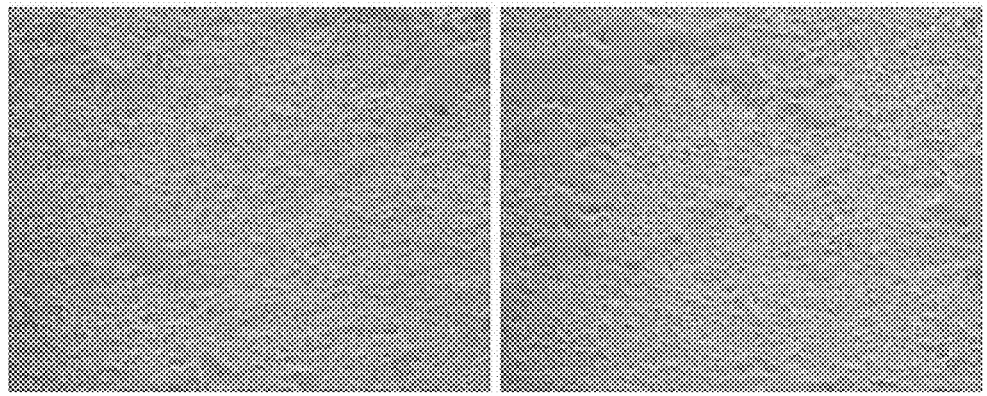
Fig. 3A  Fig. 3B
Fig. 3C  Fig. 3D
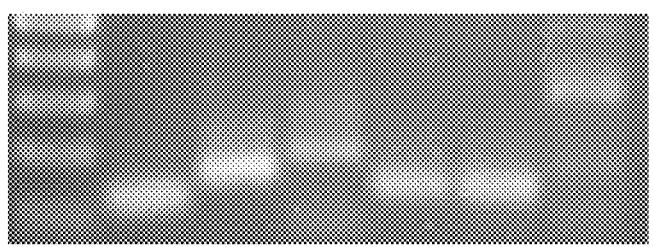
Fig. 4A
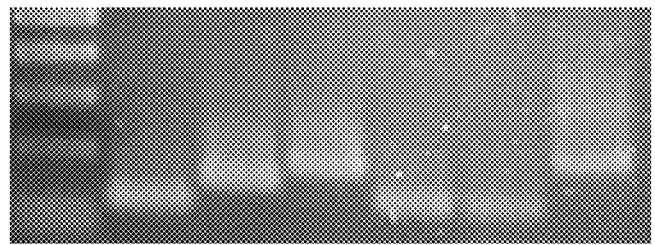
Fig. 4B

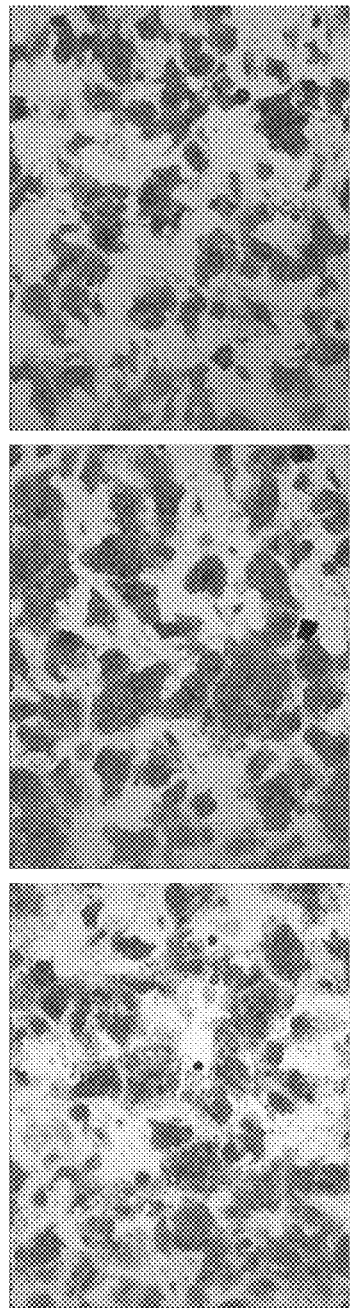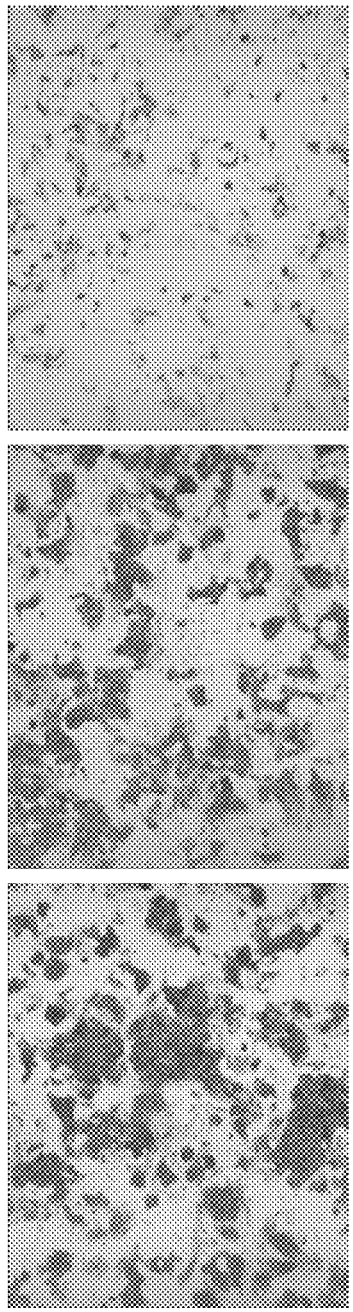

SCALABLE PRIMATE PLURIPOTENT STEM CELL AGGREGATE SUSPENSION CULTURE AND DIFFERENTIATION THEREOF

RELATED APPLICATIONS

This application is a Continuation-in-Part under 35 U.S.C. §120 of U.S. patent application Ser. No. 13/220,590, filed Aug. 29, 2011, now U.S. Pat. No. 8,445,273, issued May 21, 2013; which is a Continuation of U.S. patent application Ser. No. 12/264,760, filed Nov. 4, 2008, now U.S. Pat. No. 8,008,075, issued Aug. 30, 2011, the disclosures of which are incorporated herein by reference in the entireties.

STATEMENT REGARDING FEDERALLY SPONSORED RESEARCH OR DEVELOPMENT

Part of the work performed during development of this invention utilized U.S. Government funds from National Institutes of Health Grant No. 5 R24RR021313-05. The U.S. Government has certain rights in this invention.

FIELD OF THE INVENTION

The present invention relates to suspension cell aggregate compositions that are essentially serum and feeder-free and methods for differentiating the cell aggregate suspensions.

BACKGROUND OF THE INVENTION

To date, there is no efficient system providing for a large-scale manufacturing process ("scale-up") for mammalian pluripotent cells such as human embryonic stem cells (hESC) as described herein. To maintain hESC in an undifferentiated state in vitro, the hESC are maintained on mouse embryonic fibroblast (MEF) feeders and passaged by manual mechanical dissociation (e.g., micro-dissection) and transferring individual colony pieces. These methods are sufficient for research studies that do not require large-scale production of undifferentiated hESC or differentiated hESC, gene targeting, drug discovery, in vitro toxicology, future clinical applications require improved methods for the stable large-scale expansion of hESC, including enzymatic passaging.

Enzymatic expansion of hESC can be performed but these methods have technical disadvantages because hESC depend on cell-cell interactions as well as para- and autocrine signals for survival. Hence, hESC prefer this cellular microenvironment as compared to existing as single cells. Also, there are reports that enzymatic dissociation of hESC may lead to abnormal karyotypes and result in genetic and epigenetic changes. Thus, providing a highly supportive culture environment while at the same time allowing for robust large-scale expansion (i.e., a manufacturing process) of undifferentiated hES or differentiated hESC without compromising the pluripotency, multipotency or genetic stability over extended culture periods is essential.

Human pluripotent cells offer unique opportunities for investigating early stages of human development as well as for therapeutic intervention in several disease states, such as diabetes mellitus and Parkinson's disease. For example, the use of insulin-producing β-cells derived from hESC would offer a vast improvement over current cell therapy procedures that utilize cells from donor pancreases. Currently cell therapy treatments for diabetes mellitus, which utilize cells from donor pancreases, are limited by the scarcity of high quality islet cells needed for transplant. Cell therapy for a single Type I diabetic patient requires a transplant of approximately $8 \times 10^8$ pancreatic islet cells (Shapiro et al. 2000, *N Engl J Med* 343:230-238; Shapiro et al. 2001a, *Best Pract Res Clin Endocrinol Metab* 15:241-264; Shapiro et al. 2001, British Medical Journal 322:861). As such, at least two healthy donor organs are required to obtain sufficient islet cells for a successful transplant.

hESC thus represent a powerful model system for the investigation of mechanisms underlying pluripotent cell biology and differentiation within the early embryo, as well as providing opportunities for genetic manipulation of mammals and resultant commercial, medical and agricultural applications. Furthermore, appropriate proliferation and differentiation of hESC can potentially be used to generate an unlimited source of cells suited to transplantation for treatment of diseases that result from cell damage or dysfunction. Other pluripotent cells and cell lines including early primitive ectoderm-like (EPL) cells as described in International Patent Application WO 99/53021, in vivo or in vitro derived ICM/epiblast, in vivo or in vitro derived primitive ectoderm, primordial germ cells (EG cells), teratocarcinoma cells (EC cells), and pluripotent cells derived by dedifferentiation or by nuclear transfer will share some or all of these properties and applications. International Patent Application WO 97/32033 and U.S. Pat. No. 5,453,357 describe pluripotent cells including cells from species other than rodents. Human ES cells have been described in International Patent Application WO 00/27995, and in U.S. Pat. No. 6,200,806, and human EG cells have been described in International Patent Application WO 98/43679.

The biochemical mechanisms regulating ES cell pluripotency and differentiation are very poorly understood. However, the limited empirical data available (and much anecdotal evidence) suggests that the continued maintenance of pluripotent ES cells under in vitro culture conditions is dependent upon the presence of cytokines and growth factors present in the extracellular milieu.

While human ESCs offer a source of starting material from which to develop substantial quantities of high quality differentiated cells for human cell therapies, these cells must be obtained and/or cultured in conditions that are compatible with the expected regulatory guidelines governing clinical safety and efficacy. Such guidelines likely will require the use of media with all components sourced with cGMP. The development of such chemically defined/GMP standard conditions is necessary to facilitate the use of hESCs and cells derived from hESCs for therapeutic purposes in humans.

In addition, the eventual application of hESC based cell replacement therapies will require the development of methods that enable large scale culture and differentiation conditions that are compliant with regulatory guidelines. While several groups have reported simplified growth conditions for hESCs, there are substantial limitations with these studies. To date, however, the successful isolation, long-term clonal maintenance, genetic manipulation and germ line transmission of pluripotent cells has generally been difficult.

Most of the cell culture conditions for stem cells still contain serum replacer (KSR) in the media (Xu et al. 2005 Stem Cells, 23:315-323; Xu et al. 2005 Nature Methods, 2:185-189; Beattie et al. 2005 Stem Cells, 23:489-495; Amit et al. 2004 Biol. Reprod., 70:837-845; James et al. 2005 Development, 132:1279-1282). KSR contains a crude fraction of bovine serum albumin (BSA) rather than a highly purified source. Others have only performed short-term studies, and therefore it is not clear if their conditions would enable the maintenance of pluripotency over extended periods (Sato et al. 2004, *Nature Med.* 10:55-63; U.S. Patent Publication Nos. 2006/0030042 and 2005/0233446). Others have shown long-term maintenance of pluripotency in a chemically defined media with FGF2, activin A, and insulin, but the cells were grown on plates that were coated with human serum, which was "washed off" before plating of cells (Vallier et al. 2005 J Cell Sci., 118(Pt 19):4495-509). While FGF2 has been a component of all these media, it is not clear if it provides a primary or secondary self-renewal signal (Bendall et al. 2007 Nature 448:1015-1027); particularly as in some formulations it is necessary to use it at a high concentration (up to 100 ng/mL, Xu et al. 2005 Nature Methods, 2:185-189).

Furthermore, all of these groups have either included insulin in their media at μg/mL levels, or have insulin present due to the use of KSR. Insulin is typically considered to function in glucose metabolism and "cell survival" signaling via binding to the insulin receptor. At levels above physiological concentrations, however, insulin can also bind to the IGF1 receptor with a lower efficiency and confer classical growth factor activity through the PI3 Kinase/AKT pathway. The presence/requirement for such high levels of insulin (μg/mL levels) in KSR or these other media conditions suggests that the major activity is elicited via binding to the IGF1 receptor, which is expressed by hESCs (Sperger et al. 2003 PNAS, 100(23):13350-13355). Others have noted the expression of a full complement of IGF1R and intracellular signaling pathway members in hESCs, which is likely to signify the functional activity of this pathway (Miura et al. 2004 Aging Cell, 3:333-343). Insulin or IGF1 may elicit a major signal required for the self-renewal of hESCs, as is suggested by the fact that all conditions developed thus far for the culture of hESC contain either insulin, insulin provided by KSR, or IGF1 provided by serum. In support of this concept, it has been shown that if PI3 Kinase is inhibited in hESC cultures, the cells differentiate (D'Amour et al. 2005, Nat. Biotechnol 23:1534-41; McLean et al. 2007 Stem Cells 25:29-38).

A recent publication outlines a humanized, defined media for hESCs (Ludwig et al. Nature Biotechnology, published online Jan. 1, 2006, doi:10.1038/nbt1177). This recent formulation, however, includes several factors that are suggested to influence the proliferation of hESCs, including FGF2, TGFβ, LiCl, γ-aminobutyric acid and pipecolic acid. It is noted that this recently defined cell culture medium also contains insulin.

A self-renewal signaling paradigm for hESC based on a combination of insulin/IGF1, heregulin, Activin A signaling was previously reported by Applicant. See Wang et al. 2007 Blood 110:4111-4119. In this context we have found that an exogenous FGF2 signal is redundant and not required (Schulz & Robins 2009, supra) Schulz & Robins 2009, (In: Lakshmipathy et al. eds., Emerging Technology Platforms for Stem Cells. John Wiley & Sons, Hoboken, N.J., pp. 251-274);) Heregulin is a member of the EGF growth factor family. There are at least 14 members, including, but not limited to, EGF, TGFβ, heparin binding-EGF (hb-EGF), neuregulin-β (also named heregulin-β (HRG-β), glial growth factor and others), HRG-α, amphiregulin, betacellulin, and epiregulin. All these growth factors contain an EGF domain and are typically first expressed as transmembrane proteins that are processed by metalloproteinase (specifically, ADAM) proteins to generate soluble ectodomain growth factors. EGF family members interact with either homo- or hetero-dimers of the ErbB1, 2, 3 and 4 cell surface receptors with different affinities (Jones et al. FEBS Lett, 1999, 447:227-231). EGF, TGFα and hbEGF bind ErbB1/1 (EGFR) homodimers and ErbB1/2 heterodimers at high affinity (1-100 nM range), whereas HRG-β binds ErbB3 and ErbB4 at very high affinity (<1 nM range). Activated ErbB receptors signal through the PI3 Kinase/AKT pathway and also the MAPK pathway.

ErbB2 and ErbB3 are amongst the most highly expressed growth factor receptors in hESCs (Sperger et al. 2003, PNAS, 100:13350-13355) and HRG-β has been shown previously to support the expansion of mouse primordial germ cells (Toyoda-Ohno et al. 1999, Dev. Biol., 215:399-406). Furthermore, over expression and subsequent inappropriate activation of ErbB2 is associated with tumorigenesis (Neve et al. 2001 Ann. Oncol, 12(Suppl 1):S9-13; Zhou & Hung, 2003 Semin. Oncol. 30(5 Suppl 16):38-48; Yarden, 2001, Oncology, 61 Suppl 2:1-13). Human ErbB2 (Chromosome 17q), and ErbB3 (Chromosome 12q) are present on chromosomes that have been observed to accumulate as trisomies in some hESCs (Draper et al. 2004 Nat. Biotechnol. 22:53-4; Cowan et al. 2004 N Engl. J. Med. 350(13):1353-6; Brimble et al. 2004 Stem Cells Dev., 13:585-97; Maitra et al. 2005 Nat. Genet. 37:1099-103; Mitalipova et al. 2005 Nat. Biotechnol. 23: 19-20; Draper et al. 2004 Stem Cells Dev., 13:325-36; Ludwig et al. Nature Biotech, published online Jan. 1, 2006, doi:10.1038/nbt1177).

ErbB2 and ErbB3 (Brown et al. 2004 Biol. Reprod., 71:2003-11; Salas-Vidal & Lomeli, 2004 Dev Biol. 265:75-89) are expressed in the mouse blastocyst, although not specifically restricted to the inner cell mass (ICM), and ErbB1, EGF and TGFβ are expressed in the human blastocyst (Chia et al. 1995 Development, 1221(2):299-307). HB-EGF has proliferative effects in human IVF blastocyst culture (Martin et al. 1998 Hum. Reprod. 13:1645-52; Sargent et al. 1998 Hum. Reprod. 13(Suppl 4):239-48), and modest additional effects on mouse ES cells grown in 15% serum (Heo et al. 2006 Am. J. Phy. Cell Physiol. 290:C123-33, Epub 2005 Aug. 17. Pre- and early post-implantation development does not appear to be affected in ErbB2−/−, ErbB3−/−, Neuregulin1−/− (Britsch et al. 1998 Genes Dev., 12:1825-36), ADAM17−/− (Peschon et al. 1998 Science, 282: 1281-1284) and ADAM19−/− (Horiuchi 2005 Dev. Biol. 283:459-71) null embryos. Therefore, the importance of signaling through the ErbB receptor family in hESCs is, up to now, unclear.

Neuregulin-1 (NRG1) is a large gene that exhibits multiple splicing and protein processing variants. This generates a large number of protein isoforms, which are referred to herein collectively as neuregulin. Neuregulin is predominantly expressed as a cell surface transmembrane protein. The extracellular region contains an immunoglobulin-like domain, a carbohydrate modified region and the EGF domain. NRG1 expression isoforms have been reviewed previously (Falls 2003 Exp. Cell Res. 284:14-30). The cell membrane metalloproteases ADAM17 and ADAM19 have been shown to process the transmembrane form(s) of neuregulin-1 to soluble neuregulin/heregulin. HRG-α and -β are the cleaved ectodomains of neuregulin, containing the EGF and other domains. As the EGF domain is responsible for binding and activation of the ErbB receptors, a recombinant molecule containing only this domain can exhibit essentially all of the soluble growth factor effects of this protein (Jones et al. 1999 FEBS Lett. 447:227-31). Also, there are processed transmembrane isoforms of neuregulin that are thought to trigger juxtacrine signaling in adjacent cells via interaction of the EGF domain with ErbB receptors.

Still, an important development in the progression of hESC research toward maintaining pluripotency in culture will be the elucidation of media and cell culture conditions that are compatible with the expected regulatory guidelines governing clinical safety and efficacy. While the best outcome would be the availability of chemically defined media for hESC, components that are not chemically defined would be acceptable if they were produced to GMP standard. There is a need, therefore, to identify methods and compositions for the culture and stabilization of a population of pluripotent stem cells that are able to be used for therapeutic purposes, wherein the culture compositions are defined and/or produced to GMP standard.

The production of committed progenitor or differentiated cell types that can function following transplantation is a central promise of the potential of hESC-based therapeutic research. Using a step-wise protocol, in particular a 4-stage step-wise protocol substantially similar to that described herein and previously in Applicant's patent and non-patent publications, also referred to herein, primate pluripotent stem cells (pPSC) e.g., hESC or iPSC, are differentiable cells that can be directed to differentiate to a mixed population of pancreatic type cells by the end of stage 4. The mixture of cells contains at least cells commonly referred to as "pancreatic progenitors", or "pancreatic endoderm", or "pancreatic epithelium" both also referred to as "PE", or "PDX1-positive pancreatic endoderm", or "pancreatic endoderm cells" or "PEC" or equivalents thereof.

The cellular composition of PEC has been fully characterized as described in Applicant's prior patent and non-patent applications, including but not limited to Kroon et al. 2008 *Nature Biotechnology* 26:443-52, and U.S. Pat. Nos. 7,534,608; 7,695,965; and 7,993,920, entitled METHODS FOR MAKING INSULIN IN VIVO, and U.S. Pat. No. 8,278,106, entitled ENCAPSULATION OF PANCREATIC CELLS DERIVED FROM HUMAN PLURIPOTENT STEM CELLS, which are herein incorporated by reference in their entireties. Using flow cytometry, quantification of more than 20 samples from more than 10 different development lots of PEC showed the following types of cells. About 50% (ranges from 33-60%) of the cell mixture consisted of cells that express NKX6-1 but not Chromogranin (CHGA). About 44% (range 33-62%) poly-hormonal endocrine cells express CHGA. CHGA positive cells have been shown to develop and mature to glucagon expressing cells following in vivo transplantation or implantation. About 7% (range 1.3-13%) express PDX1 while at the same time do not express CHGA or NKX6-1 (PDX1 only population). A very small group of cells, about 1% (range 0.27-6.9%) in the mixture or population express none of the above markers: neither PDX1, nor NKX6-1, nor CHGA (or triple negative cells). Hence, PEC or equivalents thereof refers to this population or mixture of cells. PEC composition or population is also described in more detail in Example 27 and Table 12. Kroon et al. 2008, supra, Schulz et al. 2012, supra, which disclosures are all incorporated herein by reference in their entireties.

Implanted PEC, encapsulated or un-encapsulated, gives rise to functioning islet-like structures in vivo through a mechanism that appears to primarily involve the de novo commitment of pancreatic progenitors to the endocrine lineages followed by further maturation to glucose-responsive β-cells. Such grafts are therefore capable of sensing blood glucose, responding with metered release of processed human insulin, and protecting against streptozotocin (STZ)-induced hyperglycemia in mice. See Kroon et al. 2008, supra.

While other candidate pancreatic lineages have been derived from hESC, none have demonstrated substantial post-engraftment function in vivo, as defined by both long-term glucose-responsive human c-peptide secretion and protection against STZ-induced hyperglycemia. Without demonstrated function in animal models, it is difficult to gauge the scalability, or clinical potential, of these alternate protocols. See Cai J. et al. 2009 *J Mol Cell Biol* 2:50-60; Johannesson et al. 2009 *PLoS One* 4:e4794; Mfopou et al. 2010 *Gastroenterology* 138: 2233-2245; Ungrin et al. 2011 *Biotechnol Bioeng.* December 2. doi:10.1002/bit.24375; Clark et al. 2007 *Biochem Biophys Res Commun* 356:587-593; Jiang et al. 2007 *Cell Res* 17: 333-344; and Shim et al. 2007 *Diabetologia* 50:1228-1238, which are incorporated herein by reference in their entireties.

The invention described herein follows on Applicant's previous demonstration that feeder-free conditions using defined media can support single cell passaging and bulk culture of hESC. See Schulz & Robins 2009, supra; and U.S. Pat. No. 8,278,106, entitled ENCAPSULATION OF PANCREATIC CELLS DERIVED FROM HUMAN PLURIPOTENT STEM CELLS, which are herein incorporated by reference in their entireties. Critical for the progression of hESC-based technology to clinical trials is a demonstration of comparable scalability. Improvements that enhance expansion efficiencies will also save time and produce cost savings, as well as minimize the potential for population drift over time spent in culture. See Maitra et al. 2005 *Nat Genet.* 37:1099-1103, which is incorporated herein by reference in its entirety. Importantly, scaling using roller bottles as described herein, for example, along with cryopreservation of hESC, provides a defined and consistent material for product manufacture for near and long term research and development strategies.

SUMMARY OF THE INVENTION

The invention relates to compositions comprising a basal salt nutrient solution and an ErbB3 ligand, with the compositions being essentially free of serum.

The invention also relates to compositions comprising a basal salt nutrient solution and a means for stimulating ErbB2-directed tyrosine kinase activity in differentiable cells.

The invention relates to methods of culturing differentiable cells, with the methods comprising plating the differentiable cells on a cell culture surface, providing a basal salt nutrient solution to the differentiable cells and providing a ligand that specifically binds ErbB3.

The invention relates to methods of culturing differentiable cells, with the methods comprising plating the differentiable cells on a cell culture surface and providing a basal salt nutrient solution to the differentiable cells and a means for stimulating ErbB2-directed tyrosine kinase activity in the differentiable cells.

The invention also relates to methods of culturing differentiable cells, with the methods comprising providing a digest solution to a layer of differentiable cells that are contained in a culture chamber prior to digestion, where the digestion breaks apart the layer of cells into single cells. After digestion, the single cells are placed into a new tissue culture chamber with a differentiable cell culture solution, wherein the differentiable cell culture solution comprises a basal salt nutrient solution and an ErbB3 ligand. Once cultured, the single differentiable cells are placed in conditions that permit growth and division of the single cells.

The invention relates to methods for generating a hES cell aggregate in suspension from a pluripotent hES adherent culture, by culturing a hES cell in an adherent growth culture condition which allows for expansion in an undifferentiated state; disassociating the adherent hES cell culture into a single cell suspension culture; contacting the single cell suspension culture with a first differentiating culture condition which allows for formation of hES-derived cell aggregates in suspension by agitating the single cell suspension culture until such a period of time when the single cell suspension culture forms a hES-derived cell aggregate in suspension, and thereby generating a hES-derived cell aggregate in suspension. In preferred embodiments, agitation of the single cell suspension culture is performed by rotation at about 80 rpm to 160 rpm The invention also relates to methods for generating a hES-derived cell aggregate in suspension from a hES-derived single cell suspension, by culturing a hES cell in an adherent growth culture condition which allows for expansion in an undifferentiated state; contacting the undifferentiated hES cell with a first differentiating culturing condition suitable for differentiating the hES cell and resulting in an adherent hES-derived cell; disassociating the adherent hES-derived cell into a single cell suspension culture; contacting the single cell suspension culture with a second differentiating culture condition which allows for formation of hES-derived cell aggregates in suspension by agitating the single cell suspension culture until such a period of time when the single cell suspension culture forms a hES-derived cell aggregate in suspension, and thereby generating a hES-derived cell aggregate in suspension. In preferred embodiments, agitation of the single cell suspension culture is performed by rotation at about 80 rpm to 160 rpm.

The invention relates to a roller bottle containing primate pluripotent stem cell (pPSC) aggregates in suspension. In certain aspects of the invention, the pPSC aggregates are cells selected from the group consisting of human embryonic stem cells (hESC), induced pluripotent stem cells (iPSC) and/or other human pluripotent stem cells. In one embodiment, the roller bottle is not vented, but can be vented depending on the incubator or oven capabilities. In certain embodiments, the pPSC aggregates express at least one marker selected from the group consisting of OCT4, NANOG, SSEA-3, SSEA-4, Tra-1-80 and Tra-1-60.

The invention also relates to methods for generating a roller bottle containing pPSC aggregates by contacting pPSCs with a pluripotent stem cell culture condition, and agitating the culture until pPSC aggregates form, thereby generating pPSC aggregates in the roller bottle. In certain embodiments, agitation of the pPSC culture is performed by rotation at about 3 rpm, about 4 rpm, about 5 rpm, about 6 rpm, about 7 rpm, about 8 rpm, about 9 rpm, about 10 rpm, about 11 rpm, about 12 rpm, about 13 rpm, about 14 rpm, about 15 rpm, about 16 rpm, about 17 rpm, about 18 rpm, about 19 rpm, about 20 rpm, about 21 rpm, about 22 rpm, about 23 rpm, about 24 rpm, about 25 rpm, about 26 rpm, about 27 rpm, about 28 rpm, about 29 rpm and about 30 rpm. Typically, agitation of the pPSC culture is performed by rotation at about 5 rpm, about 6 rpm, about 7 rpm, about 8 rpm, about 9 rpm, about 10 rpm, about 11 rpm, and about 12 rpm.

Another aspect of the invention relates to methods for differentiating pPSC aggregates in a roller bottle by contacting differentiable or undifferentiated pPSC aggregates with a culturing condition that differentiates the pPSCs, and agitating the pPSC aggregate culture until formation of pPSC-derived aggregates, thereby generating pPSC-derived aggregates in suspension in a roller bottle. In certain embodiments, agitation of the pPSC-derived aggregates suspension culture is performed by rotation at about 3 rpm, about 4 rpm, about 5 rpm, about 6 rpm, about 7 rpm, about 8 rpm, about 9 rpm, about 10 rpm, about 11 rpm, about 12 rpm, about 13 rpm, about 14 rpm, about 15 rpm, about 16 rpm, about 17 rpm, about 18 rpm, about 19 rpm, about 20 rpm, about 21 rpm, about 22 rpm, about 23 rpm, about 24 rpm, about 25 rpm, about 26 rpm, about 27 rpm, about 28 rpm, about 29 rpm and about 30 rpm. Typically, agitation of the pPSC culture is performed by rotation at about 5 rpm, about 6 rpm, about 7 rpm, about 8 rpm, about 9 rpm, about 10 rpm, about 11 rpm, and about 12 rpm.

Still another embodiment of the invention relates to methods where fluid flow within a rolling bottle type of vessel involves rolling movement that does not require rotation or rolling the bottle. In one embodiment, the rolling type movement is substantially re-created but without the use of a rolling vessel. In another embodiment, a primate pluripotent stem cell culture has imparted fluid movement, for example, by pumping or flowing a fluid in a smooth, orderly manner with little or no turbulence. In such embodiments, any sub-current generally moves in parallel with any other nearby sub-current(s). This type of movement is also characterized as laminar flow (commonly used to move viscous fluids, especially those moving at low velocities) or streamline flow (a steady movement of fluid movement). In a yet another embodiment, the fluid movement involves one or more baffles, which distribute the fluid flow within a chamber to create a continuous, uniform suspension of cells. In a still further embodiment, the fluid movement involves one or a combination of deflector plates, distribution channels, and/or flow channels. In each embodiment, there is included at least one or more seals on the culture vessel to ensure an aseptic environment inside the vessel during cell aggregation, growth and differentiation.

The invention also relates to methods for enriching or varying the composition of the resulting cell culture and/or population of an hES-derived cell aggregate suspension by optimizing the cell density of the pluripotent cell cultures or varying the concentration of various growth factors, for example, FGF10, EGF, KGF, noggin and retinoic acid, apoptotic inhibitors, Rho-kinase inhibitors and the like.

BRIEF DESCRIPTION OF THE DRAWINGS

FIG. 1 depicts real time RT-PCR expression analysis of ADAM19, Neuregulin1, and ErbB1-3 in BG01v grown in defined conditions (8 ng/mL FGF2, 100 ng/mL LR-IGF1, 1 ng/mL Activin A). GAPDH and OCT4 control reactions are indicated.

FIG. 2 depicts the inhibition of proliferation of BG01v cells using AG879. BG01v cells were plated in 6-well trays and exposed to DMSO (A), 50 nM-20 µM AG1478 (B), or 100 mM-20 µM AG879 (C) 24 hours after plating. After 5 days in culture, the cultures were fixed and stained for alkaline phosphatase activity. AG1478 did not appear to affect proliferation at these concentrations (20 µM shown in B), but AG879 substantially slowed cell growth at 5 µM (C).

FIG. 3 depicts the morphology of BG01v cells cultured in DC-HAIF, which is defined culture media containing 10 ng/mL HRG-β, 10 ng/mL Activin A, 200 ng/mL LR-IGF1 and 8 ng/mL FGF2 (A and B), and in defined culture media (DC) containing 10 ng/mL HRG-β, 10 ng/mL Activin A, and 200 ng/mL LR-IGF1 (C and D).

FIG. 4 depicts the expression of ADAM19, Neuregulin1, and ErbB1-4 by RT-PCR in mouse ES cells (A) and MEFs (B).

FIG. 5 depicts the inhibition of ErbB1 and ErbB2 signaling in mouse ES cells. $2 \times 10^5$ Mouse R1 ES cells were plated on 1:1000 MATRIGEL™ in 10% FBS, 10% KSR with 1000 U/mL mouse LIF (ESGRO). The following day, DMSO (carrier control), 1-50 µM AG1478, or 1-50 µM AG879 was added with fresh medium. The cultures were fixed on day 8, and stained for alkaline phosphatase activity. DMSO (A) and 1-50 µM AG1478 (B and C) did not overtly inhibit proliferation. AG879 substantially inhibited cell growth at 50 µM (compare D and F) and may have slowed proliferation at 20 µM (E).

FIG. 27A); Differentiation at days 0, 2, 5, 8 and 12 in vented (V) or not-vented (NV) 490 $cm^2$ roller bottles (about 1.2 L capacity), are shown. Day 2 samples were not collected for the last 490V sample (far right column) due to loss of culture. The same d0 control was used for each roller bottle differentiation (asterisk).

DETAILED DESCRIPTION OF THE INVENTION

Figure 6A:
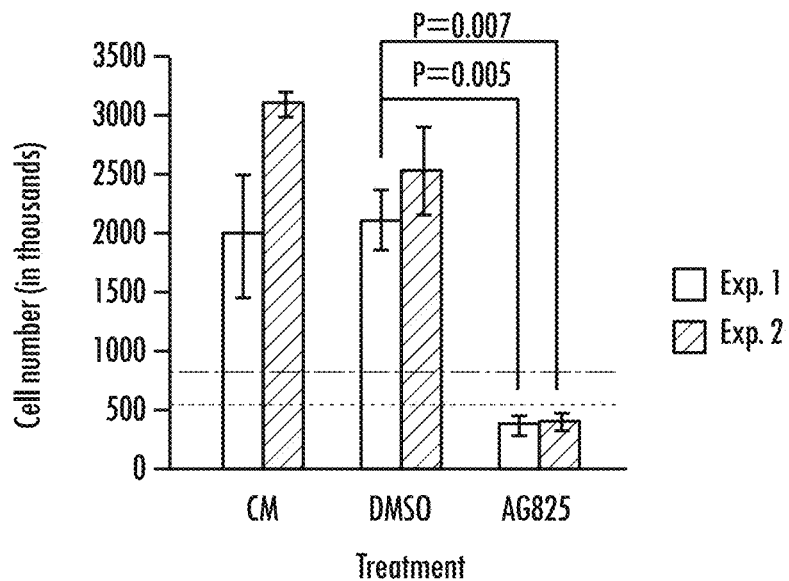
FIG. 6 depicts the inhibition of proliferation of BG02 cells grown in conditioned media (CM). (A) 50 µM AG825 inhibited proliferation of BG02 hESCs growing in CM. (B) AG825 inhibits ErbB2 Y1248 phosphorylation in hESCs. (C) Colony counting of serial passaging of CyT49 hESCs in different combinations of growth factors. (D) Cell counting analysis of the role of IGF1 and HRG in hESC proliferation using BG02 cells (left). (E) OCT4/DAPI immunostaining of a duplicate repeated experiment demonstrated that IGF1 and HRG significantly increased the proportion of OCT4+ cells compared to ActA/FGF2 conditions. (F) RTK blotting analysis of BG01 DC-HAIF hESCs starved of growth factors overnight; starved, then pulsed with DC-HAIF for 15 minutes; or steady-state cultures are shown (left). The mean and range of normalized relative intensity is plotted (right).

In contrast to previously known methods of tissue engineering which are based on seeding individual cells into polymer scaffolds, matrices and/or gels, the methods described herein use cell aggregate suspensions formed from pluripotent hES single cell suspensions or hES-derived (differentiated) single cell suspensions as the building blocks of tissue formation. Cell aggregates are often comprised of hundreds to thousands of individual cells, connected through junctional adhesions and extracellular matrix that collectively contribute to the final differentiated product. In this regard, cell aggregates can be defined as a type of tissue that provides a number of performance advantages relative to more traditional engineered tissues.

In one embodiment of the invention, methods are provided for producing hES cell aggregate suspensions from a single cell suspension of pluripotent stem cell cultures or hES-derived cell cultures. The pluripotent stem cells can be initially cultured on fibroblast feeders, or they can be feeder-free. Methods of isolating hESC and culturing such on human feeder cells was described in U.S. Pat. No. 7,432,104 entitled METHODS FOR THE CULTURE OF HUMAN EMBRYONIC STEM CELLS ON HUMAN FEEDER CELLS, which is herein incorporated in its entirety by reference. Pluripotent ES cell aggregate suspension cultures made directly or initiated from hESCs cultured on feeders avoid the need for making hESC monolayers, for example, as in adherent cultures. These methods are described in detail in Examples 17 and 18.

Other embodiments of the invention provide for methods of producing cell aggregate suspensions directly into a differentiation media, e.g., a differentiating media containing an agent, preferably a TGFβ family member, which is capable of activating a TGFβ family of receptor. Such agents include but are not limited Activin A, Activin B, GDF-8, GDF-11, and Nodal. Methods of producing cell aggregate suspension in a differentiation media is distinguished from other methods, also described herein, which provide for production of cell aggregate suspension cultures in a pluripotent stem cell media, e.g., StemPro.

Still other embodiments of the invention provide for methods of producing cell aggregate suspensions formed from differentiated hES cell cultures (also referred to as "hES-derived cell cultures" or "hES-derived cell(s)"), e.g., cells from stages 1, 2, 3, 4 and 5 as described in D'Amour et al. 2005, supra and D'Amour et al. 2006, Nature Biotech 26 2006: 1392-1401). Hence, methods for making the cell aggregates described herein are not limited to any one pluripotent or multipotent stage of a hES or hES-derived cell, rather the manner of use and need for cell type optimization will dictate which methods are preferred. These methods are described in detail in Examples 19-22.

In another embodiment of the invention, methods are provided for controlling the resulting cell composition, e.g., controlling the percentage of pancreatic endoderm cells, pancreatic endocrine cells and/or PDX1-endoderm cells, by varying the concentration of different growth factors. These methods are described in detail in Example 21.

Unless otherwise noted, the terms used herein are to be understood according to conventional usage by those of ordinary skill in the relevant art. In addition to the definitions of terms provided below, definitions of common terms in molecular biology may also be found in Rieger et al. 1991 Glossary of genetics: classical and molecular, 5th Ed., Berlin: Springer-Verlag; and in Current Protocols in Molecular Biology, F. M. Ausubel et al. Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

"About" as used herein means that a number referred to as "about" comprises the recited number plus or minus 1-10% of that recited number. For example, "about" 100 cells can mean 95-105 cells or as few as 99-101 cells depending on the situation. Whenever it appears herein, a numerical range such as "1 to 20" refers to each integer in the given range; e.g., "1 to 20 cells" means 1 cell, 2 cells, 3 cells, etc., up to and including 20 cells. Where about modifies a range expressed in non-integers, it means the recited number plus or minus 1-10% to the same degree of significant figures expressed. For example, about 1.50 to 2.50 mM can mean as little as 1.35 M or as much as 2.75M or any amount in between in increments of 0.01.

The present invention provides methods for production of hES-derived cell aggregates from hES-derived single cell suspensions. Because various mechanical and non-physiological factors effect movement and aggregation of cells in culture, the fluid mechanical microenvironment that correlates with optimal cell aggregate viability and performance, as well as to provide a normalizing variable that can be used for scale-up, it was necessary to characterize the movement of cells growing or differentiating in various culture vessels, dishes, Erlenmeyer flasks, bioreactors, bottles and the like and the effects, if any, of various media conditions on the cells. Some of these factors include but are not limited to, shear rate and shear stress, cell density and concentration of various growth factors in any cell medium.

Shear rate and shear stress are mechanical characteristics that define the fluid shear within a system. Shear rate is defined as the fluid velocity over a given distance and is expressed as $sec^{-1}$. Shear rate is proportional to shear stress where shear rate ( )=shear stress (t)/viscosity ($\mu$). Shear stress is defined as the fluid shear force acting tangentially to the cell surface and is expressed as force per unit area ($dyne/cm^2$ or $N/m^2$). Shear stress can be generated by agitated liquid moving past static cells, agitated cells moving through static liquid or by cells moving within an agitated, dynamic fluid environment. Fluid viscosity is typically measured in poise where 1 poise=1 dyne $sec/cm^2$=100 centipoise (cp). The viscosity of water, one of the least viscous fluids known, is 0.01 cp. The viscosity of a typical suspension of eukaryotic cells in media is between 1.0 and 1.1 cp at a temperature of 25° C. Both density and temperature can affect the viscosity of a fluid.

Fluid velocity also dictates whether the flow will be laminar or turbulent. Laminar flow occurs when viscous forces dominate and is characterized by smooth, even streamlines at low velocities. In contrast, high velocity and inertial forces dominate during turbulent flow, which is characterized by the appearance of eddies, vortices and chaotic fluctuations in the flow across space and time. A dimensionless value known as the Reynold's number (Re) is typically used to quantify the presence of laminar or turbulent flow. The Reynold's number is the ratio of inertial to viscous forces and is quantitated as (density*velocity*length scale)/(viscosity). Laminar flow dominates with Re<2300 while turbulent flow dominates when Re>4000. Based on this relationship with fluid velocity, the Reynold's number and thus the degree to which fluid flow is laminar or turbulent is directly proportional to the shear rate and shear stress experienced by cells in suspension. However, high shear stress conditions can be generated in both laminar and turbulent fluid environments. Initially, there is a tendency for liquid to resist movement, with the fluid closest to a solid surface experiencing attractive forces that generate a boundary layer or a region of no-flow immediately adjacent to the surface. This creates a gradient in fluid velocity from the surface to the center of the fluid flow. The steepness of the velocity gradient is a function of the speed at which the liquid is moving and distance from the boundary layer to the region of highest fluid velocity. As the liquid flow rate through or around a container accelerates, the velocity of the flow overcomes the viscosity of the liquid and the smooth, laminar gradient breaks down producing turbulent flow. Thomas et al. showed that cell lysis under turbulent conditions occurs most frequently in regions of locally high shear stress and high energy dissipation rates. See Thomas et al. (1994) Cytotechnology 15: 329-335. These regions appear randomly but are often found near the boundary layer where the velocity gradient is highest. These random fluctuations in fluid velocity can generate regions of very high shear stress that ultimately can have a negative effect on the scale-up of cell culture-based manufacturing systems. Thus, a need exists for methods that can maintain cell density and viability in a mammalian cell culture manufacturing scale-up system by controlling the major sources of shear forces in such systems.

Following methods provided by Henzler (Henzler, 2000, Particle stress in bioreactors, In *Advances in Biochemical Engineering/Biotechnology*, Scheper, T. Ed. Springer-Verlag, Berlin) and Colomer et al. (Colomer, J. et al. 2005. Experimental analysis of coagulation of particles under low-shear flow. *Water Res.* 39:2994), fluid mechanical properties of the bulk fluid in a rotating 6-well dish were calculated. The Dimensionless Stress is equal to the turbulence constant* (aggregate diameter/Kolmogorov's Microscale)^turbulence exponent. Shear Stress is equal to the Dimensionless Stress*fluid density*(kinematic viscosity*power input)^0.5. Shear Rate is equal the Shear Stress/kinematic viscosity. For calculation of the power input and Kolmogorov's Microscale, the Reynold's number is required at each rotation rate and is equal to the (rotation rate*flask diameter)^2/viscosity. As both the power input and Kolmogorov's Microscale are functions of the Reynold's Number, all shear stress and shear rate calculations vary with rotation rate.

Moreover, shear stress and shear rate are functions of the Dimensionless Stress, which depends on the diameter of forming aggregates, thus the shear stress and rate experienced by aggregates is expected to increase with time in rotation. Example calculations are shown in Example 17 for aggregate diameters between 100-200 μm and rotation speeds between 60-140 rpm. These methods were used to provide an estimation of the average shear in the bulk fluid over time. However, it is expected that the shear stress at the wall of the vessel will be the highest due to boundary effects. To estimate wall shear stress, Ley et al. proposed that wall shear stress in a 6-well dish is equal to the radius of gyration*(density*dynamic viscosity*(2*pi*rotation rate)^3)^0.5. Using this approach, the wall shear stress was calculated for rotation speeds ranging from 60 rpm to 140 rpm and is shown in Example 18. Note that, unlike the time-averaged shear stress that is experienced by aggregates in the bulk fluid, the shear stress occurring at the wall is independent of aggregate diameter.

Culture cell density is also a factor critical to the tissue function and is difficult to achieve and/or optimize in traditional tissue which are 2-dimensional (e.g., adherent engineered constructs). The effect of cell density on differentiation is described in more detail in Example 20. Cell aggregates may overcome this limitation by assuming an organized 3-dimensional (3D) architecture that more accurately reflects an in vivo cellular density and conformation. As a result, the period of time for the cells to achieve their intended structure can be significantly reduced and/or made more consistent and efficient. Moreover, cells in the 3D aggregate format may differentiate and function more optimally, as this architecture more closely resembles normal physiology than adherent cultures. In addition, the mechanical hardship involved in the manufacturing process is less damaging to cell aggregates that are free-floating in suspension culture as compared to the mechanical hardship, for example, in an adherent culture.

Typical manufacturing-scale suspension culture also utilizes continuous perfusion of media as a method for maintaining cell viability while maximizing cell density. In this context, media exchange contributes fluid shear to the culture affecting adherent cells and suspended aggregates differently. Immobile adherent cells are subject to fluid shear stress as the media flows tangentially across the cell surface. In contrast, suspended aggregates experience significantly less shear stress across the aggregate surface, as aggregates are free to tumble in response to applied shear force. It is expected that prolonged shear stress will be detrimental to adherent ES cells and that the suspended aggregate format is preferred for optimal survival and function. Thus based on a need for an efficient manufacturing process for production of pluripotent stem cells and/or multipotent progenitor cells derived from pluripotent stem cells and the above observed mechanics relating to shear rate and shear stress, the present invention provides for the first time methods of manufacturing for production of pluripotent stem cells and/or multipotent progenitor cells derived from pluripotent stem cells in suspension format, in particular, cell aggregate suspension format.

As used herein, "single cell suspension" or equivalents thereof refers to a hES cell single cell suspension or a hES-derived single cell suspension by any mechanical or chemical means. Several methods exist for dissociating cell clusters to form single cell suspensions from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Acutase and the like), or a combination of both. Further, methods and culture media conditions capable of supporting single-cell dissociation of hESC is useful for expansion, cell sorting, and defined seeding for multi-well plate assays and enable automatization of culture procedures and clonal expansion. Thus, one embodiment of the invention provides methods for generating a stable single-cell enzymatic dissociation hES cell or hES-derived cell culture system capable of supporting long-term maintenance and efficient expansion of undifferentiated, pluripotent hES cell or differentiated hESC.

As used herein, "roller bottle" or "rolling bottle" or equivalents thereof refers to a cylindrical container adapted to rotate about its axes. These containers include but are not limited to roller bottles sold through Corning, Fisher Scientific, and other manufacturers, as well as drums, barrels, and other bottle type containers capable of being rotated on its side wall, for example. Roller bottles described herein do not have to be cylindrical or have a circular cross-section. They can be non-circular, closed curve, of constant width, for example. In one embodiment, the curve is a Reuleaux triangle or a Reuleaux triangle with rounded corners as described in U.S. Pat. No. 5,866,419, which is incorporated herein by reference in its entirety. Circular cross-section roller bottles are not the only shape or geometry to provide smooth rotation because an infinite number of such curves exist and are contemplated by the invention. Hover, such curves are not generally encountered in industry because most machinery used for rotating bottles requires that the horizontal axis running perpendicular to the curve remain in a fixed location, which it does not for non-circular rollers because that have axes with a back-and-forth translation motion while rolling. This additional motion or rotation, in addition to the usual circular motion as in other cylindrical roller bottles can enhance gas exchange as compared to circular cross-section type roller bottles.

A typical cylindrical roller bottle includes a bottom wall, a top wall and a cylindrical side wall extending between the bottom and top walls. The top wall includes an opening to provide access to the interior of the roller bottle. The internal surfaces of such roller bottles provide active surfaces for cell interaction and/or attachment. Hence, the Oxford Dictionary of Biochemistry provides that roller bottles are cylindrical containers used for the culture of monolayers of adherent cells. Indeed, roller bottles are desirable for growing large amounts of cells, such as adherent cells, or for producing cell by-products, such as pharmaceutical substances that are secreted by cells. The cylindrical side wall of roller bottles can be smooth or patterned, whereby patterning extends substantially from the bottom wall to the top wall for increasing cell growth surface area and for facilitating the flow of liquid to all interior surface areas of the bottle when the bottle is rolled about the axis of the side wall.

Independent of the cross-section of the roller bottle (circular or non-circular) liquid growth medium is introduced into and contained within a roller bottle. The rotating movement of the bottle keeps the internal surfaces wetted with the liquid medium, thereby encouraging the growth of cells. Rotating rollers of an appropriate apparatus are employed to rotate roller bottles of the invention.

Roller bottles are usually constructed of either glass, stainless steel or a clear plastic, such as polystyrene, polyurethane, polyvinyl chloride, polycarbonate, polyolefins such as polypropylene, polyethylene terephthalate with glycol additives, ethylene glycol-1,4, cyclohexane dimethanol terephthalate copolyester and the like. Transparent materials are preferred, as cell growth can be monitored by placing the bottle on an inverted microscope.

Manual and automated roller bottle systems have been used for over 40 years in the pharmaceutical, biochemical, and medical fields for processes such as cell growth and infection, heterologous glycoprotein production, vaccine preparation, and high density plant cell cultivation. See Tanaka et al. 1983, *Biotechnol. Bioeng.* 25:2359; Tanaka 1987, *Process Biochem.* August, 106; Hong, et al. 1989, *Biotechnol. Prog.* 5:137; Elliot 1990, *Bioprocess Tech.* 10:207; Tsao 1992, *Annals N.Y. Acad. Sci.* 665:127; Pennell & Milstein 1992, *J. of Immun. Meth.* 146:43; Olivas et al., 1995, *Immun. Meth.* 182, 73 (1995); Singhvi et al. 1996, *Cytotechnology* 22:79; and Kunitake et al. 1997, *Biotechnology* 52:3289, which are incorporated herein by reference in their entireties. Additionally, for industrial scale production of cell culture products (i.e. vaccines), cells are frequently passaged in roller bottles prior to transfer to micro-carrier cultures for a final growth phase even when unit operation based systems are utilized. See Edy, 1984, *Adv. Exp. Med. Biol.* 172:169, which is herein incorporated by reference in its entirety.

To date, widespread use of roller bottles for culturing adherent cells can be attributed to several factors. The process relies on: (i) a horizontal cylindrical vessel containing a sufficient volume of media or fluid and axially rotated; because roller bottle scale up is a function of length, scale-up development or invention is not required, resulting in reduced developmental timelines for industry and faster introduction to market for new products; (ii) roller bottle systems allow for constant fluid-gas contact, i.e. due to the axial rotation there is at all times at least a thin layer of fluid or media coating the inner surface of the bottle as it rotates; this layer allows for increased fluid-gas exchange and the as the bottle rotates that gas returns to the cells which are in the pool of media at the bottom of the roller bottle; (iii) maintaining sterile conditions for prolonged times in large scale culture is possible because contamination of one or more roller bottles does not result in contamination of an entire lot; (iv) precise control of nutrient and waste-product levels is possible; and (v) direct monitoring of the cells, e.g. identification of certain cell markers to ensure efficient differentiation and proper specification of cells after stages 1-4 for example is relatively simple.

While not wanting to be limited to use of roller bottle or roller type vessels for culturing three-dimensional cell aggregates, it is intended that there are other means for making the cell aggregates of the invention, although not employing the motion created by a roller bottle or a cylindrical type of vessel rotating on a drum, for example. The type of motion used to aggregate pPSCs in general can be produced, for example, by aerosolizing the vessel or chamber to produce a more laminar flow. The motion can also be created by having an inlet and an outlet port to assist the inflow and outflow of the fluid medium, or even the cells themselves, to create motion similar to that achieved with the roller bottles described herein. The motion can also be achieved with the use of one or more or a combination of flow distributors. For example, such a flow distributor may include a baffle to distribute the flow of fluid or medium within the chamber and thereby create a continuous, uniform mixture of the three-dimensional cell aggregates. In another example, the flow distributor may be combination of one or more deflector plates, distribution channels, and/or flow channels, which create fluid movement similar to that found in roller bottles without necessarily occurring in a roller bottle type, cylindrical vessel or chamber. Thus, alternative means of creating fluid movement in a manner that is non-turbulent, yet generates sufficient low shear force to promote cell collision and allow the cells to adhere to each other and form the cell aggregates as described herein.

Still, certain properties of growing adherent or anchorage dependent cells in roller bottles have their disadvantages. For example, adherent cell growth by its nature requires substantial surface area for the cell to attach to and roller bottles are limited in surface area that is available for growth. The conventional method of mixing in roller bottles is rotation at a uniform rate in one direction for all purposes e.g. cell planting or seeding, cell growth and/or virus propagation and expansion. Standard rotation frequencies of most roller bottle processes for culturing adherent and anchorage dependent cells is about 0.125 rpm to 5 rpm. For these cultures, it is important that the cells come into contact with the sides of the roller bottle as rapidly as possible, since only after attachment to the vessel wall can the cells subsequently proliferate and form cell sheets. Slow cell attachment to the inner walls of the vessel leads to low viability of the cells and/or inhomogeneous planting, and hence inhomogeneous growth on the roller bottle surface. Moreover, inefficient mixing limits cell growth because the cells do not obtain adequate nutrients (e.g. oxygen) or adequate removal of toxins (e.g. carbon dioxide) from a submerged, surface-attached cell sheet as the bottle rotates. Interestingly, these disadvantages are not critical to using roller bottles for aggregation, growth, expansion and differentiation of differentiable pluripotent cells in suspension.

In view of the properties described above and further in view Applicant's own disclosure of methods for making hES cell aggregates in 6-well trays and the like, one of ordinary skill in the art would not turn to use of roller bottles for making pluripotent stem cell aggregates. See Schulz et al. 2012, *Stem Cells* 7: 1-17, e37004, and U.S. Pat. Nos. 8,153, 429 and 8,008,075, which are incorporated herein by reference in their entireties. For example, Schulz et al. 2012, supra, teaches that pluripotent stem cells can be effectively aggregated by using a circular or radial movement or motion or rotation, which is imposed over a central vortex and draws cells into a higher local density in the middle of the culture vessel, e.g. drawing cells into the center of a well of a 6-well tray, or the center of Erlenmeyer flask or the center of a bioreactor based on a rotational format. This radial vortex cannot be accomplished in roller bottles because by its nature the roller bottle rotates on its side wall and not on its base, hence it is not intuitive to transfer methods from a system that includes a central vortex motion to one that does not, such as the roller bottles as described herein.

Applicants have performed studies of static cultures using other types of motion including studies rocking, stirring and centrifugation of hES cells, and these types of motions were incapable of allowing the formation of hES cell aggregates or differentiable cell aggregates. Further, these hES or hES cell-derived aggregates that did form under these conditions did not give rise to functioning glucose responsive cell types in vivo, which is the ultimate test of any method for successful manufacturing of PEC. See at least Kroon et al. 2008, supra and Schulz et al. (2012) supra. So, it cannot be said that just movement and motion alone is sufficient to form pluripotent stem cell or hES cell suspension aggregates or differentiable cell aggregates, because it is not. These studies (data not shown) indicated that more than just fluid movement and forces generated with such movement facilitate the adhesive contact necessary for cell aggregate formation that results in the transitioning of single-cell pluripotent stem cells to stable cell-cell aggregates.

As mentioned briefly above, rotation of a roller bottle is very different from rotation of a 6-well tray, Erlenmeyer flasks, and the like which occurs about a central vortex. In a roller bottle, the majority of the culture volume remains at the bottom of the bottle when the bottle rotates on its side wall, and a thin layer of fluid or culture medium coats the inner bottle surface as the bottle rotates. This thin fluid layer has increased gas exchange as the bottle rotates and therefore increases $O_2$ levels to the culture medium overall; i.e. once the thin layer of culture media returns to the bottom of the bottle where the majority of the culture medium resides, it carries with it increases amounts of $O_2$ It is not intuitive then that this motion, especially when rotated at very low speeds that are standard in the art for adherent cells (e.g. 0.125 to 5 rpm) would allow for sufficient cell-to-cell contact or collisions while at the same time maintain the low shear-force sufficient to allow primate pluripotent stem cell (pPSC) aggregate formation, let alone differentiation of differentiable cell aggregates.

Using roller bottles to aggregate, grow, passage, expand and differentiate cells is also different from 6-well trays, Erlenmeyer flasks, bioreactors because of the different rotations speeds between the two formats. 6-well trays, Erlenmeyer flasks, bioreactors and the like for example use higher rotation speeds of about 80, 85, 90, 95, 100, 105, 110, 115 and 120 rpm, which are required for at least the purpose of preventing the cell aggregates from agglomerating or forming clusters or larger cell masses in culture. Note, that the agglomerated cell clusters (e.g., large aggregates of 300 μm or more) are not to be confused with the roughly spherical cell aggregates, which are smaller (about 100-200 μm) and uniform in size. In contrast, the aggregation, growth, passaging, expansion and differentiation of pPSCs in roller bottles is performed at relatively low rotations speeds of about 3, 4, 5, 6, 7, 8, 9, and 10 rpms. These lower rotation speeds do not create the same degree of shear force which occurs in 6-well trays, Erlenmeyer flasks, bioreactors and the like, and in view of Applicant's previous experience (see Schulz et al. 2012, supra), it was not expected that cell aggregate formation would succeed under these conditions.

An advantage of using roller bottles to aggregate, grow, passage, expand and differentiate pluripotent stem cells over that of other cell culture vessels is that once optimized in the smallest roller bottle, the methodologies will work very similarly in larger bottles without additional substantial invention. For example, by using longer bottles with the same standard cross-section, but substantially larger capacity, or by using arrays of bottles, total culture mass can be scaled using the same bottle diameter, diameter/volume ratio and rotation speed. An increase in roller bottle length (scaling) does not affect the cell aggregation or differentiation processes. So, scaling of the cell process or manufacture from 490 cm$^2$ roller bottles (11.12 cm in diameter, 17.30 cm in length including cap) to 850 cm$^2$ roller bottles (11.63 cm in diameter, 27.36 cm in length including cap) to 1750 cm$^2$ roller bottles (11.73 cm in diameter, 53.16 cm in length including cap) or greater does not involve substantially or significantly modification other than that described herein.

For at least the above reasons, scalability of cell manufacturing in roller bottles is different from the rotational platform systems of 6-well trays, Erlenmeyer flasks, bioreactors and the like. For example, in order to achieve a 1 L pluripotent stem culture of 1×10$^6$ cells/mL, about thirty (30) 6-well trays would be required. Stated in another way, instead of using eighty (80) 6-well trays (total 480 wells), the skilled artisan would only need 4, 850 cm$^2$, roller bottles. The skilled artisan will appreciate that less manipulation and labor that is needed for roller bottle culture is an improvement in manufacturing. In addition, adjustments must be made in volume, speed and rotational radius in order to achieve aggregation when using rotational platforms at different scales. Primate PSC aggregation in conical flasks can be achieved, for example, but occurs best at relatively high rotation speeds, about 150 rpm, and this causes too much turbulence and shear-force leading to increased cell death (data not shown). Merely placing a bottle or jar on a rocking platform does not produce the herein described cell suspension aggregates (data not shown). The rocking motion does not create a suitable fluid motion to support appropriate cell-cell contact and adherence, and potentially creates too much turbulence and shear-force, causing increased cell death. Similarly, square shaped bottles and 15 cm glass jars are unsuitable culture vessels to scale up pPSC aggregates formation for similar reasons (data not shown). Further, mere cell-to-cell contact alone does not cause pPSC aggregates to form because when cell pellets are recovered after single-cell suspensions of hES cells are centrifuged, cell aggregates were not observed (data not shown). Thus, discovering a truly scalable system with appropriate fluid motion that supports efficient and consistent cell aggregation (including consistent aggregate diameter) has not been at all straight forward or routine, and substantially more difficult than a skilled artisan would anticipate or expect. In fact, it has been surprising that roller bottles, which have been traditionally used for large scale-up cultures of adherent and anchorage dependent cell types, coupled with up to a 30-fold reduction in speed would provide suitable conditions for production of pPSC aggregates and differentiation as herein described at all.

As used herein, the term "contacting" (i.e., contacting a cell e.g., a differentiable cell, with a compound) is intended to include incubating the compound and the cell together in vitro (e.g., adding the compound to cells in culture). The term "contacting" is not intended to include the in vivo exposure of cells to a defined cell medium comprising an ErbB3 ligand, and optionally, a member of the TGF-β family, that may occur naturally in a subject (i.e., exposure that may occur as a result of a natural physiological process). The step of contacting the cell with a defined cell medium comprising an ErbB3 ligand, and optionally, a member of the TGF-β family, can be conducted in any suitable manner. For example, the cells may be treated in adherent culture, or in suspension culture. It is understood that the cells contacted with the defined medium can be further treated with a cell differentiation environment to stabilize the cells, or to differentiate the cells.

As used herein, the term "differentiate" refers to the production of a cell type that is more differentiated than the cell type from which it is derived. The term therefore encompasses cell types that are partially and terminally differentiated. Differentiated cells derived from hESC are generally referred to as hES-derived cells or hES-derived cell aggregate cultures, or hES-derived single cell suspensions, or hES-derived cell adherent cultures and the like.

As used herein, the term "substantially" refers to a great extent or degree, e.g. "substantially similar" in context is used to describe one method which is to great extent or degree similar to or different than another method. However, as used herein, the term "substantially free", e.g., "substantially free" or "substantially free from contaminants," or "substantially free of serum" or "substantially free of insulin or insulin like growth factor" or equivalents thereof, means that the solution, media, supplement, excipient and the like, is at least 98%, or at least 98.5%, or at last 99%, or at last 99.5%, or at least 100% free of serum, contaminants or equivalent thereof. In one embodiment, there is provided a defined culture media with no serum, or 100% serum-free, or substantially free of serum. Conversely, as used herein, the term "substantially similar" or equivalents thereof means that the composition, process, method, solution, media, supplement, excipient and the like is at least 80%, at least 85%, at least 90%, at least 95%, or at least 99% similar to that previously described in the specification herein, or in a previously described process or method incorporated herein in its entirety.

In certain embodiments of the present invention, the term "enriched" refers to a cell culture that contains more than approximately 50%, 55%, 60%, 65%, 70%, 75%, 80%, 85%, 90%, or 95% of the desired cell lineage.

As used herein, the term "effective amount" or equivalents thereof of a compound refers to that concentration of the compound that is sufficient in the presence of the remaining components of the defined medium to effect the stabilization of the differentiable cell in culture for greater than one month in the absence of a feeder cell and in the absence of serum or serum replacement. This concentration is readily determined by one of ordinary skill in the art.

As used herein, the term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCR, in situ hybridization, Western blotting, and immunostaining.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

The present invention may be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. 1989 "Molecular Cloning", Second Edition, Cold Spring Harbor Laboratory, Plainview, N.Y.; Maniatis et al. 1982 "Molecular Cloning", Cold Spring Harbor Laboratory, Plainview, N.Y.; Wu (ed.) 1993 Meth. Enzymol. 218, Part I; Wu (ed.) 1979 Meth. Enzymol. 68; Wu et al. (eds.) 1983 Meth. Enzymol. 100 and 101; Grossman and Moldave (eds.) 1980 Meth. Enzymol. 65; Miller (ed.) 1972 "Experiments in Molecular Genetics", Cold Spring Harbor Laboratory, Cold Spring Harbor, N.Y.; Old and Primrose, 1981 "Principles of Gene Manipulation", University of California Press, Berkeley; Schleif & Wensink, 1982 "Practical Methods in Molecular Biology"; Glover (ed.) 1985 "DNA Cloning" Vol. I and II, IRL Press, Oxford, UK; Hames and Higgins (eds.) 1985 "Nucleic Acid Hybridization", IRL Press, Oxford, UK; and Setlow and Hollaender 1979 "Genetic Engineering: Principles and Methods", Vols. 1-4, Plenum Press, New York. Abbreviations and nomenclature, where employed, are deemed standard in the field and commonly used in professional journals such as those cited herein.

The invention relates to compositions and methods comprising a basal salt nutrient solution and an effective amount of an ErbB3 ligand, with the compositions being essentially free of serum. The compositions and methods of the present invention are useful for culturing cells, in particular, differentiable cells. It is understood that at different points during culturing the differentiable cells, various components may be added to the cell culture such that the medium can contain components other than those described herein. It is, however, contemplated that at least at one point during the preparation of the culture, or during the culture of the differentiable cells, the defined medium comprises a basal salt nutrient solution and a means for activating ErbB2-directed tyrosine kinase.

Although a basal salt nutrient solution as described herein is employed to maintain cell growth and viability of hESC, in other embodiments of the invention, alternative stem cell culture medias to maintain pluripotency or for differentiation of the pluripotent cells, work in substantially similar means, including but not limited to KSR (Invitrogen), or xeno-free KSR (Invitrogen), StemPro® (Invitrogen), mTeSR™1 (StemCell Technologies) and HEScGRO (Millipore), DMEM based media, and the like.

In another embodiment, hESC are cultured in the defined media described herein in the absence and/or presence of extracellular matrix proteins (ECM), e.g., MATRIGEL. Human ES cells cultured in the absence of ECM contain about 0.5 to 10% human serum (hS) or hS retentate fractions from a 300K and/or 100K cut-off spin column (Microcon). The hES cell aggregate suspensions can be produced by directly incubating the hESC into the media containing hS or hS retentate fractions; or after incubating the culture vessels with the hS or hS retentate fractions for about 30 min., 1 hour, 2 hours, 3 hours, 4, hours, 5 hours, 6 hours, 12 hours, and 24 hours at 37° C. The plating efficiency for the hESC in the hS or hS retentate fraction containing media was comparable to that observed in hESC cultured in DC-HAIF as described in PCT/US2007/062755, or cultured in DC-HAIF media using MATRIGEL™ as an ECM, or other similar matrices. Methods for culturing hESC in a defined media substantially free of serum is described in U.S. patent application Ser. No. 11/8875,057, filed Oct. 19, 2007, entitled METHODS AND COMPOSITIONS FOR FEEDER-FREE PLURIPOTENT STEM CELL MEDIA CONTAINING HUMAN SERUM, which is herein incorporated in its entirety by reference.

Still in another embodiment, hES cell aggregate suspensions were cultured in a media substantially free of serum and further in the absence of exogenously added fibroblast growth factor (FGF). This is distinguished from U.S. Pat. No. 7,005,252 (Thomson), which requires culturing hESC in a media without serum but containing exogenously added growth factors, including FGF.

Cellular regulation can be effected through the transduction of extracellular signals across the membrane that, in turn, modulates biochemical pathways within the cell. Protein phosphorylation represents one course by which intracellular signals are propagated from molecule to molecule resulting finally in a cellular response. These signal transduction cascades are highly regulated and often overlapping as evidenced by the existence of many protein kinases as well as phosphatases. It has been reported that in humans, protein tyrosine kinases are known to have a significant role in the development of many disease states including diabetes, cancer and have also been linked to a wide variety of congenital syndromes. Serine threonine kinases, e.g., Rho kinases, are a class of enzymes, which if inhibited can have relevance to the treatment of human disease, including diabetes, cancer, and a variety of inflammatory cardiovascular disorders and AIDS. The majority of inhibitors identified/designed to date act at the ATP-binding site. Such ATP-competitive inhibitors have demonstrated selectivity by virtue of their ability to target the more poorly conserved areas of the ATP-binding site.

The Rho kinase family of small GTP binding proteins contains at least 10 members including Rho A-E and G, Rac 1 and 2, Cdc42, and TC10. The inhibitors are often referred to as ROK or ROCK inhibitors, and they are used interchangeably herein. The effector domains of RhoA, RhoB, and RhoC have the same amino acid sequence and appear to have similar intracellular targets. Rho kinase operates as a primary downstream mediator of Rho and exists as two isoforms: α (ROCK2) and β (ROCK1). Rho kinase family proteins have a catalytic (kinase) domain in their N-terminal domain, a coiled-coil domain in their middle portion, and a putative pleckstrin-homology (PH) domain in their C-terminal domain. The Rho-binding domain of ROCK is localized in the C-terminal portion of the coiled-coil domain and the binding the GTP-bound form of Rho results in enhancement of kinase activity. The Rho/Rho-kinase-mediated pathway plays an important role in the signal transduction initiated by many agonists, including angiotensin II, serotonin, thrombin, endothelin-1, norepinephrine, platelet-derived growth factor, ATP/ADP and extracellular nucleotides, and urotensin II. Through the modulation of its target effectors/substrates Rho kinase plays an important role in various cellular functions including smooth muscle contraction, actin cytoskeleton organization, cell adhesion and motility and gene expression. By virtue of the role that Rho kinase protein play in mediating a number of cellular functions perceived to be associated with the pathogenesis of arteriosclerosis, inhibitors of this kinase may also be useful for the treatment or prevention of various arteriosclerotic cardiovascular diseases and involved in endothelial contraction and enhancement of endothelial permeability which is thought to progress to atherosclerosis. Hence, in other embodiments of the invention, agents which promote and/or support cell survival are added to various cell culture media, for example, Rho-kinase inhibitors Y-27632, Fasudil, and H-1152P and ITS (insulin/transferrin/selenium; Gibco). These cell survival agents function, in part, by promoting re-association of dissociated hES cell or hES-derived cultures, e.g., foregut endoderm, pancreatic endoderm, pancreatic epithelium, pancreatic progenitor populations and the like, particularly dissociated pancreatic endoderm and pancreatic progenitor populations. Increase in survival of hES or hES-derived cells was achieved independently of whether the cells were produced from cell aggregates in suspension or from adherent plate cultures (with or with no extracellular matrix, with or without serum, with or without feeders). Increase in survival of these cell populations facilitates and improves purification systems using a cell-sorter and, therefore allows improved recovery of the cells. Use of Rho kinase inhibitors such as Y27632 may allow for expansion of hES-derived cell types as well by promoting their survival during serial passaging dissociated single cells or from cryogenic preservation. Although, Rho kinase inhibitors such as Y27632 have been tested on hES and hES-derived cell cultures, Rho kinase inhibitors can be applied to other cell types, for example, in general, epithelial cells including but not limited to intestinal, lung, thymus, kidney as well as neural cell types like pigmented retinal epithelium.

As used herein, the term "differentiable cell" is used to describe a cell or population of cells that can differentiate into at least partially mature cells, or that can participate in the differentiation of cells, e.g., fuse with other cells, that can differentiate into at least partially mature cells. As used herein, "partially mature cells", "progenitor cells", "immature cells", "precursor cells", "multipotent cells" or equivalents thereof and also includes those cells which are terminally differentiated, e.g., definitive endoderm cells, PDX1-negative foregut endoderm cells, PDX1-positive pancreatic endoderm cells which further include PDX1-positive pre-pancreatic endoderm cells and PDX1-positive pancreatic endoderm tip cells. All are cells that exhibit at least one characteristic of the phenotype, such as morphology or protein expression, of a mature cell from the same organ or tissue but can further differentiate into at least one other cell type. For example, a normal, mature hepatocyte typically expresses such proteins as albumin, fibrinogen, alpha-1-antitrypsin, prothrombin clotting factors, transferrin, and detoxification enzymes such as the cytochrome P-450s, among others. Thus, as defined in the present invention, a "partially mature hepatocyte" may express albumin or another one or more proteins, or begin to take the appearance or function of a normal, mature hepatocyte.

In contrast to cell aggregates produced by previously known methods that may vary in both size and shape, the cell aggregates and methods described herein have a narrow size and shape distribution, i.e., the cell aggregates are substantially uniform in size and/or shape. The size uniformity of the cell aggregates is critical for differentiation performance and homogeneity of the culture. Applying basic mass transport analysis to the aggregates, it is expected that diffusion of oxygen and nutrients into the center of large aggregates will be slow compared to diffusion into smaller aggregates, assuming equal permeability. As differentiation of aggregated ES cells into pancreatic lineage cells is dependent on the temporal application of specific growth factors, a culture with a mixture of aggregates of different diameters is likely to be de-synchronized as compared to a uniform (size and shape) culture of cell aggregates. This mixture of cell aggregates gives rise to heterogeneity and may result in poor differentiation performance and ultimately not lend itself to being amenable to manufacturing, scale-up, and production. The cell aggregates used herein can be of various shapes, such as, for example, a sphere, a cylinder (preferably with equal height and diameter), or rod-like among others. Although other shaped aggregates may be used, in one embodiment of the invention, it is generally preferable that the cell aggregates be spherical or cylindrical. In another embodiment, the cell aggregates are spherical and substantially uniform in size and shape. For instance, if the cell aggregates differ in size or are not uniform, it will be difficult to reliably manufacture and perform large scale-up processes of the cells. Hence, as used herein, the phrase "substantially uniform" or "substantially uniform in size and shape" or equivalents thereof, refers to the spread in uniformity of the aggregates which is not more than about 20%. In another embodiment, the spread in uniformity of the aggregates is not more than about 15%, 10% or 5%.

Although the exact number of cells per aggregate is not critical, it will be recognized by those skilled in the art that the size of each aggregate (and thus the number of cells per aggregate) is limited by the capacity of oxygen and nutrients to diffuse to the central cells, and that this number may also vary depending on cell type and the nutritive requirements of that cell type. Cell aggregates may comprise a minimal number of cells (e.g., two or three cells) per aggregate, or may comprise many hundreds or thousands of cells per aggregate. Typically, cell aggregates comprise hundreds to thousands of cells per aggregate. For purposes of the present invention, the cell aggregates are typically from about 50 microns to about 600 microns in size, although, depending on cell type, the size may be less or greater than this range. In one embodiment, the cell aggregates are from about 50 microns to about 250 microns in size, or about 75 to 200 microns in size, and preferably they are about 100 to 150 microns in size. In contrast, cylindrical or non-spherical cell aggregates which may occur in suspension are those aggregates whereby the diameter, as based on the minor and major axes (e.g., X, Y and Z), are not equal. These non-spherical cell aggregates tend to be larger in size, about 500 microns to 600 microns in diameter and height. However, in the methods described herein, these non-spherical hES cell aggregates become spherical once differentiation is initiated if they were not already. Non-spherical cell aggregates include but are not limited to cylindrical and cuboidal cell aggregates, but are still uniform in size and shape.

Many cell types may be used to form the cell aggregates described herein. In general, the choice of cell type will vary depending on the type of three-dimensional construct to be engineered (e.g. various organ structures including pancreas, liver, lung, kidney, heart, bladder, blood vessels, and the like). For example, if the three dimensional structure is a pancreas, the cell aggregates will advantageously comprise a cell type or types typically found in a pancreas (e.g., endocrine cells such as insulin, glucagon, ghrelin, somatostatin type cells, as well as endothelial cells, smooth muscle cells, etc.). One skilled in the art can choose an appropriate cell type(s) for the cell aggregates, based on the type of three-dimensional tissue or organ to be desired. Non-limiting examples of suitable cell types include stem cells (e.g. adult and embryonic), contractile or muscle cells (e.g., striated muscle cells and smooth muscle cells), neural cells (e.g., glial, dendritic and neurons), connective tissue (including bone, cartilage, cells differentiating into bone forming cells and chondrocytes, and lymph tissues), parenchymal cells, epithelial cells (including endothelial cells that form linings in cavities and vessels or channels, exocrine secretory epithelial cells, epithelial absorptive cells, keratinizing epithelial cells (e.g. keratinocytes and corneal epithelial cells), extracellular matrix secretion cells, mucosal epithelial cells, renal epithelial cells, lung epithelial cells, mammary epithelial cells and the like, and undifferentiated cells (such as embryonic cells, stem cells, and other precursor cells), among others.

The cell aggregates described herein can be homo-cellular aggregates or hetero-cellular aggregates. As used herein, "homo-cellular", "mono-cellular" cell aggregates or equivalents thereof refers to a plurality of cell aggregates in suspension, wherein each cell aggregate comprises a plurality of living cells of substantially a single cell type, e.g. methods for producing hES cell aggregates described herein can be substantially homo-cellular, consisting substantially of pluripotent hESC, consisting of substantially of definitive endoderm cells, foregut endoderm cells, consisting substantially of pancreatic endoderm cells, which can further include PDX1-positive pre-pancreatic endoderm cells, PDX1-positive pancreatic endoderm cells, PDX1-positive pancreatic endoderm tip cells, pancreatic endocrine precursor cells, pancreatic endocrine cells and the like.

As used herein, the term "essentially" or "substantially" means either a de minimus or a reduced amount of a component or cell present in any cell aggregate suspension type, e.g., cell aggregates in suspension described herein are "essentially or substantially homogenous", "essentially or substantially homo-cellular" or are comprised of "essentially hESC", "essentially or substantially definitive endoderm cells", "essentially or substantially foregut endoderm cells", "essentially or substantially PDX1-negative foregut endoderm cells", "essentially or substantially PDX1-positive pre-pancreatic endoderm cells", "essentially or substantially PDX1-positive pancreatic endoderm or progenitor cells", "essentially or substantially PDX1-positive pancreatic endoderm tip cells", "essentially or substantially pancreatic endocrine precursor cells", "essentially or substantially pancreatic endocrine cells" and the like.

Some of the substantially homo-cellular cell aggregate suspension cultures are, for example, hES-derived cell aggregate suspension cultures which comprise less than about 50% hESCs, less than about 45% hESCs, less than about 40% hESCs, less than about 35% hESCs, less than about 30% hESCs, less than about 25% hESCs, less than about 20% hESCs, less than about 15% hESCs, less than about 10% hESCs, less than about 5% hESCs, less than about 4% hESCs, less than about 3% hESCs, less than about 2% hESCs or less than about 1% hESCs of the total hES-derived cells in the culture. Stated in another way, hES-derived cell aggregate suspension cultures, e.g., PDX1-negative foregut endoderm, PDX-positive pre-pancreatic endoderm cells, PDX1-positive pancreatic endoderm or progenitor cells, PDX1-positive pancreatic tip cells, pancreatic endocrine progenitor cells and pancreatic endocrine cells, comprise at least 50%, at least 55%, at least 60%, at least 65%, at least 70%, at least 75%, at least 80%, at least 85%, at least 90%, or at least 95%, As used herein, "hetero-cellular", "multi-cellular" or equivalents thereof refers to cell aggregates whereby each individual cell aggregate comprises a plurality of cells of at least two, three, four, five, six or more cell types, or at least one cell type and a non-cellular component, e.g., extracellular matrix (ECM) material (e.g., collagen, fibronectin, laminin, elastin, and/or proteoglycans). Such ECM components can be naturally secreted by the cells, or alternately, the cells can be genetically manipulated by any suitable method known in the art to vary the expression level of ECM material and/or cell adhesion molecules, such as selectins, integrins, immunoglobulins, and cadherins, among others. In another embodiment, either natural ECM material or any synthetic component that imitates ECM material can be incorporated into the aggregates during aggregate formation. For example, methods for production of hES-derived cell aggregates such as pancreatic epithelial or pancreatic endoderm cell aggregates (or stage 4 cell aggregates) described herein consists substantially of pancreatic epithelial or endoderm cells, but may also consist in small cell numbers other non-pancreatic epithelial type cells, or other endoderm progenitors, and even pancreatic endocrine secreting cells (e.g., insulin secreting cells).

To be clear, the homo- or hetero-cellular aggregates described herein and produced by the suspension methods described herein, are not the same cell aggregates described in the art and by others and referred to as embryoid bodies (EBs). Embryoid bodies are clearly distinguished from the herein described cell aggregates because EBs are cell aggregates of differentiated and undifferentiated cells that appear when ES cells overgrow in monolayer cultures, or are maintained in suspension cultures in undefined media or are differentiated via non-directed protocols (i.e. random differentiation) towards multiple germ layer tissues. In contrast, the present invention, discussed in detail in Examples 17 and 20, enzymatically dissociates hESC on adherent plate cultures to make a single cell suspension and then brings the cells together to form cell aggregates; then using these cell aggregates suspension cultures for differentiation substantially as described in D'Amour et al. 2005, supra, & D'Amour et al. 2006, supra. Other differences between EBs and the cell aggregates of this invention are further discussed below.

Still other methods describe making embryoid bodies (EBs). As used herein, the term "embryoid bodies", "aggregate bodies" or equivalents thereof, refer to aggregates of differentiated and undifferentiated cells that appear when ES cells overgrow in monolayer cultures, or are maintained in suspension cultures in undefined media or are differentiated via non-directed protocols towards multiple germ layer tissues. That is, EBs are not formed from a single cell suspension of pluripotent stem cells as described herein; nor are EBs formed from adherent cultures of hES-derived multipotent cells. These features alone make the present invention clearly distinguishable from an embryoid body.

Embryoid bodies are a mixture of different cell types, typically from several germ layers, distinguishable by morphological criteria. Embryoid bodies typically refer to a morphological structure comprised of a population of cells, the majority of which are derived from embryonic stem (ES) cells that have undergone non-directed differentiation, i.e., such as that which occurs when undifferentiated cells are exposed to high concentrations of serum in the absence of defined growth factors. Under culture conditions suitable for EB formation (e.g., the removal of Leukemia inhibitory factor for mouse ES cells, or other, similar blocking factors), ES cells proliferate and form small masses of cells that begin to differentiate. First, corresponding to about days 1-4 of differentiation for human ES cells, the small mass of cells forms a layer of endodermal cells on the outer layer, and is considered a "simple embryoid body". Secondly, corresponding to about days 3-20 post differentiation for human ES cells, "complex embryoid bodies" are formed, which are characterized by extensive differentiation of ectodermal and mesodermal cells and derivative tissue. As used herein, EBs includes both simple and complex EBs unless otherwise required by context. The determination of when embryoid bodies have formed in a culture of ES cells is routinely made by persons of skill in the art by, for example, visual inspection of the morphology. Floating masses of about 20 cells or more depending on the culture conditions are considered to be EBs. See, e.g., Schmitt et al. (1991) Genes Dev. 5, 728-740; Doetschman et al. 1985, *J. Embryol. Exp. Morph.* 87:27-45. The term also refers to equivalent structures derived from primordial germ cells, which are primitive cells extracted from embryonic gonadal regions; see e.g., Shamblott et al. 1998, *Proc. Natl. Acad. Sci. USA* 95: 13726. Primordial germ cells, sometimes also referred to in the art as EG cells or embryonic germ cells, when treated with appropriate factors form pluripotent ES cells from which embryoid bodies can be derived; see e.g., U.S. Pat. No. 5,670,372; and Shamblott et al. supra.

Various methods for making EBs exist, e.g. spin embryoid bodies as described by Ng et al. 2008 *Nature Protocols* 3:468-776 and EBs made from single cell suspensions which were plated onto micro-patterned extracellular matrix islands as described in Bauwens et al. 2008, *Stem Cells* 26:2300-10, Epub 2008 Jun. 26. However, these methods are cost-prohibitive and less efficient for large scaled production (manufacturing) of hESC and hES-derived cells because they require too many steps before scale-up production can actually commence. For example, Bauwens et al. first have to seed hESC on a growth factor reduced MATRIGEL™ before the cells can be selected to start a suspension culture. The time and cost of this method makes it cumbersome because customized micro-patterned tissue culture plates are required. Additionally, the method employed by Ng et al. is also not cost-efficient for large scale-up manufacturing of hESC and hES-derived cells because of the use of centrifuges in order to create a more uniform EB. These methods are limited by surface area constraints, which also impacts their scalability. Lastly, in all these methodologies, the cell aggregates are not made from single cell suspensions of pluripotent stem cells as in the present invention.

Embryoid bodies are cell aggregates, unlike the cell aggregates described in this invention, that are made up of numerous cell types from the three germ layers and are typically created by exposing aggregates of undifferentiated ES cells to non-directed differentiation signals, such as 20% fetal bovine serum. The result of this non-directed methodology is a mixture of cell types that is intended to mimic normal embryo development in vitro. While this approach is useful at the basic research level for examining embryo development, it is not amenable to any large-scale cell therapy manufacturing process where cell yield, population identity, population purity, batch consistency, safety, cell function and cost of goods are primary concerns. Moreover, regardless of any enrichment strategies employed to purify a given cell type from an embryoid body, the differentiation protocol does not provide a directed approach that will generate a large population of a single cell type. Subsequently, contaminant populations will always predominate and will hamper any attempt to purify a specific population. All previous work on creating and differentiating aggregates of ES cells has one or more of the following components in their methodology: 1) use of mouse rather than human ES cells, 2) forced aggregation protocols that rely on centrifugation to aggregate cells rather than normal cell adhesion processes, 3) aggregation of cell chunks in static conditions, 4) non-single cell dissociation or scraping of cells off surfaces to create aggregates, 5) non-direct differentiation of cell aggregates using 15-20% fetal calf serum, resulting in the formation of an embryoid body and cell types of all germ layers, 6) formation in "hanging drop" conditions that can only be performed at a small scale. To our knowledge, the only study that does not utilize 15-20% FCS to differentiate embryoid bodies describes a protocol where cell aggregates are formed by forced aggregation, then aggregates are immediately differentiated using media appropriate for mesoderm (Ng et al. 2005, *Blood* 106:1601). However, in this work, the researchers transferred the embryoid bodies to non-aggregate adherent culture after 10-12 days in static aggregate culture making comparisons to the current application irrelevant. In contrast to all previous work, the current application presents an approach that 1) dissociates human ES cells to single cells then creates aggregates by rotational culture at shear rates optimized for improve control of aggregate diameter and cell survival, 2) directly differentiates the ES cell aggregates to definitive endoderm then foregut endoderm, then pre-pancreatic foregut endoderm, then pancreatic endoderm and finally pancreatic endocrine cells. This differentiation protocol generates definitive endoderm and pancreatic lineage populations with high efficiency and minimal contaminant populations. Moreover, this approach to ES cell aggregation and differentiation does not create embryoid bodies, in direct contrast to all other published research.

In contrast to embryoid bodies, which are a mixture of differentiated and undifferentiated cells and typically consist of cells from several germ layers and go through random differentiation, the cell aggregates described herein are essentially or substantially homo-cellular, existing as aggregates of pluripotent, multipotent, bipotent, or unipotent type cells, e.g., embryonic cells, definitive endoderm, foregut endoderm, PDX1 positive pancreatic endoderm, pancreatic endocrine cells and the like.

The present invention addresses the above problems by providing a cost efficient manufacturing process or methods capable of reproducibly producing cell aggregates that are substantially uniform in size and shape using a process that can easily be applied to large scale manufacturing. In one particular embodiment, the differentiable cells are expanded in a suspension culture, using the cell media of the present invention. In another particular embodiment, the differentiable cells can be maintained and expanded in suspension, i.e., they remain undifferentiated or are prevented from further differentiating. The term "expand" in the context of cell culture is used as it is in the art, and refers to cellular proliferation and increase the number of cells, preferably increase in number of viable cells. In a specific embodiment, the cells are expanded in a culture suspension by culturing for more than about one day, i.e., about 24 hours. In a more specific embodiment, the cells are expanded in a suspension culture by culturing for at least 1, 2, 3, 4, 5, 6, 7 days, or at least 2, 3, 4, 5, 6, 7, 8 weeks.

The differentiation culture conditions and hES-derived cell types described herein are substantially similar to that described in D'Amour et al. 2006, supra. D'Amour et al. 2006, describes a 5 step differentiation protocol: stage 1 (results in substantially definitive endoderm production), stage 2 (results in substantially PDX1-negative foregut endoderm production), stage 3 (results in substantially PDX1-positive foregut endoderm production), stage 4 (results in substantially pancreatic endoderm or epithelium or pancreatic endocrine progenitor production) and stage 5 (results in substantially hormone expressing endocrine cell production). Importantly, for the first time, all these cell types can be produced by suspension methods described herein.

As used herein, "definitive endoderm (DE)" refers to a multipotent endoderm lineage cell that can differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express or fail to significantly express certain markers. In some embodiments, one or more markers selected from SOX17, CXCR4, MIXL1, GATA4, HNF3beta, GSC, FGF17, VWF, CALCR, FOXQ1, CMKOR1, CRIP1 and CER are expressed in definitive endoderm cells. In other embodiments, one or more markers selected from OCT4, alpha-fetoprotein (AFP), Thrombomodulin (TM), SPARC, SOX7 and HNF4alpha are not significantly expressed in definitive endoderm cells. Definitive endoderm cell populations and methods of production thereof are also described in U.S. patent application Ser. No. 11/021,618, entitled DEFINITIVE ENDODERM, filed Dec. 23, 2004, which is hereby incorporated in its entirety.

Still other embodiments of the present invention relate to cell cultures and cell aggregates termed "PDX1-negative foregut endoderm cells", "foregut endoderm cells" or equivalents thereof. PDX1-negative foregut endoderm cells are also multipotent and can give rise to various cells and tissues including but not limited to thymus, thyroid, parathyroid, lungs/bronchi, liver, pharynx, pharyngeal pouches, parts of the duodenum and Eustachian tube. In some embodiments, the foregut endoderm cells express increased levels of SOX17, HNF1B, HNF1 alpha, FOXA1 as compared to non foregut endoderm cells e.g., definitive endoderm or PDX-positive endoderm which do not appreciably express these markers. PDX1-negative foregut endoderm cells also express low to no levels of PDX1, AFP, SOX7 and SOX1. PDX1-negative foregut endoderm cell populations and methods of production thereof are also described in U.S. patent application Ser. No. 11/588,693, entitled PDX1-expressing dorsal and ventral foregut endoderm, filed Oct. 27, 2006 which is hereby incorporated herein by reference in its entirety.

Other embodiments of the present invention relate to cell cultures of "PDX1-positive pancreatic foregut endoderm cells," "PDX1-positive pre-pancreatic endoderm," or equivalents thereof. PDX1-positive pre-pancreatic endoderm cells are multipotent and can give rise to various cells and/or tissues including but not limited to stomach, intestine and pancreas. In some embodiments, the PDX1-positive pre-pancreatic endoderm cells express increased levels of PDX1, HNF6, SOX9 and PROX1 as compared to non pre-pancreatic endoderm cells which do not appreciably express these markers. PDX1-positive pre-pancreatic endoderm cells also express low to no levels of NKX6.1, PTF1A, CPA, and cMYC.

Other embodiments of the present invention relate to cell cultures of "PDX1-positive pancreatic endoderm cells," "PDX1-positive pancreatic progenitor," "pancreatic epithelium", "PE" or equivalents thereof. PDX1-positive pancreatic progenitor cells are multipotent and can give rise to various cells in the pancreas including but not limited to acinar, duct and endocrine cells. In some embodiments, the PDX1-positive pancreatic progenitor cells express increased levels of PDX1 and NKX6.1 as compared to non pre-pancreatic endoderm cells which do not appreciably express these markers. PDX1-positive pancreatic progenitor cells also express low to no levels of PTF1A, CPA, cMYC, NGN3, PAX4, ARX and NKX2.2, INS, GCG, GHRL, SST, and PP.

Alternatively, other embodiments of the present invention relate to cell cultures of "PDX1-positive pancreatic endoderm tip cells," or equivalents thereof. In some embodiments, the PDX1-positive pancreatic endoderm tip cells express increased levels of PDX1 and NKX6.1 similar to PDX1-positive pancreatic progenitor cells, but unlike PDX1-positive pancreatic progenitor cells, PDX1-positive pancreatic endoderm tip cells additionally express increased levels of PTF1A, CPA and cMYC. PDX1-positive pancreatic endoderm tip cells also express low to no levels of NGN3, PAX4, ARX and NKX2.2, INS, GCG, GHRL, SST, and PP.

Yet, other embodiments of the present invention relate to cell cultures of "pancreatic endocrine precursor cells," "pancreatic endocrine progenitor cells" or equivalents thereof. Pancreatic endocrine progenitor cells are multipotent and give rise to mature endocrine cells including alpha, beta, delta and PP cells. In some embodiments, the pancreatic endocrine progenitor cells express increased levels of NGN3, PAX4, ARX and NKX2.2 as compared to other non-endocrine progenitor cell types. Pancreatic progenitor cells also express low to no levels of INS, GCG, GHRL, SST, and PP.

Still other embodiments of the present invention relate to cell cultures of "pancreatic endocrine cells," "pancreatic hormone secreting cells", "pancreatic islet hormone-expressing cell," or equivalents thereof that refer to a cell, which has been derived from a pluripotent cell in vitro, e.g. alpha, beta, delta and/or PP cells or combinations thereof. The endocrine cells can be poly-hormonal or singly-hormonal, e.g. expressing insulin, glucagon, ghrelin, somatostatin and pancreatic polypeptide or combinations thereof. The endocrine cells can therefore express one or more pancreatic hormones, which have at least some of the functions of a human pancreatic islet cell. Pancreatic islet hormone-expressing cells can be mature or immature. Immature pancreatic islet hormone-expressing cells can be distinguished from mature pancreatic islet hormone-expressing cells based on the differential expression of certain markers, or based on their functional capabilities, e.g., glucose responsiveness in vitro or in vivo. Pancreatic endocrine cells also express low to no levels of NGN3, PAX 4, ARX and NKX2.2.

Most of above cell types are epithelialized as compared to mesenchymal definitive endoderm cells. In some embodiments, the pancreatic endoderm cells express one or more markers selected from Table 3 and/or one or more markers selected from Table 4 of related U.S. patent application Ser. No. 11/588,693 entitled PDX1 EXPRESSING DOSAL AND VENTRAL FOREGUT ENDODERM, filed Oct. 27, 2006, and also U.S. patent application Ser. No. 11/115,868, entitled PDX1-expressing endoderm, filed Apr. 26, 2005, which are hereby incorporated herein by reference in their entireties.

The invention contemplates compositions and methods useful for differentiable cells, regardless of their source or of their plasticity. The "plasticity" of a cell is used herein roughly as it is in the art. Namely, the plasticity of a cell refers to a cell's ability to differentiate into a particular cell type found in tissues or organs from an embryo, fetus or developed organism. The "more plastic" a cell, the more tissues into which the cell may be able to differentiate. "Pluripotent cells" include cells and their progeny, which may be able to differentiate into, or give rise to, pluripotent, multipotent, oligopotent and unipotent cells, and/or several, if not all, of the mature or partially mature cell types found in an embryo, fetus or developed organism. "Multipotent cells" include cells and their progeny, which may be able to differentiate into, or give rise to, multipotent, oligopotent and unipotent progenitor cells, and/or one or more mature or partially mature cell types, except that the mature or partially mature cell types derived from multipotent cells are limited to cells of a particular tissue, organ or organ system. For example, a multipotent hematopoietic progenitor cell and/or its progeny possess the ability to differentiate into or give rise to one or more types of oligopotent cells, such as myeloid progenitor cells and lymphoid progenitor cells, and also give rise to other mature cellular components normally found in the blood. "Oligopotent cells" include cells and their progeny whose ability to differentiate into mature or partially mature cells is more restricted than multipotent cells. Oligopotent cells may, however, still possess the ability to differentiate into oligopotent and unipotent cells, and/or one or more mature or partially mature cell types of a given tissue, organ or organ system. One example of an oligopotent cell is a myeloid progenitor cell, which can ultimately give rise to mature or partially mature erythrocytes, platelets, basophils, eosinophils, neutrophils and monocytes. "Unipotent cells" include cells and their progeny that possess the ability to differentiate or give rise to other unipotent cells and/or one type of mature or partially mature cell type.

Differentiable cells, as used herein, may be pluripotent, multipotent, oligopotent or even unipotent. In certain embodiments of the present invention, the differentiable cells are pluripotent differentiable cells. In more specific embodiments, the pluripotent differentiable cells are selected from the group consisting of embryonic stem cells, ICM/epiblast cells, primitive ectoderm cells, primordial germ cells, and teratocarcinoma cells. In one particular embodiment, the differentiable cells are mammalian embryonic stem cells. In a more particular embodiment, the differentiable cells are human embryonic stem cells.

The invention also contemplates differentiable cells from any source within an animal, provided the cells are differentiable as defined herein. For example, differentiable cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Of course, the invention contemplates using differentiable cells from any animal capable of generating differentiable cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

The differentiable cells of the present invention can be derived using any method known to those of skill in the art. For example, human pluripotent cells can be produced using dedifferentiation and nuclear transfer methods. Additionally, the human ICM/epiblast cell or the primitive ectoderm cell used in the present invention can be derived in vivo or in vitro. Primitive ectodermal cells may be generated in adherent culture or as cell aggregates in suspension culture, as described in WO 99/53021. Furthermore, the human pluripotent cells can be passaged using any method known to those of skill in the art, including, manual passaging methods, and bulk passaging methods such as enzymatic or non-enzymatic passaging.

In certain embodiment, when ES cells are utilized, the embryonic stem cells have a normal karyotype, while in other embodiments, the embryonic stem cells have an abnormal karyotype. In one embodiment, a majority of the embryonic stem cells have a normal karyotype. It is contemplated that greater than 50%, 55%, 60%, 65%, 70%, 75%, 80%, 85%, 90% or greater than 95% of metaphases examined will display a normal karyotype.

In another embodiment, a majority of the embryonic stem cells have an abnormal karyotype. It is contemplated that greater than 50%, 55%, 60%, 65%, 70%, 75%, 80%, 85%, 90% or greater than 95% of metaphases examined will display an abnormal karyotype. In certain embodiments, the abnormal karyotype is evident after the cells have been cultured for greater than 5, 6, 7, 8, 9, 10, 11, 12, 13, 14, 15, or 20 passages. In one specific embodiment, the abnormal karyotype comprises a trisomy of at least one autosomal chromosome, wherein the autosomal chromosome is selected from the group consisting of chromosomes 1, 7, 8, 12, 14, and 17. In another embodiment, the abnormal karyotype comprises a trisomy of more than one autosomal chromosome, wherein at least one of the more than one autosomal chromosomes is selected from the group consisting of chromosomes 1, 7, 8, 12, 14, and 17. In one embodiment, the autosomal chromosome is chromosome 12 or 17. In another embodiment, the abnormal karyotype comprises an additional sex chromosome. In one embodiment, the karyotype comprises two X chromosomes and one Y chromosome. It is also contemplated that translocations of chromosomes may occur, and such translocations are encompassed within the term "abnormal karyotype." Combinations of the foregoing chromosomal abnormalities and other chromosomal abnormalities are also encompassed by the invention.

The compositions and methods comprise a basal salt nutrient solution. As used herein, basal salt nutrient solution refers to a mixture of salts that provide cells with water and certain bulk inorganic ions essential for normal cell metabolism, maintain intra- and extra-cellular osmotic balance, provide a carbohydrate as an energy source, and provide a buffering system to maintain the medium within the physiological pH range. Examples of basal salt nutrient solutions include, but are not limited to, Dulbecco's Modified Eagle's Medium (DMEM), Minimal Essential Medium (MEM), Basal Medium Eagle (BME), RPM1 1640, Ham's F-10, Ham's F-12, α-Minimal Essential Medium (aMEM), Glasgow's Minimal Essential Medium (G-MEM), and Iscove's Modified Dulbecco's Medium, and mixtures thereof. In one particular embodiment, the basal salt nutrient solution is an approximately 50:50 mixture of DMEM and Ham's F12.

It is contemplated that the composition can further comprise trace elements. Trace elements can be purchased commercially, for example, from Mediatech. Non-limiting examples of trace elements include but are not limited to compounds comprising, aluminum, chloride, sulfate, iron, cadmium, cobalt, chromium, germanium, sodium, potassium, calcium, phosphate and magnesium. Specific example of compounds containing trace elements include but are not limited to, $AlCl_3$, $AgNO_3$, $Ba(C_2H_3O_2)_2$, $CdCl_2$, $CdSO_4$, $CoCl_2$, $CrCl_3$, $Cr_2(SO_4)_3$, $CuSO_4$, ferric citrate, $GeO_2$, KI, KBr, LI, molybdic acid, $MnSO_4$, $MnCl_2$, NaF, $Na_2SiO_3$, $NaVO_3$, $NH_4VO_3$, $(NH_4)_6MO_7O_{24}$, $NiSO_4$, RbCl, selenium, $Na_2SeO_3$, $H_2SeO_3$, selenite.2Na, selenomethionone, $SnCl_2$, $ZnSO_4$, $ZrOCl_2$, and mixtures and salts thereof. If selenium, selenite or selenomethionone is present, it is at a concentration of approximately 0.002 to approximately 0.02 mg/L. In addition, hydroxylapatite may also be present.

It is contemplated that amino acids can be added to the defined media. Non-limiting examples of such amino acids are Glycine, L-Alanine, L-Alanyl-L-Glutamine, L-Glutamine/Glutamax, L-Arginine hydrochloride, L-Asparagine-$H_2O$, L-Aspartic acid, L-Cysteine hydrochloride-$H_2O$, L-Cystine 2HCl, L-Glutamic Acid, L-Histidine hydrochloride-$H_2O$, L-Isoleucine, L-Leucine, L-Lysine hydrochloride, L-Methionine, L-Phenylalanine, L-Proline, L-Hydroxyproline, L-Serine, L-Threonine, L-Tryptophan, L-Tyrosine disodium salt dihydrate, and L-Valine. In certain embodiments, the amino acid is L-Isoleucine, L-Phenylalanine, L-Proline, L-Hydroxyproline, L-Valine, and mixtures thereof.

It is also contemplated that the defined medium can comprise ascorbic acid. Preferably ascorbic acid is present at an initial concentration of approximately 1 mg/L to approximately 1000 mg/L, or from approximately 2 mg/L to approximately 500 mg/L, or from approximately 5 mg/L to approximately 100 mg/L, or from approximately 10 mg/L to approximately 100 mg/L or approximately at 50 mg/L.

In addition, the compositions and methods may also comprise other components such as serum albumin, transferrin, L-glutamine, lipids, antibiotics, β-Mercaptoethanol, vitamins, minerals, ATP and similar components may be present. Examples of vitamins that may be present include, but are not limited to vitamins A, $B_1$, $B_2$, $B_3$, $B_5$, $B_6$, $B_7$, $B_9$, $B_{12}$, C, $D_1$, $D_2$, $D_3$, $D_4$, $D_5$, E, tocotrienols, $K_1$ and $K_2$. One of skill in the art can determine the optimal concentration of minerals, vitamins, ATP, lipids, essential fatty acids, etc., for use in a given culture. The concentration of supplements may, for example, be from about 0.001 μM to about 1 mM or more. Specific examples of concentrations at which the supplements may be provided include, but are not limited to about 0.005 μM, 0.01 μM, 0.05 μM, 0.1 μM, 0.5 μM, 1.0 μM, 2.0 μM, 2.5 μM, 3.0 μM 4.0 μM, 5.0 μM, 10 μM, 20 μM, 100 μM, etc. In one specific embodiment, the compositions and methods comprise vitamin $B_6$ and glutamine. In another specific embodiment, the compositions and methods comprise vitamin C and an iron supplement. In another specific embodiment, the compositions and methods comprise vitamin $K_1$ and vitamin A. In another specific embodiment, the compositions and methods comprise vitamin $D_3$ and ATP. In another specific embodiment, the compositions and methods comprise vitamin $B_{12}$ and transferrin. In another specific embodiment, the compositions and methods comprise tocotrienols and β-Mercaptoethanol. In another specific embodiment, the compositions and methods comprise glutamine and ATP. In another specific embodiment, the compositions and methods comprise an omega-3 fatty acid and glutamine. In another specific embodiment, the compositions and methods comprise an omega-6 fatty acid and vitamin $B_1$. In another specific embodiment, the compositions and methods comprise α-linolenic acid and $B_2$.

The compositions of the present invention are essentially serum free. As used herein, "essentially serum free" refers to the absence of serum in the solutions of the present invention. Serum is not an essential ingredient to the compositions and methods of the present invention. Thus, the presence of serum in any of the compositions should only be attributable to impurities, e.g., from the starting materials or residual serum from the primary cell culture. For example, essentially serum free medium or environment can contain less than 10, 9, 8, 7, 6, 5, 4, 3, 2, or 1% serum wherein the presently improved bioactive maintenance capacity of the medium or environment is still observed. In a specific embodiment of the present invention, the essentially serum free composition does not contain serum or serum replacement, or only contains trace amounts of serum or serum replacement from the isolation of components of the serum or serum replacement that are added to the defined media.

The compositions and methods of the present invention also comprise a means for stimulating ErbB2 tyrosine kinase activity within differentiable cells. In one specific embodiment, the compositions and methods of the present invention comprise the presence of at least one ErbB3 ligand. Typically, an ErbB3 ligand will bind the ErbB3 receptor and dimerize with the ErbB2 receptor. The ErbB2 receptor is, in turn, generally responsible for intracellular tyrosine kinase activity within the differentiable cell.

As used herein, "ErbB3 ligand" refers to a ligand that binds to ErbB3, which in turn dimerizes to ErbB2, thus activating the tyrosine kinase activity of the ErbB2 portion of the ErbB2/ErbB3 heterodimeric receptor. Non-limiting examples of ErbB3 ligands include Neuregulin-1; splice variants and isoforms of Neuregulin-1, including but not limited to HRG-β, HRG-α, Neu Differentiation Factor (NDF), Acetylcholine Receptor-Inducing Activity (ARIA), Glial Growth Factor 2 (GGF2), and Sensory And Motor Neuron-Derived Factor (SMDF); Neuregulin-2; splice variants and isoforms of Neuregulin-2, including but not limited to NRG2-β; Epiregulin; and Biregulin.

In one embodiment, the means for stimulating ErbB2-directed tyrosine kinase activity comprise at least one ErbB3 ligand that is selected from the group consisting of Neuregulin-1, Heregulin-β (HRG-β), Heregulin-α (HRG-α), Neu differentiation factor (NDF), acetylcholine receptor-inducing activity (ARIA), glial growth factor 2 (GGF2), motor-neuron derived factor (SMDF), Neuregulin-2, Neuregulin-2β (NRG2-β), Epiregulin, Biregulin and variants and functional fragments thereof. In another specific embodiment, the compositions and methods of the present invention comprise more than one means for stimulating ErbB2-directed tyrosine kinase activity, such as, but not limited to, using more than one ErbB3 ligand.

In a more specific embodiment of the compositions and methods of the present invention, the ErbB3 ligand is HRG-β or a variant or functional fragment thereof. In one embodiment, the species from which the culture additive protein, polypeptide or variant or functional fragment thereof derives is the same as the species of cells that are cultured. For example, if mouse ES cells are cultured, an HRG-β with an amino acid sequence that is identical to the *mus musculus* HRG-β sequence can be used as an additive in culture and is considered to be "of the same species." In other embodiments, the species from which the biological additive derives is different from the cells being cultured. For example, if mouse ES cells are cultured, an HRG-β with an amino acid sequence that is identical to the human HRG-β sequence from can be used as an additive in culture and is considered to be "of different species."

As used herein, a "functional fragment" is a fragment or splice variant of a full length polypeptide that exerts a similar physiological or cellular effect as the full length polypeptide. The biological effect of the functional fragment need not be identical in scope or strength as the full-length polypeptide, so long as a similar physiological or cellular effect is seen. For example, a functional fragment of HRG-β can detectably stimulate ErbB2-directed tyrosine kinase.

As used herein, the term "variant" includes chimeric or fusion polypeptides, homologs, analogs, orthologs, and paralogs. In addition, a variant of a reference protein or polypeptide is a protein or polypeptide whose amino acid sequence is at least about 80% identical to the reference protein or polypeptide. In specific embodiments, the variant is at least about 85%, 90%, 95%, 95%, 97%, 98%, 99% or even 100% identical to the reference protein or polypeptide. As used herein, the terms "correspond(s) to" and "corresponding to," as they relate to sequence alignment, are intended to mean enumerated positions within the reference protein or polypeptide, e.g., wild-type human or mouse neuregulin-1, and those positions in the modified protein or polypeptide that align with the positions on the reference protein or polypeptide. Thus, when the amino acid sequence of a subject protein or polypeptide is aligned with the amino acid sequence of a reference protein or polypeptide, the sequence that "corresponds to" certain enumerated positions of the reference protein or polypeptide sequence are those that align with these positions of the reference sequence, but are not necessarily in these exact numerical positions of the reference sequence. Methods for aligning sequences for determining corresponding amino acids between sequences are described below.

A polypeptide having an amino acid sequence at least, for example, about 95% "identical" to a reference an amino acid sequence encoding, for example TGF-β, is understood to mean that the amino acid sequence of the polypeptide is identical to the reference sequence except that the amino acid sequence may include up to about five modifications per each 100 amino acids of the reference amino acid sequence encoding the reference TGF-β. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exists several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, et al. 1984 *Nucleic Acids Research* 12:387), BLASTP, ExPASy, BLASTN, FASTA (Atschul et al. 1990, *J Molec Biol* 215:403) and FASTDB. Examples of methods to determine identity and similarity are discussed in Michaels & Garian 2000, *Current Protocols in Protein Science*, Vol 1, John Wiley & Sons, Inc., which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (1990, *Comp. App. Biosci.* 6:237-245, incorporated by reference herein). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at the 5' or 3' ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The invention also provides chimeric or fusion polypeptides. As used herein, a "chimeric polypeptide" or "fusion polypeptide" comprises at least a portion of a member of the reference polypeptide operatively linked to a second, different polypeptide. The second polypeptide has an amino acid sequence corresponding to a polypeptide which is not substantially identical to the reference polypeptide, and which is derived from the same or a different organism. With respect to the fusion polypeptide, the term "operatively linked" is intended to indicate that the reference polypeptide and the second polypeptide are fused to each other so that both sequences fulfill the proposed function attributed to the sequence used. The second polypeptide can be fused to the N-terminus or C-terminus of the reference polypeptide. For example, in one embodiment, the fusion polypeptide is a GST-IGF-1 fusion polypeptide in which an IGF-1 sequence is fused to the C-terminus of the GST sequences. Such fusion polypeptides can facilitate the purification of recombinant polypeptides. In another embodiment, the fusion polypeptide can contain a heterologous signal sequence at its N-terminus. In certain host cells (e.g., mammalian host cells), expression and/or secretion of a polypeptide can be increased through use of a heterologous signal sequence.

In addition to fragments and fusion polypeptides, the present invention includes homologs and analogs of naturally occurring polypeptides. "Homologs" are defined herein as two nucleic acids or polypeptides that have similar, or "identical," nucleotide or amino acid sequences, respectively. Homologs include allelic variants, orthologs, paralogs, agonists, and antagonists as defined hereafter. The term "homolog" further encompasses nucleic acid molecules that differ from a reference nucleotide sequence due to degeneracy of the genetic code and thus encode the same polypeptide as that encoded by the reference nucleotide sequence. As used herein, "naturally occurring" refers to a nucleic or amino acid sequence that occurs in nature.

An agonist of a polypeptide can retain substantially the same, or a subset, of the biological activities of the polypeptide. An antagonist of a polypeptide can inhibit one or more of the activities of the naturally occurring form of the polypeptide.

In another more specific embodiment of the compositions and methods of the present invention, the ErbB3 ligand is HRG-β or a variant or a functional fragment thereof. Additional, non-limiting examples of ErbB3 ligands are disclosed in U.S. Pat. Nos. 6,136,558, 6,387,638, and 7,063,961, which are incorporated by reference.

Heregulins are generally classified into two major types, alpha and beta, based on two variant EGF-like domains that differ in their C-terminal portions. These EGF-like domains, however, are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF) is the rat equivalent of human HRG. Like the HRG polypeptides, NDF has an immunoglobulin (Ig) homology domain followed by an EGF-like domain and lacks a N-terminal signal peptide. Presently, there are at least six distinct fibroblastic pro-NDFs, classified as either alpha or beta polypeptides, based on the sequences of the EGF-like domains. Isoforms 1 to 4 are characterized on the basis of a variable stretch between the EGF-like domain and transmembrane domain. Thus it appears that different NDF isoforms are generated by alternative splicing and may perform distinct tissue-specific functions. See European Patent No. 505 148; and International Patent Publication Nos. WO 93/22424 and WO 94/28133, which are incorporated by reference.

In one embodiment of the present invention, the compositions and methods are free of exogenous insulin and insulin substitutes. The phrase "exogenous insulin or insulin substitutes" is used herein to indicate insulin or insulin substitutes that is/are not intentionally added to the compositions or methods of the present invention. Thus, in certain embodiments of the present invention, the methods and compositions are free of insulin or insulin substitutes that are intentionally supplied. The compositions or methods may, however, not necessarily be free of endogenous insulin. As used herein, "endogenous insulin" indicates that the cultured cells may be producing insulin of their own accord when cultured according to the methods of the present invention. Endogenous insulin also may be used to indicate residual impurities from the primary cell culture or impurities from the starting materials. In specific examples, the compositions and methods of the present contain less than 50, 45, 40, 35, 30, 25, 20, 15, 10, 9, 8, 7, 6, 5, 4, 3, 2, or 1 μg/mL of insulin.

As used herein, the term "insulin" refers to the protein, or variant or fragment thereof that binds to the insulin receptor in normal physiological concentrations and can induce signaling through the insulin receptor. The term "insulin" encompasses a protein having the polypeptide sequence of native human insulin, or of other mammalian insulin, or of any homologs or variants to these sequences. Additionally, the term insulin encompasses polypeptide fragments that are capable of binding to the insulin receptor to induce signaling through the insulin receptor. The term "insulin substitute" refers to any zinc containing compound that may be used in place of insulin to give substantially similar results as insulin. Examples of insulin substitutes include, but are not limited to zinc chloride, zinc nitrate, zinc bromide, and zinc sulfate.

To be clear, insulin-like growth factors are not insulin substitutes or homologs of insulin, as contemplated in the present invention. Accordingly, in another specific embodiment, the compositions and methods of the present invention comprise the use of at least one insulin-like growth factor (IGF) or a variant or a functional fragment thereof. In another embodiment, the compositions and methods of the present invention are free of any exogenous insulin-like growth factors (IGFs). In specific embodiments, the compositions and methods of the present invention contain less than 200, 150, 100, 75, 50, 25, 20, 15, 10, 9, 8, 7, 6, 5, 4, 3, 2, or 1 ng/mL of IGF-1.

As used herein, the term "activator of IGF-1R" refers to mitogens that play a pivotal role in regulating cell proliferation, differentiation, and apoptosis. The effects of an activator of IGF-1R are typically mediated through IGF-1R, although they can be mediated through other receptors. The IGF-1R is also involved in cell transformation induced by tumor virus proteins and oncogene products, and the interaction is regulated by a group of specific binding proteins (IGFBPs). In addition, a large group of IGFBP proteases hydrolyze IGFBPs, resulting in the release of bound IGFs that then resume their ability to interact with IGF-IR. For the purpose of this invention, the ligands, the receptors, the binding proteins, and the proteases are all considered to be activators of IGF-1R. In one embodiment, the activator of IGF-1R is IGF-1, or IGF-2. In a further embodiment, the activator of IGF-1R is an IGF-1 analog. Non-limiting examples of IGF-1 analogs include LongR3-IGF1, Des(1-3)IGF-1, [Arg$^3$]IGF-1, [Ala$^{31}$]IFG-1, Des(2,3)[Ala$^{31}$]IGF-1, [Leu$^{24}$]IGF1, Des(2,3)[Leu$^{24}$]IGF-1, [Leu$^{60}$]IGF-1, [Ala$^{31}$][Leu$^{60}$]IGF-1, [Leu$^{24}$][Ala$^{31}$]IGF-1, and combinations thereof. In a further embodiment, the IFG-1 analog is LongR3-IGF1, which is a recombinant analog of human insulin growth factor-1. It is contemplated that LongR3-IGF1 is initially present at a concentration of approximately 1 ng/mL to approximately 1000 ng/mL, more preferably approximately 5 ng/mL to approximately 500 ng/mL, more preferably approximately 50 ng/mL to approximately 500 ng/mL, more preferably approximately 100 ng/mL to approximately 300 ng/mL, or at a concentration of approximately 100 ng/mL.

In certain embodiments, the compositions and methods of the present invention comprise transforming growth factor beta (TGF-β) or a TGF-β family member or variants or functional fragments thereof. As used herein, the term "member of the TGF-β family" or the like refers to growth factors that are generally characterized by one of skill in the art as belonging to the TGF-β family, either due to homology with known members of the TGF-β family, or due to similarity in function with known members of the TGF-β family. In particular embodiments of the invention, if the member of the TGF-β family is present, the TGF-β family member or variant or functional fragment thereof activates SMAD 2 or 3. In certain embodiments, the member of the TGF-β family is selected from the group consisting of Nodal, Activin A, Activin B, TGF-13, bone morphogenic protein-2 (BMP2) and bone morphogenic protein-4 (BMP4). In one embodiment, the member of the TGF-β family is Activin A.

It is contemplated that if Nodal is present, it is initially present at a concentration of approximately 0.1 ng/mL to approximately 2000 ng/mL, more preferably approximately 1 ng/mL to approximately 1000 ng/mL, more preferably approximately 10 ng/mL to approximately 750 ng/mL, or more preferably approximately 25 ng/mL to approximately 500 ng/mL. It is contemplated that if used, Activin A is initially present at a concentration of approximately 0.01 ng/mL to approximately 1000 ng/mL, more preferably approximately 0.1 ng/mL to approximately 100 ng/mL, more preferably approximately 0.1 ng/mL to approximately 25 ng/mL, or most preferably at a concentration of approximately 10 ng/mL. It is contemplated that if present, TGF-β is initially present at a concentration of approximately 0.01 ng/mL to approximately 100 ng/mL, more preferably approximately 0.1 ng/mL to approximately 50 ng/mL, or more preferably approximately 0.1 ng/mL to approximately 20 ng/mL.

In additional embodiments of the present invention, the compositions and methods of the present invention are free of activators of FGF receptors. There are currently at least 22 known members of the family of fibroblast growth factors, with these factors binding to one of at least one of four FGF receptors. As used herein, the term "activator of an FGF receptor" refers to growth factors that are generally characterized by one of skill in the art as belonging to the FGF family, either due to homology with known members of the FGF family, or due to similarity in function with known members of the FGF family. In certain embodiments, the activator of an FGF receptor is an FGF, such as, but not limited to α-FGF and FGF2. In particular embodiments, the compositions and methods are free of exogenous FGF2. The phrase "exogenous FGF2" is used herein to indicate fibroblast growth factor 2, i.e., basic FGF that is not intentionally added to the compositions or methods of the present invention. Thus, in certain embodiments of the present invention, the methods and compositions are free of intentionally supplied FGF2. The compositions or methods may, however, not necessarily be free of endogenous FGF2. As used herein, "endogenous FGF2" indicates that the cultured cells may be producing FGF2 of their own accord when cultured according to the methods of the present invention. "Endogenous FGF2" also may be used to indicate residual impurities from the primary cell culture or impurities from the starting materials. In specific examples, the compositions and methods of the present contain less than 10, 9, 8, 7, 6, 5, 4, 3, 2, or 1 ng/mL of FGF2.

It is contemplated, however, that the compositions and methods of the invention can include at least one activator of an FGF receptor, including any of the FGF polypeptides, functional fragments thereof or variants thereof. It is contemplated that if FGF2 is present, it is initially present at a concentration of approximately 0.1 ng/mL to approximately 100 ng/mL, more preferably approximately 0.5 ng/mL to approximately 50 ng/mL, more preferably approximately 1 ng/mL to approximately 25 ng/mL, more preferably approximately 1 ng/mL to approximately 12 ng/mL, or most preferably at a concentration of approximately 8 ng/mL. In another specific embodiment, the compositions and methods of the invention can include at least one activator of an FGF receptor, other than FGF2. For example, the compositions and methods of the present invention may comprise at least one of FGF-7, FGF-10 or FGF-22 or variants or functional fragments thereof. In specific embodiments, a combination of at least two of FGF-7, FGF-10 and FGF-22, or variants or functional fragments thereof, are present. In another embodiment, all three of FGF-7, FGF-10 and FGF-22, or variants or functional fragments thereof, are present. It is contemplated that if any of FGF-7, FGF-10 or FGF-22 or variants or functional fragments are present, each is initially present at a concentration of approximately 0.1 ng/mL to approximately 100 ng/mL, more specifically from approximately 0.5 ng/mL to approximately 50 ng/mL, more specifically from approximately 1 ng/mL to approximately 25 ng/mL, more specifically from approximately 1 ng/mL to approximately 12 ng/mL, or most specifically at a concentration of approximately 8 ng/mL.

In additional certain embodiments, the compositions and methods of the present invention comprise serum albumin (SA). In specific embodiments, the SA is either bovine SA (BSA) or human SA (HAS). In still more specific embodiments, the concentration of the SA is more than about 0.2%, volume to volume (v/v), but less than about 10% v/v. In even more specific embodiments, the concentration of SA is more than about 0.3%, 0.4%, 0.5%, 0.6%, 0.7%, 0.8%, 0.9%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.4%, 4.6%, 4.8%, 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6% and 9.8% (v/v).

In additional embodiments, the compositions and methods comprise at least one insoluble substrate. For example, the differentiable cells may be placed on a cell culture surface that comprises such compounds as, but is not limited to, polystyrene, polypropylene. The surface may, in turn, be coated with an insoluble substrate. In specific embodiments, the insoluble substrate is selected from the group consisting of a collagen, a fibronectin and fragments or variants thereof. Other examples of insoluble substrates include, but are not limited to, fibrin, elastin, fibronectins, laminins and nidogens.

Accordingly, the cell culture environments and methods of the present invention comprise plating the cells in an adherent culture. As used herein, the terms "plated" and "plating" refer to any process that allows a cell to be grown in adherent culture. As used herein, the term "adherent culture" refers to a cell culture system whereby cells are cultured on a solid surface, which may in turn be coated with an insoluble substrate that may in turn be coated with another surface coat of a substrate, such as those listed below, or any other chemical or biological material that allows the cells to proliferate or be stabilized in culture. The cells may or may not tightly adhere to the solid surface or to the substrate. The substrate for the adherent culture may comprise any one or combination of polyornithine, laminin, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). Furthermore, the substrate for the adherent culture may comprise the matrix laid down by a feeder layer, or laid down by the pluripotent human cell or cell culture. As used herein, the term "extracellular matrix" encompasses solid substrates such as but not limited to those described above, as well as the matrix laid down by a feeder cell layer or by the pluripotent human cell or cell culture. In one embodiment, the cells are plated on MATRIGEL™-coated plates. In another embodiment, the cells are plated on fibronectin-coated plates. In certain embodiments, if the cells are plated on fibronectin, the plates are prepared by coating with 10 μg/mL human plasma fibronectin (Invitrogen, #33016-015), diluted in tissue grade water, for 2-3 hours at room temperature. In another embodiment, serum can be placed in the medium for up to 24 hours to allow cells to plate to the plastic. If using serum to promote the attachment of the cells, the media is then removed and the compositions, which are essentially serum-free, are added to the plated cells.

The compositions and methods of the present invention contemplate that the differentiable cells are cultured in conditions that are essentially free of a feeder cell or feeder layer. As used herein, a "feeder cell" is a cell that grows in vitro, that is co-cultured with a target cell and stabilizes the target cell in its current state of differentiation. As used herein, a "feeder cell layer" can be used interchangeably with the term "feeder cell." As used herein, the term "essentially free of a feeder cell" refers to tissue culture conditions that do not contain feeder cells, or that contain a de minimus number of feeder cells. By "de minimus", it is meant that number of feeder cells that are carried over to the instant culture conditions from previous culture conditions where the differentiable cells may have been cultured on feeder cells. In one embodiment of the above method, conditioned medium is obtained from a feeder cell that stabilizes the target cell in its current state of differentiation. In another embodiment, the defined medium is a non-conditioned medium, which is a medium that is not obtained from a feeder cell.

As used herein, the term "stabilize," when used in reference to the differentiation state of a cell or culture of cells, indicates that the cells will continue to proliferate over multiple passages in culture, and preferably indefinitely in culture, where most, if not all, of the cells in the culture are of the same differentiation state. In addition, when the stabilized cells divide, the division typically yield cells of the same cell type or yield cells of the same differentiation state. A stabilized cell or cell population in general, does not further differentiate or de-differentiate if the cell culture conditions are not altered, and the cells continue to be passaged and are not overgrown. In one embodiment, the cell that is stabilized is capable of proliferation in the stable state indefinitely, or for at least more than 2 passages. In a more specific embodiment, the cells are stable for more than 3 passages, 4 passages, 5 passages, 6 passages, 7 passages, 8 passages, 9 passages, more than 10 passages, more than 15 passages, more than 20 passages, more than 25 passages, or more than 30 passages. In one embodiment, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, stem cells are maintained in culture in a pluripotent state by routine passage in the defined medium until it is desired that they be differentiated. As used herein, the term "proliferate" refers to an increase in the number cells in a cell culture.

In certain embodiments, the compositions and methods comprise an inactivator of BMP signaling. As used herein, an "inactivator of BMP signaling" refers to an agent that antagonizes the activity of one or more BMP proteins or any of their upstream or downstream signaling components through any of its possible signaling pathways. The compound(s) used to inactivate BMP signaling can be any compound known in the art, or later discovered. Non-limiting examples of inactivators of BMP signaling include dominant-negative, truncated BMP receptor, soluble BMP receptors, BMP receptor-Fc chimeras, noggin, follistatin, chordin, gremlin, cerberus/DAN family proteins, ventropin, high dose activin, and amnionless.

In certain embodiments, the compositions and methods can comprise at least one hormone, cytokine, adipokine, growth hormone or variant or functional fragment thereof. It is currently contemplated that in certain embodiments, the growth hormone present in the defined medium will be of the same species as the differentiable cells that are cultured with the defined media. Thus, for example, if a human cell is cultured, the growth hormone is human growth hormone. The use of growth hormone that is from a species different than the cultured cells is also contemplated. Preferably the hormone, cytokine, adipokine and/or growth hormone is present at an initial concentration of approximately 0.001 ng/mL to approximately 1000 ng/mL, more preferably approximately 0.001 ng/mL to approximately 250 ng/mL, or more preferably approximately 0.01 ng/mL to approximately 150 ng/mL.

Examples of cytokines and adipokines that may be included in the compositions and methods of the present invention include, but are not limited to, the four α-helix bundle family of cytokines, the interleukin-1 (IL-1) family of cytokines, the IL-17 family of cytokines and the chemokine family of cytokines Of course, the invention contemplates members and subclasses of each of these families of cytokines, such as, but not limited to, the CC chemokines, the CXC chemokines, the C chemokines and the $CX_3C$ chemokines, interferons, interleukins, lymphotoxins, c-kit ligand, granulocyte-macrophage colony-stimulating factor (GM-CSF), monocyte-macrophage colony-stimulating factor (M-CSF), granulocyte colony-stimulating factor (G-CSF), leptin, adiponectin, resistin, plasminogen activator inhibitor-1 (PAI-1), tumor necrosis factor-alpha (TNFα), tumor necrosis factor-beta (TNFβ), leukemia inhibitory factor, visfatin, retinol binding protein 4 (RBP4), erythropoietin (EPO), thrombopoietin (THPO). Of course, one of skill in the art will understand that the invention contemplates variants or functional fragments of the above-listed factors.

The present invention relates to methods of culturing differentiable cells, with the methods comprising plating differentiable cells on a cell culture surface, providing a basal salt nutrient solution to the cells and providing a means for stimulating ErbB2-directed tyrosine kinase activity in the cells.

In one embodiment, differentiable cells are contacted with at least one of the compositions of the invention in the absence of serum or serum replacement, and in the absence of a feeder cell layer, such that the cells are maintained in an undifferentiated state for at least one month. Pluripotency can be determined through characterization of the cells with respect to surface markers, transcriptional markers, karyotype, and ability to differentiate to cells of the three germ layers. These characteristics are well known to those of ordinary skill in the art.

The embodiments of this invention describe various differentiable pPSC including human pluripotent stem cells such as hESC including but not limited to CyT49, CyT203, CyT25, BG01, BG02 and MELT, and induced pluripotent stem (iPS) cells such as iPSC-482c7 and iPSC-603 (Cellular Dynamics International, Inc., Madison, Wis.) and iPSC-G4 and iPSC-B7 (Shinya Yamanaka, Center for iPS Cell Research, Kyoto University); studies using G4 and B7 are described in detail in U.S. patent application Ser. No. 12/765,714, entitled CELL COMPOSITIONS DERIVED FROM DEDIFFERENTIATED REPROGRAMMED CELLS, filed Apr. 22, 2010, which is incorporated by reference herein in its entirety. Certain of these human pluripotent stem cells are registered with national registries such as the National Institutes of Health (NIH) and listed in the NIH Human Stem Registry (e.g., CyT49 Registration No. #0041). Information on CyT49 and other available cell lines can also found on the worldwide web at stemcells.nih.gov/research/registry. Still other cell lines, e.g., BG01 and BG01v, are sold and distributed to the third parties by WiCell®, an affiliate of the Wisconsin International Stem Cell (WISC) Bank (Catalog name, BG01) and ATCC (Catalog No. SCRC-2002), respectively. While other cell lines described herein may not be registered or distributed by a biological repository such as WiCell® or ATCC, such cell lines are available to the public directly or indirectly from the principle investigators, laboratories and/or institutions. Public requests for cell lines and reagents, for example, are customary for those skilled in the art in the life sciences. Typically, transfer of these cells or materials is by way of a standard material transfer agreement between the proprietor of the cell line or material and the recipient. These types of material transfers occur frequently in a research environment, particularly in the life sciences. In fact, Applicant has transferred cells since the time they were derived and characterized, including CyT49 (2006), CyT203 (2005), CyT25 (2002), BG01 (2001), BG02 (2001), BG03 (2001) and BG01v (2004) through such agreements with commercial and non-profit industry partners and collaborators. The date in parenthesis indicates the date when the cell line or material was publically availability.

In August 2006, Klimanskaya et al. demonstrated that hESC can be derived from single blastomeres, hence keeping the embryo intact and not causing their destruction. Biopsies were performed from each embryo using micromanipulation techniques and nineteen (19) ES-cell-like outgrowths and two (2) stable hESC lines were obtained. These hESC lines were able to be maintained in an undifferentiated state for over six (6) months, and showed normal karyotype and expression of markers of pluripotency, including Oct-4, SSEA-3, SSEA-4, TRA-1-60, TRA-1-81, nanog and alkaline phosphatase. These hESC can differentiate and form derivatives of all three (3) embryonic germ layers both in vitro and form in teratomas in vivo. These methods to create new stem cell lines without destruction of embryos addresses the ethical concerns of using human embryos. See Klimanskaya et al. 2006 *Nature* 444:481-5, Epub 2006 Aug. 23, which is incorporated herein by reference in its entirety.

The present studies used certain CyT or BG hES cell lines, however, subsequent to the initial filing on Jun. 16, 2006 of the provisional priority application, U.S. Patent Application No. 60/805,039, other investigators have published reports using the originally described methods or variations thereof, using other human pluripotent stem cell lines, including but not limited to H7, H9, HUES7, H1, HSF6, chHES-8 (eh=China), chHES-20, and chHES-22, H9, BG01, BG02, HUES4, HUES8, HUES9, and HUES 2; other induced pluripotent (iPS) stem cells lines such as DiPS-H1 & DIPS-H2 (T1-diabetes specific iPS cells) and other iPS cells described in U.S. Patent Publication No. 2010-0272695, entitled CELL COMPOSITIONS DERIVED FROM DEDIFFERENTIATED REPROGRAMMED CELLS, filed Apr. 22, 2010, incorporated by reference herein in its entirety; and human pluripotent stem cells such as human parthenogenetic stem cell (hpSC). See e.g., D'Amour et al. 2005, *Nature Biotechnology* 23:1534-1541; Cai et al. 2007, *Hepatology*, 45:1229-39; King et al. 2008, *Regen. Med.* 3:175-80; Zhou et al. 2008, *Stem Cells & Development* 17:737-750; Brunner et al. 2009, *Genome Res.* 19:1044-1056; Maehr et al. 2009, *PNAS* 106: 15768-15773; Argawal et al. 2008, *Stem Cells* 26:1117-1127; Bingham et al. 2009, *Stem Cells & Devel* 18:1-10; Borowiak et al. 2009, *Cell Stem Cell* 4:348-358; Chen et al. 2009, *Nature Chem Biology* 5:258:265; Revazova et. al. 2007, *Cloning Stem Cells* 9:432-449; Turovets et. al. 2011, *Differentiation* 81:292-8, Epub 2011 Feb. 8, which are incorporated herein by reference in their entireties. Thus, abundant evidence has been provided by the research community at large to establish that the methods of the present invention are not limited to the pluripotent cells described herein.

Tables 1 and 2 are non-exhaustive lists of certain hESC and iPSC, respectively, which are available worldwide for research and/or commercial purposes, and are suitable for use in the methods and compositions of the present invention. The information in Tables 1 and 2 was derived from the literature and publically available databases including, for example, the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained.

TABLE 1

Human ES cell lines

| Institution (Country) | Name |
|---|---|
| U.S.A. | |
| BresaGen, Inc., Athens, Georgia (USA) | BG01, BG02, BG03; BG04; BG01v |
| Invitrogen (USA) | BG01v/hOG |
| CyThera, Inc., San Diego, California (USA) | CyT49, CyT203, CyT25 |
| Geron Corporation, Menlo Park, California (USA) | GE01, GE07, GE09, GE13, GE14, GE91, GE92 (H1, H7, H9, H13, H14, H9.1, H9.2) |
| University of California, San Francisco, California (USA) | UC01, UC06 (HSF-1, HSF-6); UCSFB1, UCSFB2, UCSFB3, UCSFB4, UCSFB5, UCSFB6, UCSFB7, UCSFB8, UCSFB9 & UCSFB10 |
| Wisconsin Alumni Research Foundation, Madison, Wisconsin (USA) | WA01, WA07, WA09, WA13, WA14 (H1, H7, H9, H13, H14) |
| Children's Hospital Corporation (USA) | CHB-1, CHB-2 CHB-3 CHB-4, CHB-5, CHB-6, CHB-8, CHB-9, CHB-10, CHB-11 & CHB-12 |
| The Rockefeller University (USA) | RUES1, RUES2 & RUES3 |
| Harvard University (USA) | HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, |

TABLE 1-continued

Human ES cell lines

| Institution (Country) | Name |
|---|---|
| | HUES23, HUES24, HUES25, HUES26, HUES27; HUES28; HUES48; HUES49; HUES53; HUES55 & HUES 56 |
| Mt Sinai Hosp-Samuel Lunenfeld Research Institute (USA) | CA1 & CA2 |
| Children's Memorial Hospital (USA) | CM-1, CM-2, CM-5, CM-6, CM-7, CM-8, CM-11, CM-12, CM-13, CM-14, CM-16 |
| The University of Texas Health Science Center at Houston (USA) | CR1 & CR2 |
| California Stem Cell, Inc. (USA) | CSC14 |
| University of Connecticut School of Medicine/Dentistry (USA) | CSC14, CT1, CT2, CT3, & CT4 |
| The Third Affiliated Hospital of Guangzhou Medical College (USA) | FY-3PN; FY-hES-1; FY-hES-3; FY-hES-5; FY-hES-7 & FY-hES-8 |
| Advanced Cell Technology, Inc. (USA) | MA 01; MA 09; MA 42; MA 50; MA135; NED 1; NED 2; NED 3 & NED 4 |
| Stanford University (USA) | MFS5 |
| New York University School of Medicine (USA) | NYUES1; NYUES2; NYUES3; NYUES4; NYUES5; NYUES6 & NYUES7 |
| Reprogenetics, LLC (USA) | RNJ7 |
| University of California, Los Angeles (USA) | UCLA1; UCLA2 & UCLA3 |
| Eastern Virginia Medical School (USA) | ES-76; ES-78-1; ES-78-2 |
| Reproductive Genetics Institute (USA) | RG-222; RG-230; RG-249; RG-308; RG-313; RG-148; DYSTROPHIA MYOTONICA 1 (DM1), affected, 46,XY; RG-153; DYSTROPHIA MYOTONICA 1 (DM1), affected, 46,XX; RG-170; MUSCULAR DYSTROPHY, BECKER TYPE (BMD), affected, 46,XY; RG-186; HUNTINGTON DISEASE (HD), affected, 46,XX; RG-194; HUNTINGTON DISEASE (HD), affected, 46,XY; RG-233; HEMOGLOBIN BETA LOCUS (HBB), affected (HbS/HbS - sickle cell anemia), 46,XX; RG-245; EMERY-DREIFUSS MUSCULAR DYSTROPHY, X-LINKED (EDMD), carrier, 47,XXY; RG-246; EMERY-DREIFUSS MUSCULAR DYSTROPHY, X-LINKED (EDMD), affected, 46,XY; RG-271; TORSION DYSTONIA 1 (DYT1), AUTOSOMAL DOMINANT, affected (N/GAG del), 46,XY; RG-283; MUSCULAR DYSTROPHY, DUCHENNE TYPE (DMD), affected, 46,XY; RG-288; CYSTIC FIBROSIS (CF), affected (deltaF508/deltaF508), 46,XY; RG-289; CYSTIC FIBROSIS (CF), affected (deltaF508/deltaF508), 46,XX; RG-301; MUSCULAR DYSTROPHY, DUCHENNE TYPE(DMD) affected, 46,XY; RG-302; MUSCULAR DYSTROPHY, DUCHENNE TYPE (DMD), carrier, 46,XX; RG-315; NEUROFIBROMATOSIS, TYPE I (NF1), affected (R19 47X/N), 46,XY; RG-316; TUBEROUS SCLEROSIS, TYPE 1(TSC1), affected (N/IVS7 + 1 G-A); RG-316; TUBEROUS SCLEROSIS, TYPE 1(TSC1), affected (N/IVS7 + 1 G-A); RG-320; TUBEROUS SCLEROSIS, TYPE 1(TSC1), affected (N/IVS7 + 1 G-A); RG-326; POPLITEAL PTERYGIUM SYNDROME (PPS), affected (R84H/N), 46,XY; RG-328; FACIOSCAPULOHUMERAL MUSCULAR DYSTROPHY 1A (FSHD), affected, 46,XY; RG-330; FACIOSCAPULOHUMERAL MUSCULAR DYSTROPHY 1A (FSHD), affected, 46,XY; RG-333; FACIOSCAPULOHUMERAL MUSCULAR DYSTROPHY 1A (FSHD), affected, 46,XX; RG-356; HEMOGLOBIN ALPHA LOCUS (HBA), affected (-alpha/--), 46,XX; RG-357; EMERY-DREIFUSS MUSCULAR DYSTROPHY, X-LINKED (EDMD), affected, 46,XY; RG-358; EMERY-DREIFUSS MUSCULAR DYSTROPHY, X-LINKED (EDMD), affected, 46,XY; RG-399; FACIOSCAPULOHUMERAL MUSCULAR DYSTROPHY 1A (FSHD), affected, 46,XX; RG-401; FACIOSCAPULOHUMERAL MUSCULAR DYSTROPHY 1A (FSHD), affected, 46,XX; RG-402; FACIOSCAPULOHUMERAL MUSCULAR DYSTROPHY 1A (FSHD), affected, 46,XX; |

TABLE 1-continued

Human ES cell lines

| Institution (Country) | Name |
|---|---|
| | RG-403; FACIOSCAPULOHUMERAL MUSCULAR DYSTROPHY 1A (FSHD), affected; |
| | RG-404; SPINAL MUSCULAR ATROPHY, TYPE I (SMA1), affected, 46,XY; |
| | RG-406; TORSION DYSTONIA 1, AUTOSOMAL DOMINANT (DYT1), affected (N/GAG del); |
| | RG-413; BREAST CANCER, FAMILIAL (BRCA2), affected (N/IVS7 GT del) & MULTIPLE ENDOCRINE NEOPLASIA, TYPE I (MEN1), affected (N/3036 4bp del); |
| | RG-414; MULTIPLE ENDOCRINE NEOPLASIA, TYPE I (MEN1), affected (N/3036 4bp del); |
| | RG-415; HUNTINGTON DISEASE (HD), affected; |
| | RG-416; CYSTIC FIBROSIS (CF), affected (deltaF508/1717-1 G-A); |
| | RG-417; CYSTIC FIBROSIS (CF), affected (deltaF508/1717-1 G-A); |
| | RG-418; HEMOGLOBIN BETA LOCUS (HBB), affected (cd8 + G/619del); |
| | RG-420; HEMOGLOBIN BETA LOCUS (HBB), affected (cd8 + G/619del); |
| | RG-422; CYSTIC FIBROSIS (CF), affected (N1303K/deltaF508); |
| | RG-423; CYSTIC FIBROSIS (CF), carrier (N/deltaF508); |
| | RG-424; MULTIPLE ENDOCRINE NEOPLASIA, TYPE 2 (MEN2B), affected (M918T/N); |
| | RG-426; PELIZAEUS-MERZBACHER DISEASE (PMLD), affected; |
| | RG-428; TUBEROUS SCLEROSIS, TYPE 1 (TSC1), affected (N/IVS7 + 1 G-A) |
| South American | |
| Instituto de Biociencias, São Paulo (Brazil) | BR-1 |
| Middle East | |
| Technion-Israel Institute of Technology, Haifa (Israel) | TE03, TE04, TE06 (I 3, I 4, I 6) |
| Hadassah University Hospital (Israel) | HAD 1; HAD 2; HAD 3; HAD 4; HAD 5; HAD 6 |
| Hebrew University of Jerusalem | HEFX1 |
| Technion-Israel Institute of Technology | I3; I3.2; I3.3; 14; 16; 16.2; J3; J3.2 |
| Royan Institute (Iran) | ARMD.1.H.iPSC.2; BOM.1.H.iPSC.1; CNS.1.H.iPSC.10; CNS.2.H.iPSC.7; FHC.1.H.iPSC.3; GSD.1.H.iPSC.7; HER.1.H.iPSC.1; LCA.1.H.iPSC.1; LHON.1.H.iPSC.5; R.1.H.iPSC.1; R.1.H.iPSC.4; R.1.H.iPSC.9; Royan H1; Royan H10; Royan H2; Royan H3; Royan H4; Royan H5; Royan H6; Royan H7; Royan H8; Royan H9; RP.1.H.iPSC.2; RP2.H.iPSC.3; TYR.1.H.iPSC.1; USH.1.H.iPSC.6 |
| Europe | |
| Cellartis AB, Gotenberg (Sweden) | SA001, SA002 (Sahlgrenska 1, Sahlgrenska 2); SA002.2; SA003; AS034.1; AS034.1.1; AS034.2; AS038; AS046; FC018; ASo85; AS094; SA111; SA121; SA142; SA167; SA181; SA191; SA196; SA202; SA203; SA211; SA218; SA240; SA279; SA348; SA352; SA399; SA461; SA502; SA506; SA521; SA540; SA611 |
| Karolinska Institutet (Sweden) | HS181; HS207; HS235; HS237; HS293; HS306; HS346; HS351; HS356; HS360; HS361; HS362; HS363; HS364; HS366; HS368; HD380; HS382; HS400; HS401; HS402; HS415; HS420; HS422; HS426; HS429; HS429A; HS429B; HS429C; HS429D; HS475; HS480; HS481; HS539 |
| Göteborg University, Göteborg (Sweden) | SA04-SA19 (Sahlgrenska 4-Sahlgrenska 19) |
| Karolinska Institute, Stockholm (Sweden) | KA08, KA09, KA40, KA41, KA42, KA43 (hICM8, hICM9, hICM40, hICM41, hICM42, hICM43) |
| Geneva University (Switzerland) | CH-ES1 |
| University of Basel (Switzerland) | CH-ES3; CH-ES3; CH-ES5 |
| Roslin Cells Ltd (UK) | RC2; RC3; RC4; RC5 |
| University of Newcastle upon Tyne (UK) | NCL-1; NCL-2; NCL-3; NCL-4; NCL-5; NCL-6; NCL-7; NCL-8; NCL-9 |
| Roslin Institute (Edinburgh) & Geron Corporation (UK) | RH1; RH2; RH3; RH4; RH5; RH6; RH7; RH9; |
| University of Manchester (UK) | Man 2 |
| King's College London (UK) | KCL-001 (formerly WT3) |
| The University of Sheffield, Sheffield (UK) | SHEF-1; SHEF-2; SHEF-3; SHEF-4; SHEF-5; SHEF-6; SHEF-7; SHEF-8 |
| Universities of Edinburgh & Oxford; University of Cambridge (UK) | Edi-1; Edi-2; Edi-3; Edi-4 |

TABLE 1-continued

Human ES cell lines

| Institution (Country) | Name |
|---|---|
| Roslin Cells Ltd, Roslin Institute, Universities of Edinburgh & Manchester, Central Manchester & Manchester Children's University Hospitals NHS Trust (UK) | RCM-1; RC-1; RC-2; RC-3; RC-4; RC-5; RC-6; RC-7; RC-8; RC-9; RC-10 |
| King's College London & Guy's Hospital Trust/Charitable Foundation of Guy's & St Thomas (UK) | KCL-003-CF1 (formerly CF1); KCL-005-HD1; KCL008-HD-2; KCL009-trans-1; KCL-001 (WT-3); KCL-001 (WT-4) |
| Stem Cell Sciences Ltd, Australia (SCS) & Australian Stem Cell Centre (ASCC) | MEL-1; MEL-2; MEL-3; MEL-4 |
| University of Edinburgh (UK) | CB660 |
| Axordia Ltd. (UK) | Shef-1; Shef-2; Shef-3; Shef-4; Shef-5; Shef-6; Shef-7 |
| University of Nottingham (UK) | Nott-1; Nott-2 |
| Centre of Regenerative Medicine in Barcelona (Spain) | ES-2; ES-3; ES-4; ES-5; ES-6; ES-7; ES-8; ES-9; ES-10; ES-11EM; cFA404-KiPS4F-1; cFA404-KiPS4F-3; KiPS3F-7; KiPS4F-1; KiPS4F-8 |
| Principe Felipe Centro de Investigacion (Spain) | VAL-3; VAL-4; VAL-5; VAL-6M; VAL-7; VAL-8; VAL-9; VAL-10B |
| Université Libre de Bruxelles (Belgium) | ERA-1; ERA2; ERA-3; ERAMUC-1; ERAMUC-1 |
| Vrije Universiteit Brussel (Belgium) | VUB01; VUB02; VUB06; VUB07; VUB03__DM1; VUB04__CF; VUB05__HD; VUB08__MFS; VUB09__FSHD; VUB10__SCA7; VUB11__FXS; VUB13__FXS; VUB14; VUB19__DM1; VUB20__CMT1A; VUB22__CF; VUB23__OI; VUB24__DM1; VUB26; VUB27; VUB28__HD__MFS |
| Central Manchester and Manchester Children's University Hospitals NHS (UK) | Man 1; Man 2 |
| Université Paris-Sud 11 (France) | CL01; CL02; CL03; PB04; PB05; PB05-1; PB06; PB06-1; PB07; PB08; PB09; PB10 |
| INSERM (France) | OSCAR; STR-I-155-HD; STR-I-171-GLA; STR-I-189-FRAXA; STR-I-203-CFTR; STR-I-209-MEN2a; STR-I-211-MEN2a; STR-I-221-Sca2; STR-I-229-MTMX; STR-I-231-MTMX; STR-I-233-FRAXA; STR-I-251-CFTR; STR-I-301-MFS; STR-I-305-APC; STR-I-315-CMT1a; STR-I-347-FRAXA; STR-I-355-APC; STR-I-359-APC |
| Masaryk University (Czech Republic) | CCTL 6; CCTL 8; CCTL 9; CCTL 10; CCTL 12; CCTL 13; CCRL 14 |
| Aalborg University (Denmark) | CLS1; CLS2; CLS3; CLS4 |
| University of Copenhagen (Denmark) | LRB001; LRB002; LRB003; LRB004; LRB005; LRB006; LRB007; LRB008; LRB009; LRB010; LRB011; LRB013; LRB014; LRB016; LRB017; LRB018; |
| University of Southern Denmark | KMEB1; KMEB2; KMEB3; KMEB4; KMEB |
| University of Helsinki (Finland) | FES21; FES22; FES29; FES30; FES61; FES75 |
| University of Tampere (Finland) | Regea 06/015; Regea 06/040; Regea 07/027; Regea 07/046; Regea 08/013; Regea 08/017; Regea 08/023; Regea 08/056 |
| Leiden University Medical Center (Netherlands) | HESC-NL1; HESC-NL2; HESC-NL3; HESC-NL4 |
| Russian Academy of Sciences (Russia) | ESM01; ESM02; ESM03; |
| Instanbul Memorial Hospital (Turkey) | MINE: NS-2; NS-3; NS-4; NS-5; NS-6; NS-7; NS-8; NS-9; NS-10; OZ-1; OZ-2; OZ-3; OZ-4; OZ-5; OZ-6; OZ-7; OZ-8 |
| Australia | |
| Monash University (Australia) | Envy |
| Prince of Wales Hospital, Sydney (Australia) | E1C1; E1C2; E1C3; E1C4; Endeavour 1; Endeavour 2; hES3.1; hES3.2; hES3.3 |
| Sydney IVF Limited (Australia) | SIVF01; SIVF03; SIVF05; SIVF06; SIVF07; SIVF08; SIVF09; SIVF10; SIVF11; SIVF12; SIVF13 |
| Asia | |
| Kyoto University (Japan) | 201B1; 201B2; 201B3; 201B6; 201B7; 243H1; 243H7; 246G1; 246G3; 246G4; 246G5; 246G6; khES-1; khES-2; khES-3; |
| Singapore Stem Cell Consortium | ESI-013; ESI-014; ESI-017; ESI-027; ESI-035; ESI-049; ESI-051; ESI-053 |
| ES Cell International Pte Ld (Singapore) | ES01, ES02, ES03, ES04, ES05, ES06 (HES-1, HES-2, HES-3, HES-4, HES-5, HES-6 |
| Maria Biotech Co. Ltd. - Maria Infertility Hospital Medical Institute, Seoul (Korea) | MB01, MB02, MB03; MB04; MB05; MB06; MB07; MB08; MB09 |
| MizMedi Hospital - Seoul National University, Seoul (Korea) | MI01 (Miz-hES1); Miz-hES2; Miz-hES3; Miz-hES4; Miz-hES5; Miz-hES6; Miz-hES7; Miz-hES8; Miz-hES9; Miz-hES10; Miz-hES11; Miz-hES12; Miz-hES13; Miz-hES14; Miz-hES15; |
| Pochon CHA University College of Medicine (Korea) | CHA-hES3; CHA-hES4 |
| Seoul National University (Korea) | SNUhES1; SNUhES2; SNUhES3; SNUhES4; SNUhES11; SNUhES16 |

TABLE 1-continued

Human ES cell lines

| Institution (Country) | Name |
|---|---|
| National Centre for Biological Sciences/Tata Institute of Fundamental Research, Bangalore (India) | NC01, NC02, NC03 (FCNCBS1, FCNCBS2, FCNCBS3); BJN-hem19; BJN-hem20 |
| Reliance Life Sciences, Mumbai (India) | RL05, RL07, RL10, RL13, RL15, RL20, RL21 (RLS ES 05, RLS ES 07, RLS ES 10 |
| National Institute for Research in Reproductive Health (India) | KIND-1; KIND-2 |
| Tata Institute of Fundamental Research (India) | FCNCBS1; FCNCBS2; FCNCBS3 |
| Kaohsiung Medical University (Taiwan) | T1; T2; T3; T4; T5 |
| Central South University (China) | chESC-3 (H3); chESC-8; chESC-20; chESC-22; EBNA1 + H9 |
| Graduate University of Chinese Academy of Sciences (China) | hPES-1; hPES-2 |
| Huazhong University of Science and Technology (China) | hES-8; hES18 |
| Peking University Third Hospital (China) | B4; B7; PKU1; PKU2 |
| Shanghai Jiao Tong University School of Medicine (China) | SHhES1 |
| Shanghei Second Medical University (China) | SH1; SH2; SH4; SH7; SH28; SH35; SH35a; SH38; SH39; SH42 |
| Sun Yat-sen University (China) | CHES-1; SYSU-1; SYSU-2 |
| Sun Yat-sen University Second Affiliated Hospital (China) | CHE-1; CHE-2; CHE-3 |
| The Third Affiliated Hospital of Guangzhou Medical College (China) | FY-hES-5; FY-hES-9; FY-hES-10;; FY-hES-11 |

TABLE 2

Listing of human induced pluripontent stem (hIPS) cell lines

| Institution | Cell Line |
|---|---|
| University of Wisconsin - Madison (USA) | 1. IPS(FORESKIN)-1 (Normal; 46XY; Yu, J., et al. [Thomson]2007, *Science*. 2007 318: 1917-20.)<br>2. IPS(FORESKIN)-2 (Normal; 46XY; Yu, J., et al. supra).<br>3. IPS(FORESKIN)-3 (Normal; 46XY Yu, J. et al. supra).<br>4. IPS(FORESKIN)-4 (Normal; 46XY; Yu, J. et al. supra).<br>5. IPS(IMR90)-1 (Normal; 46XX; Yu, J. et al. supra).<br>6. IPS(IMR90)-2 (Normal; 46XX; Yu, J. et al. supra).<br>7. IPS(IMR90)-3 (Normal; 46XX; Yu, J. et al. supra).<br>8. IPS(IMR90)-4 (Normal; 46XX; Yu, J. et al. supra).<br>9. IPS-SMA-3.5 (Normal; 46XY; Type 1 Spinal Muscular Atrophy; Ebert et al. 2009, *Nature*. 457: 277-80)<br>10. IPS-SMA-3.6 (Normal; 46XY; Type 1 Spinal Muscular Atrophy; Ebert et al. 2009, supra)<br>11. IPS-WT (Normal; 46XX; Type 1 Spinal Muscular Atrophy; Ebert et al. 2009, supra) |
| University of California, Los Angeles (USA) | 1. IPS-1 (Karumbayaram, S. et al. 2009, Stem Cells 27: 806-811; Lowry, et al.. 2008, *Proc Natl Acad Sci* USA. 105: 2883-8)<br>2. IPS-2 (Karumbayaram, et al. 2009, supra; Lowry et al. 2008, supra)<br>3. IPS-5 (Lowry et al. 2008, supra)<br>4. IPS-7 (Lowry et al. 2008, supra)<br>5. IPS-18 (Karumbayaram et al. 2009, supra; Lowry et al. 2008, supra)<br>6. IPS-24 (Lowry et al. 2008, supra)<br>7. IPS-29 (Lowry et al. 2008, supra) |
| Mt. Sinai Hospital (Samuel Lunenfeld Research Institute; USA) | 1. (Woltjen et al. 2009, *Nature*. 458: 766-70)<br>2. 61 (Woltjen et al. 2009, supra)<br>3. 66 (Woltjen et al. 2009, supra)<br>4. 67 (Woltjen et al. 2009, supra)<br>5. HIPSC117 (Kaji et al. 2009, *Nature* 458: 771-5)<br>6. HIPSC121 (Kaji et al. 2009, supra)<br>7. HIPSC122 (Kaji et al. 2009, supra) |
| Children's Hospital - Boston (USA) | 1. 551-IPS8 (Park et al. 2008, Nature 451: 141-6).<br>2. ADA-IPS2 ((ADA-SCID) Adenosine Deaminase Deficiency-related Severe Combined Immunodeficiency (GGG > AGG, exon 7, ADA gene); Park et al. 2008, *Stem Cells Cell* 134: 877-86) |

TABLE 2-continued

Listing of human induced pluripontent stem (hIPS) cell lines

| Institution | Cell Line |
|---|---|
| | 3. ADA-IPS3 ((ADA-SCID) Adenosine Deaminase Deficiency-related Severe Combined Immunodeficiency (GGG > AGG, exon 7, ADA gene); (Park et al. 2008, supra)<br>4. BJ1-IPS1 (Park et al. 2008, supra)<br>5. BMD-IPS1 (Male; (BMD) Becker Muscular Dystrophy (Unidentified mutation in dystrophin); (Park et al. 2008, supra)<br>6. BMD-IPS4 (Normal; 46XY; (BMD) Becker Muscular Dystrophy (Unidentified mutation in dystrophin); (Park et al. 2008, supra)<br>7. DH1CF16-IPS1 (Normal; 46XY; (Park et al. 2008, supra)<br>8. DH1CF32-IPS2 (Male; Park et al. 2008, supra)<br>9. DH1F-IPS3-3(Normal; 46XY; Park et al. 2008, supra)<br>10. DMD-IPS1 ((Normal; 46XY; DMD) Duchenne Muscular Dystrophy (Deletion of exon 45-52, dystrophin gene; Park et al. 2008, supra)<br>11. DMD-IPS2 (Male; (DMD) Duchenne Muscular Dystrophy (Deletion of exon 45-52, dystrophin gene; (Park et al. 2008, supra)<br>12. DS1-IPS4 (Male; Down syndrome (Trisomy 21); Park et al. 2008, supra)<br>13. DS2-IPS1 (Male; Down syndrome (Trisomy 21); (Park et al. 2008, supra)<br>14. DS2-IPS10 (Male; Down syndrome (Trisomy 21); Park et al. 2008, supra)<br>15. GD-IPS1(Male; (GD) Gaucher Disease type III (AAC > AGC, exon 9, G-insertion, nucleotide 84 of cDNA, GBA gene; Park et al. 2008, supra)<br>16. GD-IPS3 (Male; (GD) Gaucher Disease type III (AAC > AGC, exon 9, G-insertion, nucleotide 84 of cDNA, GBA gene; Park et al. 2008, supra)<br>17. HFIB2-IPS2 (Park, I. H., et al. 2008. Generation of human-induced pluripotent stem cells Nat Protoc. 3: 1180-6; Park et al. 2008, supra)<br>18. HFIB2-IPS4 (Park, I. H., et al. 2008. Generation of human-induced pluripotent stem cells Nat Protoc. 3: 1180-6; Park et al. 2008, supra)<br>19. HFIB2-IPS5 (Park, I. H., et al. 2008. Generation of human-induced pluripotent stem cells Nat Protoc. 3: 1180-6; Park et al. 2008, supra)<br>20. JDM-IPS1 (Normal, 46XX; Juvenile diabetes mellitus (multifactorial); Park et al. 2008, supra)<br>21. JDM-IPS1 (Normal, 46XX; Juvenile diabetes mellitus (multifactorial); Park et al. 2008, supra)<br>22. JDM-IPS2 (Female; Juvenile diabetes mellitus (multifactorial); Park et al. 2008, supra)<br>23. JDM-IPS3 (Female; Juvenile diabetes mellitus (multifactorial); Park et al. 2008, supra)<br>24. LNSC-IPS2 (Female; Lesch-Nyhan syndrome (carrier, heterozygosity of HPRT1; Park et al. 2008, supra)<br>25. MRC5-IPS7 (Male; Park et al. 2008, supra)<br>26. MRC5-IPS12 (Normal; 46XY; Park et al. 2008, supra)<br>27. MRC5-IPS1 (Male; Park et al. 2008, supra)<br>28. PD-IPS1 (Male; Parkinson disease (multifactorial); Park et al. 2008, supra)<br>29. SBDS-IPS1 (Male; Swachman-Bodian-Diamond syndrome (IV2 + 2T > C and IV3 − 1G > A, SBDS gene; Park et al. 2008, supra)<br>30. SBDS-IPS2<br>31. SBDS-IPS3 (Normal; 46XY; Swachman-Bodian-Diamond syndrome (IV2 + 2T > C and IV3 − 1G > A, SBDS gene; Park et al. 2008, supra) |
| Harvard University (USA) | 1. A29a (46XX; (ALS) Amyotrophic Lateral Sclerosis (L144F [Leu144 > Phe] dominant allele of the superoxide dismutase (SOD1) gene; Caucasian; Dimos et al. 2008, *Science* 321: 1218-21)<br>2. A29b (46XX; (ALS) Amyotrophic Lateral Sclerosis (L144F [Leu144 > Phe] dominant allele of the superoxide dismutase (SOD1) gene; Caucasian; Dimos, J. T., et al. 2008, supra)<br>3. A29c (46XX; (ALS) Amyotrophic Lateral Sclerosis (L144F [Leu144 > Phe] dominant allele of the superoxide dismutase (SOD1) gene; Caucasian; Dimos, J. T. et al. 2008, supra) |
| Salk Institute (USA) | 1. HAIR-IPS1 (Aasen, et al. [Belmonte, J. C.] 2008, *Nat Biotechnol*. 26: 1276-84)<br>2. HAIR-IPS2 (Aasen, T., et al. 2008, supra) |
| Royan Institute (Iran) | 1. R.1.H.iPSC.1(OCT4, Sox2, KLF4, c-Myc; Human fibroblasts)<br>2. BOM.1.H.iPSC.1 (OCT4, Sox2, KLF4, c-Myc; Human fibroblasts)<br>3. FHC.1.H.iPSC.3 (OCT4, Sox2, KLF4, c-Myc; Human fibroblasts)<br>4. GSD.1.H.iPSC.7 (OCT4, Sox2, KLF4, c-Myc; Human fibroblasts)<br>5. TYR.1.H.iPSC.1 (OCT4, Sox2, KLF4, c-Myc; Human fibroblasts)<br>6. HER.1.H.iPSC.1 (OCT4, Sox2, KLF4, c-Myc; Human fibroblasts)<br>7. R.1.H.iPSC.4 (OCT4, Sox2, KLF4, c-Myc; Human fibroblasts)<br>8. R.1.H.iPSC.9 (OCT4, Sox2, KLF4, c-Myc; Human fibroblasts)<br>9. RP2.H.iPSC.3 (OCT4, Sox2, KLF4, c-Myc; iPS cells)<br>10. LCA.1.H.iPSC.1 (OCT4, Sox2, KLF4, c-Myc; iPS cells)<br>11. USH.1.H.iPSC.6 (OCT4, Sox2, KLF4, c-Myc; Human fibroblasts)<br>12. RP.1.H.iPSC.2 (OCT4, Sox2, KLF4, c-Myc; Human fibroblasts)<br>13. ARMD.1.H.iPSC.2 (OCT4, Sox2, KLF4, c-Myc; Human fibroblasts)<br>14. LHON.1.H.iPSC.5 (OCT4, Sox2, KLF4, c-Myc; iPS cells)<br>15. CNS.1.H.iPSC.10 (OCT4, Sox2, KLF4, c-Myc; iPS cells)<br>16. CNS.2.H.iPSC.7 (OCT4, Sox2, KLF4, c-Myc; iPS cells) |

TABLE 2-continued

Listing of human induced pluripontent stem (hIPS) cell lines

| Institution | Cell Line |
|---|---|
| Centre of Regenerative Medicine in Barcelona (Spain) | 1. KiPS4F-1 (OCT4, Sox2, KLF4, c-Myc; human foreskin keratinocytes; 46XY)<br>2. KiPS3F-7 (OCT4, Sox2, KLF4); human foreskin keratinocytes)<br>3. KiPS4F-8 (OCT4, Sox2, KLF4, c-Myc human foreskin keratinocytes; 46XY)<br>4. cFA404-KiPS4F-1 (OCT4, Sox2, KLF4, c-Myc; Epidermal keratinocytes; 46XY)<br>5. cFA404-KiPS4F-3 (OCT4, Sox2, KLF4, c-Myc; Epidermal keratinocytes; 46XY) |
| Université Paris-Sud 11 (France) | 1. PB03 (Oct4, Sox2, Lin28, Nanog; Primary Amniocytes; 46XX; Lentivirus)<br>2. PB04 (Oct4, Sox2, Lin28, Nanog; Primary Amniocytes; Beta-Thalassemia affected; 46XY; Lentivirus)<br>3. PB05-1 (Oct4, Sox2, Lin28, Nanog; Primary Amniocytes; Beta-Thalassemia affected; 46XY; Lentivirus)<br>4. PB05 (Oct4, Sox2, Lin28, Nanog; Primary Amniocytes; Beta-Thalassemia affected; 46XY; Lentivirus)<br>5. PB06 (Oct4, Sox2, Lin28, Nanog; Primary Amniocytes; Down Syndrome; 47XY, +21; Lentivirus)<br>6. PB06-1 (Oct4, Sox2, Lin28, Nanog; Primary Amniocytes; Down Syndrome; 47XY, +21; Lentivirus)<br>7. PB07 (OCT4, Sox2, KLF4, c-Myc; Primary Amniocytes; 46XY; Retrotivirus)<br>8. PB08 (OCT4, Sox2, KLF4, c-Myc; Primary Amniocytes; 46XY; Retrotivirus)<br>9. PB09 (Oct4, Sox2, Lin28, Nanog; Primary Amniocytes; 46XY; Lentivirus)<br>10. PB10 (Oct4, Sox2; Primary Amniocytes46XY, Lentivirus) |
| Kyoto University (Japan) | 1. 201B1 (human fibroblast; 46XX)<br>2. 201B2 (human fibroblast; 46XX)<br>3. 201B3 (human fibroblast; 46XX)<br>4. 201B6 (human fibroblast; 46XX)<br>5. 201B7 (human fibroblast; 46XX)<br>6. 243H1 (human fibroblast)<br>7. 243H7 (human fibroblast)<br>8. 246B1 (Normal, 46XX)<br>9. 246B2 (Normal, 46XX)<br>10. 246B3 (Normal, 46XX)<br>11. 246B4 (Normal, 46XX)<br>12. 246B5 (Normal, 46XX)<br>13. 246B6 (Normal, 46XX)<br>14. 246G1 (human fibroblast; Takahashi et al. 2007, Cell 131: 861-72)<br>15. 246G3 (human fibroblast; Takahashi et al. 2007, supra)<br>16. 246G4 (human fibroblast; Takahashi et al. 2007, supra)<br>17. 246G5 (human fibroblast; Takahashi et al. 2007, supra)<br>18. 246G6 (human fibroblast; Takahashi et al. 2007, supra)<br>19. 253F1 (Normal, 46XX; Takahashi et al. 2007, supra)<br>20. 253F2 (Normal, 46XX; Takahashi et al. 2007, supra)<br>21. 253F3 (Normal, 46XX; Takahashi et al. 2007, supra)<br>22. 253F4 (Normal, 46XX; Takahashi et al. 2007, supra)<br>23. 253F5 (Normal, 46XX; Takahashi et al. 2007, supra) |
| Shanghai Institutes for Biological Sciences (China) | 1. HAFDC-IPS-6 (Li et al. 2009, *Hum Mol Genet.* 2009 18: 4340-9)<br>2. IPS-S (Liao et al. 2008, *Cell Res.* 18: 600-3) |

With regard to iPSCs (induced pluripotent stem cells), Applicant has previously described in detail cell aggregate suspension differentiation in U.S. patent application Ser. No. 12/765,714 (U.S. Patent Publication No. 2010-0272695), entitled CELL COMPOSITIONS DERIVED FROM DEDIFFERENTIATED REPROGRAMMED CELLS, filed Apr. 22, 2010, which is incorporated herein by reference in its entirety. Human iPSC aggregation is described in more detail in Example 27. U.S. Patent Publication No. 2010-0272695 and Example 27 herein, describes inclusion of at least a Rho kinase or ROCK inhibitor in the cell culture medium to enhance, increase, and/or promote growth, survival, proliferation and cell-cell adhesion of cells. For example, when employing Y-27632 the concentration can range from about 0.01 to about 1000 µM, typically about 0.1 to about 100 µM, and frequently about 1.0 to about 50 µM, and most often about 5 to 20 µM. When Fasudil/HA1077 is used, it can be used at about two or three-fold the aforementioned Y-27632 concentration. When H-1152 is used, it can be used at about a fraction, e.g., about 1/10th, 1/20th, 1/30th, 1/40th, 1/50th or 1/60th, of the amount of the aforementioned Y-27632 concentration. The concentration of ROCK-inhibitor used will depend, in part, on the bioactivity and potency of the inhibitor and the conditions in which it is used. Further, the time or stage for treating with the ROCK inhibitor is particularly not limited provided the desired effects such as the enhancing, increasing, and/or promoting growth, survival, proliferation and cell-cell adhesion of cells is achieved.

The cell aggregates described herein can be suspended in any physiologically acceptable medium, typically chosen according to the cell type(s) involved. The tissue culture media may comprise, for example, basic nutrients such as sugars and amino acids, growth factors, antibiotics (to minimize contamination) and the like. In another embodiment, the differentiable cells are cultured in suspension, using the cell media described herein. The term "suspension" as used in the context of cell culturing is used as it is in the art. Namely, cell culture suspensions are cell culture environments where the cells or cell aggregates do not adhere to a surface. One of skill in the art will be familiar with suspension culture techniques, including, but not limited to, the use of equipment such as flow hoods, incubators and/or equipment used to keep the cells in constant motion, e.g., rotator platforms, shakers, etc, if necessary. As used herein, cells are "in motion" if they are moving, or if their immediate environment is moving relative to the cells. If the cells are kept "in motion", the motion will, in one embodiment, be a "gentle motion" or "gentle agitation" that is designed to avoid or prevent exposing the cells to shear stress.

A variety of methods of making cell aggregates are known in the art such as, for example, the "hanging drop" method wherein cells in an inverted drop of tissue culture medium sink to the bottom of the drop where they aggregate; shaking cell suspensions in a laboratory flask; and various modifications of these techniques. See, e.g., Timmins et al. 2004, *Angiogenesis* 7:97-103; Dai et al. 1996, *Biotech Bioeng* 50:349-56; Foty et al. 1996, *Development* 122:1611-20; Forgacs et al. 2001, *J. Biophys.* 74, 2227-2234; Furukawa et al. 1998, *Cell Transplantation* 10:441-45; Glicklis et al. 2004. *Biotech Bioeng* 86:672-80; Carpenedo et al. 2007, *Stem Cells* 25:2224-34; and Korff et al. 2001, *FASEB J.* 15:447-57, which are herein incorporated in their entirety be reference. More recently, cell aggregates have been formed by scraping micropatterned colonies into suspension, centrifuging colonies out of microtiter plates and into suspension or using pipets to dislodge and suspend colonies grown in patterned microwells (Ungrin et al. 2008 *PLoS ONE* 3:1-12; Bauwens et al, 2008 *Stem Cells, Published online Jun. 26*, 2008). Although such methods can be used to produce cell aggregates described herein, the cell aggregates produced herein are optimized for synchronous directed-differentiation as described in D'Amour et al. 2006, supra, Also, unlike these other methods, the methods for producing the cell aggregates in suspension described herein are amenable to large scale manufacturing.

In general, the cell medium compositions of the present invention are refreshed at least once every day, but the medium can be changed more often or less often, depending of the specific needs and circumstances of the suspension culture. In vitro, cells are usually grown in culture media in a batch mode (i.e., are batch fed) and exposed to various media conditions. As described herein, the cells exist in a dish-culture as either adherent cultures or as cell aggregates in suspension, and maintained in contact with a surrounding culture medium; and the waste media being replaced periodically. In general, the culture medium may be refreshed about every 1, 2, 3, 4, 5, 6, 7, 8, 9, 10, 11, 12, 13, 14, 15, 16, 17, 18, 19, 20, 21, 22, 23 or 24 hours, or any fraction thereof. In additional examples, the medium may be refreshed less often such as, but not limited to, every 1.1, 1.2, 1.3, 1.4, 1.5, 1.6, 1.7, 1.8, 1.9 or every 2 or more days, or any time frame in between.

Yet, in another embodiment of the invention, perfusion methods are employed to prevent degradation of growth factors and other agents which have to be replaced frequently; or perfusion as a means to deplete waste products from the culture media over a period of time. For example, U.S. Pat. No. 5,320,963 describes a bioreactor for perfusion culture of suspension cells. U.S. Pat. No. 5,605,822 describes a bioreactor system, employing stromal cells to provide growth factors, for growth of HSC cells in culture by perfusion. U.S. Pat. No. 5,646,043 describes growth of HSC cells by continuous and periodic perfusion including media compositions for growth of HSC cells. U.S. Pat. No. 5,155,035 describes a bioreactor for suspension culture of cells by fluid media rotation. These references are all incorporated herein in their entireties.

In general, the cells that are cultured in suspension in the medium compositions of the present invention are "split" or "passaged" every week or so, but the cells can be split more often or less often, depending on the specific needs and circumstances of the suspension culture. For example, the cells may be split every 1, 2, 3, 4, 5, 6, 7, 8, 9, 10, 11, 12, 13, 14 or more days, or any time frame in between. As used herein, the term "split" or "passaged" in the context of cell culture is used as it is in the art. Namely, cell culture splitting, or passaging, is the collection of cells from a previous culture and subsequent transfer of a smaller number of collected (harvested) cells into a new cell culture vessel. In general, passaging cells allows the cells to continue to grow in a healthy cell culture environment. One of skill in the art will be familiar with the process and methods of cell culture passaging, which may, but not necessarily, involve the use of enzymatic or non-enzymatic methods that may be used to disaggregate cells that have clumped together during their growth expansion.

In some instances, a degree of cell death may occur in the cultured (suspended and adherent) cells immediately after passaging. In one embodiment, the differentiable cells can "recover" from passaging, by delaying the refreshing of the cell medium for more than 24 hours. Thereafter, the cell medium may be changed more frequently. In another embodiment, the cell culture medium can further comprise an inhibitor of cell death. For example, Wantanabe et al. recently disclosed the use of a Rho-associated kinase inhibitor, Y27632, to protect human ES cells after dissociation. See Wantanabe et al. *Nat. Biotechnol.*, 25:681-686 2007, which is incorporated by reference. In additional embodiments, the cell culture medium may comprise caspase inhibitors, growth factors or other trophic factors to prevent or attenuate cell death immediately after passaging. Specific examples of compounds that may be used include, but are not limited to, HA 1077, Dihydrochloride, Hydroxyfasudil, Rho Kinase Inhibitor, Rho-Kinase Inhibitor II, Rho Kinase Inhibitor III, Kinase Inhibitor IV and Y27632 all of which are commercially available. In still another embodiment, the compounds or factors used to prevent or attenuate cell death during or immediately after cell passaging may be removed from the cell culture medium after the cells have recovered from the passaging process. In an additional embodiment, undifferentiated ES cells aggregate effectively in standard base media and do not require Y27632 or other interventions to maintain viability during dissociation and aggregation.

In additional embodiments, the compositions and methods of the present invention may also comprise the presence or use of surfactants. In one particular embodiment, the compositions and methods comprise at least one surfactant in the context of a suspension culture. Surfactants are well-known in the art and, generally speaking, are amphiphilic in nature. In specific embodiments, the present invention comprises the use of at least one surfactant that is either anionic, cationic, non-ionic or zwitterionic. The concentration of the surfactant used in the compositions and methods of the present invention is a matter of routine screening and optimization. For example, Owen et al. reported the use of surfactants in cell culture techniques for HeLa cells and human amniotic cells. See Owen et al. *J. Cell. Sci.*, 32:363-376 (1978), which is incorporated by reference. Examples of surfactants that may be used include, but are not limited to, Sodium dodecyl sulfate (SDS), ammonium lauryl sulfate, and other alkyl sulfate salts, Sodium laureth sulfate (SLES), Alkyl benzene sulfonate, Soaps, or fatty acid salts, Cetyl trimethylammonium bromide (CTAB) (hexadecyl trimethyl ammonium bromide), and other alkyltrimethylammonium salts, Cetylpyridinium chloride (CPC), Polyethoxylated tallow amine (POEA), Benzalkonium chloride (BAC), Benzethonium chloride (BZT), Dodecyl betaine, Dodecyl dimethylamine oxide, Cocamidopropyl betaine, Coco ampho glycinate, Alkyl poly(ethylene oxide), Copolymers of poly(ethylene oxide) and polypropylene oxide) such as Pluronic F68, Alkyl polyglucosides, such as, but not limited to, Octyl glucoside, Decyl maltoside, Fatty alcohols, Cetyl alcohol, Oleyl alcohol, Cocamide MEA, cocamide DEA and cocamide TEA and/or Polyoxyethylene-sorbitane monolaurate (Tween)

The embodiments described herein provide methods for large-scale manufacturing of proliferating and/or differentiating hESC by maintaining a low shear environment thereby maintaining operating cell density in the system and minimizing fluid shear stresses. In particular, the present invention provides methods for maintaining a low shear environment in a eukaryotic cell manufacturing scale-up system by culturing a cell suspension in a 60 mm dish, 6-well plate, a rotating bottle, a bioreactor (e.g., spinner flasks), a vessel and the like. Alternatively, continuous perfusion systems for culturing cells requires agitation or movement in the bioreactor or vessel to provide suspension of the cells, oxygenation and a supply of fresh nutrients, e.g., for growth and/or differentiation. To obtain cell suspension, bioreactor vessels typically use one or more movable mechanical agitation devices that are also a potential source of shear stress.

Establishing and maintaining a constant, optimized agitating shear rate is important for maintaining cell growth and viability. For example increased shear rate is deleterious in the following aspects: (1) excessive shear increases energy consumption, (2) excessive shear interferes with diffusion at the membrane surface, (3) excessive shear can deprive certain compounds of their bioactivities, and (4) excessive shear can deform cell membranes beyond the threshold bursting tension leading to cell lysis. It therefore is desirable to maintain shear within an optimal range of 5 to 500 $sec^{-1}$, depending on the diameter of the cell aggregate and the sensitivity of the particular cell line to single cell dissociation and shear. Exemplary shear rates produced by configurations useful in the methods of the invention are shown in Example 17 for aggregate diameters between 100-200 μm and rotation speeds between 60-140 rpm for a 6-well dish. These values estimate the time averaged shear stress that occurs in the bulk fluid during rotation. However, it is expected that the shear stress at the wall of the vessel will be higher due to boundary effects. Using the method of Ley et al. supra, the wall shear stress was calculated for rotation speeds ranging from 60 rpm to 140 rpm and is shown in Examples 17-19.

Still, other examples of means or devices for generating a gently agitated cell suspension exist and are well known to one skilled in the art including impellers, such as propellers, or other mechanical means, bladders, fluid or gas flow-based means, ultrasonic standing wave generators, rocking or rotating platforms or combinations thereof which produce a cell suspension. In the methods of the invention, a rotating platform is an exemplary means for suspending the cells in the media when cells are in 6-well plates, generating a shear rate of less than 400 $sec^{-1}$. Regardless of rotator type or mechanism for generating agitated mixed fluid suspensions, the estimated time-averaged shear rate and shear stress in the bulk fluid provides a normalizing factor by which all fluid mixing devices can be related. While the flow regimes amongst the devices may vary in their profile and extent of laminar or turbulent flow, shear calculations provide a basis for equating flow in devices that produce mixing by different mechanisms. For example, for a 125 mL spinner flask with an impeller diameter of 4 cm, a vessel width of 6.4 cm, an impeller angle of 90 degrees, and an impeller width of 0.1 cm, a impeller rotation speed of 135 rpm will generate the same time-average shear rate and shear stress in the bulk fluid as 6-well dish with 5 mL media rotating at 100 rpm for aggregates of 100 μm in diameter.

The method of the present invention can also be used to maintain a low shear environment in a manufacturing scale-up system for periods of time ranging from 1, 2, 3, 4, 5, 6, 7, 8, 9, 10, 11, 12, 13, 14, 15, 16, 17, 18, 19, 20, 21, 23, 24, 25, 26, 27, 28, 29, 30 days, to more than 40 days, to more than 50 days. An exemplary operating time is at least about 1, 2, 3, 4, 5, 6, 7, 8, 9, 10, 11, 12, 13, 14, 15, 16, 17, 18, 19, 20, 21, 23, 24, 25, 26, 27, 28, 29, 30 days to more than 40 days, to more than 50 days.

It is contemplated that the differentiable cells can be passaged using enzymatic, non-enzymatic, or manual dissociation methods prior to and/or after contact with the defined medium of the invention. Non-limiting examples of enzymatic dissociation methods include the use of proteases such as trypsin, collagenase, dispase, and ACCUTASE™. In one embodiment, ACCUTASE™ is used to passage the contacted cells. When enzymatic passaging methods are used, the resultant culture can comprise a mixture of singlets, doublets, triplets, and clumps of cells that vary in size depending on the enzyme used. A non-limiting example of a non-enzymatic dissociation method is a cell dispersal buffer. Manual passaging techniques have been well described in the art, such as in Schulz et al. 2004 *Stem Cells,* 22:1218-38. The choice of passaging method is influenced by the choice of extracellular matrix, if one is present, and is easily determined by one of ordinary skill in the art.

In one specific embodiment, methods of culturing differentiable cells comprise providing a dissociation solution to a layer of differentiable cells that are contained in a culture chamber prior to dissociation, where the dissociation breaks apart the layer of cells into single cells. After dissociation, the single cells are placed into a new tissue culture chamber with a stem cell culture solution, wherein the stem cell culture solution comprises a basal salt nutrient solution and an ErbB3 ligand. Once cultured, the single stem cells are placed in conditions that permit growth and division of the single cells. In another specific embodiment, the methods of culturing differentiable cells comprise providing a dissociation solution to an aggregation differentiable cells that are contained in a culture chamber prior, where the dissociation breaks apart the aggregates of cells into single cells or smaller aggregates of cells.

The disaggregation solution used in the methods of the present invention can be any disaggregation solution capable of breaking apart or disaggregating the cells into single cells, without causing extensive toxicity to the cells. Examples of disaggregation solutions include, but are not limited to, trypsin, ACCUTASE™, 0.25% Trypsin/EDTA, TrypLE, or VERSENE™ (EDTA) and trypsin. The methods of the present invention need not result in every cell of the confluent layer or suspension being disaggregated into single cells, provided that at least a few single cells are disaggregated and capable of being re-cultured.

Either at the beginning of culture, or after passaging, the differentiable cells can be seeded at any density, including a single cell in a culture chamber. The cell density of the seeded cells may be adjusted depending on a variety of factors, including but not limited to the use of adherent or suspension cultures, the specific recipe of the cell culture media used, the growth conditions and the contemplated use of the cultured cells. Examples of cell culture densities include, but are not limited to, $0.01 \times 10^5$ cells/mL, $0.05 \times 10^5$ cells/mL, $0.1 \times 10^5$ cells/mL, $0.5 \times 10^5$ cells/mL, $1.0 \times 10^5$ cells/mL, $1.2 \times 10^5$ cells/mL, $1.4 \times 10^5$ cells/mL, $1.6 \times 10^5$ cells/mL, $1.8 \times 10^5$ cells/mL, $2.0 \times 10^5$ cells/mL, $3.0 \times 10^5$ cells/mL, $4.0 \times 10^5$ cells/mL, $5.0 \times 10^5$ cells/mL, $6.0 \times 10^5$ cells/mL, $7.0 \times 10^5$ cells/mL, $8.0 \times 10^5$ cells/mL, $9.0 \times 10^5$ cells/mL, or $10.0 \times 10^5$ cells/mL, or more, e.g., up to $5\times10^7$ cells/mL have been cultured with good cell survival, or any value in between.

In addition to the above, as used herein, the term "operating cell density" or "operational cell density" or equivalents thereof refers to that cell density at which a manufacturing process or system will be operated to obtain the production of a proliferating or differentiating hES cell culture. Such cell densities are those at which nutrients such as vitamins, minerals, amino acids or metabolites, as well as environmental conditions such as oxygen tension, that are supplied to the system are sufficient to maintain cellular viability. Alternatively, such cell densities are those at which waste products can be removed from the system at a rate sufficient to maintain cellular viability. Such cell densities can be readily determined by one of ordinary skill in the art.

Operating cell densities that may be maintained are those from at least about $0.5\times10^6$ cells/mL. In a typical scale-up system operating cell densities may be between about $0.5\times10^6$ cells/mL and about $25\times10^6$ cells/mL. Exemplary densities can be between about $2.5\times10^6$ cells/mL, $22\times10^6$ cells/mL and up to $5\times10^7$ cells/mL. In the method of the invention, cell viability is at least about 40%, 45%, 50%, 55%, 60%, 65%, 70%, 75%, 80%, 85%, 90%, 95% and up to about 100%. Other scale-up system operating cell densities and acceptable cell viability levels will be recognized by those skilled in the art and can be determined by techniques well known to those of skill in the art. For example, batch (batch fed), fed-batch and continuous feed configurations, cell densities may be between about $0.5\times10^6$ cells/mL and $15\times10^6$ cells/mL.

Differentiable cells may also be utilized to screen for molecules or factors that influence their plasticity or other characteristics. For example, differentiable cells could be used to identify agents that induce apoptosis, differentiation or proliferation, as well as similar effects in differentiated lineages that have been generated from the differentiable cells.

Because the compositions and methods of the present invention allow for single cell passaging, differentiable cells have been successfully cultured in high-throughput settings, such as, but not limited to, 96-well plates and 384-well plates. FIG. 16 shows the morphology and alkaline phosphatase staining of BG02 cells that were cultured in DC-HAIF in both a 96-well and 384-well plate, using the methods described herein. Briefly, hESCs cells that were split, using ACCUTASE™, and plated in 96-well and 384-well plates and cultured showed a similar plating efficiency as what is observed using other culture dishes. In addition, the cells formed colonies, and were expanded successfully over 5 days in the smaller environments. These smaller cultures remained morphologically undifferentiated, and stained uniformly positive for alkaline phosphatase, a marker of undifferentiated cells. Furthermore, hESCs could also be grown in 96-well culture devices (not shown) that provide real-time measurements of impedance, which can be used to measure cell proliferation and viability using the RT-CEST™ methods from ACEA Biosciences, Inc. (www.aceabio.com). Such an approach would enable a label-free identification and quantitation of subtle or immediate effects on differentiable cells, as well as measurements of proliferation, apoptosis and changes to morphology, in real time.

The compositions and methods of the invention may contain virtually any combination of the components set out above or described elsewhere herein, provided the compositions and methods comprise a basal salt nutrient solution and a means for stimulating ErbB2 directed tyrosine kinase activity. As one skilled in the art would recognize, the components of the compositions and methods of the invention will vary according to the protocol design. Accordingly, one embodiment of the present invention relates to culturing differentiable cells in 96-well plates and/or 384-well plates. Indeed, using the methods and compositions of the present invention, the cell culture chamber, i.e., the culture dish, is no longer limited to specific dimensions. Thus, the methods described herein are in no way limited to specific culture chamber dimensions and/or means and devices to generate hES cells.

The compositions and methods described herein have several useful features. For example, the compositions and methods described herein are useful for modeling the early stages of human development. Furthermore, the compositions and methods described herein can also serve for therapeutic intervention in disease states, such as neurodegenerative disorders, diabetes mellitus or renal failure, such as by the development of pure tissue or cell type.

The cell types that differentiate from differentiable cells have several uses in various fields of research and development including but not limited to drug discovery, drug development and testing, toxicology, production of cells for therapeutic purposes as well as basic science research. These cell types express molecules that are of interest in a wide range of research fields. These include the molecules known to be required for the functioning of the various cell types as described in standard reference texts. These molecules include, but are not limited to, cytokines, growth factors, cytokine receptors, extracellular matrix, transcription factors, secreted polypeptides and other molecules, and growth factor receptors.

It is contemplated that the differentiable cells of the invention can be differentiated through contact with a cell differentiation environment. As used herein, the term "cell differentiation environment" refers to a cell culture condition wherein the differentiable cells are induced to differentiate, or are induced to become a human cell culture enriched in differentiated cells. Preferably, the differentiated cell lineage induced by the growth factor will be homogeneous in nature. The term "homogeneous," refers to a population that contains more than approximately 50%, 60%, 70%, 80%, 85%, 86%, 87%, 88%, 89%, 90%, 91%, 92%, 93%, 94%, 95%, 96%, 97%, 98%, or 99% of the desired cell lineage.

A cell differentiating medium or environment may be utilized to partially, terminally, or reversibly differentiate the differentiable cells of the present invention. In accordance with the invention the medium of the cell differentiation environment may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiation environment can also contain supplements such as L-Glutamine, NEAA (non-essential amino acids), P/S (penicillin/streptomycin), N2, B27 and β-mercaptoethanol (β-ME). It is contemplated that additional factors may be added to the cell differentiation environment, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

The compositions described herein are useful for the screening of test compounds to determine whether a test compound modulates pluripotency, proliferation, and/or differentiation of differentiable cells. Pluripotency, proliferation and/or differentiation of differentiable cells can be readily ascertained by one of ordinary skill in the art. Non-limiting methods include examining cell morphology, the expression of various markers, teratoma formation, cell counts and measurements of impedance.

The progression of the differentiable cells to the desired cell lineage, or its maintenance in an undifferentiated state can be monitored by quantitating expression of marker genes characteristic of the desired cell lineage as well as the lack of expression of marker genes characteristic of differentiable cell types. One method of quantitating gene expression of such marker genes is through the use of quantitative PCR (Q-PCR). Methods of performing Q-PCR are well known in the art. Other methods that are known in the art can also be used to quantitate marker gene expression. Marker gene expression can be detected by using antibodies specific for the marker gene of interest.

In certain embodiments, the screening method encompasses methods of identifying a compound capable of modulating pluripotency, proliferation and/or differentiation of a differentiable cell, comprising (a) providing a differentiable cell; (b) culturing the cell in a composition comprising a basal salt nutrient solution and an ErbB3 ligand, wherein the composition is essentially serum free; (c) contacting the cell with a test compound; and determining whether an increase or decrease in pluripotency, proliferation and/or differentiation occurs in the cell contacted with the compound, said increase being an indication that the compound modulates pluripotency, proliferation and/or differentiation. In certain embodiments, the ErbB3 ligand is HRG-1β. In other embodiments, the ErbB3 ligand can be substituted with a test compound, to determine the effects of the test compound. For example, the effects on pluripotency, proliferation and/or differentiation that occur with the test compound can be compared to the effects on pluripotency, proliferation and/or differentiation that occurs with the ErbB3 ligand to determine the effects of the test compound on the differentiable cells. It is contemplated that any of the compositions described herein can be used in the screening methods of the present invention.

In yet another embodiment, the cells can be cultured in the absence of an ErbB3 ligand (ErbB2-directed tyrosine kinase activity) to determine the effects of the absence of an ErbB3 ligand (ErbB2-directed tyrosine kinase activity) on the cells.

Using the methods described herein, compositions comprising the desired cell lineage that are substantially free of other cell types can be produced. Alternatively, compositions comprising mixtures of the differentiable cells and the desired cell lineage can also be produced.

In some embodiments of the present invention, cells of the desired cell lineage can be isolated by using an affinity tag that is specific for such cells. One example of an affinity tag specific for a target cell is an antibody that is specific to a marker polypeptide that is present on the cell surface of the target cell but which is not substantially present on other cell types that would be found in a cell culture produced by the methods described herein.

The present invention also relates to kits, wherein the kit comprises a basal salt nutrient solution and at least one compound capable of stimulating ErbB2-directed tyrosine kinase activity. In one embodiment, the kits comprise at least one ErbB3 ligand, as described herein. In another embodiment, the kits comprise more than one ErbB3 ligand. In another embodiment, the kits comprise at least one of TGF-β or a TGF-β family member or a variant or functional fragment thereof as described herein. In yet another embodiment, the kits comprise more than one of TGF-β or a TGF-β family member or a variant or functional fragment thereof. In still another embodiment, the kits comprise at least one fibroblast growth factor or variant or functional fragment thereof. In another embodiment, the kits comprise more than one fibroblast growth factor or variant or functional fragment thereof. In a specific embodiment, the kits comprise at least one of FGF-7, FGF-8, FGF-10, FGF-22 or variants or functional fragments thereof. In another embodiment, the kits comprise serum albumin. In still another embodiment, the kits comprise serum and/or at least one insoluble substrate as described herein and/or at least one disaggregation solution.

The kits of the invention may contain virtually any combination of the components set out above or described elsewhere herein. As one skilled in the art would recognize, the components supplied with kits of the invention will vary with the intended use for the kits. Thus, kits may be designed to perform various functions set out in this application and the components of such kits will vary accordingly.

Throughout this application, various publications are referenced. The disclosures of all of these publications and those references cited within those publications in their entireties are hereby incorporated by reference into this application in their entirety in order to more fully describe the state of the art to which this invention pertains.

EXAMPLES

The human embryonic stem cell line BG01v (BresaGen, Inc., Athens, Ga.) was used in some of the experiments described herein. The BG01v hESC line is a karyotypically variant cell line, which exhibits stable karyotype containing specific trisomies (karyotype: 49, XXY,+12,+17). Parent cultures were maintained as described previously (Schulz et al. 2003, *BMC Neurosci.,* 4:27; Schulz et al. 2004, *Stem Cells* 22:1218-38; Rosler et al. 2004, *Dev. Dynamics,* 229:259-274; Brimble et al. 2004 *Stem Cells Dev.* 13:585-596). Briefly, the cells were grown in dishes coated with MATRIGEL™ or fibronectin, in conditioned media from mouse embryonic fibroblasts (MEFs) (MEF-CM) comprising DMEM:F12 with 20% KSR, 8 ng/mL FGF2, 2 mM L-Glutamine, 1× non-essential amino acids, 0.5 U/mL penicillin, 0.5 U/mL streptomycin, 0.1 mM β-mercaptoethanol (Sigma, St. Louis, Mo., USA), with collagenase passaging.

The defined culture (DC) media tested herein comprised DMEM/F12, 2 mM Glutamax, 1× non-essential amino acids, 0.5 U/mL penicillin, 0.5 U/mL streptomycin, 10 µg/mL transferrin (all from Invitrogen, Carlsbad, Calif., USA) 0.1 mM β-mercaptoethanol (Sigma), 0.2% fatty acid-free Cohn's fraction V BSA (Serologicals), 1× Trace Element mixes A, B and C (Cellgro) and 50 µg/mL Ascorbic Acid (Sigma). Variable levels of recombinant growth factors were used, including FGF2 (Sigma), LongR3-IGF1 (JRH Biosciences), Heregulin-13 EGF domain (HRGl3, Peprotech), TGFβ (R&D systems), nodal (R&D systems), LIF (R&D systems), EGF (R&D systems), TGFα (R&D systems), HRGα (R&D systems), BMP4 (R&D systems), and Activin A (R&D Systems). LongR3-IGF1 is a modified version of IGF1 that has reduced affinity for IGF1 binding proteins, some of which are expressed in hESCs. DC-HAIF is the defined culture media as above, containing 10 ng/mL HRG-β, 10 ng/mL Activin A, 200 ng/mL LR-IGF1 and 8 ng/mL FGF2. DC-HAI is defined culture media as above containing 10 ng/mL HRG-β, 10 ng/mL Activin A, and 200 ng/mL LR-IGF1. In both DC-HAIF and DC-HAI, the LR-IGF1 component can, of course be replaced with IFG1.

MATRIGEL™ coated dishes were prepared by diluting Growth Factor Reduced BD MATRIGEL™ matrix (BD Biosciences, Franklin Lakes, N.J., USA) to a final concentration range of about 1:30 to about 1:1000 in cold DMEM/F-12. In one embodiment, the concentration of MATRIGEL™ is about 1:200. 1 mL/35 mm dish was used to coat dishes for 1-2 hours at room temperature or at least overnight at 4° C. Plates were stored up to one week at 4° C. MATRIGEL™ solution was removed immediately before use.

For the tested conditions, parent cultures were plated into 6-well dishes for comparison of multiple conditions. Cultures were typically plated directly into the test conditions. The cultures were assessed every day and graded based on morphological criteria 4 to 5 days after plating. The grading scale of 1 to 5 involved examining the whole culture and assessing overall proportion of undifferentiated colonies, their relative size, and proportion of colonies or parts of colonies exhibiting obvious differentiation. Grade 5 indicates "ideal" cultures, with large undifferentiated colonies and negligible differentiation. Grade 4 indicates a very good culture, but with some obvious differentiation. Grade 3 indicates an acceptable culture, but with around half the colonies exhibiting obvious differentiation. Grade 2 cultures are predominantly differentiated, with occasional putative undifferentiated cells. Grade 1 cultures contain differentiated colonies or the cultures did not adhere or did not survive. Cultures that exhibited good expansion of undifferentiated cells were passaged to assess longer-term culture in these conditions.

Example 1

Expression of ErbB1-3, Nrg1 and ADAM19 in BG01v Cells

Real time RT-PCR was used to demonstrate expression of ErbB1-3, Neuregulin and ADAM-19 in BG01v cells (FIG. 1). BG01v cells cultured in DC media as described above, containing 100 ng/mL LongR3-IGF1 (LR-IGF1), 8 ng/mL FGF2 and 1 ng/mL Activin A were harvested and RNA was prepared using the RNeasy mini kit (Qiagen) according to the manufacturer's instructions. First strand cDNA was prepared using the iScript kit (Biorad) and real time PCR was carried out using a MJ Research Opticon thermal cycler.

TaqMan assays on demand (Applied Biosystems) for ADAM19 (Hs00224960_m1), EGFR (Hs00193306_m1), ErbB2 (Hs00170433_m1), ErbB3 (Hs00176538_m1), NRG1 (Hs00247620_m1), OCT4 (Hs00742896_s1) and control GAPDH were used with TaqMan universal PCR (Applied Biosystems). The real time amplification plots are shown in FIG. 1, demonstrating expression of these transcripts in undifferentiated BG01v cells.

Example 2

Inhibition of ErbB2 Slows Proliferation of BG01v Cells

The EGF domain family of ligands bind to the ErbB family of receptor tyrosine kinases. To examine the effect of known inhibitors of ErbB tyrosine kinases in hESCs, BG01v cells were plated in 6 well trays on MATRIGEL™ diluted at 1:1000, in defined culture medium (DC) containing 100 ng/mL LongR3-IGF1, 8 ng/mL FGF2 and 1 ng/mL Activin A. On the next day, DMSO (carrier control), 50 nM-20 µM AG1478 (an ErbB1 inhibitor), or 100 nM-20 µM AG879 (an ErbB2 inhibitor) was added with fresh medium. The cells were cultured for an additional 5 days, with daily media changes. The cultures were then fixed and stained for alkaline phosphatase activity.

Subconfluent colonies of AP+ BG01v cells observed (FIGS. 2A, and B) in control and AG1478 cultured cells, indicating that neither DMSO nor AG1478 (50 nM-20 µM) had an apparent affect on cell proliferation. AG879, however, substantially inhibited cell growth at 5 µM (FIG. 2C) and caused cell death at 20 µM (not shown). The cultures grown in AG879 did not appear to differentiate and appeared to maintain a pluripotent morphology and alkaline phosphatase activity, indicating that AG879 appeared to inhibit proliferation without inducing differentiation, suggesting that BG01v cells are reliant on ErbB2 signaling for cell survival. Conversely, BG01v cells grown in similar conditions as above do not appear to be reliant on ErbB1 signal for proliferation.

Example 3

BG01v cells are Maintained in Defined Media Containing Heregulin

Expression of ErbB2 and ErbB3 and the inhibition of proliferation with AG879 suggested that BG01v cells have active endogenous ErbB signaling and that they may also respond to exogenous HRG-13. BG01v cells were grown in DC medium containing 10 ng/mL HRG-13, 200 ng/mL LongR3-IGF1, 8 ng/mL FGF2 and 10 ng/mL Activin A, on MATRIGEL™ diluted 1:1000 (FIGS. 3A and B). These cells were grown for 4 passages, or >20 days, exhibited undifferentiated morphology and did not show elevated spontaneous differentiation.

Furthermore, BG01v cells were also maintained for 2 passages, or >13 days, in DC medium comprising 10 ng/mL HRGβ, 200 ng/mL LongR3-IGF1, and 10 ng/mL Activin A. These cultures proliferated normally and exhibited very low spontaneous differentiation, demonstrating that BG01v cells could be maintained in defined conditions with HRGβ in the absence of FGF2.

Example 4

The Role of ErbB2-Directed Tyrosine Kinase in ES Cells

RT-PCR demonstrated that mESCs express ADAM19, Neuregulin1 (Nrg1), and ErbB1-4 (FIG. 4A). In mESCs, ErbB2 and 3 appeared to be expressed at higher levels than ErbB1, with low levels of ErbB4 being detected. These data suggest that endogenous HRG-β could be involved in driving mESC self-renewal.

The expression of the ErbB receptor transcripts in mouse embryonic fibroblasts (MEFs) was also examined (FIG. 4B). MEFs are a heterogenous population of cells derived from E12.5-13.5 viscera that have been used historically to maintain mouse and human EC cells and ES cells. Expression of Nrg1 and Adam19 in this population suggests that the HRG-β ectodomain is also present in MEF-conditioned media and may exert significant effects upon pluripotency.

AG1478 and AG879 were used to examine the role of HRG/ErbB signaling in mouse ES cells. R1 mouse ES cells were maintained in standard conditions in DMEM, 10% FBS, 10% KSR, 0.5 U/mL penicillin, 0.5 U/mL streptomycin, 1×NEAA, 1 mM sodium pyruvate, 1000 U/mL LIF (ES-GRO), 0.1 mM β-ME, and were passaged with 0.5% trypsin/EDTA. $2\times10^5$ cells/well were plated in 6 well trays on MATRIGEL™ diluted at 1:1000. The day after plating, DMSO (carrier control), 1-50 μM AG1478, or 1-50 μM AG879 was added with fresh medium. The cells were cultured an additional 8 days, with daily media changes. The cultures were then fixed and stained for alkaline phosphatase activity.

DMSO and 1-50 μM AG1478 had no apparent affect on cell proliferation, with subconfluent colonies of alkaline phosphatase positive mESCs observed (FIGS. 5A-C). However, AG879 substantially inhibited cell growth at 50 μM (compare FIGS. 5D and 5F) and may have slowed proliferation at 20 μM (FIG. 5E). mESCs grown in AG879 did not appear to differentiate and maintained a pluripotent morphology, and alkaline phosphatase activity.

The results indicate that AG879 appeared to inhibit proliferation, without inducing differentiation, of mESCs, suggesting that mESCs require ErbB2 signaling for proliferation. Conversely, mESCs do not appear to be reliant on an ErbB1 signal for proliferation. The concentration of AG879 required to inhibit proliferation was ~10× higher for mESCs than that for BG01v cells grown in defined conditions, indicating that either the serum used in the mESC conditions may have interfered with the activity of the drug, that AG879 has a lower affinity for the mouse ErbB2 tyrosine kinase than for human ErbB2 tyrosine kinase, or that ErbB2 may play slightly different roles with the different species of ES cells.

Figure 6B:
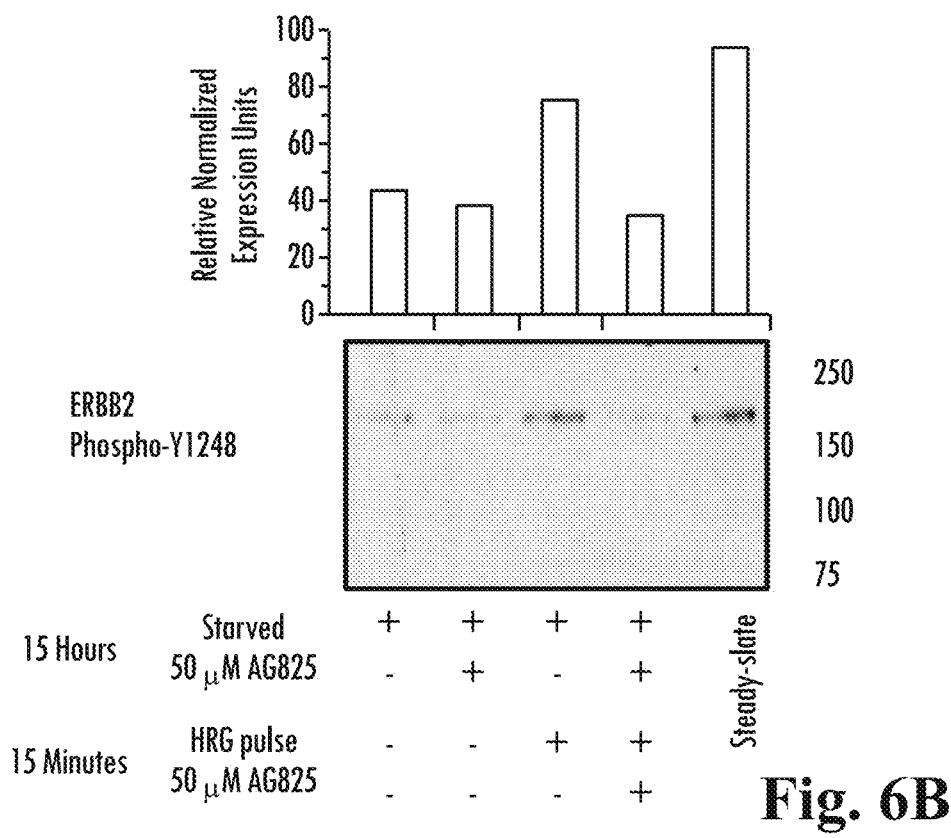
Figure 6C:
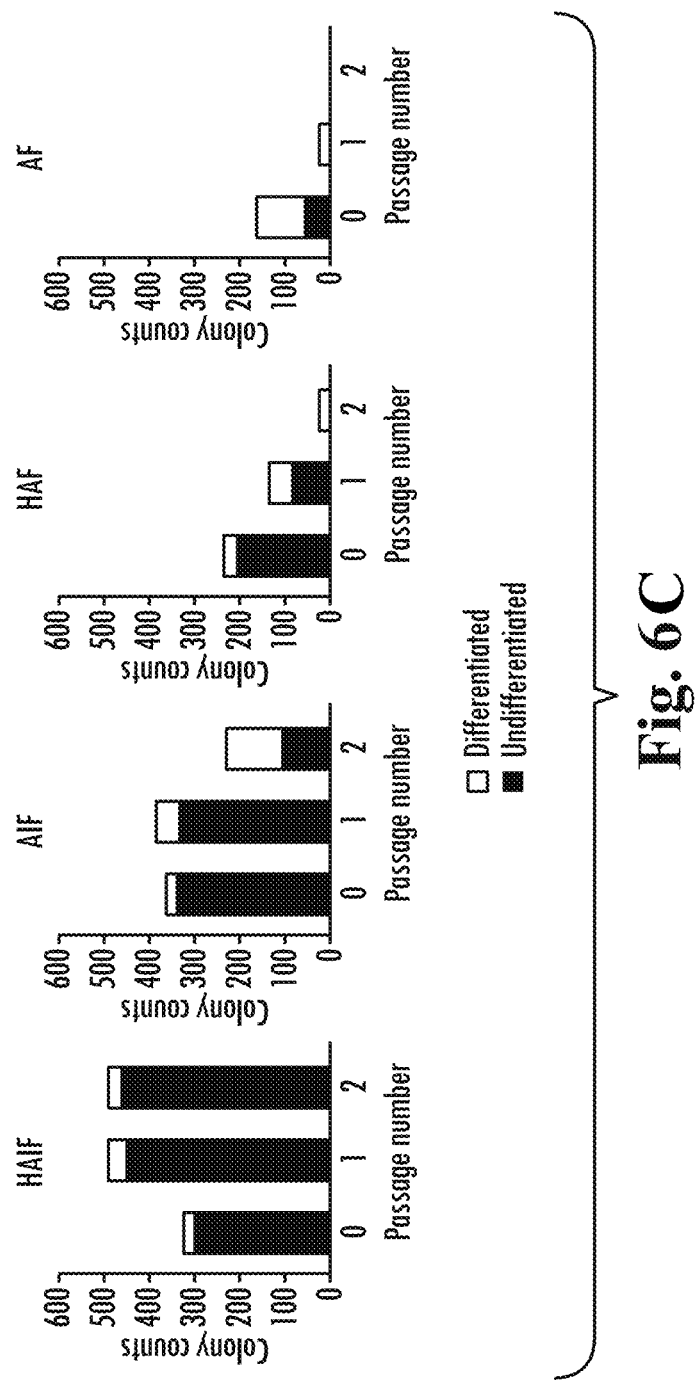
Figure 6D:
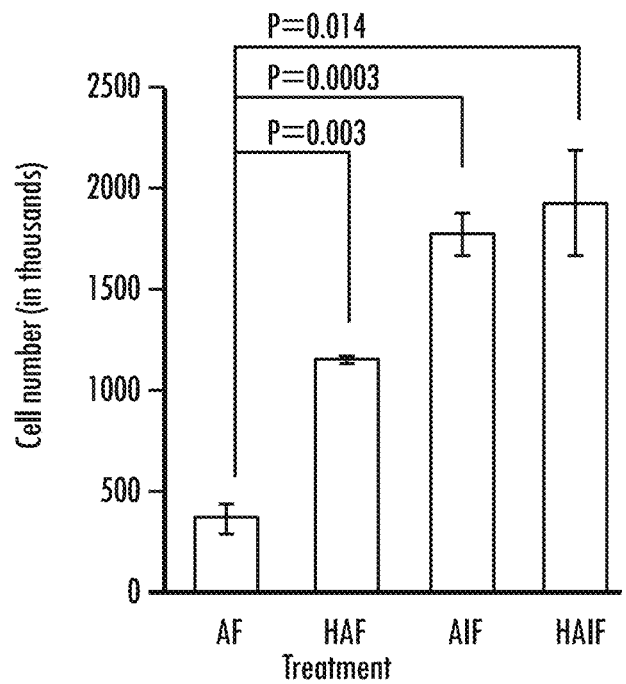
Figure 6E:
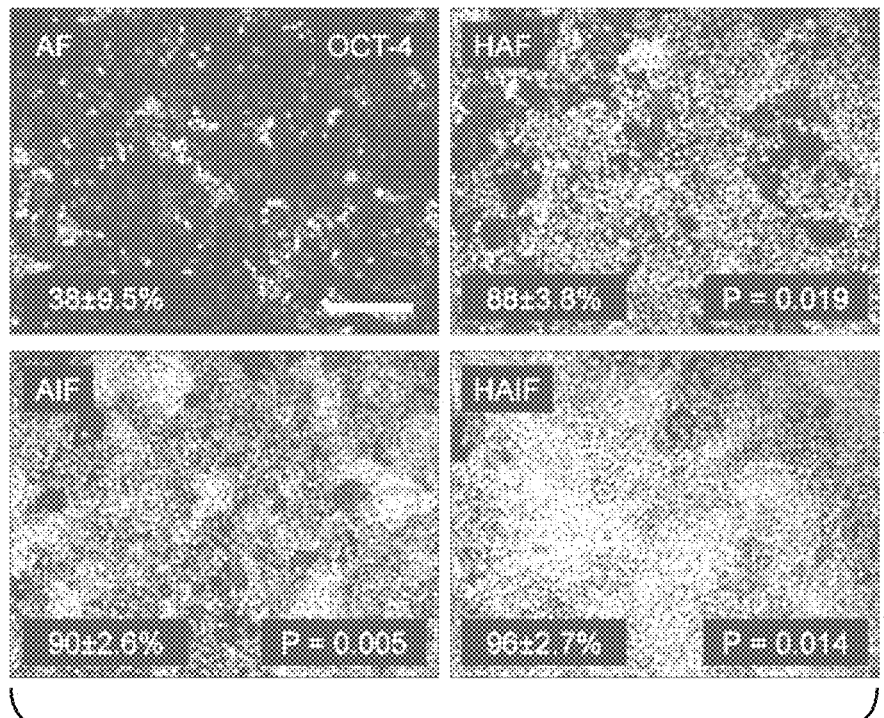
Figure 6F:
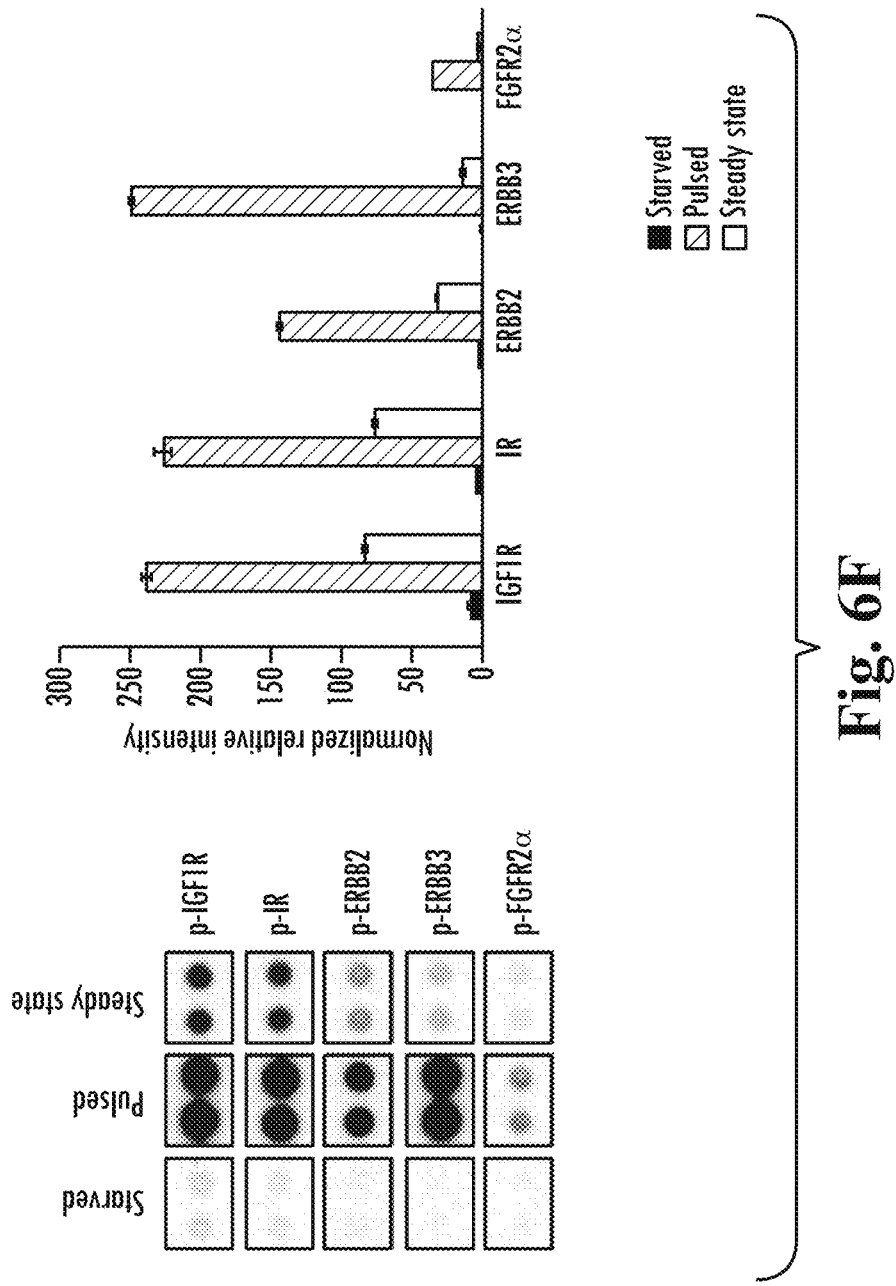

Another highly selective inhibitor of the ErbB2 tyrosine kinase, tyrphostin AG825 (Murillo, et al. 2001, *Cancer Res* 61:7408-12), was used to investigate the role of ErbB2 in human ESCs. AG825 significantly inhibited proliferation of hESCs growing in conditioned medium (CM) (FIG. 6A). AG825 inhibited proliferation without widespread cell death, and viable hESCs could be maintained for >5 days (not shown). Western blotting showed that AG825 inhibited autophosphorylation of ErbB2 at tyrosine-1248 in starved/heregulin (HRG) pulsed hESCs growing in DC-HAIF (FIG. 6B). Thus, disruption of ErbB2 signaling severely inhibited hESC proliferation. To establish hESCs in defined growth conditions, cultures could be passaged directly from CM conditions into DC-HAIF and exhibited minimal spontaneous differentiation (FIG. 6C). Colony and cell-counting assays confirmed that LongR3-IGF1 and HRG played the major roles in self-renewal and proliferation in the context of one of the embodiments of the present invention (FIG. 6D, 6E). Phosphorylation of IGF1R, IR, FGF2α, ErbB2, and ErbB3 was also observed in both steady-state DC-HAIF cultures, and in starved cultures that were pulsed with DC-HAIF (FIG. 6F).

Example 5

Culture of Mouse ES Cells in Defined Conditions

To further examine the role of HRG/ErbB2 signaling in mouse ES cells, the proliferation of R1 ES cells was examined in DC medium using a combination of growth factors. $1\times10^5$ cells/well were plated in 6-well trays, coated with 0.2% gelatin, in DC containing combinations of 10 ng/mL HRG-β, 100 ng/mL LongR3-IGF1, 1 ng/mL Activin A, 1000 U/mL mouse LIF or 10 ng/mL BMP4 (Table 3, below). Proliferation was observed over 8 days.

Viable colonies only grew in conditions containing at least LIF/HRG-β or LIF/BMP4 (Table 3). No additional obvious benefit was observed when LongR3-IGF1 or Activin were added to these combinations. Normal proliferation was observed in a control parental culture, and no viable colonies were observed in defined media without any growth factors.

TABLE 3

| HRG | IGF | Activin | LIF | BMP4 | Growth |
|-----|-----|---------|-----|------|--------|
| + |   |   |   |   | No |
| + |   |   | + |   | Yes |
| + | + |   |   |   | No |
| + | + |   | + |   | Yes |
| + | + | + |   |   | No |
| + | + | + | + |   | Yes |
| + |   | + |   |   | No |
| + |   | + | + |   | Yes |
|   |   |   | + | + | Yes |
| + |   |   | + | + | Yes |

Figure 7A:
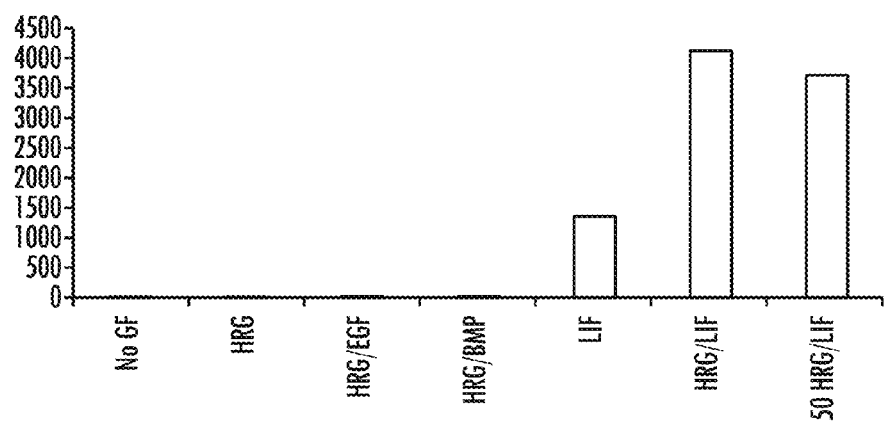
FIG. 7 depicts mouse ES cells grown in defined conditions with different growth factor combinations. (A) shows the scoring of AP+ colonies after $2 \times 10^5$ cells were grown in different growth factor combinations for 8 days. (B-G) show 4× magnification images of AP+ colonies grown in different growth factor combinations.
Figures 7B, 7C, 7D:
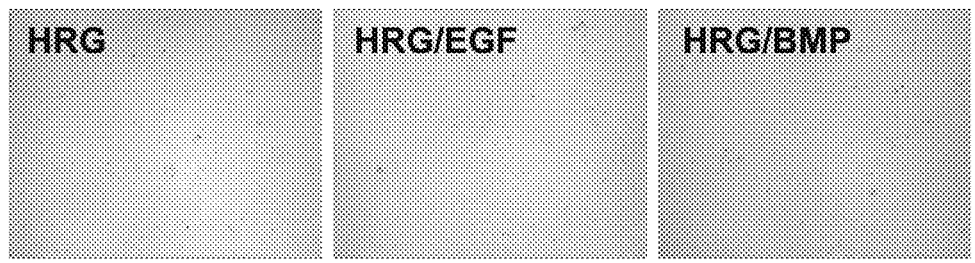
Figures 7E, 7F, 7G:
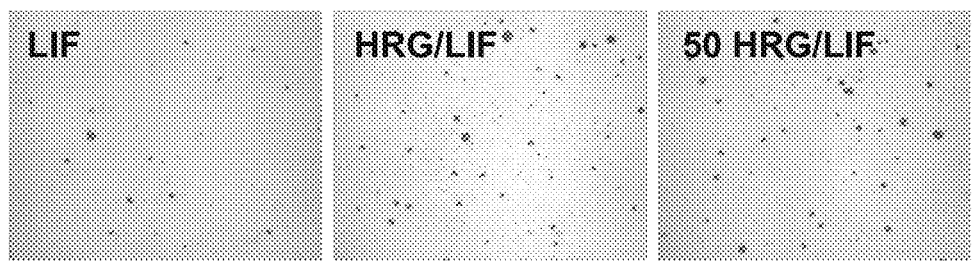

A quantitative assay was performed by plating $2\times10^5$ cells/well in 6-well trays on 1:1000 MATRIGEL™, in selected combinations of 10 or 50 ng/mL HRG-β, 10 ng/mL EGF, 1000 U/mL LIF or 10 ng/mL BMP4. The cultures were grown for 8 days, fixed, and the number of alkaline phosphatase colonies was counted (FIG. 7A). No colonies were observed in defined conditions without growth factors, and <45 colonies were observed with HRG-13, HRG-β/EGF and HRG-β/BMP combinations. While 1358 colonies were observed in LIF alone, 4114 and 3734 colonies were observed in the 10 ng/mL HRG-β/LIF and 50 ng/mL HRG-β/LIF combinations, respectively. This indicated that in defined conditions, LIF alone provided a substantial pluripotency signal, and HRG-β exhibited a large synergistic effect with LIF, more than doubling the number of proliferating mESC colonies in this assay. Low magnification images of this assay also indicate this synergistic proliferative effect (FIGS. 7B-G).

Example 6

Figure 8A:
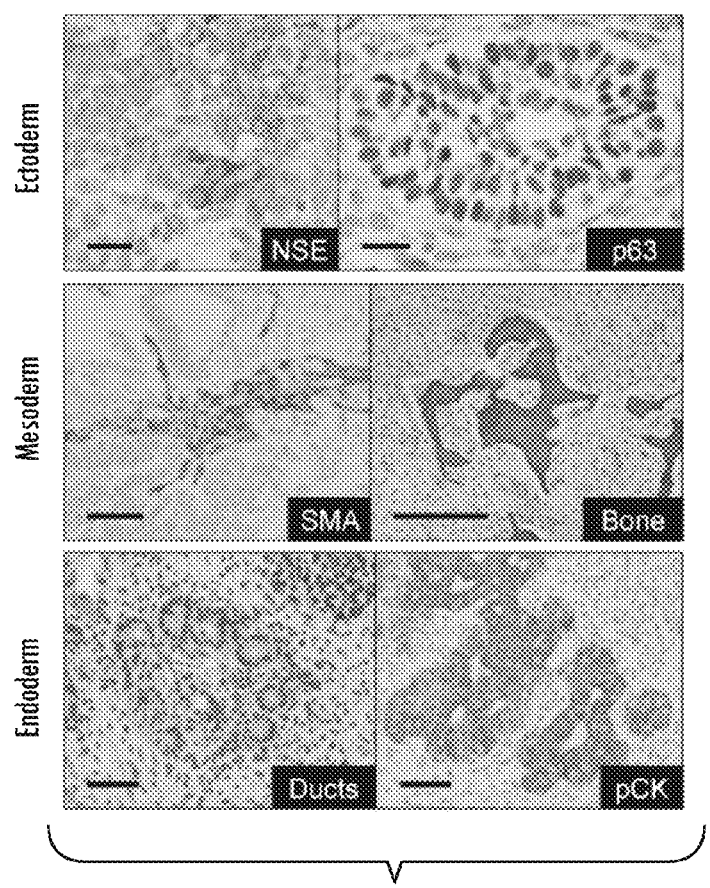
FIG. 8 depicts the characterization of human ES cells that are maintained in DC-HAIF medium. (A) Analysis of teratomas from BG02 DC-HAIF p25 cells demonstrated pluripotent differentiation potential to ectoderm, mesoderm and endoderm. (B) Immunostaining of BG02 cells cultured in 15% FCS/5% KSR that have differentiated. (C) Venn diagram of the distribution of transcripts detected using high density Illumina Sentrix Human-6 Expression Beadchips containing 47,296 transcript probes in BG02 cells maintained in CM (64 passages) or DC-HAIF (10 or 32 passages in defined media). (D) Scatterplot analysis demonstrating that the transcriptional profile of BG02 DC-HAIF p32 cells is highly similar to that of BG02 cells maintained in CM (top), and was not substantially altered in early and late passage cultures in DC-HAIF (bottom). (E) Hierarchical clustering dendrogram of relative gene expression in different populations generated using the Beadstudio software.
Figure 8B:
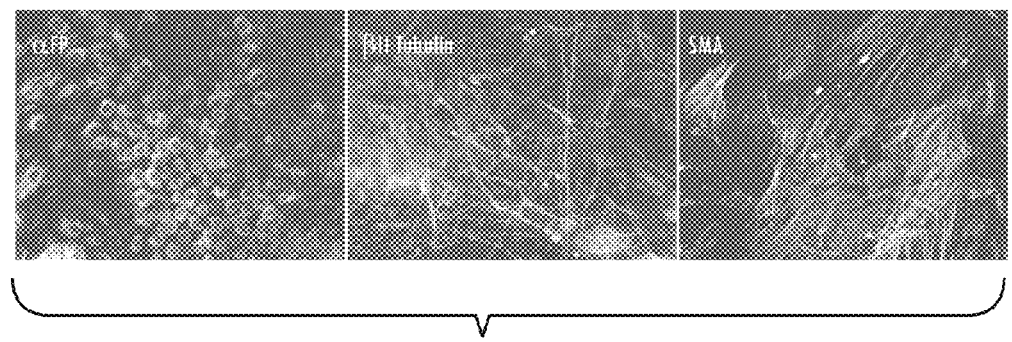
Figure 8C:
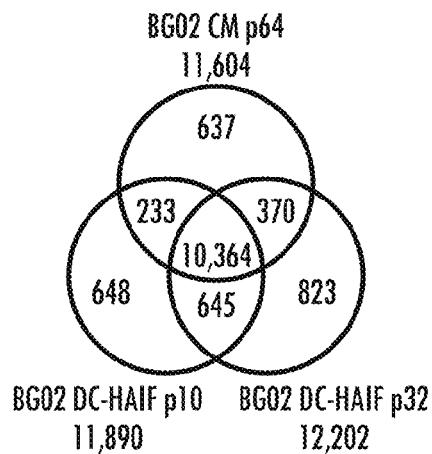
Figure 8D:
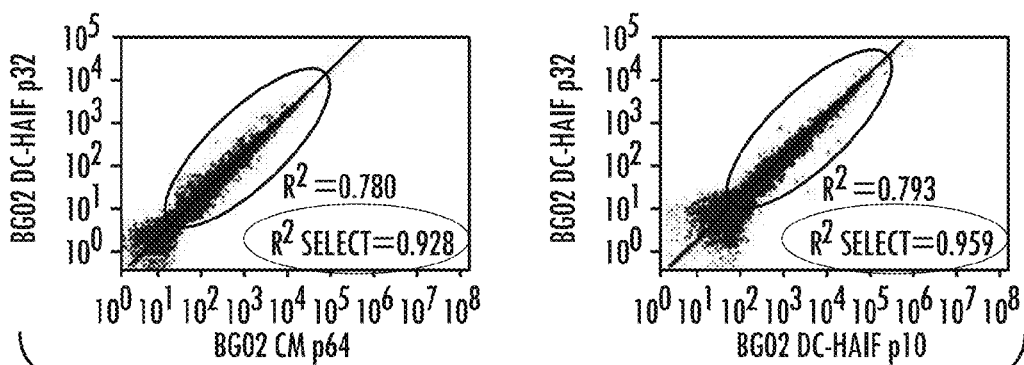
Figure 8E:
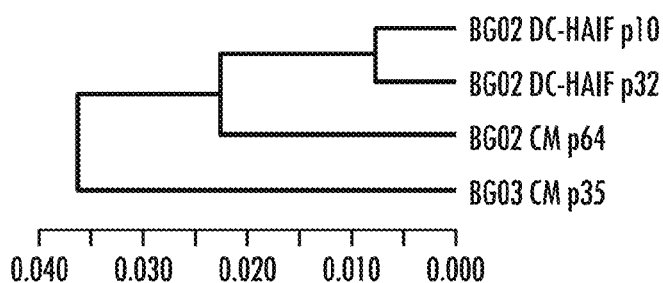

Characterization of Pluripotency of Human Embryonic Stem Cells (hESCs) Maintained in DC-HAIF Multiple approaches were used to confirm the maintenance of plasticity of hESCs in DC-HAIF. BG02 cells cultured in DC-HAIF for 6 months (25 passages) maintained the potential to form complex teratomas (FIG. 8A) and representatives of the three germ layers in vitro (FIG. 8B). Transcriptional analyses were used to compare global expression in hESCs cells (Liu et al. 2006, *BMC Dev Biol* 6:20) maintained in CM and DC-HAIF. Greater than 11,600 transcripts were detected in BG02 cells grown in DC-HAIF for 10 and 32 passages, and BG02 cells grown in CM for 64 passages. There were about 10364 transcripts common to all populations (FIG. 8C), including known hESC markers such as CD9, DNMT3, NANOG, OCT4, TERT and UTF1 (not shown). High correlation coefficients were observed in comparisons of CM and DC-HAIF cultures ($R^2$select=0.928), as well as in early and late passage cells ($R^2$select=0.959) (FIG. 8D). Hierarchical clustering analysis demonstrated that BG02 cells maintained in DC-HAIF grouped tightly and retained a close similarity to BG02 and BG03 cells maintained in CM (FIG. 8E). These data are consistent with previous analyses showing that undifferentiated hESCs clustered tightly compared to embryoid bodies or fibroblasts (Liu et al. 2006, *BMC Dev Biol* 6:20). Thus, cells maintained in the compositions of the present invention are able to maintain key markers of pluripotency. Accordingly, the compositions of the present invention can be used as a simple medium for supporting self-renewal of differentiable cells.

Example 7

Figure 9A:
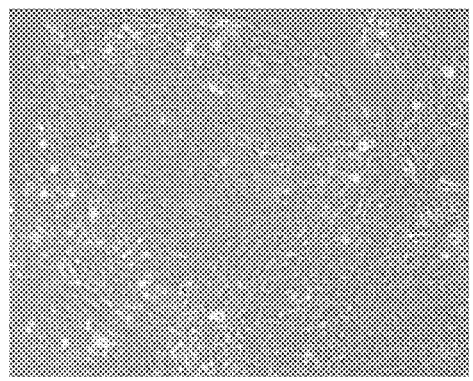
FIG. 9 depicts the morphology of cells cultured on humanized extracellular matrices (ECMs) in the presence of DC-HAIF medium. (A) CyT49 cells (diluted 1:200) growing on growth factor-reduced MATRIGEL™ (diluted 1:200). CyT49 cells could also grow on tissue culture dishes coated with (B) whole human serum, (C) human fibronectin, and (D) VITROGROT™.
Figure 9B:
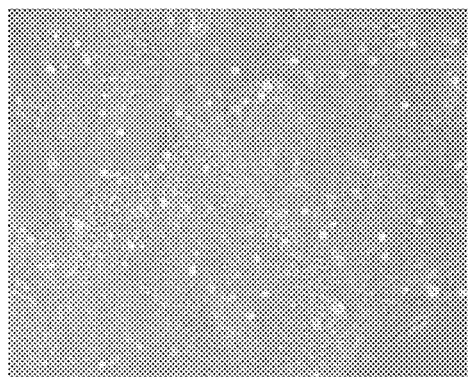
Figure 9C:
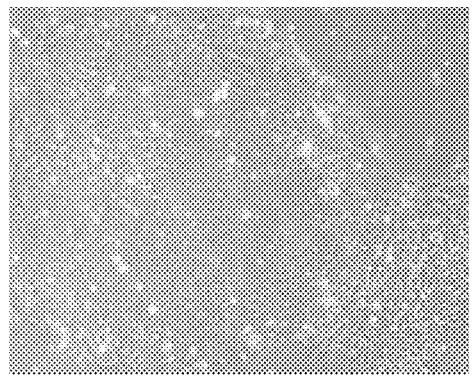
Figure 9D:
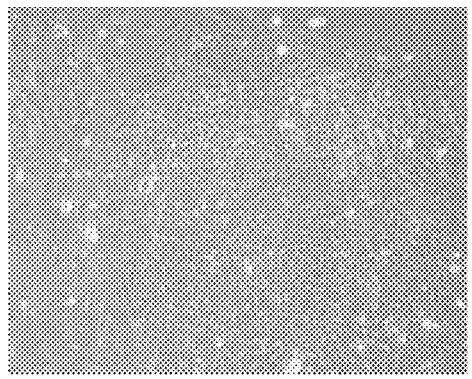

Maintenance of Human Embryonic Stem Cells (hESCs) on Humanized Extracellular Matrices (ECMs) in DC-HAIF To investigate the role of ErbB2 signaling and develop a defined media for hESCs, DC-HAIF cultures were initially expanded on culture dished coated with growth factor-reduced MATRIGEL™ 1:30, but could also be maintained successfully long-term on this substrate diluted 1:200 (FIG. 9A), or 1:1000. BG02 and CyT49 hESCs could also be maintained for >5 passages on tissue culture dishes coated with human serum (FIG. 9B); human fibronectin (FIG. 9C); or VITROGRO™ (FIG. 9D), which is a proprietary humanized ECM.

Example 8

Single Cell Passaging of Human Embryonic Stem Cells (hESCs)

Figure 10A:
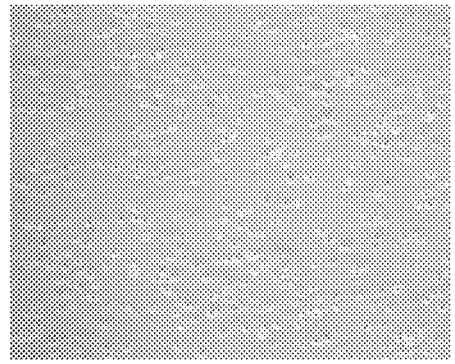
FIG. 10 depicts the single-cell passaging of human ES cells. (A-D) Staged imaging of BG02 cells after passaging with ACCUTASE™ and plating about $5 \times 10^5$ cells in a 60 mm culture dish. (A) 1.5 hours after initial plating, showing viable cells adhering to the dish. (B) At 20 hours post-plating, the large majority of cells have aggregated to form small colonies. These colonies expand by proliferation by day 4, post-plating (C), and over the course of 5-6 days to form an epithelial-like monolayer covering the entire dish (D). (E) Normal male karyotype demonstrated in a BG02 culture passaged 19 times with ACCUTASE™ in DC-HAIF.
Figure 10B:
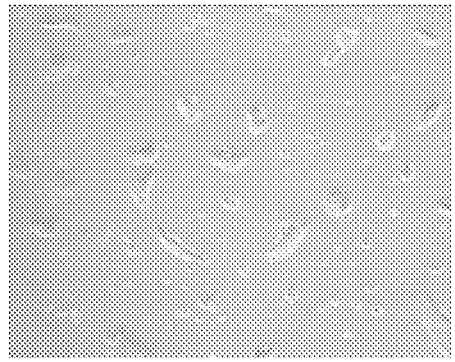
Figure 10C:
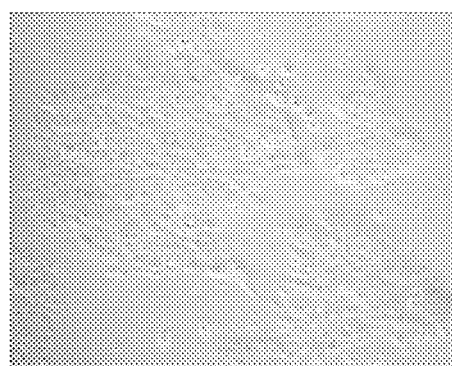
Figure 10D:
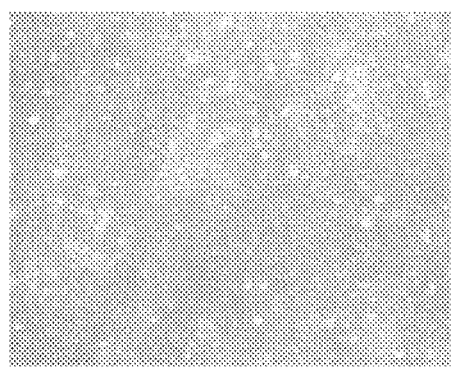
Figure 10E:
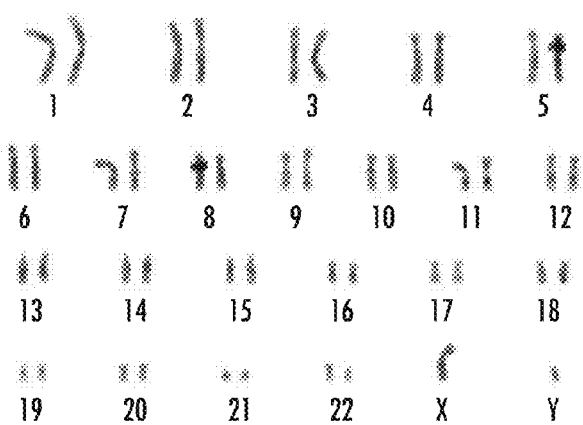
Figures 11A, 11B:
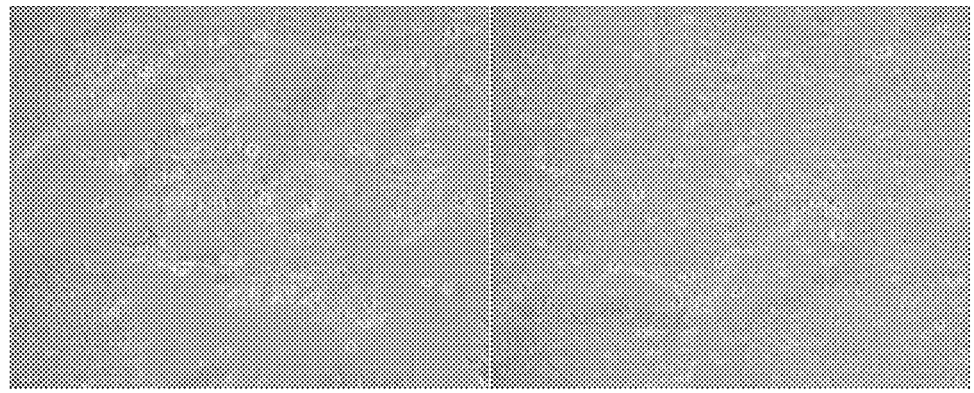
FIG. 11 depicts cell morphology after single cell passaging of human ES cells using (A) ACCUTASE™, (B) 0.25% Trypsin/EDTA, (C) TrypLE, or (D) Versene.
Figures 11C, 11D:
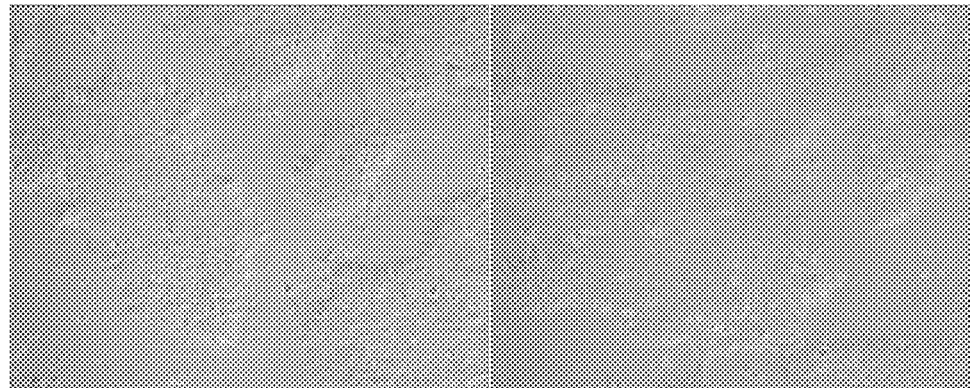

Multiple research groups have demonstrated that certain triplodies, notably of hChr12 and 17, are accumulated in hESCs under certain sub-optimal culture conditions (Baker et al. 2007, *Nat. Biotech.* 25:207-15). The appearance of triploidies seems to be most directly related to poor cell survival when cultures are split to single cells at passaging, providing a presumed strong selective growth advantage for cells harboring these aneuploidies. Conversely, hESCs growing in one embodiment of the present invention, DC-HAIF, maintained high viability at plating after being split to single cells (FIG. 10A-D). BG01 and BG02 cells maintained a normal karyotype (FIG. 10E) after being passaged with ACCUTASE™ for >18 and 19 passages respectively. The maintenance of normal karyotype in cells demonstrated that disaggregation of hESC cultures to single cells did not inherently lead to the accumulation of these trisomies in hESCs maintained in DC-HAIF. BG01 and BG02 cultures were also passaged by disaggregation to single cells with multiple passaging agents (FIG. 11). Cultures were split with ACCUTASE™, 0.25% Trypsin/EDTA, TrypLE, or VERSENE™ (EDTA) for 5 passages and karyotyped. The data demonstrate that culturing and passaging hESCs in the compositions of the present invention maintained a normal karyotype in at least two human embryonic cell lines, using a variety of cell disaggregation reagents.

Figure 12A:
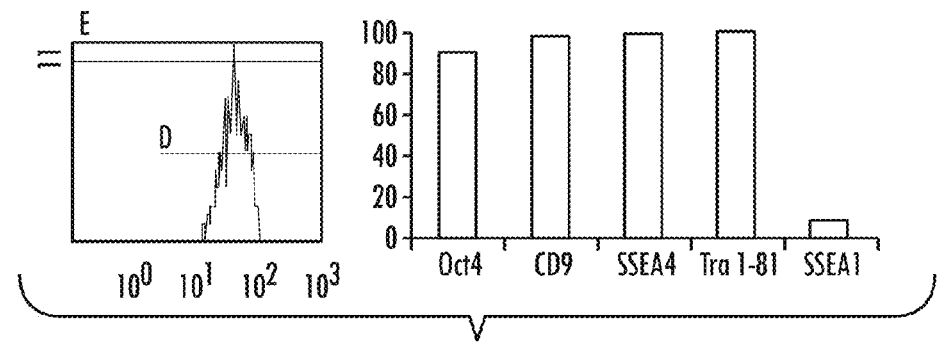
FIG. 12 depicts the large-scale growth of human ES cells cultured in DC-HAIF. (A) Flow cytometric analysis of BG02 cells after expansion to $>10^{10}$ cells. >85% of cells expressed OCT4, CD9, SSEA-4, TRA-1-81. (B) RT-PCR analysis of expression of markers of pluripotency OCT4, NANOG, REX1, SOX2, UTF1, CRIPTO, FOXD3, TERT and DPPA5. Markers of differentiated lineages, α-fetoprotein (AFP), MSX1 and HAND1 were not detected. (C) Fluorescence in situ hybridization (FISH) using human chromosome-specific repeats demonstrated maintenance of normal copy numbers for hChr 12, 17, X and Y.
Figure 12B:
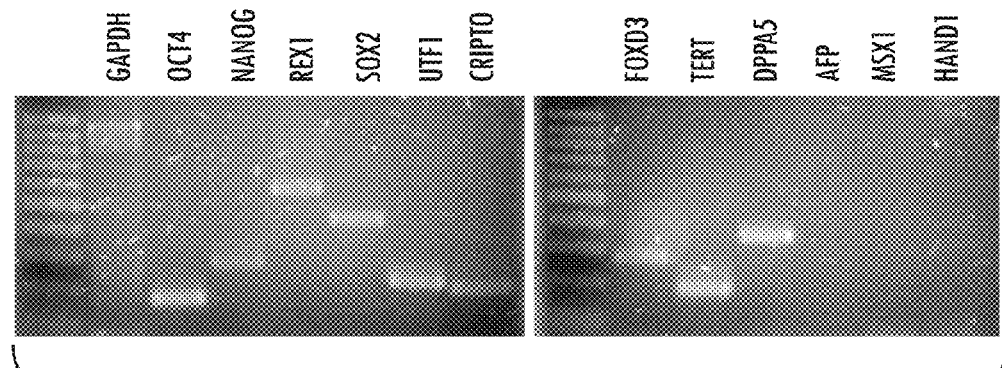
Figure 12C:
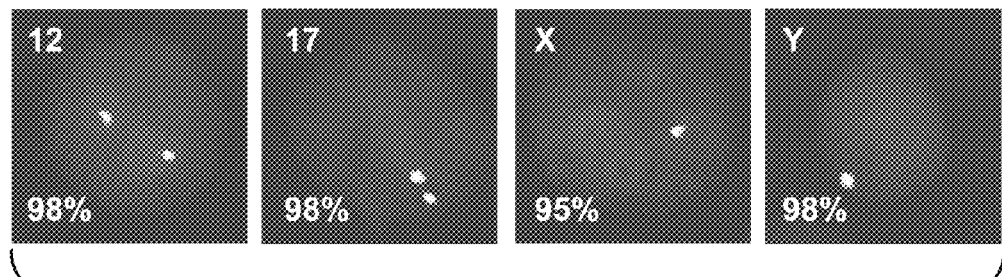

Large-scale expansion of undifferentiated hESCs is also possible, using the compositions of the present invention. A starting confluent culture of BG02 cells in a 60 mm plate was expanded in DC-HAIF through 4 passages to generate >1.12× $10^{10}$ cells in 20 days in a single experiment. The cultures remained undifferentiated, as demonstrated by >85% of the cells in the batch maintaining expression of markers of pluripotency such as OCT4, CD9, SSEA-4, TRA-1-81 when examined by flow cytometry (FIG. 12A). Expression of other markers of pluripotency was also observed by RT-PCR analysis, while markers of differentiated lineages α-fetoprotein, MSX1 and HAND1 were not detected (FIG. 12B). Fluorescence in situ hybridization analysis demonstrated that the cells cultured and passaged in DC-HAIF maintained expected copy numbers for hChr12 (98% 2-copy), hChr17 (98% 2-copy), hChrX (95% 1-copy) and hChrY (98% 1-copy) (FIG. 12C). Karyotyping analysis also demonstrated that a normal euploid chromosome content and banding profile was maintained in these cells.

Example 9

Insulin and IGF1 Exert Different Effects on hESCs when Applied at Physiological Concentrations Essentially all of the reported culture conditions for hESCs to date include supraphysiological levels of insulin, which can stimulate both IR and IGF1R. To distinguish the activities that insulin and insulin-substitutes exert, compared to IGF1, hESCs are cultured in defined media conditions in physiological levels of these growth factors. The concentrations of insulin and IGF1 are titrated from about 0.2 to about 200 ng/mL and cell proliferation is monitored by counting cells after 5 days. Cultures that expand successfully are serially passaged 5 times. Physiological levels of IGF1 support the expansion of hESC cultures, whereas physiological levels of insulin do not, indicating that the activity of insulin or insulin-substitutes cannot replace IGF1, and that IGF1 and insulin (or insulin substitutes) represent separate classes of biological activities with regard to action on hESCs.

Example 10

Methods for Screening the Effects of Supplements

To initially examine the effects of Vitamin $B_{12}$ and Vitamin $B_6$ on the growth or differentiation hESCs growing at an intermediate density, BG02 cells are split using ACCUTASE™ and 1×$10^5$ cells/well are plated in 6-well trays in defined culture (DC) media. The DC media contains 10 ng/mL HRG-β, 200 ng/mL LongR3-IGF1, and 10 ng/mL FGF10. Vitamin $B_6$ (0.5 µM) and/or Vitamin $B_{12}$ (0.5 µM) are added to experimental wells. Cell numbers in each condition are counted after 7 days. Cell counting and colony counting of both experimental and control wells will provide insight on the effects of Vitamin $B_6$ and Vitamin $B_{12}$ on cell growth.

In addition, markers of differentiation, such as OCT4 can be assayed in the experimental well to determine the effects of the additives and supplements to the differentiation state of the differentiable cells.

Example 11

Culturing of hESCs in the Absence of FGF2

Figure 13A:
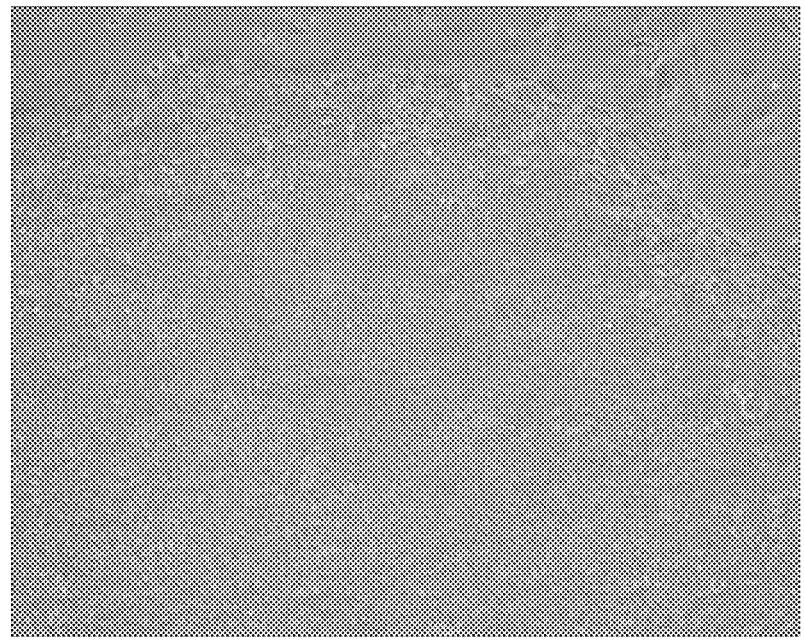
FIG. 13 depicts the morphology (A) and normal karyotype (B) of hESC BG02 cells grown in defined media comprising HRG-β and IGF1, but in the absence of FGF2 for 7 passages, or >2 months.
Figure 13B:
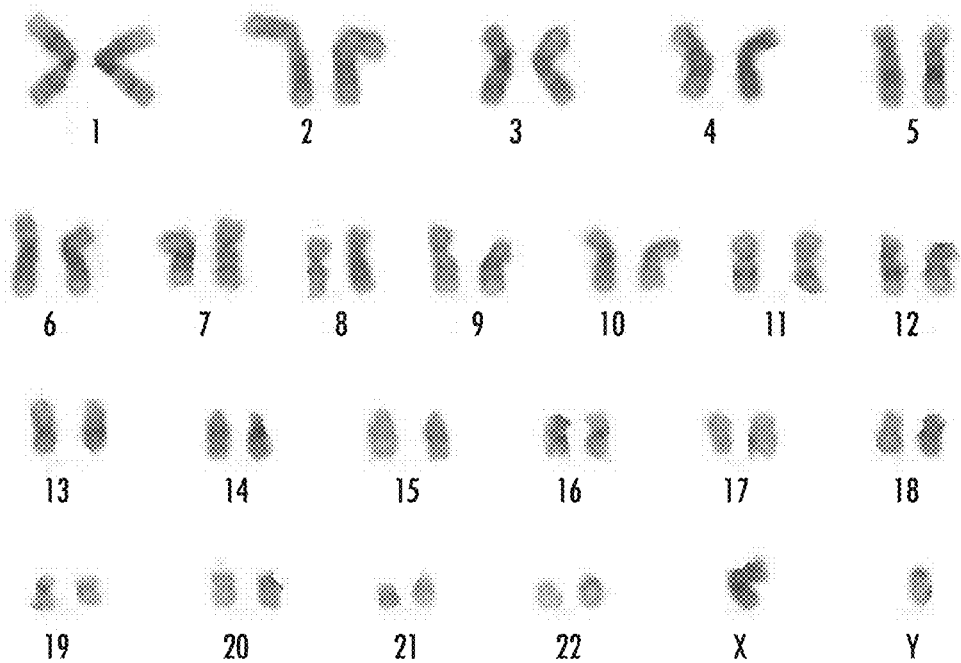
Figure 20:
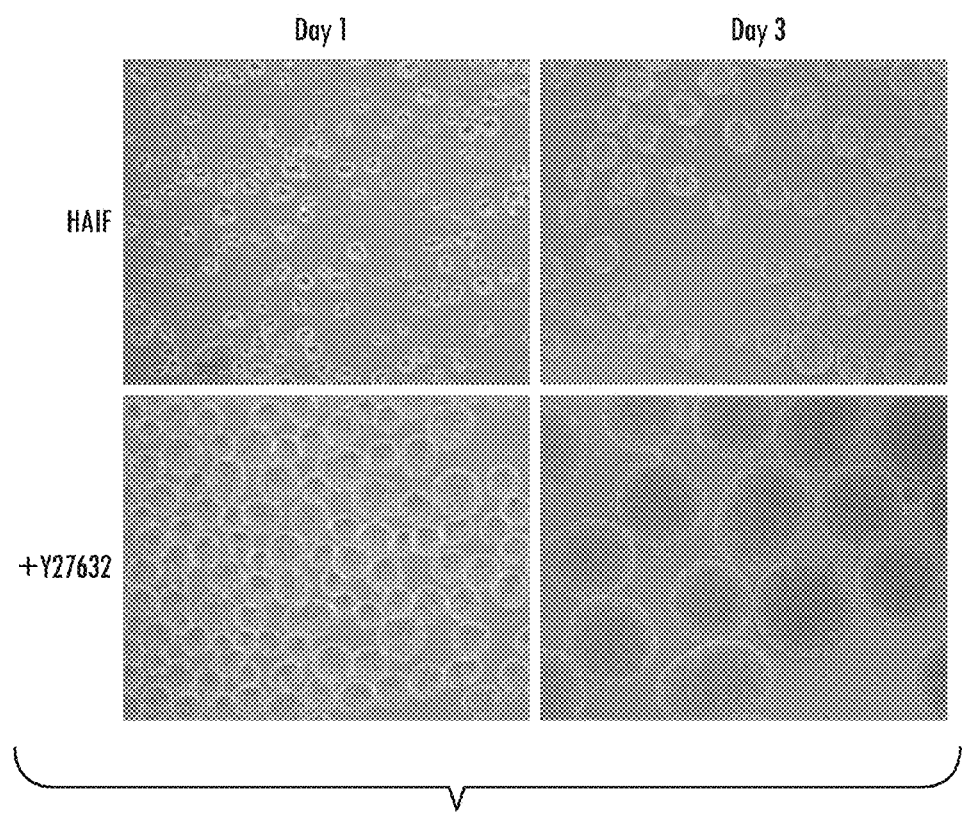
FIG. 20 depicts the enhancement of hESC aggregation in the presence of Y27632 in suspension culture. $2 \times 10^6$ BG02 cells were seeded in 3 mL DC-HAIF or DC-HAIF+Y27632, in 6-well trays, in an incubator on a rotating platform at 100 rpm. Images of aggregates were captured on days 1 and 3.

BG02 cells were maintained long term in DC-HAI, for 20 passages (FIG. 13A), and BG01 cells were also serially passaged in DC-HAI, both in the absence of FGF2. The cultures did not deteriorate or exhibit overt differentiation, and exhibited normal expansion of undifferentiated colonies throughout the culture period. The maintenance of a normal male karyotype in a BG02 culture was demonstrated after 6 passages in DC-HAI (FIG. 13B, 20/20 normal metaphase spreads).

Figure 14:
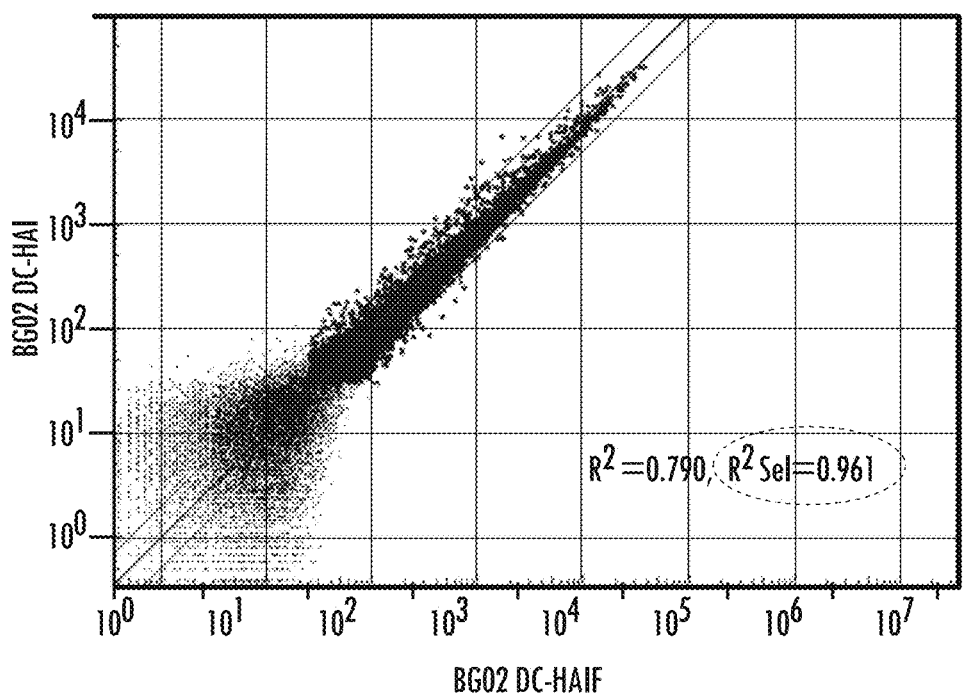
FIG. 14 depicts a scatter plot analysis of transcripts from hESCs (BG02) that are maintained in DC-HAIF (32 passages) or DC-HAI (10 passages). A large proportion of the expressed transcripts were detected in both samples, and transcription was not substantially altered by culturing hESCs in the absence of exogenous FGF2. Correlation coefficients ($R^2$) were generated using all detected transcripts with an expression level of >0 (all dots), or with transcripts exhibiting a detection confidence level of >0.99 ($R^2$ select, dots indicated by dashed oval). Angled lines delineate the mean and limits of a 2-fold difference.
Figure 15:
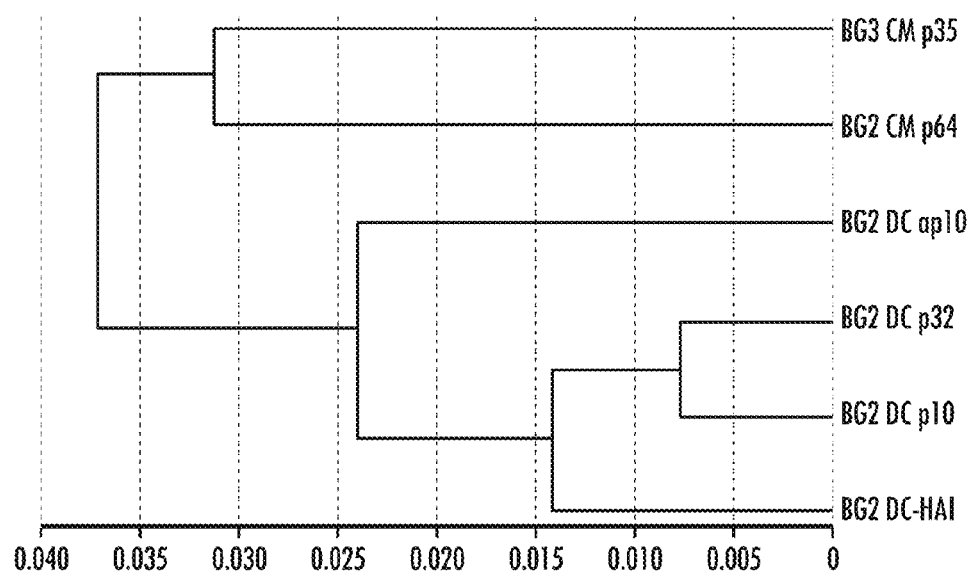
FIG. 15 depicts a hierarchical clustering dendrogram of relative gene expression in different populations of early and late passage BG02 cells maintained in DC-HAIF. Cells clustered tightly (~0.0075) and retained a close similarity to BG02 and BG03 cells maintained in conditioned medium (CM) (~0.037). BG02 cells maintained in DC-HAI also clustered tightly with the other hESC populations examined. By way of explanation in FIG. 15, CM is Conditioned Medium; DC is defined culture medium, DC-HAIF as defined above; ap is ACCUTASE™ single cell passaging; DC-HAI is identical to DC-HAIF as defined herein, except without FGF2.
Figure 16A:
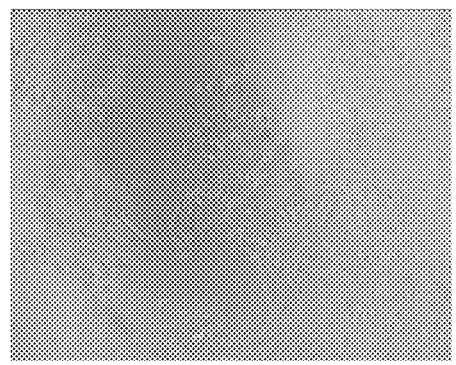
FIG. 16 depicts the morphology and alkaline phosphatase staining of BG02 cells cultured in DC-HAIF in 96-well and 384-well plates. (A) Phase contrast imaging and (B) alkaline phosphatase staining of BG02 cells ($10^4$ cells/well) growing in one well of a 96-well plate. (C) Phase contrast imaging and (D) alkaline phosphatase staining of BG02 cells ($10^3$ cells/well) growing in one well of a 384-well plate.
Figure 16B:
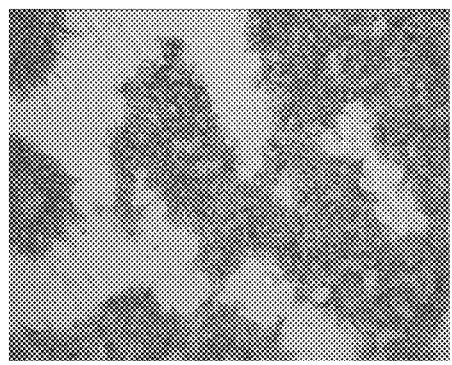
Figure 16C:
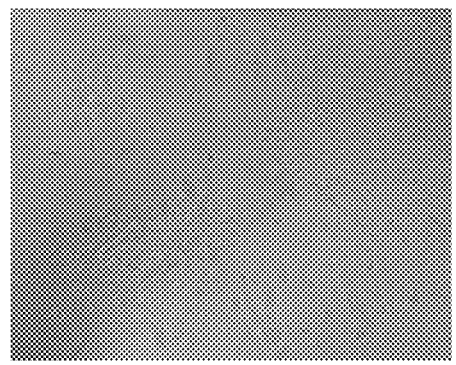
Figure 16D:
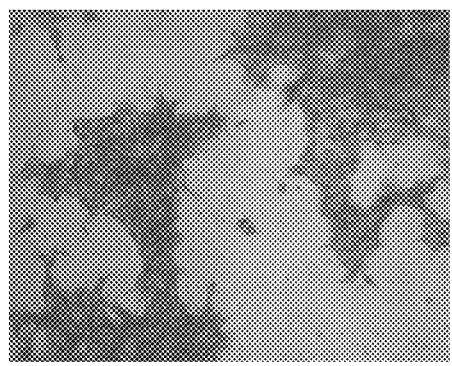

Transcriptional analyses were used to compare global expression in hESCs cells maintained in DC-HAIF and DC-HAI. Total cellular RNA was isolated from hESCs using Trizol (Invitrogen) and was treated with DNase I (Invitrogen) according to the manufacturer's suggested protocol. Sample amplification was performed with 100 ng of total RNA using the Illumina RNA Amplification kit and labeling was achieved by incorporation of biotin-16-UTP (Perkin Elmer Life and Analytical Sciences) at a ratio of 1:1 with unlabeled UTP. Labeled, amplified material (700 ng per array) was hybridized to Illumina Sentrix Human-6 Expression Beadchips containing 47,296 transcript probes according to the manufacturer's instructions (Illumina, Inc.). Arrays were scanned with an Illumina Bead Array Reader confocal scanner and primary data processing, background subtraction, and data analysis were performed using Illumina BeadStudio software according to the manufacturer's instructions. A minimum detection confidence score of 0.99 (a computed cutoff indicating the target sequence signal was distinguishable from the negative controls) was used to discriminate the presence or absence of transcript expression. Data analysis was performed using parallel approaches described for other hESC samples (Liu et al. 2006, *BMC Dev Biol* 6:20). Hierarchical clustering was performed as described previously (Liu et al. 2005, *BMC Dev Biol* 6:20), and was based on average linkage and Euclidean distances as the similarity metric using differentially expressed genes identified by ANOVA ($p<0.05$). Detailed descriptions of the sensitivity and quality control tests used in array manufacture and algorithms used in the Bead studio software are available from Illumina, Inc (San Diego, Calif.). The majority of transcripts detected were expressed in both DC-HAIF and DC-HAI BG02 cultures, including known hESC markers such as CD9, DNMT3, NANOG, OCT4, TERT and UTF1 (not shown). High correlation coefficients were observed in comparisons of DC-HAIF and DC-HAI cultures ($R^2$ select=0.961) (FIG. 14). Hierarchical clustering analysis demonstrated that BG02 cells maintained in DC-HAI grouped tightly and retained a close similarity to cells maintained in DC-HAIF, as well as BG02 and other hESC lines in multiple culture formats (FIG. 15). These data are consistent with previous analyses showing that undifferentiated hESCs clustered tightly compared to embryoid bodies or fibroblasts (Liu et al. 2006, BMC Dev Biol 6:20).

Furthermore, BG02 cells maintained in DC-HAI differentiated to representatives of mesoderm, endoderm and ectoderm in complex teratomas formed in SCID-beige mice (not shown), formally demonstrating the maintenance of pluripotency in cultures grown in the absence of exogenous FGF2.

To examine if exogenous FGF2 was required in the context of single cell passaging, BG01 cells were passaged with ACCUTASE™ and grown in defined conditions containing only 10 ng/mL HRG-β and 200 ng/mL LongR3-IGF1 (DC-HI). These DC-HI cultures were maintained for 10 passages, and did not exhibit overt differentiation or a slowing of proliferation.

These studies clearly demonstrated that the provision of exogenous FGF2 is not required when hESCs are maintained in defined media minimally containing heregulin and IGF1. Furthermore cultures absent FGF2 retained key properties of pluripotency, including transcriptional profile and differentiation to mesoderm, endoderm and ectoderm in vivo.

Example 12

Suspension Cultures

Starting cultures of BG02 cells were maintained in DC-HAIF medium on dishes coated with 1:200 matrigel, as described herein and were split by passaging with ACCUTASE™. To initiate suspension culture, BG02 cells were disaggregated with ACCUTASE™ and placed in low attachment 6-well trays at a density of 1.6, 3, or $6\times10^5$ cells/mL (0.5, 1, or $2\times10^6$ cells in 3 mL volumes) in DC-HAIF medium. The trays were placed on a rotating platform at 80-100 rpm in a humidified incubator with 5% $CO_2$. Under these conditions hESCs coalesced into small spheres of morphologically viable cells within 24 hours.

Figure 17:
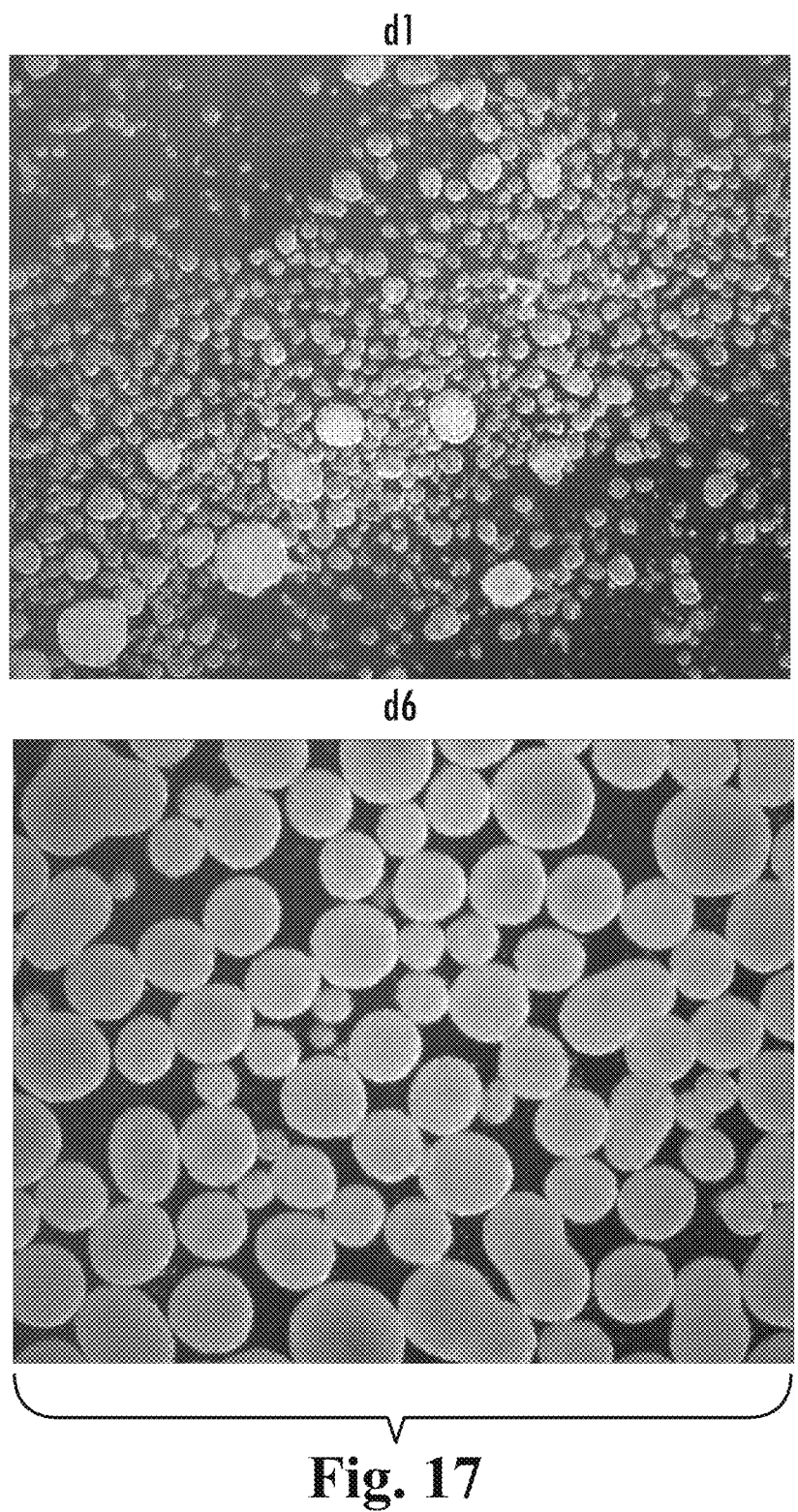
FIG. 17 depicts dark field images of BG02 grown in DC-HAIF in suspension culture. Day 2 and day 6 cultures are shown. The images were captured using 4× magnification

The medium in the wells was changed on the second day, and every day thereafter. Suspension aggregates continued to proliferate, growing larger over time without obvious signs of differentiation (FIG. 17). Some of the spheres continued to aggregate over the course of the culture, as some aggregates became much larger than the majority. In addition, non-spherical aggregates could be observed in the process of merging during the first few days of the culture. To limit this continued aggregation, 38 µg/mL DNaseI was included in some suspension cultures for the first 24 hours. This approach appeared to be conducive to the initial aggregation, with relatively larger, but fewer, aggregates formed in the presence of DNaseI. It is not clear, however, if the DNaseI treatment reduced the subsequent merging of spheres and exposure to DNaseI consistently made these aggregates harder to break up when splitting.

Suspension cultures were disaggregated with ACCUTASE™ approximately every 7 days and new spheres were established. While the densities varied in different experiments, spheres established within this range of densities ($1.6-6\times10^5$ cells/mL) could be maintained in culture for more than 12 passages, or >80 days, without morphological signs of differentiation. FISH analyses of serially passaged suspension hESCs were also performed to assess the chromosome number for common aneuplodies. BG02 cells that had been grown in suspension for 6 passages exhibited normal counts for hChr 12 (96% two copy, n=788), hChr 17 (97% two copy, n=587), hChr X (97% one copy, n=724) and hChr Y (98% one copy, n=689).

Example 13

Expansion of Differentiable Cells in Suspension Culture

Unlike embryoid body culture in the presence of serum or inducers of differentiation, suspension aggregates of hESCs in DC-HAIF did not appear to differentiate. Obvious visceral endoderm was not observed, neither was the formation of structures resembling proamniotic cavities, both classic signs of embryoid body differentiation. To examine the lack of differentiation more closely, cultures were plated back into adherent conditions on MATRIGEL™ diluted 1:200 and cultured in DC-HAIF. These cultures were also primarily undifferentiated, and did not exhibit obvious morphological signs of increased differentiation such as the presence of larger, flattened cells, or structured regions.

Figure 18:
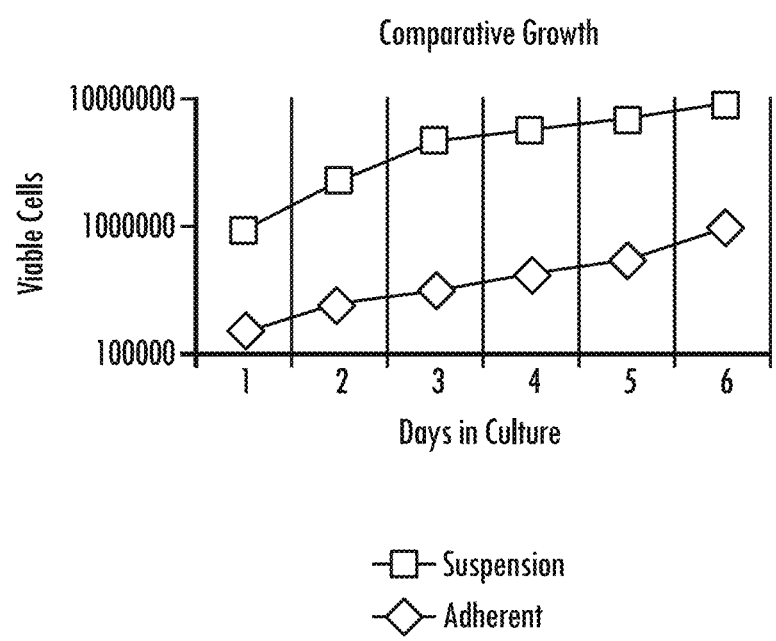
FIG. 18 depicts the growth rates in adherent and suspension cultures in DC-HAIF. $1 \times 10^6$ BG02 cells were plated into parallel wells in adherent and suspension culture and cell counts were performed on days 1-6.
Figure 19:
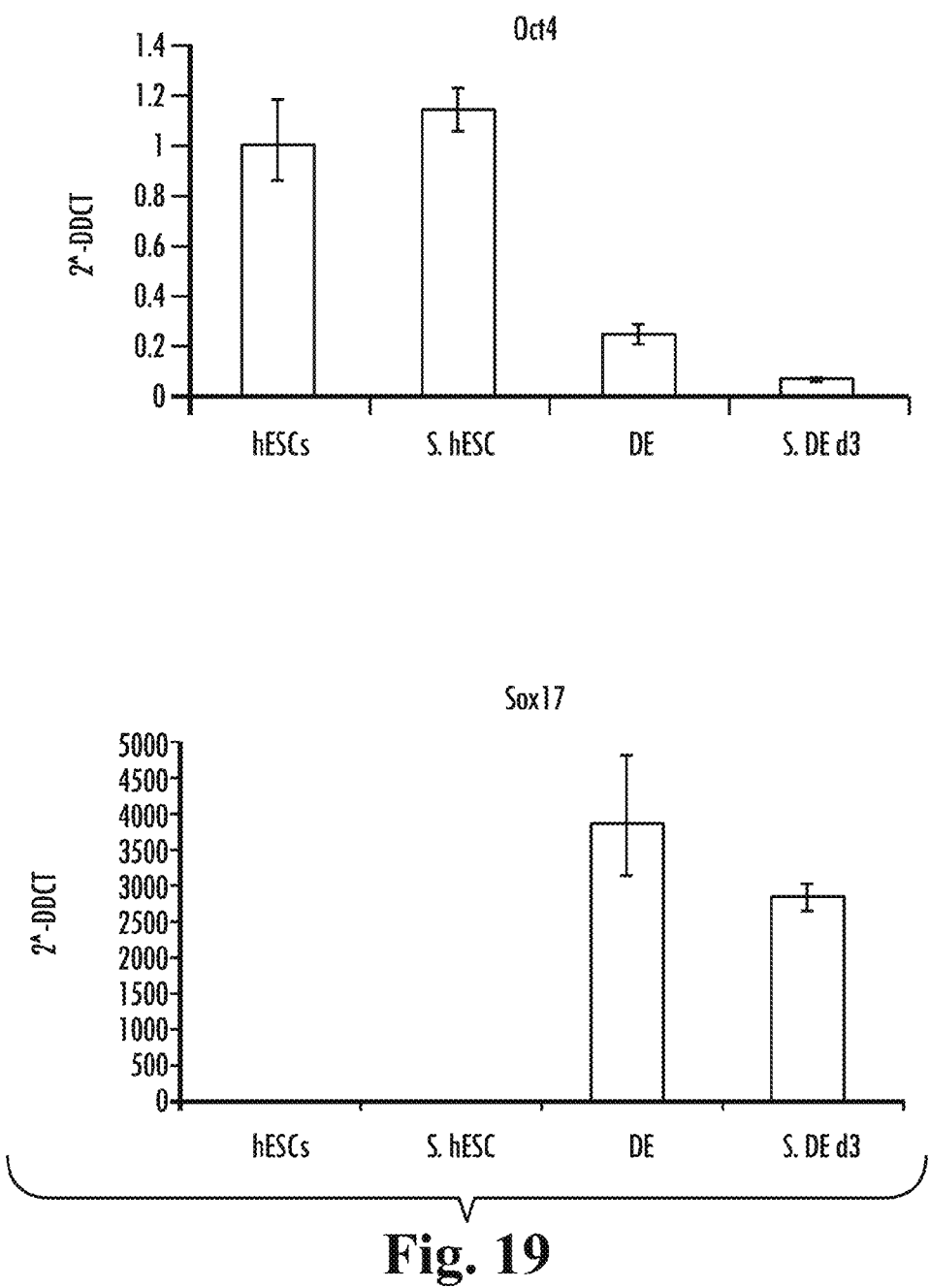
FIG. 19 depicts qPCR analysis of suspension and adherent hESCs. BG02 cells growing in suspension (S. hESCs) and adherent (hESCs) culture exhibited comparable levels of OCT4, and lacked SOX17 expression. Adherent cells differentiated to definitive endoderm (DE), and suspension hESCs differentiated to definitive endoderm in suspension (S. DE d3), both exhibited the expected marked down regulation of OCT4 and up regulation of SOX17 expression

Cell counting was used to assess the relative growth rates of cells in suspension compared to adherent culture. In this experiment, an adherent culture of BG02 cells was passaged with ACCUTASE™, and about $1\times10^6$ cells were placed in parallel suspension or adherent culture wells. Individual wells were counted on days 1-6 and plotted on a log scale (FIG. 18). While a higher initial proportion of hESCs were viable after 24 hours in adherent culture (~90% vs ~14%), growth rates were comparable thereafter. This indicated that hESCs could proliferate just as rapidly in suspension culture as in traditional adherent culture. Cell counts performed during passaging allow one to gauge the amount of expansion possible in this simple suspension system. In several cultures seeded with $5 \times 10^5$ cells, approximately $10^7$ cells, or more, were generated after 7 days. The expansion after 7 days in suspension culture equated to about a 20-fold or more expansion, with the largest expansion observed being ~24× the input cell number.

Example 14

Characteristics of Differentiable Cells Expanded in Suspension Culture

Quantitative RT-PCR (qPCR) was used to compare gene expression in hESCs grown in suspension and adherent culture in DC-HAIF. Comparable levels of OCT4, a marker of pluripotent cells, were observed in both culture formats, confirming that cultures maintained in suspension were primarily undifferentiated. SOX17, a marker of definitive endoderm, was not expressed in either population of hESCs. The qPCR analysis also examined the potential of suspension hESCs to differentiate to definitive endoderm, as aggregates in suspension. Adherent and suspension hESCs were differentiated using parallel conditions. hESC cultures were treated with RPMI containing 2% BSA, 100 ng/mL Activin A, 8 ng/mL FGF2 and 25 ng/mL Wnt3A for 24 hours, followed by 2 days in the same medium without Wnt3A. The expression of OCT4 was downregulated, and expression of SOX17 upregulated similarly in both definitive endoderm samples compared to undifferentiated hESCs. This differentiation analysis confirmed that hESCs cultured in suspension in DC-HAIF maintained their differentiation potential, as evidenced by the likely formation of definitive endoderm.

Example 15

Addition of an Apoptosis Inhibitor in Suspension Culture

To attenuate the loss of cells after initial passaging in suspension, an inhibitor of apoptosis was added to the medium. Cells were passaged as in Example 12, except that Y-27632, an inhibitor of p160-Rho-associated coiled-coil kinase (ROCK), was added to the medium.

Figure 21:
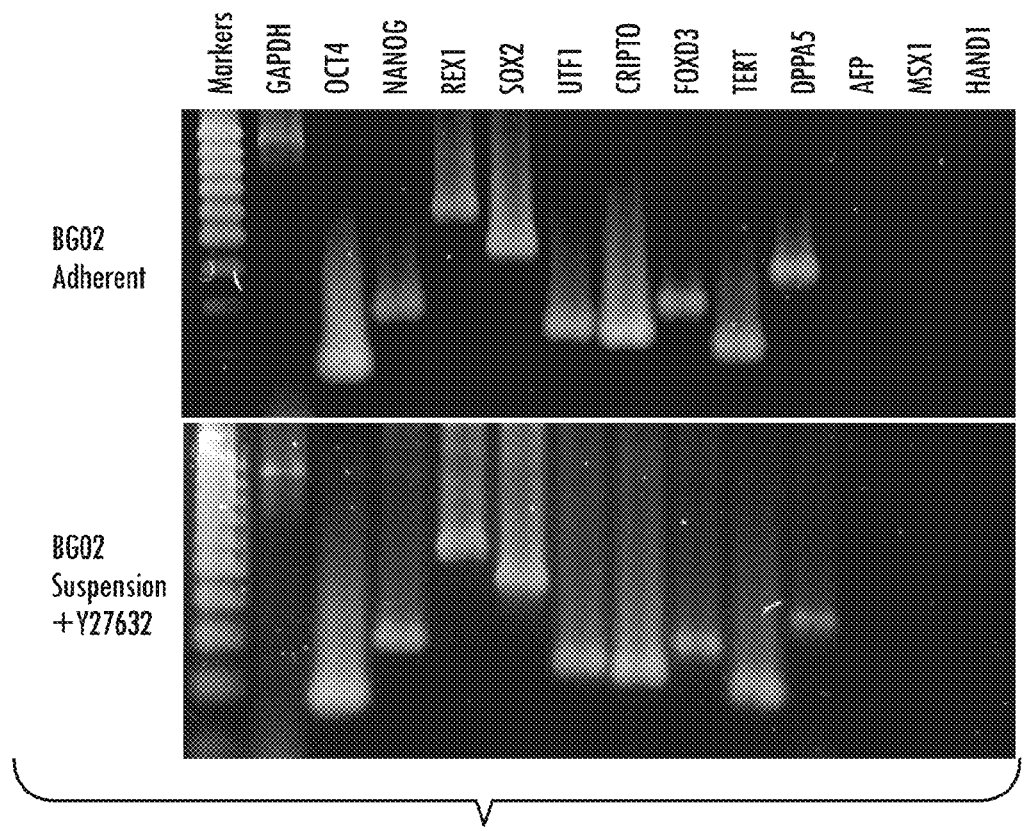
FIG. 21 depicts RT-PCR analysis of suspension aggregates in the presence of Y27632. RT-PCR was performed on the expanded cultures to assess expression of markers of pluripotency. Expression of OCT4, NANOG, REX1, SOX2, UTF1, CRIPTO, FOXD3, TERT AND DPPA5 was detected, whereas markers of differentiated lineages AFP, MSX1 and HAND1 were not detected.
Figure 22A:
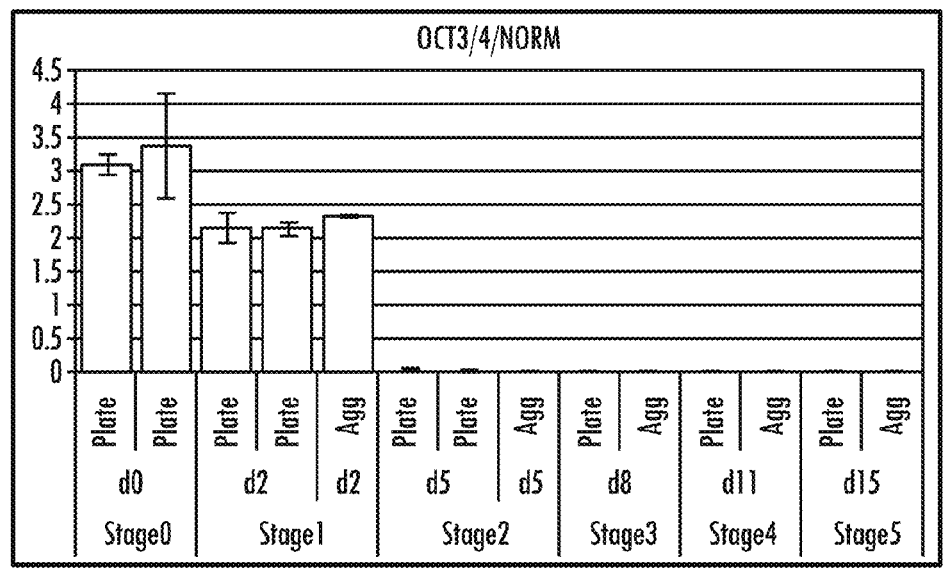
FIGS. 22 A-P are bar charts showing the expression patterns of marker genes OCT4 (panel A), BRACH (panel B), SOX17 (panel C), FOXA2 or HNF3beta (panel D), HNF1beta (panel E), PDX1 (panel F) NKX6.1 (panel G), NKX2.2 (panel H), INS (panel I), GCG (panel J), SST (panel K), SOX7 (panel L), ZIC1 (panel M), AFP (panel N), HNF4A (panel O) and PTF1A (panel P), which is not an exhaustive list but markers which can be used to identify pluripotent human embryonic stem (hES) cells (stage0, d0), definitive endoderm cells (stage1; d2), PDX1-negative foregut endoderm cells (stage2; d5), PDX1-positive endoderm cells (stage3, d8), pancreatic endoderm cells (stage4; d11), pancreatic endocrine precursors and/or hormone secreting cells (stage5; d15).
Figure 22B:
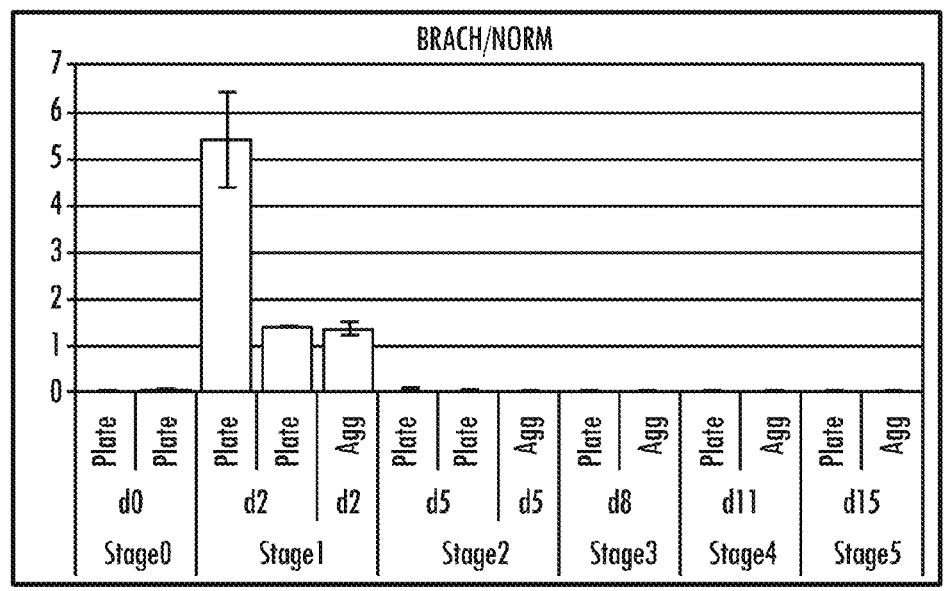
Figure 22C:
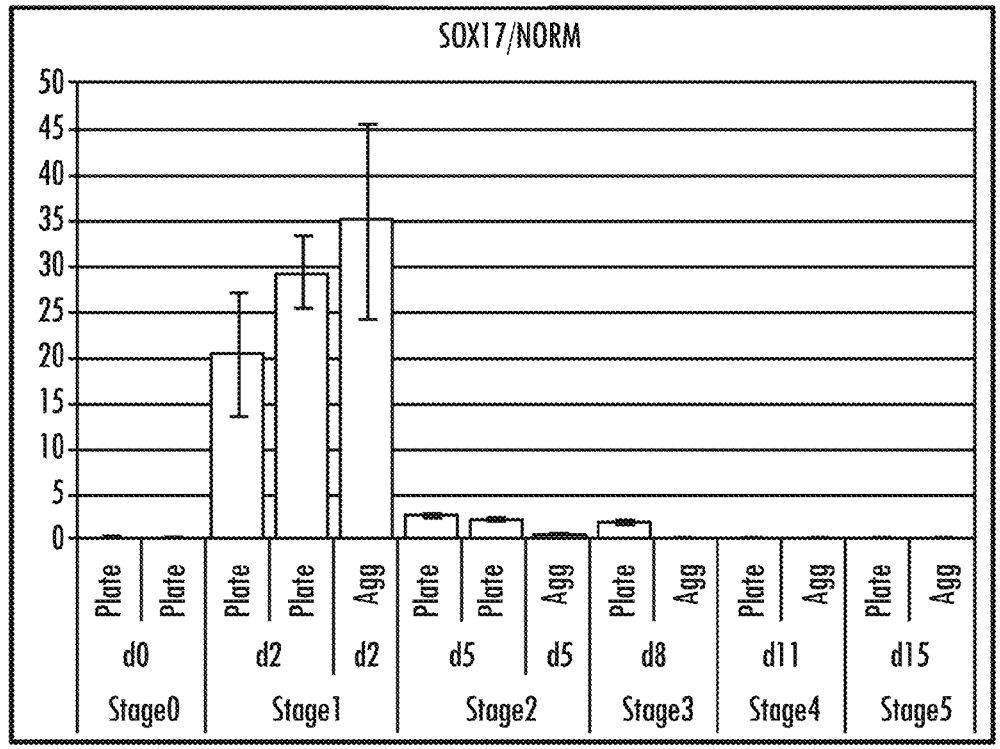
Figure 22D:
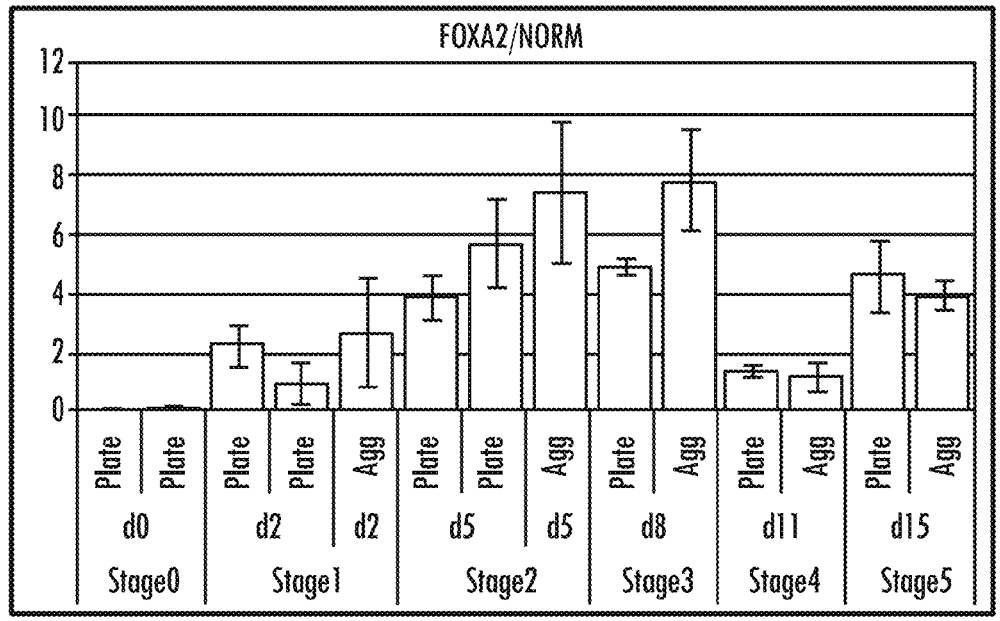
Figure 22E:
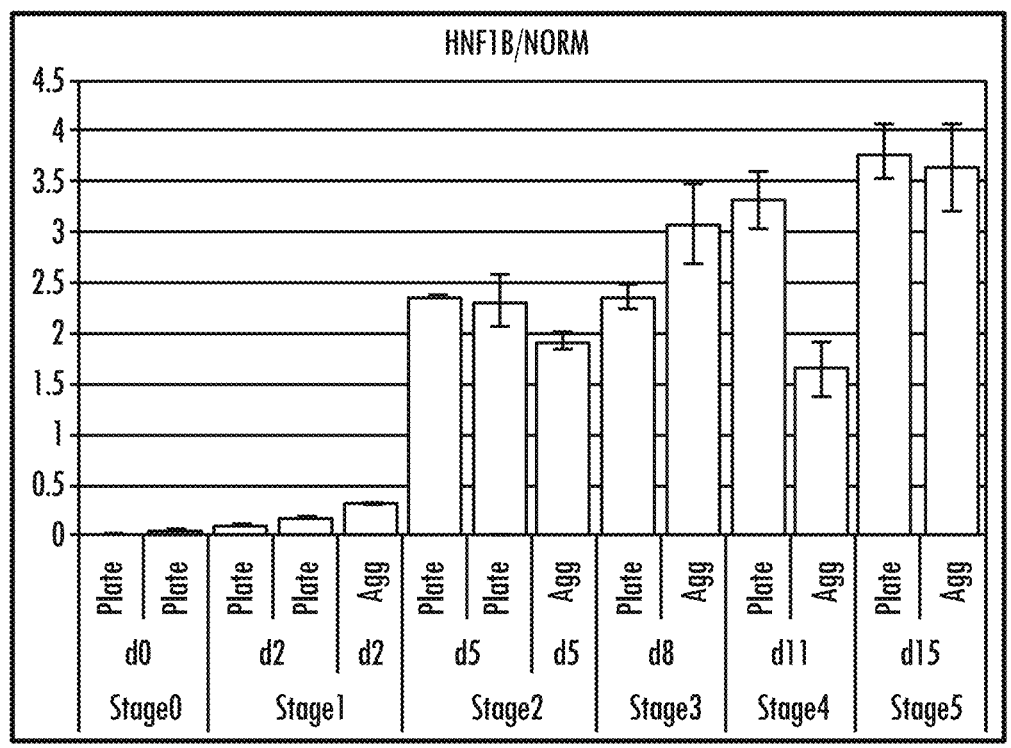
Figure 22F:
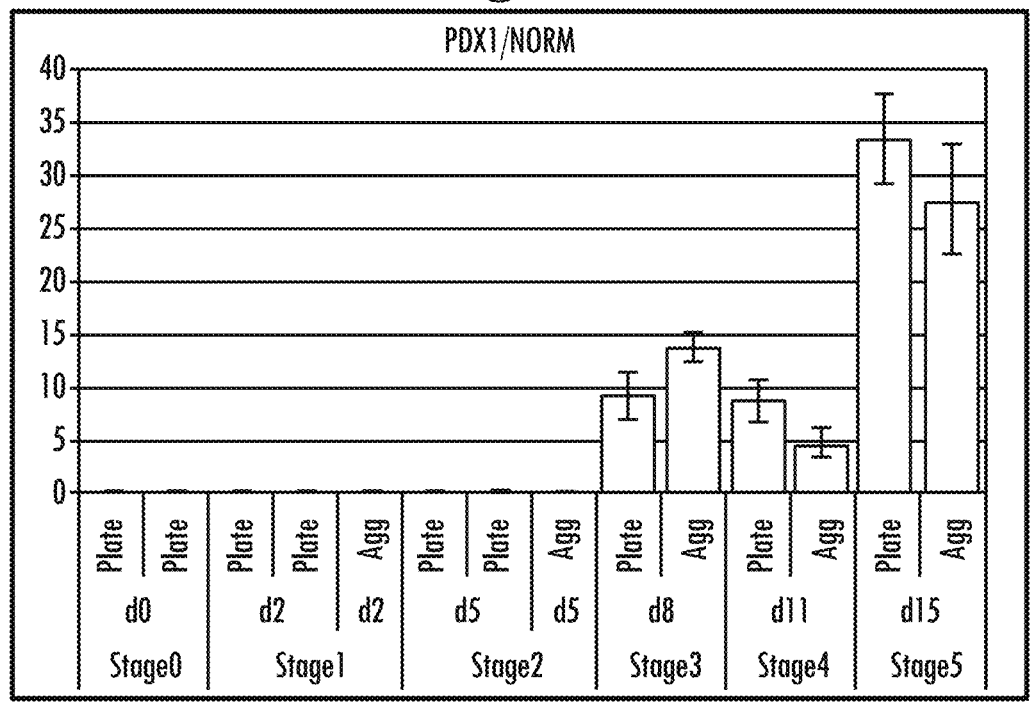
Figure 22G:
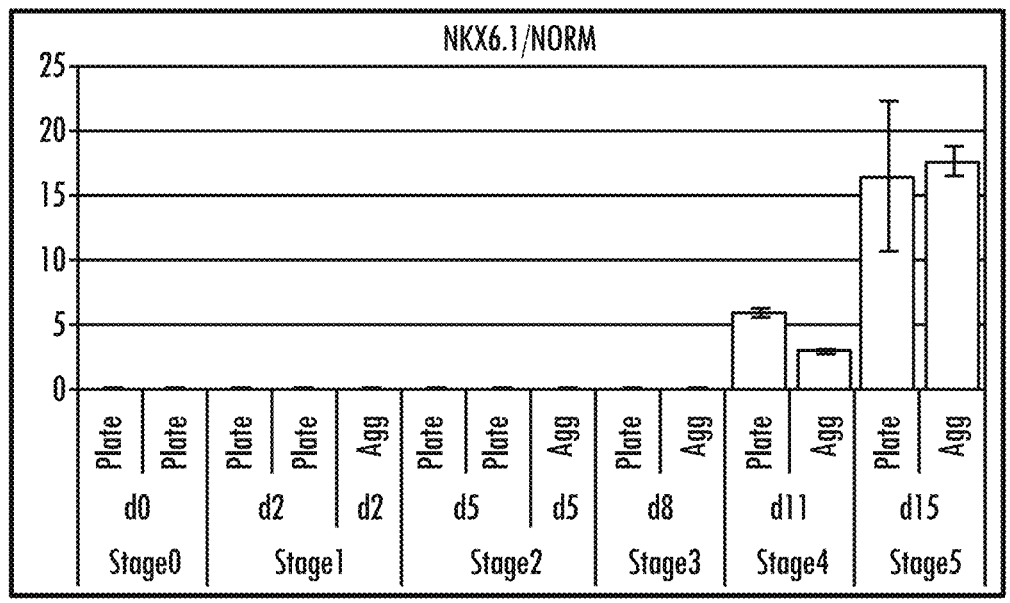
Figure 22H:
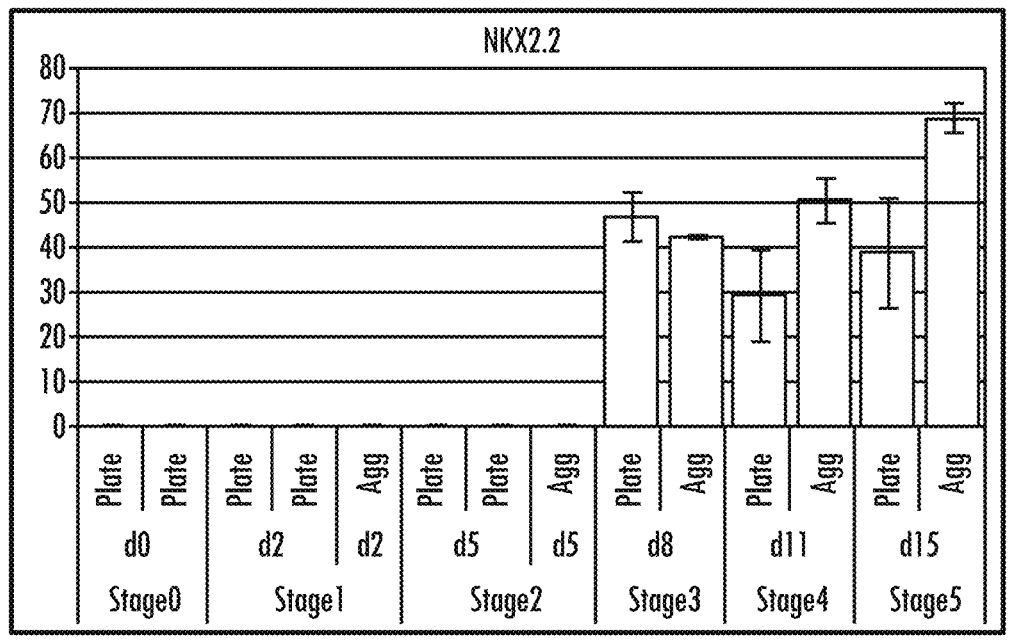
Figure 22I:
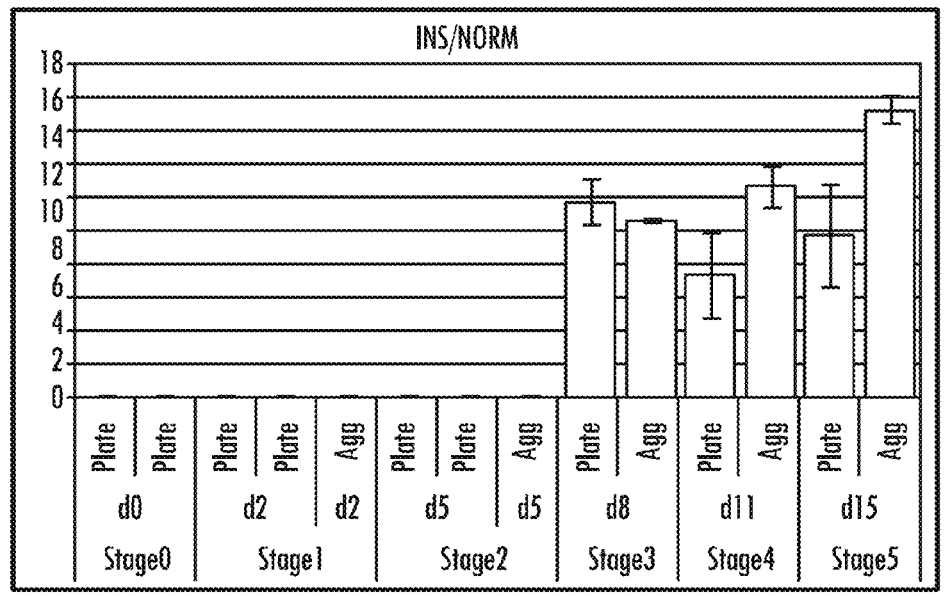
Figure 22J:
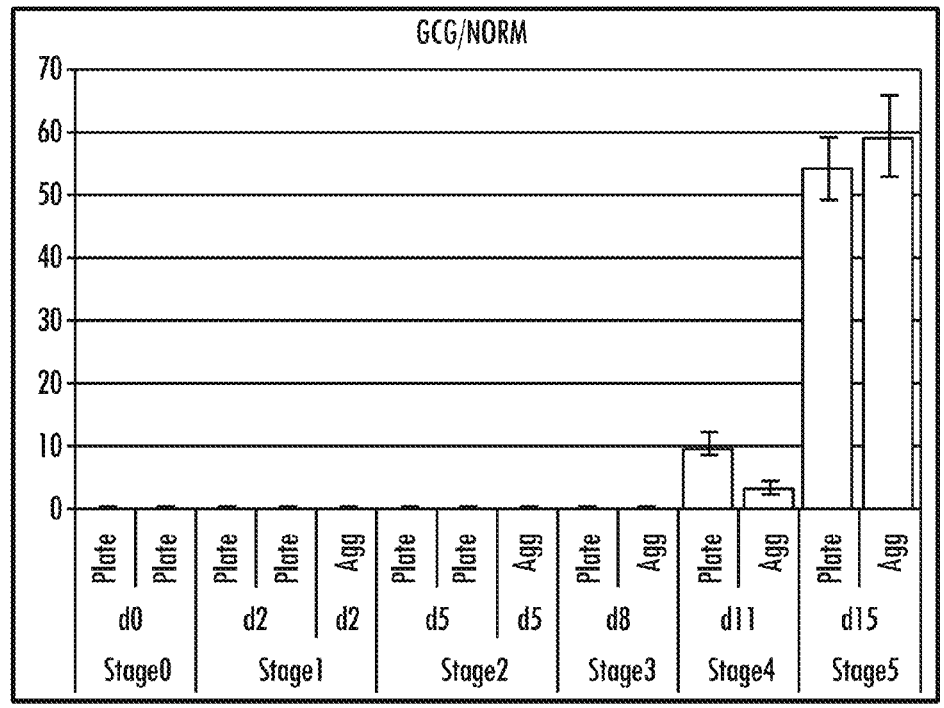
Figure 22K:
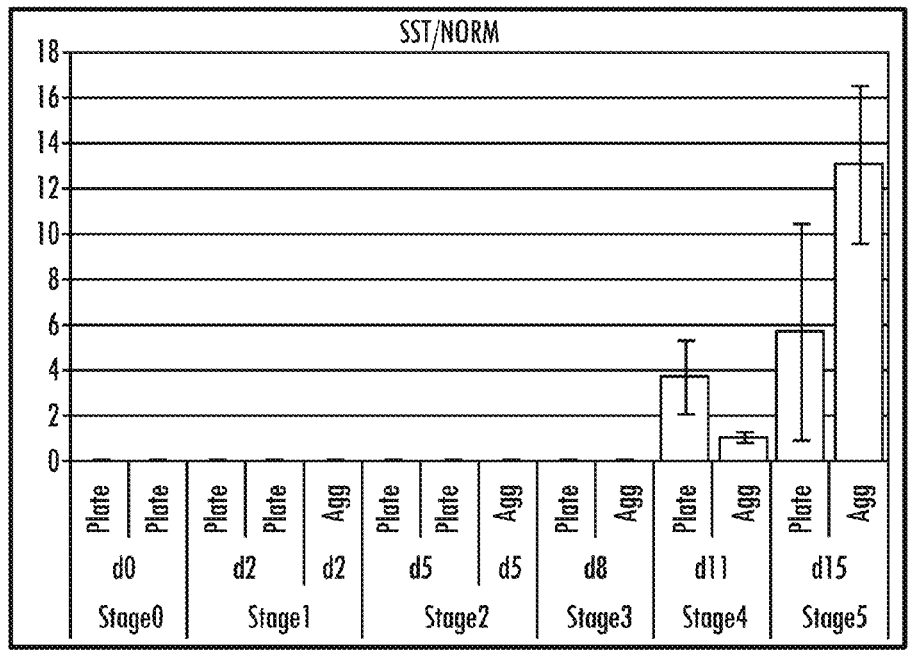
Figure 22L:
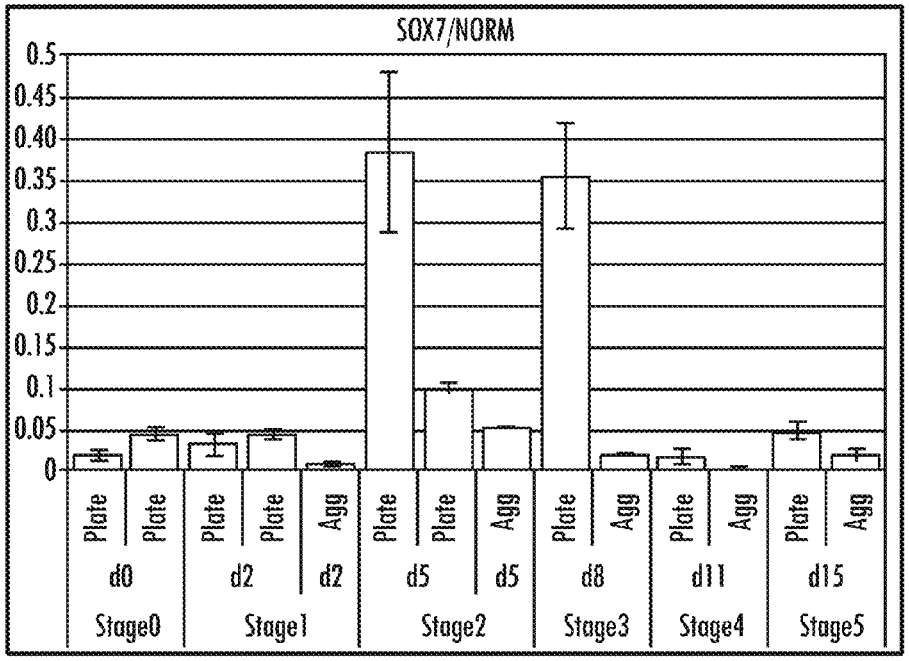
Figure 22M:
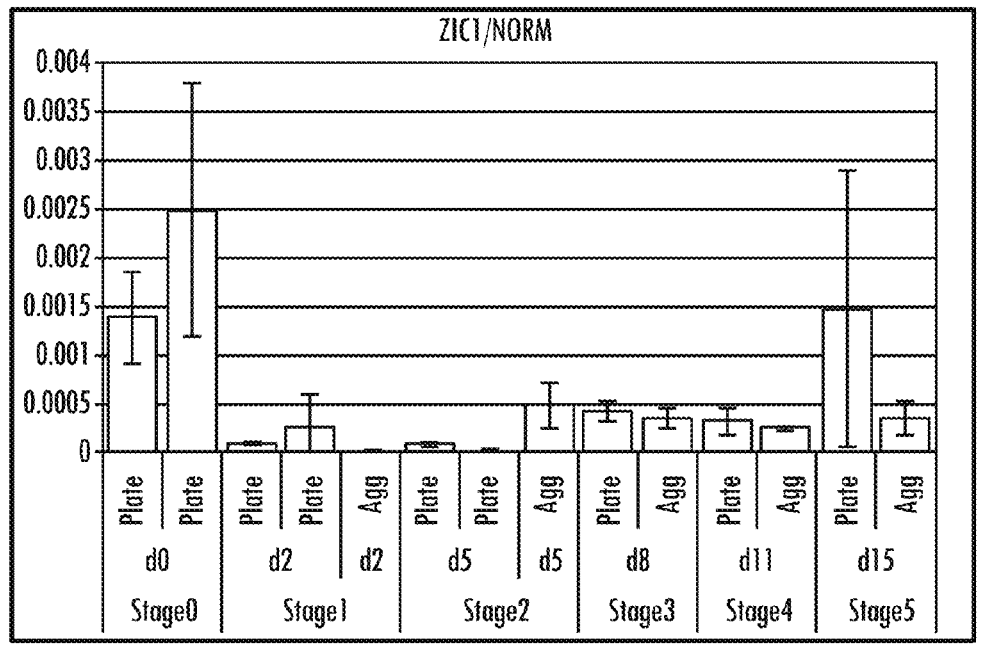
Figure 22N:
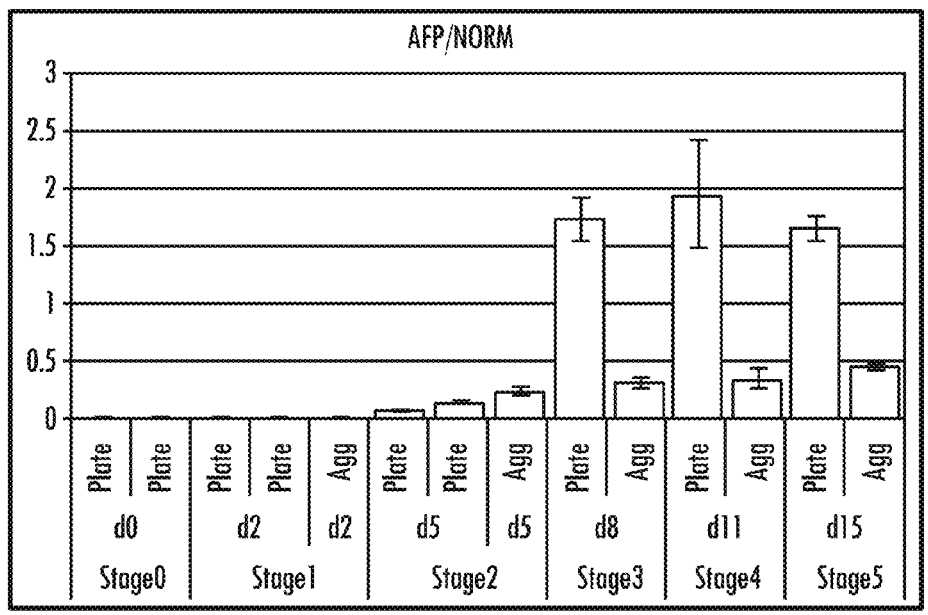
Figure 22O:
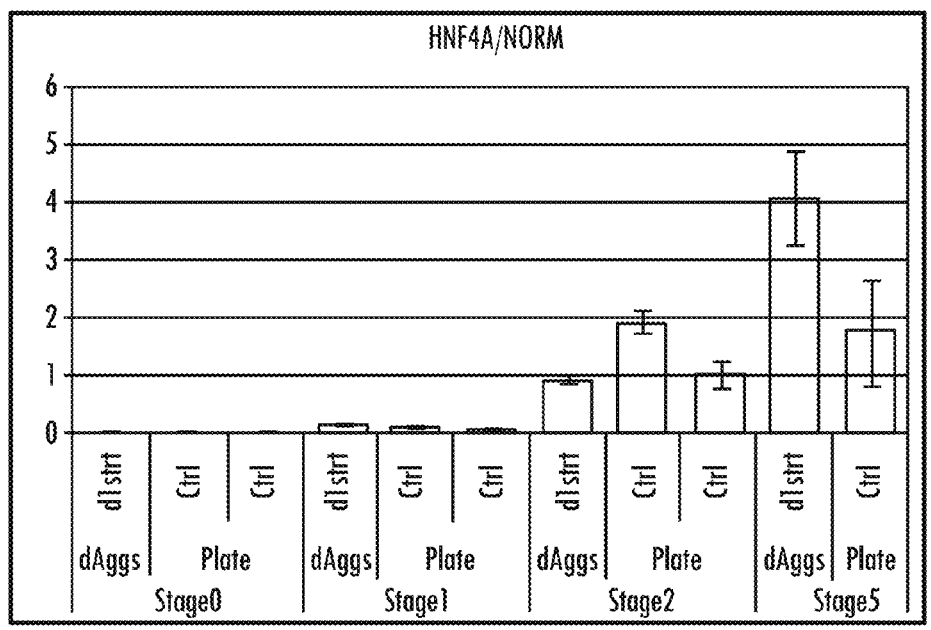
Figure 22P:
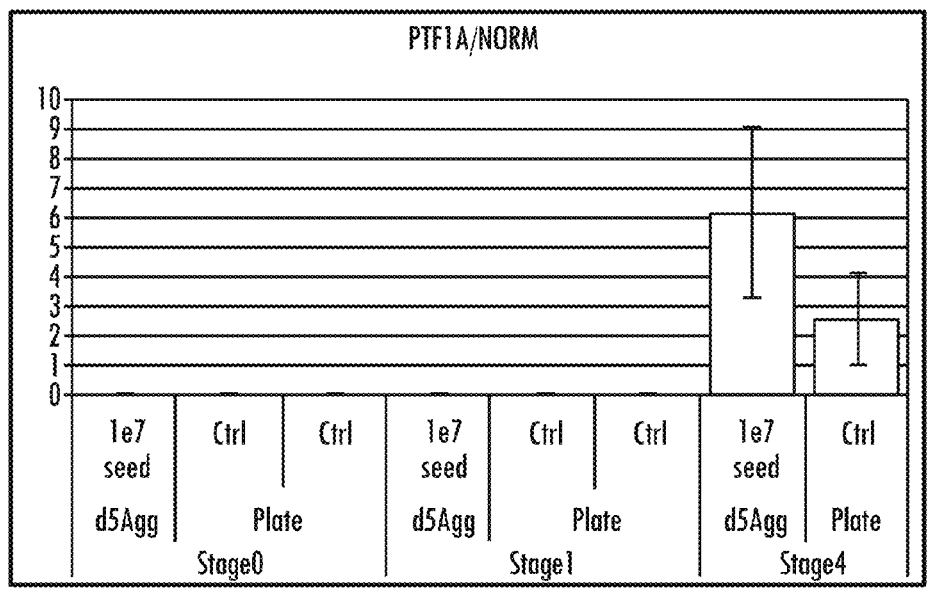

Suspension aggregates of BG02 cells were formed by seeding $2 \times 10^6$ single cells in 6-well dishes in 3 mL DC-HAIF medium, at 100 rpm on a rotating platform in an incubator (Table 4, Experiment A). 10 µM Y27632 ROCK inhibitor was added to test wells for the course of the experiment and the cultures observed daily and counted after 24 hours (day 1) and after 4 or 5 days. As shown in FIG. 20, addition of Y27632 had a profound effect on the initial aggregation phase of suspension culture. Compared to cells aggregated in medium without inhibitor, much larger aggregates were formed in the presence of Y27632 (FIG. 20). Cell counting confirmed that more viable cells were present in the presence of inhibitor (Table 4, Experiment A). This difference in cell number persisted throughout the course of the culture period, with more cells also observed on day 4, compared to cultures without inhibitor. As with previous suspension culture experiments, cells exposed to Y27632 could also be serially passaged, and maintained in an undifferentiated state (not shown). When the aggregates were split again, almost twice as many cells were observed with Y27632 treatment (Table 4 Experiment A). RT-PCR analysis demonstrated that BG02 cells grown in suspension culture in the presence of Y27632 remained undifferentiated (FIG. 21).

As previous experiments had shown that growth rates of cells in suspension and adherent culture were similar after the initial 24 hours, an experiment was performed where Y27632 was removed after this initial period (Table 4, Experiment B). Consistent with these previous observations, Y27632 enhanced initial survival and aggregation of hESCs after initial passage, but removing the inhibitor after 24 hours did not negatively impact the number and viability count of cells analyzed on day 5. $1.4 \times 10^7$ (+Y27632) and $1.8 \times 10^7$ (+/−Y27632) viable cells were generated when inhibitor was present compared to $3.9 \times 10^6$ cells in untreated cultures. This analysis confirmed that Y27632 had the largest impact during the first 24 hours of suspension hESC culture.

Because of the enhanced survival and aggregation observed in the presence of Y27632, an experiment was performed to examine if it was possible to reduce the number of cells used to seed suspension cultures (Table 4, Experiment C). Previous experiments had indicated that seeding ES cells at a low density of about $5 \times 10^5$ cells per 3 mL DC-HAIF, or less, did not work well. To determine if addition of a ROCK inhibitor would allow cell seeding at lower densities, a range of cell concentrations (from about $2 \times 10^6$ total cells down to about $1 \times 10^5$ total cells was used to seed suspension cultures in 6-well trays cells in 3 mL DC-HAIF. 10 µM Y27632 was added to all conditions, and the cell number and viability assessed on day 5. Successful aggregation and expansion was observed even at low seeding densities. An approximately 13 fold expansion of viable cells was observed even in cultures that were only seeded with $1 \times 10^5$ cells Inhibition of ROCK with Y27632 therefore facilitated initial survival of hESCs at much lower densities in this suspension system.

TABLE 4

Suspension Cultures with and without an Apoptosis Inhibitor

| Expt. | Treatment | Seeding | Cell counts: total (viable, %) | | |
|---|---|---|---|---|---|
| | | | p0, day 1 | p0, day 4 | p1, day 4 |
| A | HAIF | $2 \times 10^6$ | $1.9 \times 10^6$ ($3.5 \times 10^5$, 19%) | $1.8 \times 10^6$ ($1.3 \times 10^6$, 75%) | $2.5 \times 10^6$ ($2.2 \times 10^6$, 88%) |
| | +Y27632 | $2 \times 10^6$ | $1.6 \times 10^6$ ($1.2 \times 10^6$, 74%) | $7.8 \times 10^6$ ($7.1 \times 10^6$, 91%) | $4.6 \times 10^6$ ($4.2 \times 10^6$, 91%) |
| | | | | p0, day 5 | |
| B | HAIF | $2 \times 10^6$ | $2.9 \times 10^6$ ($5.5 \times 10^5$, 26%) | $4.8 \times 10^6$ ($3.9 \times 10^6$, 81.3%) | |
| | +Y27632 | $2 \times 10^6$ | $1.9 \times 10^6$ ($1.4 \times 10^6$, 73%) | $1.5 \times 10^7$ ($1.4 \times 10^7$, 92%) | |
| | +/−Y27632 | $2 \times 10^6$ | N/A | $1.9 \times 10^7$ ($1.8 \times 10^7$, 96%) | |
| | | | | p0, day 5 | |

TABLE 4-continued

Suspension Cultures with and without an Apoptosis Inhibitor

| Expt. | Treatment | Seeding | Cell counts: total (viable, %) | |
|---|---|---|---|---|
| C | +Y27632 | $2 \times 10^6$ | $1.9 \times 10^6$ ($1.6 \times 10^6$, 84%) | $1.4 \times 10^7$ ($1.2 \times 10^7$, 90%) |
| | | $1 \times 10^6$ | $8.7 \times 10^5$ ($6.6 \times 10^5$, 76%) | $8.6 \times 10^6$ ($7.8 \times 10^6$, 91%) |
| | | $5 \times 10^5$ | $4.6 \times 10^5$ ($3.5 \times 10^5$, 75%) | $5.7 \times 10^6$ ($5.3 \times 10^6$, 93%) |
| | | $2.5 \times 10^5$ | $2.6 \times 10^5$ ($2.3 \times 10^5$, 91%) | $2.7 \times 10^6$ ($2.5 \times 10^6$, 91%) |
| | | $10^5$ | $6.8 \times 10^4$ ($5.4 \times 10^4$, 79%) | $1.4 \times 10^6$ ($1.3 \times 10^6$, 92%) |

Expt. = Experiment;
p0 = passage 0;
p1 = passage 1;
N/A = not available;
Cell counts and percentages are rounded to 1 and 0 decimal places, respectively.

Example 16

Suspension Cultures in Various Media

To determine if suspensions of ES cells could be cultured in the absence of FGF2 and/or Activin A, ES cells were cultured in a variety of media, with and without these factors. Table 5 shows cell counting results from suspension cultures and indicate that suspension cultures could be successfully expanded in the absence of exogenous FGF2 (HAI conditions), as well as without exogenous FGF2 or Activin A (HI conditions). The addition of Y27632 increased the yield of cells generated by day 5 in all conditions. In addition, the cells in each media were successfully passaged with no morphological signs of differentiation.

TABLE 5

Suspension Cultures in Various Media

| Treatment | Seeding | Cell counts: total (viable, %) p0, day 5 | Fold Expansion |
|---|---|---|---|
| HAIF | $2 \times 10^6$ | $7.7 \times 10^6$ ($6.5 \times 10^6$, 83%) | 3.25 |
| HAI | $2 \times 10^6$ | $7.0 \times 10^6$ ($6.3 \times 10^6$, 91%) | 3.15 |
| HI | $2 \times 10^6$ | $6.4 \times 10^6$ ($5.3 \times 10^6$, 83%) | 2.65 |
| HAIF + Y27632 | $2 \times 10^6$ | $1.5 \times 10^7$ ($1.3 \times 10^7$, 90%) | 6.5 |
| HAI + Y27632 | $2 \times 10^6$ | $1.5 \times 10^7$ ($1.3 \times 10^7$, 91%) | 6.5 |
| HI + Y27632 | $2 \times 10^6$ | $1.9 \times 10^7$ ($9.2 \times 10^6$, 49%) | 4.6 |

Example 17

Optimized Shear Rate Results in Increased Survival, Uniform Density and Size of Suspension Cell Aggregates It is contemplated that any cell line that can be maintained in a suspension cell culture will benefit from and can be utilized in accordance with the systems, methods and apparatus disclosed herein. Cells include, but are not limited to, mammalian cells, including but not limited to human cell lines CyT49, CyT203, CyT25, BG01 and BG02, mouse, dog, and non-human primate stem cell lines, as well as others.

Results provided herein indicate that cell proliferation and differentiation can be maintained at control levels or attenuated, depending on the operating parameters of the reactor apparatus, particularly rate of culture flow and provided shear force. The shear force exerted on cell culture can have significant effects on cell proliferation. A symmetrical system, such as a rotating platform employed herein, provides a uniform, primarily laminar, shear stress around the vessel, while an asymmetrical system and mounting, such as a stirred-tank bioreactor, has regions of turbulent flow that are characterized by locally high shear stress. As such, if the bio-reactor or cell-culture apparatus is not a symmetrical system, the direction of culture flow affects both the nature and the degree of a shear stress that results from rotation.

Of course, optimal rotational speeds are culture specific and can vary depending upon cell count in the cell culture, the viscosity of culture media, type of media, the robustness of the particular cells in suspension (some cells being able to withstand a higher level of shear forces than others) etc. Optimal rotational speeds are easily determined for the particular set of conditions at hand. In particular, rotational speeds described and contemplated herein are useful in order to maintain laminar flow conditions. Therefore, the experiments described herein were under conditions where: 1) cell proliferation and differentiation was maintained at or near control levels; and 2) conditions at which cell proliferation and differentiation was attenuated. The following is a general method which works well for maintaining hES cell aggregate cultures or differentiated hES cell aggregate cultures. One skilled in the art can optimize the size and shape of the cell aggregates based on the description provided herein.

Table 6 below describes shear rate and stress as it relates to the diameter (μm) of the cell aggregates. Human ES cells were aggregated for 1, 2, 3 and/or 4 days at various rotation speeds using an orbital rotator (Barnstead LabLine Multipurpose Rotator): 60 rpm, 80 rpm, 100 rpm, 120 rpm, 130 rpm, 140 rpm, 150 rpm and 160 rpm. Table 6 also demonstrates that the effective shear rate experienced by the cell aggregates depends on the diameter of that cell aggregate.

TABLE 6

Size of cell aggregates is dependent on shear rate and shear stress

| Aggregate Diameter (μm) | Rotation Rate (rpm) | Dimensionless Stress | Shear Stress (dynes/cm 2) | Shear Rate (1/sec) |
|---|---|---|---|---|
| 200 | 140 | 0.94 | 3.16 | 322.24 |
| | 120 | 0.76 | 2.06 | 210.12 |
| | 100 | 0.59 | 1.24 | 126.82 |
| | 80 | 0.43 | 0.66 | 67.05 |
| | 60 | 0.29 | 0.30 | 30.17 |
| 175 | 140 | 0.72 | 2.42 | 246.72 |
| | 120 | 0.58 | 1.58 | 160.87 |
| | 100 | 0.45 | 0.95 | 97.10 |
| | 80 | 0.33 | 0.50 | 51.33 |
| | 60 | 0.22 | 0.23 | 23.10 |

TABLE 6-continued

Size of cell aggregates is dependent on shear rate and shear stress

| Aggregate Diameter (μm) | Rotation Rate (rpm) | Dimensionless Stress | Shear Stress (dynes/cm^2) | Shear Rate (1/sec) |
|---|---|---|---|---|
| 150 | 140 | 0.53 | 1.78 | 181.26 |
|  | 120 | 0.43 | 1.16 | 118.19 |
|  | 100 | 0.33 | 0.70 | 71.34 |
|  | 80 | 0.24 | 0.37 | 37.71 |
|  | 60 | 0.16 | 0.17 | 16.97 |
| 125 | 140 | 0.37 | 1.23 | 125.88 |
|  | 120 | 0.30 | 0.80 | 82.08 |
|  | 100 | 0.23 | 0.49 | 49.54 |
|  | 80 | 0.17 | 0.26 | 26.19 |
|  | 60 | 0.11 | 0.12 | 11.79 |
| 100 | 140 | 0.24 | 0.79 | 80.56 |
|  | 120 | 0.19 | 0.51 | 52.53 |
|  | 100 | 0.15 | 0.31 | 31.71 |
|  | 80 | 0.11 | 0.16 | 16.76 |
|  | 60 | 0.07 | 0.07 | 7.54 |

To determine how rotation speed controls the diameter of ES aggregates, we generated ES aggregates by rotation at 100 rpm, 120 rpm or 140 rpm. Aggregate diameters were quantitated from 5× phase contrast images taken after 2 days in rotation culture. For the 100 rpm culture, the average diameter+/−SD was 198 μm+/−21 μm. For the 120 rpm culture, the average diameter+/−SD was 225 μm+/−28 μm. For the 140 rpm culture, the average diameter+/−SD was 85 μm+/−15 μm. Each diameter distribution is statistically significant (p<0.001) using ANOVA and the Tukey Multiple Comparison post-test. As shown in Table 6, the shear rate increases exponentially from 60 rpm to 140 rpm, e.g., the shear rate for a 100 μm diameter aggregate was approximately 30 sec-1 at 100 rpm and approximately 80 sec-1 at 140 rpm, which is about a 3-fold increase. Typically, rotation speeds above 140 rpm resulted in larger, less uniform hES cell aggregates. Cell aggregate cultures can also be cultured initially at reduced rotation speeds, e.g., 60 rpm to 80 rpm for about 1 day, and then cultured at a higher rotation speed thereafter (e.g., 100 rpm-140 rpm or more) without any deleterious effects to the size and or shape of the cell aggregates.

It is important to note, that although the diameters of the cell aggregates varied accordingly with the shear rate, there were no profound effects in gene expression among the various conditions, i.e. different rotation speeds and/or different size and shaped cell aggregates. That is, the signature markers observed for the pluripotent hESC or the hES-derived cell types (e.g., definitive endoderm, foregut endoderm, PDX1-endoderm, pancreatic endoderm and endocrine cells) were consistent with that described in D'Amour et al. supra and related applications incorporated herein by their reference.

To determine the effect of rotation speed, shear rate and shear stress on cell survival or cell viability, it was demonstrated that survival was improved by a single day at reduced speeds (e.g., 60 rpm to 80 rpm). For example, cell survival was at least 60% or higher at rotation speeds between 60 rpm to 140 rpm. Also, the number of cell aggregates was higher at d1, d2 and d3 in the reduced rotation speed cultures as compared to higher rotation speeds (e.g., 100 rpm or higher). There was also significant disruption and disaggregation when cell aggregates were cultured at the higher rotation speeds (e.g., 140 rpm or higher). Taken together, these data indicated that cell survival is increased when the cell aggregates were first cultured for at least a single day at reduced rotation speed, however, there was no significant drop in cell survival when rotation speeds were increased to 100 rpm to 140 rpm; although, differentiation at rotation speeds less than 140 rpm is preferred.

Figure 23:
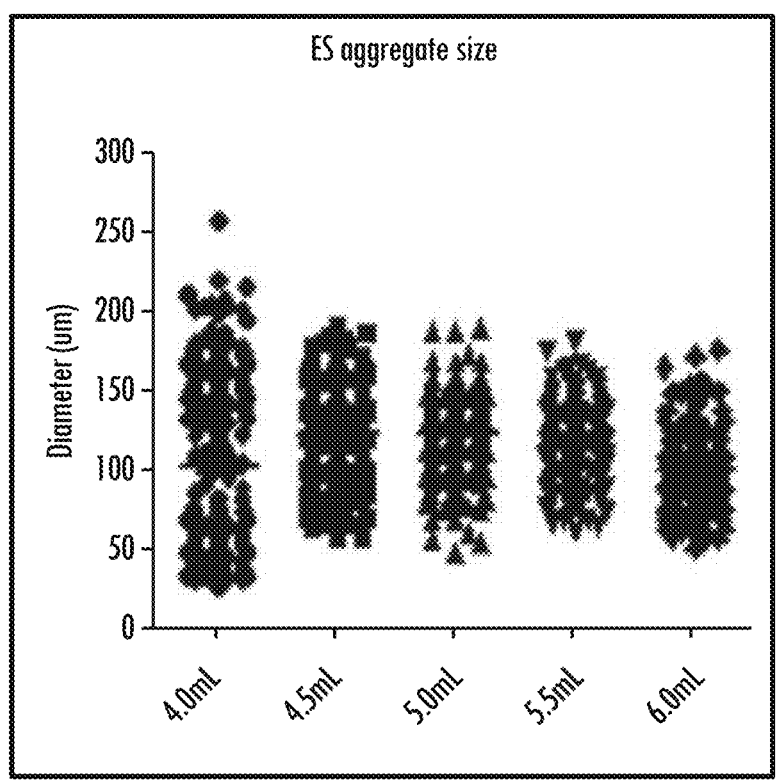
FIG. 23 is a graph showing the range of the diameters of the cell aggregates in suspension (microns) in relationship to the total volume (mL) of media in the culture.

Also, culture volume affects shear rate and shear stress which in turn, as discussed above, affects uniformity of size and shape of the cell aggregates. For example, when single cell suspension cultures are initiated to form cell aggregates in 6 mL as compared to those initiated in 4 mL resulted in a more uniformly sized and shaped cell aggregates. See FIG. 23, whereby the diameters of the cell aggregates varied from less than 50 microns to greater than 250 microns when cultured using 4 mL, whereas when cultured in 6 mL, the diameters had a tighter range and ranged from greater than 50 microns to less 200 microns. Although the described cell aggregates were initiated from single cell suspension cultures made from adherent hES cell cultures, cell aggregate suspension cultures initiated from hES-derived adherent plate cultures would be expected to behave similarly. Thus, the volume of the media is likely independent of the stage whereby cell aggregate suspension cultures are initiated.

Moreover, hES cell aggregates can be cultured in a variety of different media conditions. For example, hES cell aggregate cultures can be maintained in StemPro® containing media, in DMEM/F12 containing media; or DMEM/F12 containing 20% Knockout serum replacement (KSR, Invitrogen) media; or either StemPro® and DMEM/F12 media further containing 20 ng/mL FGF (R&D Systems) and 20 ng/mL Activin A (R&D Systems); or StemPro® and DMEM/F12 media further containing 10 ng/mL Heregulin B. Alternatively, any of the media mentioned herein and those commercially available can also be supplemented with xeno-free KSR (Invitrogen). Lastly, cell aggregates were also produced and cultured in any of the above media and further not containing exogenous FGF.

Example 18 hES Cell Aggregates in Suspension can Differentiate to Endoderm-Lineage Type Cells Human embryonic stem (hES) cells were maintained and differentiated in vitro to definitive endoderm (stage 1), foregut endoderm and PDX1 endoderm substantially as described in D'Amour et al. 2006, supra, and U.S. Patent Publication Numbers 2005/0266554, 2005/0158853, 2006/0003313, 2006/0148081, 2007/0122905 and 2007/0259421, which are herein incorporated in their entireties.

Briefly, undifferentiated pluripotent hES adherent (plate) cells were maintained on mouse embryo fibroblast feeder layers (Millipore, formerly Chemicon or Specialty Media) or on human serum coated 60 mm plates (0.1 to 20% final concentration; Valley Biomedical) in DMEM/F12 (Mediatech) supplemented with 20% KnockOut serum replacement (Invitrogen/Gibco), 1 mM nonessential amino acids (Invitrogen/Gibco), Glutamax (Invitrogen/Gibco), penicillin/streptomycin (Invitrogen/Gibco), 0.55 mM 2-mercaptoethanol (Invitrogen/Gibco) and 4 ng/mL to 20 ng/mL recombinant human FGF2 (R&D Systems). Alternatively, the above media can be supplemented with KSR Xeno-free (Gibco) and human serum. Also, human serum has been added to the culture after the hESC have been seeded on uncoated culture plates. Low dosages of Activin A (2-25 ng/mL, R&D Systems) were added to the growth culture medium to help maintain undifferentiated growth. Adherent pluripotent hESC at day 0 (d0) express high levels of pluripotent protein marker, OCT 4. See FIG. 1, panel A, plate controls at d0.

The cells were either manually or enzymatically passaged again substantially as described in D'Amour et al. 2006, supra. The suspension cultures were dissociated and transferred to a conical tube and centrifuged at 1000 rpm for about 5 minutes. The supernatant was removed and a standard cell count using a ViCell Cell Analyzer was performed. Typical cell numbers from a 60 mm plate range from $3 \times 10^6$ to $12 \times 10^6$ cells, depending on cell line, and the number of days in culture prior to passage. Once the number of cells in the primary cell suspension was determined, the suspension was further diluted with StemPro® or media containing xeno-free KSR as described above to a final volume of $1 \times 10^6$ cells/mL. This volume can be increased to $>4 \times 10^6$ cells/mL but may require more frequent feeding. ROCK inhibitor Y27632 (Axxora) was added to the cell suspension to a final concentration of about 1-15 µM, typically 10 µM, and the tube was mixed by gentle inversion. In some cases, Y27632 was not added to the suspension in order to control the rate of aggregate formation. The resuspended cells were then distributed equally into each well of a low binding 6-well dish (about 5 mL of cell suspension per well) and placed on the rotating platform at 100 rpm to 140 rpm for about 1-4 days prior to differentiation.

During this culturing period, hES cell aggregates formed and the cultures were fed at least 1-2 times daily by replacing 4 mL of media with 4 mL of fresh StemPro® media minus Y27632, or any of the described media supplemented with xeno-free KSR. Media exchanges ("feeding") should be performed as quickly as possible to disrupt or prevent any agglomeration and to break the surface tension that may cause aggregates to float during rotation. Also, to optimize growth and uniformity of the size and shape of the cell aggregates, the cell aggregates should not be removed from the rotating platform or apparatus for any long period of time. Thus, hES cell aggregates can be produced from hES cell adherent cultures which have been well established in the art.

The hES cell aggregates can now be directly differentiated as aggregates in suspension and substantially as described in D'Amour et al. 2006, supra. Briefly, the StemPro® (minus Y27632) media or any of the described media supplemented with xeno-free KSR was removed from the wells (e.g. aspirated), and the hES cell aggregates washed with 5 mL of RMPI with no serum (Cat. 15-040-CV; Mediatech), Penicillin/Streptomycin (Invitrogen) and Glutamax (Invitrogen) (also referred to as RMPI, Pen/Strep and Glutamax media), 0% FBS, 1% PenStrep, 1% Glutamax. The 6-well dish was then placed back on the rotating platform for 1-2 minutes before the wash media was removed. This was repeated at least twice or until insulin and/or IGF-I has been sufficiently removed, because although necessary for maintenance of pluripotency and ES self renewal, the same factors are detrimental to controlled, synchronous, lineage-directed differentiation. Differentiation to all endoderm-lineages by adding and removing various exogenous mitogens was performed at 100 rpm substantially as described by D'Amour et al. 2006, supra, and described in more detail below.

Differentiation to Definitive Endoderm (Stage 1)

Human ES cell aggregates were differentiated in RPMI, 100 ng/mL activin A and varying concentrations of FBS (US Defined FBS, HyClone, catalogue no. SH30070.03), and 25 ng/mL-75 ng/mL Wnt3a for the first day, and in RMPI, Pen/Strep and Glutamax media, further containing 100 ng/mL activin A and varying concentrations of FBS (HyClone) for the second and third days (d0 to d2). In most differentiation experiments FBS concentrations were 0% for the first 24 hours (d1), 0.2% for the second 24 hours (d2), and 0.2% for the third 24 hours (d3), if a three day stage 1 protocol was used or desired. Preferably a two day stage 1 protocol is performed.

QPCR analysis of hES-derived cell aggregates in suspension culture at the end of a 2 day stage 1 protocol indicated highly efficient directed differentiation of hES aggregates to definitive endoderm as compared to the adherent plate controls. Cell aggregates were formed at 100 rpm, 120 rpm and 140 rpm. In some experiments hES-derived aggregates were transferred to bioreactors (spinner flasks) prior to differentiation. Adherent hES cell cultures as well as hES cell cultures differentiated to definitive endoderm cells were used as controls. Increased expression levels of SOX17 and FOXA2 were observed in the cell aggregates in suspension and the adherent culture and as compared to undifferentiated hES cell aggregates and adherent plate controls. See FIG. 22, panels C(SOX17) & D (FOXA2) at stage 1 (d2). Moreover, expression levels of SOX7, a gene associated with contaminating extra-embryonic and visceral endoderm, was significantly reduced in the definitive endoderm cell aggregates as compared to the definitive endoderm adherent plate controls. See FIG. 22, panel L at stage 1 (d2).

Flow cytometric analyses using CXCR4 and HNF3beta (FoxA2) protein indicated that directed differentiation of ES cell-derived aggregates resulted in aggregates that were at least 97% CXCR4-positive, at least 97% HNF3beta-positive and at least 95% CXCR4/HNF3beta co-positive.

To further evaluate the efficiency of hES cell aggregate differentiation, cryosections of ES-derived cell aggregates were examined for SOX17 and HNF3beta expression using immunocytochemistry and confocal microscopy. Image analysis of the stained cryosections demonstrated that greater than ~90% of all cells at the end of stage 1 (definitive endoderm cells) expressed HNF3beta and/or SOX17.

These data all indicate that highly efficient differentiation of ES cells as cell aggregates can be achieved, and based on the expression levels of signature definitive endoderm markers, the methods for producing definitive endoderm as described herein are more efficient compared to differentiation of adherent plate cultures.

Differentiation to PDX1-Negative Foregut Endoderm cells (Stage 2)

Human definitive endoderm cell aggregates from stage 1, were briefly washed in PBS+/+ and then differentiated in RMPI, Pen/Strep and Glutamax media, further containing 2% FBS, and 25 ng-50 ng/mL KGF (R&D Systems) for another 2 or 3 days. In some experiments 5 µM SB431542 (Sigma Aldrich, Inc.) or 2.5 µM TGF-beta Inhibitor IV (Calbiochem) was added during the first day of stage 2; and alternatively with RMPI, Pen/Strep and Glutamax media/0.2% FBS/ITS (insulin/transferrin/selenium).

QPCR analysis was performed substantially as discussed above. Increased expression levels of HNF1beta and HNF4alpha were observed in the cell aggregate cultures as compared to the adherent plate controls. See FIG. 22, panels E (HNF1B) and panel O (HNF4alpha) at stage 2 (d5). Methods of producing the specific stage 0, 1, 2 and 5 hES or hES-derived cell aggregates (or "dAggs" for differentiated aggregates) were slightly modified in panel O. Differentiated cell aggregates in this context refers to differentiated hES or hES-derived cell aggregate cultures which were initiated from adherent plate control cultures, of the corresponding stage, from which they were derived. For example, at stage 1, differentiated cell aggregates ("dAggs") suspension cultures were started from a stage 0 adherent plate and incubated in any of the media described herein for about 24 h on a rotating platform at 100 rpm to 140 rpm. These differentiated cell aggregates were then further differentiated to stage 1 definitive endoderm cells with the corresponding adherent plate controls. FIG. 22, panel O, shows that there is no significant HNF4alpha (HNF4A) expression in either the stage 1 differentiated cell aggregates or the adherent plate controls. In contrast, a similar method was carried out for stage 2 samples and produced increased expression level of HNF4A. HNF4A expression is also robust for stage 5 samples.

Moreover, expression levels of genes associated with extra-embryonic endoderm (SOX7) was significantly reduced in the hES-derived cell aggregate cultures as compared to the plate controls. See FIG. 22, panel L at stage 2 (d5). Thus, demonstrating that directed differentiation of PDX1-negative foregut endoderm cells by way of cell aggregates in suspension culture removes extra-embryonic endoderm contaminants.

Taken together, these data all indicate that directed differentiation of hES cell aggregates is highly efficient, and based on the expression levels of signature PDX1-negative foregut endoderm markers, the methods for producing foregut endoderm cells are improved as compared to differentiation with adherent plate cultures.

Differentiation to PDX1-Positive Foregut Endoderm Cells (Stage 3)

Foregut endoderm cells from stage 2 were further differentiated in RMPI with no serum, Glutamax (Invitrogen) and penicillin/streptomycin (Invitrogen), plus 0.5×B27-supplement (Invitrogen/Gibco), and either 1 µM to 2 µM retinoic acid (RA, Sigma) and 0.25 nM KAAD-cyclopamine (Toronto Research Chemicals) for 1 to 3 days; or 1 µM to 2 µM retinoic acid, 0.25 nM KAAD-cyclopamine plus 50 ng/mL noggin (R&D systems). Alternatively, 0.2 µM to 0.5 µM RA and 0.25 nM KAAD-cyclopamine was added to the media for one day. Still, in some experiments no RA or KAAD-cyclopamine was added to the cell aggregate cultures. Still in other embodiments effective concentrations of 0.1-0.2% BSA were added.

Increased expression levels of PDX1 were observed in hES-derived cell aggregates as compared to the adherent plate controls. See FIG. 22, panel F (PDX1) at stage 3 (d8). Moreover, expression levels of genes associated with extra-embryonic endoderm (50×7) and visceral endoderm (AFP) was significantly reduced in the hES-derived cell aggregate cultures as compared to the plate controls. See FIG. 22, panel L (SOX7) and panel N (AFP) at stage 3 (d8). Thus, demonstrating that directed differentiation to produce PDX1-positive foregut endoderm cells by way of cell aggregates in suspension culture removes extra-embryonic endoderm contaminants.

Taken together, these data indicate that the directed differentiation of hES cell aggregates is highly efficient, and based on the expression levels of signature PDX1-positive endoderm markers, the methods for producing PDX1-positive endoderm are improved as compared to the adherent culture controls as compared to the adherent plate controls.

Differentiation to Pancreatic Endoderm or Pancreatic Endocrine Progenitor Cells (Stage 4)

At stage 4, RA is withdrawn from the stage 3 cultures, the cultures were washed once with DMEM plus B27 (1:100 Gibco), and then the wash is replaced with either DMEM+1XB27 supplement alone or with any combinations of or any or all of the following factors: Noggin (50 ng/mL), FGF10 (50 ng/mL), KGF (25-50 ng/mL), EGF (25-50 ng/mL), 1-5% FBS for 4-8 days. In cases where no RA was added, noggin at 30-100 ng/mL (R&D systems) was added to the media for 1-9 days. Further, in some experiments FGF10 at 25 ng/mL was also added.

Increased expression levels of NKX6.1 and PDX-1 and PTF1A was observed in the ES cell-derived aggregates and the corresponding adherent plate controls. See FIG. 22, panel F (PDX1), panel G (NKX6.1) and panel P (PTFA1) at stage 4 (d11). In FIG. 22, panel P, the bar chart depicts results from methods for determining whether hES and/or hES-derived cell aggregates in suspension were affected by the number of cells in an adherent plate culture from which they were derived. Although Panel P only shows results for $1 \times 10^7$ cells, cell-aggregate suspension cultures were started from various seed counts, e.g. $1 \times 10^6$ to $2 \times 10^7$ cells. All were substantially similar and produced cell aggregate cultures which had good viability and little cell death. For example, at stage 4, differentiated cell aggregate suspension cultures ("dAggs") were started from a d5 (stage 2) adherent plate, and again incubated in any of the media described herein for about 24 h on a rotating platform at 100 rpm to 140 rpm. These differentiated cell aggregates were then further differentiated to stage 4 pancreatic endoderm type cells expressing PTF1A (panel P). As compared to the corresponding stage 4 adherent plate controls, there was increased expression of PTF1A.

Moreover, expression levels of AFP were significantly reduced in the hES-derived cell aggregates as compared to the adherent plate controls. See FIG. 22, panel N at stage 4 (d11). Thus, demonstrating that directed differentiation to produce PDX1-positive pancreatic endoderm cells by way of cell aggregates in suspension culture removes visceral endoderm contaminants.

Flow cytometric analyses using NKX6.1, HNF3beta and Chromogranin (CHG) protein indicated that directed differentiation of hES-derived cell aggregates resulted in cell aggregates that were at least 53% CHG-positive, at least 40% NKX6.1 and CHG co-positive, and small amount of HNF3beta and other types of cells.

Cryosections of hES-derived aggregates were examined for NKX6.1, PDX1 and NKX2.2 expression using immunocytochemistry and confocal microscopy at the end of stage 4. Image analysis indicated highly efficient differentiation of aggregated cells to pancreatic endoderm (or PDX1-positive pancreatic endoderm), with nearly all cells expressing PDX1 and a large populations of cells expressing NKX6.1 (approximately 40% of cells) and/or NKX2.2 (approximately 40% of cells).

Differentiation to Hormone Expressing Endocrine Cells (Stage 5)

For stage 5 differentiation, stage 4 differentiated cell aggregates were continued in either CMRL (Invitrogen/Gibco) or RMPI, Pen/Strep and Glutamax media, and 0.5×B27-supplement. In some experiments media was also supplemented with human serum (Valley Biomedical) or fetal bovine serum at concentrations ranging from 0.2-5% during stage 5.

Again, similar to the cell types from the stages 2-4, increased expression of genes associated with the specific cell type was observed as compared to the adherent plate controls. For example, increased expression levels of hormones insulin (INS), glucagon (GCG) and somatostatin (SST) were observed. See FIG. 22, panel I (INS), panel J (GCG) and panel K (SST) at stage 5 (d15). Moreover, expression levels of AFP and ZIC1, a gene associated with ectoderm, was significantly reduced in the hES-derived cell aggregates as compared to the adherent plate controls. See FIG. 22, panel M (ZIC1) and panel N (AFP) at stage 5 (d15). Thus, demonstrating that directed differentiation to produce pancreatic endocrine cells by way of cell aggregates in suspension culture removes ectoderm and visceral endoderm contaminants.

Production of hES-derived hormone expressing endocrine aggregate cells was confirmed by flow cytometric analyses on Day 23 of the described protocol. Aggregates were initially formed at 140 rpm in 5 mL DMEM/F12, alternatively comprising knockout serum replacement (KSR; Gibco/Invitrogen compare 0063 for consistency) or xeno-free KSR (Invitrogen) and then differentiated at 100 rpm. Analysis of NKX6.1, Chromogranin A, insulin, glucagon and somatostatin protein expression indicates that ES cell-derived aggregates are comprised of ~20% NKX6.1+/Chromogranin A– pancreatic epithelium and ~74% Chromogranin A+ endocrine tissue. Moreover, 11% of the cells express insulin, 14% express glucagon and 11% express somatostatin. Of these, 68% of the insulin+ cells are single positive, 70% of the glucagon+ cells are single positive and 52% of the somatostatin-positive cells are single positive. This degree of single hormone positivity exceeds the values described for adherent cultures which were mostly polyhormonal cells.

To further evaluate the efficiency of aggregate differentiation to hormone expressing endocrine cells, cryosections of ES-derived aggregates were examined for glucagon, insulin and somatostatin expression using immunocytochemistry and confocal microscopy during stage 5. Image analysis of cryosections at 20× indicates highly efficient differentiation of aggregated cells to hormone positivity, with nearly all cells expressing glucagon, somatostatin or insulin. Also, in contrast to previous adherent culture experiments, a majority of the cells in the aggregate appear to express a single hormone, as occurs in vivo during development.

Example 19

Adherent Cultures from Various Stages can Form Cell Aggregates and Differentiate to Pancreatic Endoderm Type Cells The following demonstrates that production of hES-derived cell aggregates can be initiated not just from pluripotent hESC but cell aggregates can be initiated directly into a differentiation media (day 0 cell aggregates) as well as from differentiated or hES-derived cells, for example, cell aggregates can be produced from stages 1, 2, 4 and 5 or hES-derived cells.

Day 0 Cell Aggregates

Cell aggregates produced on the first day (d0) of stage 1: Adherent pluripotent hESC were grown, manually or enzymatically passaged, disassociated, counted, pelleted and the pellet resuspended to a final volume of about $1 \times 10^6$ cells/mL to $4 \times 10^6$ cells/mL in differentiation media base containing RMPI, Pen/Strep and Glutamax media, and further containing 100 ng/mL activin A, and 25 ng/mL-75 ng/mL Wnt3a, 0.2% of FBS (HyClone). This volume can be increased to >$4 \times 10^6$ cells/mL but may require more frequent feeding. Sometimes DNase was included at a concentration of 10-50 ng/mL. In some cases the ROCK inhibitor Y27632 (Axxora) was added to the cell suspension to a final concentration of 1-15 µM, typically 10 µM. Still in other cases about 1:2000 to 1:5000 of ITS (insulin/transferrin/selenium, Gibco) was added to the cultures. Both the Rho-kinase inhibitor and ITS were added to support cell survival. Resuspended cells were distributed equally into each well of a low binding 6-well dish substantially as described above, and placed on the rotating platform at 100 rpm to 140 rpm overnight. During this culturing period, cell aggregates of uniform size and shape were formed. Consequently, the higher density cultures effectively enriched or substantially enriched for PDX1-positive pancreatic endoderm or PDX-positive pancreatic progenitor type cells. Further details are provided in Example 21.

Cell aggregates produced on d0 of stage 1, were then fed up to 1-2× daily with further differentiation media containing RMPI, Pen/Strep and Glutamax media, and further containing 100 ng/mL activin A and 0.2% of FBS (HyClone) for the next 2-3 days. Subsequent steps (stages 2-5) of the protocol are substantially as described above for ES aggregates.

Stage 1—Day 2 to Day 3

Cell aggregates produced on d2-d3 of stage 1: Adherent hESC were grown and passaged substantially as described above and then differentiated to stage 1 substantially as described in D'Amour et al. 2006, supra.

Adherent cultures at the end of stage 1 (about d2 or d3 into the differentiation protocol; definitive endoderm type cells) were washed 1× with PBS–/– and disassociated to single cells with 2 mL of pre-warmed Accutase for about 2-5 minutes at 37° C. using a 1 mL or 5 mL pipet. Then 4 mL of 10% FBS in RMPI, Pen/Strep and Glutamax media was added and the single cell suspension filtered through a 40 micron blue filter (BD Biosciences) into a 50 mL conical tube. The cells were counted and pelleted (centrifuged) substantially as described above.

The cell pellet was then resuspended in RMPI, Pen/Strep and Glutamax media, further containing 2% FBS, plus DNase (50-100 µg/mL, Roche Diagnostics) and 100 ng/mL activin A. Alternatively the cell pellet was resuspended in RMPI, Pen/Strep and Glutamax media, plus 2% FBS, and DNase (50-100 µg/mL), 25 ng-50 ng/mL KGF (R&D Systems). In some experiments 5 µM SB431542 (Sigma Aldrich, Inc.) or 2.5 µM TGF-beta Inhibitor IV (Calbiochem) was included with the KGF). In some experiments Y27332 (10 µM) was included. Resuspended cells were distributed equally into each well of a low binding 6-well dish substantially as described above, and placed on the rotating platform at 100 rpm to 140 rpm overnight, during which time cell aggregates of uniform size and shape were formed.

Cell aggregates produced at the end of stage 1 were then further differentiated. Subsequent steps (stages 2-5) of the protocol are substantially as described above for ES aggregates above in Examples 17 and 18.

Stage 2—Day 5 to Day 6

Cell aggregates produced on d5-d6 at stage 2: Adherent hESC were grown and passaged substantially as described above and then differentiated to stage 2 substantially as described in D'Amour et al. 2006, supra. For stage 2, adherent cells from stage 1 were briefly washed in PBS+/+ and then further differentiated in RPMI supplemented with 2% FBS, Glutamax, penicillin/streptomycin, and 25 ng-50 ng/mL KGF (R&D Systems) for 3 days. In some experiments 5 µM SB431542 (Sigma Aldrich, Inc.) or 2.5 µM TGF-beta Inhibitor IV (Calbiochem) was added during the first day of stage 2.

Adherent cultures at the end of stage 2 (about d5 or d6 into the differentiation protocol; foregut type cells) were disassociated to single cells, counted and pelleted substantially as described above. The cell pellet was then resuspended in differentiation media containing DMEM, Pen/Strep and Glutamax media, further containing 1×B27-supplement and DNase (50-100 µg/mL, Roche Diagnostics) and no FBS or 1-2% FBS or 0.5%-10% human serum (hS) and either 1 µM to 2 µM retinoic acid (RA, Sigma) and 0.25 nM KAAD-cyclopamine (Toronto Research Chemicals); or 1 µM to 2 µM retinoic acid, 0.25 nM KAAD-cyclopamine plus 50 ng/mL noggin (R&D systems); or 0.25 nM KAAD-cyclopamine plus 100 ng/mL noggin; or 100 ng/mL noggin; or 0.2 µM to 0.5 µM RA and 0.25 nM KAAD-cyclopamine; or 0.2 µM to 0.5 µM RA and 0.25 nM KAAD-cyclopamine plus 50 ng/mL noggin. In some experiments Y27332 (10 µM) was included.

Resuspended cells were distributed equally into each well, and placed on the rotating platform at 100 rpm to 140 rpm overnight, during which time cell aggregates of uniform size and shape were formed.

The cell aggregates produced at the end of stage 2 were further differentiated on the rotating platform and fed 1-2× daily for 0-2 additional days with DMEM, Pen/Strep and Glutamax media, further containing 1×B27-supplement either 1 μM to 2 μM retinoic acid (RA, Sigma) and 0.25 nM KAAD-cyclopamine (Toronto Research Chemicals); or 1 μM to 2 μM retinoic acid, 0.25 nM KAAD-cyclopamine plus 50 ng/mL noggin (R&D systems); or 0.25 nM KAAD-cyclopamine plus 100 ng/mL noggin; or 100 ng/mL noggin; or 0.2 μM to 0.5 μM RA and 0.25 nM KAAD-cyclopamine; or 0.2 μM to 0.5 μM RA and 0.25 nM KAAD-cyclopamine plus 50 ng/mL noggin.

Cell aggregates produced at the end of stage 2 were then further differentiated to stages 3, 4 and 5 substantially as described above.

Stages 4 and 5—Day 10 to Day 30

Cell aggregates produced on d10-d14 at stage 4: Again, adherent hESC were grown and passaged substantially as described above and then differentiated to stage 2 substantially as described above and in D'Amour et al. 2006, supra.

For stage 3, adherent cells from stage 2 were further differentiated in DMEM, Pen/Strep and Glutamax media, further containing 1×B27-supplement, and either 1 μM to 2 μM RA and 0.25 nM KAAD-cyclopamine for 1 to 3 days. In other cases, 50 ng/mL noggin was added along with the RA and KAAD-cyclopamine. Alternatively, 0.2 μM to 0.5 μM of RA and 0.25 nM of KAAD-cyclopamine was added to the media for just one day. Still, in other experiments no RA or KAAD-cyclopamine was added on any day. At stage 4, cells were fed 1-2× daily with DMEM supplemented with Glutamax, penicillin/streptomycin, and 1×B27-supplement. Stage 4 cells can be further differentiated to stage 5 cells as already described in Examples 17 and 18.

Adherent cultures at either stage 4 (about d10-d14 into the differentiation protocol; pancreatic epithelial and endocrine type cells) or stage 5 (about day 16 to day 30 into the differentiation protocol; endocrine precursor and endocrine cells) were similarly dissociated into single cells, counted, and pelleted. The cell pellet was then resuspended in DMEM CMRL supplemented Pen/Strep and Glutamax, and 1×B27-supplement and DNase (50-100 μg/mL, Roche Diagnostics) and 0-2% FBS. In some experiments Y27332 (10 μM) was included which supported cell survival. Cells were equally distributed into 6-well plates and placed on a rotating platform at 100 rpm to 140 rpm form 4 hours to overnight substantially as described above.

Furthermore, the cell aggregates produced at stage 2 and at stage 5 as in Examples 17-19 were effectively enriched for pancreatic cell types as compared with adherent plate cultures from which they were derived. For example, in one typical experiment cell aggregates produced at stage 2 and analyzed by flow cytometry at stage 4 consisted of at least 98% pancreatic cell types (73% Chromogranin A positive endocrine cells and 25% NRx6.1 positive pancreatic endoderm (PE)), and 2% non-pancreatic cell types; whereas the adherent plate cultures from which the cell aggregates were derived consisted of about 73% pancreatic cell types (33% Chromogranin A positive endocrine cells and 40% NRx6.1 positive PE), and 27% non-pancreatic cell types. Thus, aggregation at stage 2 can effectively enrich for progenitors that give rise to pancreatic cell-types, and deplete for non-pancreatic cell types.

Similarly, in a typical experiment, cell aggregates produced at stage 5 and analyzed by flow cytometry consisted of at least 75% Chromogranin A positive endocrine cell types, whereas the adherent plate culture from which the cell aggregates were derived consisted of about 25% Chromogranin A positive endocrine cell types. Hence, aggregation at stage 5 can effectively enrich pancreatic endocrine cells.

The methods described herein, therefore, provide methods for improving not only efficiency of directed-differentiation of hESC in cell aggregate suspensions, but also provides methods for reducing hES-derived pancreatic cell types (or aggregates) having contaminant populations (e.g. ectoderm, trophectoderm, visceral endoderm, and extra-embryonic endoderm) and at the same time enrichment of pancreatic cell types (e.g. pancreatic endoderm and endocrine cells).

Example 20

Cell Density Effects hES Cell Differentiation Outcome

The following demonstrates that variations in cell densities effect differentiation outcomes within a given media and growth factor condition. The differentiation efficiency outcomes which result from adjustments in cell density reflects varying concentrations of endogenously produced signaling molecules and the concentration dependent affect of these molecules in influencing cellular differentiation.

Human ES cell aggregates and hES-derived cell aggregates, including d0 cell aggregates produced directly in differentiation media, were generated substantially as described above. After about five (5) days of differentiation through stages 1 and 2, the differentiating cell aggregates were pooled and re-aliquoted into individual wells at different seeding densities, e.g., a 28 mL suspension of foregut endoderm stage cell aggregate suspension was seeded or re-aliquoted at 4, 6, 8 or 10 mL per well (a 2.5-fold range of cell densities). This cell distribution was carried out in duplicate and one set of wells was fed with a stage 3 media (DMEM/PenStrep/Glutamax+1% B27 supplement (vol/vol)+0.25 uM KAAD-cyclopamine+3 nM TTNPB) containing noggin at 50 ng/mL and the other set of wells contained noggin at 25 ng/mL. Stage 3 proceeded for 3 days with daily media exchange. Cell samples were taken in duplicate for real-time QPCR analysis at the end of the three days of stage 3 (or about day 8) and again at after stage 4 (or about day 14).

Figure 24A:
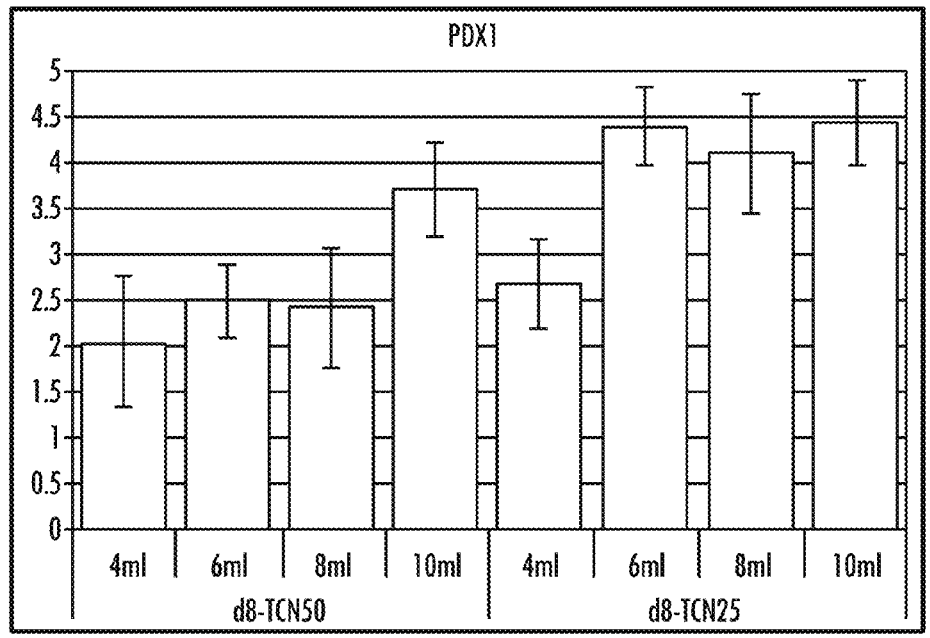
FIGS. 24 A-D are bar charts showing the expression patterns of marker genes PDX1 (panel A) NKX6.1 (panel B), NGN3 (panel C) and NKX2.2 (panel D) in hES-derived cells in relationship to the cell density of the hES cell cultures from which they were derived.
Figure 24B:
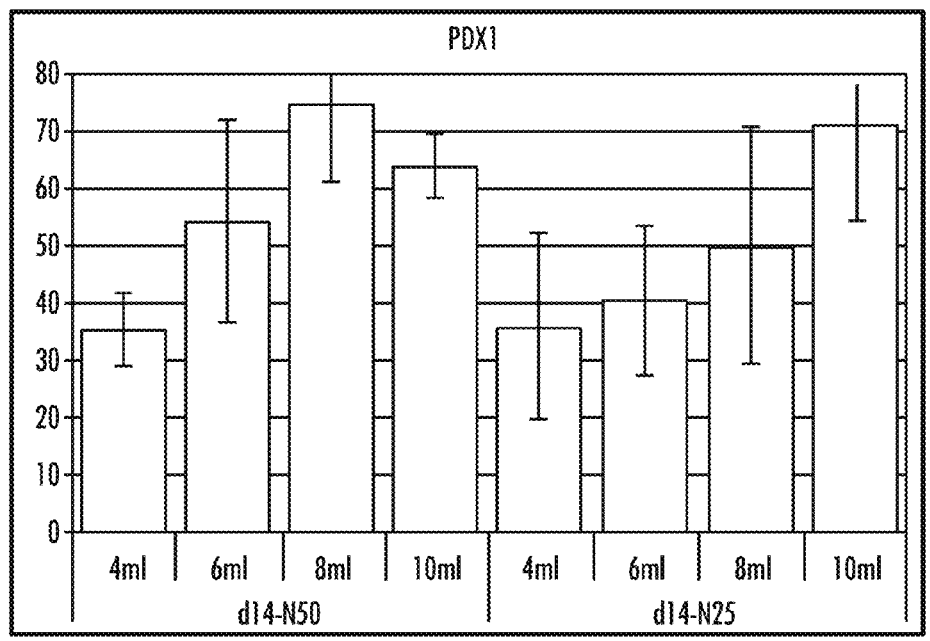
Figure 24C:
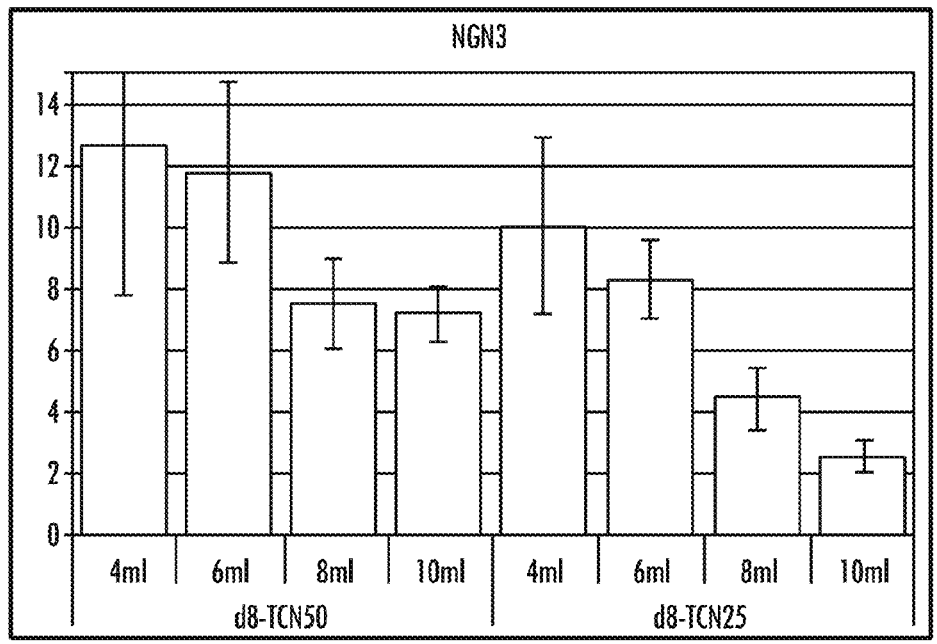
Figure 24D:
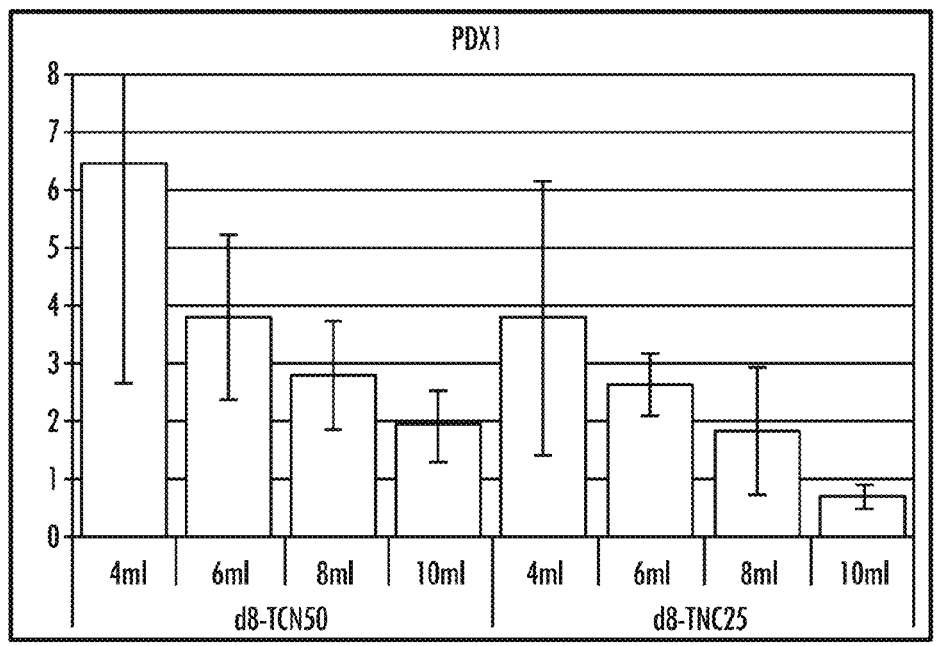

The cell density and noggin concentration used during stage 3 had different effects on the expression of those genes which are indicative of pancreatic endoderm progenitors and/or endocrine progenitors or precursors. Briefly, there is a linear relationship between increase in cell density and a corresponding increase in pancreatic progenitor cell types (e.g., pancreatic endoderm, pancreatic epithelium, PDX1-positive pancreatic endoderm). For example, after stage 3 (or day 8), an increase in cell density had a corresponding increase in the cell numbers of pancreatic progenitors as indicated by enhanced gene expression of PDX1 and NKX6-1. See FIGS. 24A & 24B. In contrast, there was an inverse relationship between increase in cell density and a corresponding reduction in endocrine progenitor cell types after stage 4 (or day 14). For example, as the cell density decreased there was reduced expression of at least NGN3 and NKX2-2 after stage 3 (or day 8). See FIGS. 24C & 24D.

Yet, lower concentrations of noggin (e.g., 25 ng/mL) at any given cell density resulted in reduced endocrine progenitor cell types as indicated by reduced expression of NGN3 and NKX2-2. See FIGS. 24C & 24D. This cell density independent effect of noggin in the cell cultures suggests that endogenously produced BMP signals from the cells are antagonized by the exogenously added noggin. The impact of endogenously produced signals on differentiation outcome is likely not limited to just BMP, but other growth factors and/or agents secreted by the cells into the medium can have similar or contrasting effects, alone or in combination with exogenous growth factors and/or agents.

Example 21

Optimization of Cell Aggregate Suspension Cultures to Generate Enriched Pancreatic Endoderm or Endocrine Cell Types The cell composition of hES-derived cell aggregate populations is optimized for certain cell types by controlling the concentration of various growth factors and/or agents. The pancreatic cell compositions described herein were hES-derived cell aggregate suspensions which were made from single cell suspension cultures, which were derived from hES cell adherent cultures, d0 cell aggregates (cell aggregates initiated from hES adherent cultures but directly into a differentiation media and not a pluripotent stem cell media), or from hES-derived cell adherent cultures at various stages of differentiation substantially as described in the previous examples. During stage 4, cell aggregates were exposed to different concentrations of the factors: NOGGIN (N), KGF (K), FGF10 (F), and EGF (E). The cell composition of the differentiated hES cell aggregates was assessed by flow cytometry analysis using a panel of markers including CHGA, NKX6.1, and PDX1. The total percentage of endocrine cells, pancreatic endoderm cells, PDX1+ endoderm cells, and non-pancreatic cells in any cell population is shown in Table 6.

The data in Table 6 demonstrates that by controlling the concentration and ratios of certain growth factors, the resulting composition can be optimized for certain cell types. For example, the percentage of pancreatic endoderm type cells was increased as compared to endocrine type cells by lowering the concentration of KGF and EGF (e.g., K(25)E(10) and 71% vs. 22.1%). In contrast, high concentrations of KGF and EGF and inclusion of Noggin and FGF10 (e.g., N(50)F(50)K(50)E(50)) decreased the number of pancreatic endoderm type cells, the total number being comparable to that of endocrine type cells (e.g., 39.6% vs. 40.1%). Noggin and KGF in higher concentrations (e.g., N(50)K(50)) or not adding growth factor increased the population of endocrine type cells in the resulting population as compared to pancreatic endoderm cell types. Also, the percentage of non-pancreatic cell types (i.e. non PDX1-positive type cells) can be significantly reduced by reducing the levels of KGF and EGF (e.g., K(25)E(10); 1.51%) or not adding any growth factor (1.53%).

Thus, Table 7 clearly demonstrates that at least varying the concentrations of different growth factors in the culture medium at certain stages of differentiation (e.g., stage 4) significantly increases and/or decreases certain populations of pancreatic endoderm, endocrine, PDX1-positive endoderm or non-pancreatic cell types.

TABLE 7

The effects of growth factors on cell composition

| Aggregation Stage | Factors in Stage 4 Media (ng/mL) | Endocrine CHGA+ | Pancreatic Endoderm CHGA- NKX6.1+ PDX1+ | PDX1+ Endoderm CHGA- NKX6.1- PDX1+ | Non-Pancreatic CHGA- NKX6.1+/- PDX1- | Total |
|---|---|---|---|---|---|---|
| ESC | K(25)E(10) | 22.1 | 71.0 | 3.0 | 4.0 | 100.1 |
| ESC | K(25)E(10) | 29.0 | 67.1 | 2.37 | 1.61 | 100.0 |
| Stage 1 Day 0 | K(25)E(10) | 25.4 | 68.9 | 2.87 | 2.01 | 99.2 |
| Stage 1 Day 0 | N(50)K(50)F(50)E(50) | 40.1 | 39.6 | 13.30 | 6.85 | 99.9 |
| Stage 1 Day 0 | None added | 69.4 | 27.4 | 1.46 | 1.53 | 99.8 |
| Stage 1 Day 0 | N(50)K(50) | 52.2 | 30.4 | 13.9 | 3.48 | 99.9 |
| Stage 1 Day 0 | K(25)E(10) | 38.8 | 50.8 | 2.17 | 8.22 | 100.0 |
| Stage 2 Day 5 | N(50)K(50) | 42.3 | 42.3 | 12.2 | 3.20 | 99.9 |
| Stage 2 Day 5 | K(25)E(10) | 28.3 | 59.4 | 7.36 | 4.97 | 100.0 |

Still other methods exist for enriching or purifying for particular hES-derived cells types as described in U.S. patent application Ser. No. 12/107,020, entitled METHODS FOR PURIFYING ENDODERM AND PANCREATIC ENDODERM CELLS DERIVED FROM HESC, filed Apr. 8, 2008, which is herein incorporated in its entirety by reference. This application describes methods for enriching various hES-cell types including all the cell types resulting in each of stages 1, 2, 3, 4 and 5 as described in D'Amour et al. 2005, supra and 2006, supra. The application uses various antibodies including but not limited to CD30, CD49a, CD49e, CD55, CD98, CD99, CD142, CD165, CD200, CD318, CD334 and CD340.

Methods for enriching the hES-derived cells or cell aggregates are not limited to methods employing antibody affinity means, but can include any method which is available to or will be well known to one of ordinary skill in the art that allows for enrichment of a certain cell type. Enrichment can be achieved by depleting or separating one cell type from the another cell type or culture.

Example 22

Cell Aggregate Suspensions of Pancreatic Endoderm Mature In Vivo and are Responsive to Insulin To demonstrate that the methods for making and manufacturing cell aggregate suspensions as described herein provides pancreatic progenitor cells which function in vivo, the above hES-derived cell aggregates in Examples 17-21 (e.g., PDX1-positive endoderm, pancreatic endoderm, pancreatic epithelium, endocrine precursors, endocrine cells, and the like) have been transplanted into animals. Methods of transplantation into normal and diabetic-induced animals, determination of in vivo glucose responsiveness of the animals and therefore insulin production of the mature transplanted cells in vivo, were performed substantially as described in Kroon et al. 2008, supra and U.S. patent application Ser. No. 11/773,944, entitled METHODS OF PRODUCING PANCREATIC HORMONES, filed Jul. 5, 2007, which are incorporated herein in their entireties. Substantially similar levels of human C-peptide were observed in the sera of these animals at similar time periods as indicated in Kroon et al. 2008, supra and U.S. patent application Ser. No. 11/773,944, supra.

The methods, compositions, and devices described herein are presently representative of preferred embodiments and are exemplary and are not intended as limitations on the scope of the invention. Changes, alternatives, modifications and variations therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

It is appreciated that certain features of the invention, which are, for clarity described in the context of the separate embodiments, may also be provided in combination in a single embodiment. For example, methods for making hES-derived cell aggregates in suspension can be generated and optimized to produce any endoderm lineage cell type, e.g., a pancreatic lineage type cell, a liver lineage type cell, an epithelial lineage type cell, a thyroid lineage cell and a thymus lineage cell, and therefore is not limited to the hES-derived cell types specifically described therein. Conversely, various features of the invention, which are, for brevity, described in the context of a single embodiment, may also be provided separately or in any suitable subcombination. For example, it is apparent to one skilled in the art that the described methods for generating hES and hES-derived cell aggregates from adherent plate cultures or from suspension, from undifferentiated adherent plate cultures or from suspension, and from differentiated adherent plate cultures or from cell aggregates in suspension are just exemplary but that a combination of the methods may also be employed.

Example 23

Cryopreservation and Banking of Human Pluripotent Stem Cells and Pancreatic Progenitor Cells Adherent hES cell cultures were harvested according to the described passaging protocol described in Example 24, pooled and counted. Cell pellets were re-suspended in pre-warmed about 50% hESC culture medium (without growth factors)/50% human serum. An equal volume of about 80% hESC culture medium (without growth factors)/20% DMSO was added drop-wise, with swirling. 1 mL of cells was distributed to 1.8 mL cryovials for freezing at −80° C. in Nalgene Mr. Frosty containers for about 24 hours, before transferring to liquid $N_2$. Substantially similar methods were performed under cGMP.

The above methods describe cryopreservation of pluripotent or differentiable stem cells. Cryopreservation of cells differentiated from pluripotent stem cells, for example, pancreatic progenitor cells were previously described in detail in U.S. patent application Ser. No. 12/618,659, entitled ENCAPSULATION OF PANCREATIC LINEAGE CELLS DERIVED FROM HUMAN PLURIPOTENT STEM CELLS, filed Nov. 13, 2009, which application and related applications are incorporated herein by reference in their entireties.

Example 24

Adherent Culture, Passaging & Expansion of Undifferentiated Human Pluripotent Stem Cells in Various Culture Vessels Including Roller Bottles A major bottleneck for manufacture of an cell aggregate-based cell therapy product, in particular one derived from human pluripotent stem cells, is the formation of the 3-dimensional cellular aggregate in suspension. Specifically, the bottleneck is taking monolayer adherent pluripotent stem cells and converting them into pluripotent stem cell aggregates, i.e. suspension aggregate cultures. As described above, hES cell aggregates in 6-well trays can be formed, for example, and subsequently differentiated in either 6-well trays or other culture vessel formats, e.g. bioreactors, bottles and the like. The embodiments of the invention described in the following Examples, provides methods for growth, passage and expansion of pluripotent stem cells as cell aggregates in suspension as well as for differentiating the cell aggregates in roller bottles. See Example 25.

Culture and Expansion of Human Pluripotent Stem Cells.

Upon thaw, or at regular passaging, dissociated hESC were plated at 50,000 or 33,000 cells/cm² for three and four day growth cycles, respectively, in different cell culture vessels. hESC growth media (XF HA) consisted of DMEM/F12 containing GlutaMAX, supplemented with 10% v/v of Xeno-free KnockOut Serum Replacement, 1% v/v non-essential amino acids, 0.1 mM 2-mercaptoethanol, 1% v/v penicillin/streptomycin, 10 ng/mL heregulin-1β and 10 ng/mL activin A. On the day of plating only (one day treatment), cell attachment was facilitated by including about 10% (vol/vol) of non-heat inactivated human AB serum (Valley Biomedical) simultaneously with the addition of xeno-free culture medium as described previously. A standardized plating volume of 0.2 mL/cm² was used for different tissue culture plates, T-flasks and cell factories as described at least in Table 8 below. The volume of growth media used was increased for each additional day of feeding and is also indicated in Table 8.

TABLE 8

Culture & Expansion of adherent hES cell Cultures

| Vessel Type S.A. | 60 mm 19.6 cm² | T75 80 cm² | T175 175 cm² | Triple T175 525 cm² | 2-stack 1272 cm² | 5-stack 3180 cm² |
|---|---|---|---|---|---|---|
| Plating | 4 | 16 | 35 | 105 | 260 | 650 |
| d1 | 5.5 | 22 | 50 | 150 | 350 | 875 |
| d2 | 7 | 28 | 60 | 180 | 450 | 1100 |
| d3 | 8.5 | 35 | 80 | 240 | 550 | 1350 |

Volumes in mL; SA: surface area.

Passaging Human Pluripotent Stem Cells.

On the day of passaging, cultures were fed with fresh growth medium and cultured for 4-8 hours before dissociation. Cultures were washed with PBS (Life Technologies) and dissociated for 6 minutes at about 37° C. using pre-warmed ACCUTASE (Innovative Cell Technologies). In some experiments the ACCUTASE was added, and then immediately aspirated (i.e. less than 4-6 minutes), such that cell dissociation was achieved in the residual reagent, at a minimal working volume, which is preferred when working with certain culture vessels, including cell factories, to minimize the number of media exchange steps. After exposure to ACCUTASE, 3× volume of cold hESC media (without heregulin or activin) was added and the cells were dissociated and collected. Dissociated cells were gently collected using 3× volume of cold hESC media (without heregulin or activin), counted using a ViCell automated cell counter (BD Biosciences), or a hemocytometer, centrifuged for 5 minutes at 200×g and the cell pellet re-suspended in fresh growth medium at $1-10\times10^6$ cells/mL for subsequent plating under the same culturing conditions.

Table 8 describes a variety of culture vessels and media volumes that have been used, however, the skilled artisan will appreciate that other culture vessels not specifically described can be used for growth, passage, and expansion of human pluripotent stem cells based on the detailed descriptions described herein. For example, see Example 25 for methods of suspension differentiation in a roller bottle.

In some studies, the passaged hESCs were added to new, uncoated 6-well tray culture vessels, without cell attachment, and rotated to form aggregates, as described above. Typically, StemPro® hESC SFM medium (Life Technologies) supplemented with 10 ng/mL heregulin-1β and 10 ng/mL activin A, or XF-HA medium, was used for suspension culture of hESC. Cell culture was performed in humidified incubators at 37° C. and 8% $CO_2$.

In order to test the aggregation of pluripotent stem cells in a rolling bottle format, single cell suspensions of $10^6$ hESC/mL prepared substantially as described above for hESC aggregation from adherent hESC cultures or directly from vials of frozen cells that were thawed, washed and suspended in culture medium, were placed in different vessels, each with a tubular shape which could be rotated while placed on its side. 50 mL tubes containing 10 mL cell suspension and 150 mL bottles containing either 30 mL or 120 mL of cell suspension were placed in a hybridization oven at about 37° C. and rotated at about 5 rpm. Rotation was achieved using a built-in, variable speed, mechanical bottle rotator. In the initial studies, the ovens were not gassed with $CO_2$. For purposes of cell aggregation control, simultaneous studies were performed using 6-well trays. Based on aggregate diameter and morphology, pluripotent stem cell aggregates were formed successfully in the rolled bottle format and the control 6-well tray format. Pluripotent stem cell aggregates were also formed in previous experiments using plastic jars. These studies demonstrated that aggregation could proceed effectively in a vessel format that was completely different from rotational culture in 6-well trays, with respect to speed, vessel shape and fluid dynamics. Furthermore, this rolling bottle format would likely be scalable without substantial optimization of the methods described herein, to bypass a critical bottleneck area.

Example 25

Pluripotent Stem Cell Aggregation and Differentiation in Roller Bottles

Figure 25:
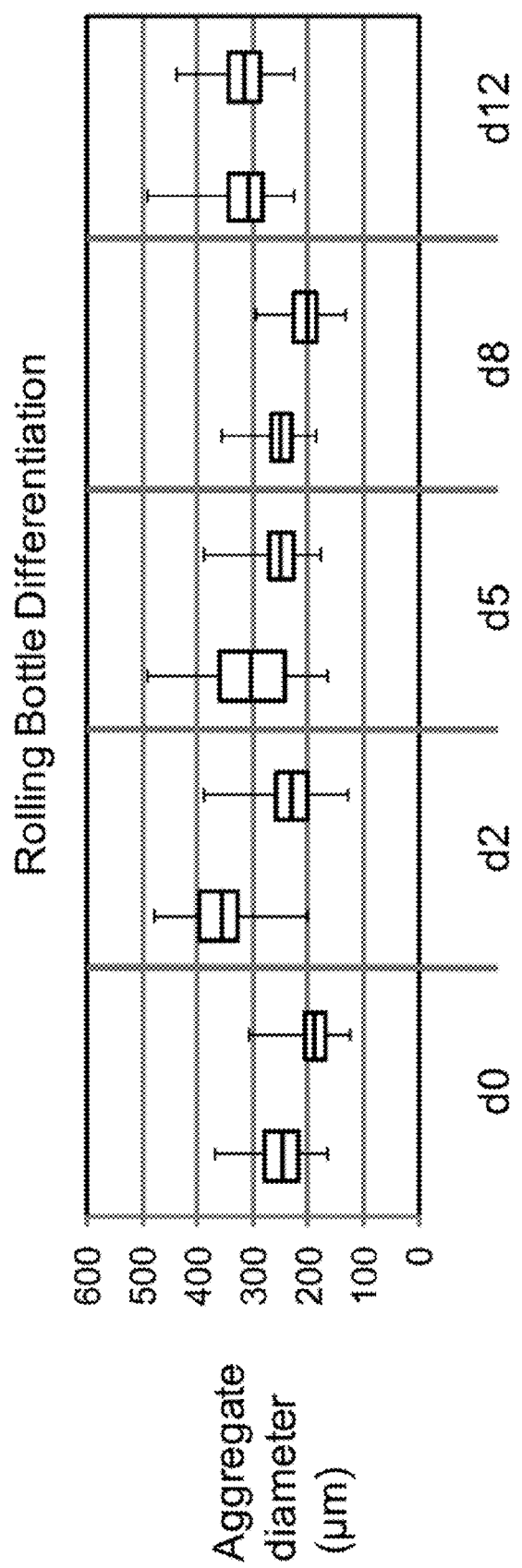
FIG. 25 is a chart showing cell aggregate diameters of pluripotent cells at day zero (d0) and differentiating cell aggregates at days 2, 5, 8 and 12 (d2, d5, d8 and d12, respectively). Cell aggregate sizes were measured and plotted showing the minimum, maximum, 2nd and 3rd quartile, and median. Each day shows the plot for cell aggregates formed from $1\times10^6$ cells/mL (left) and $2\times10^6$ cells/mL (right).
Figure 26A:
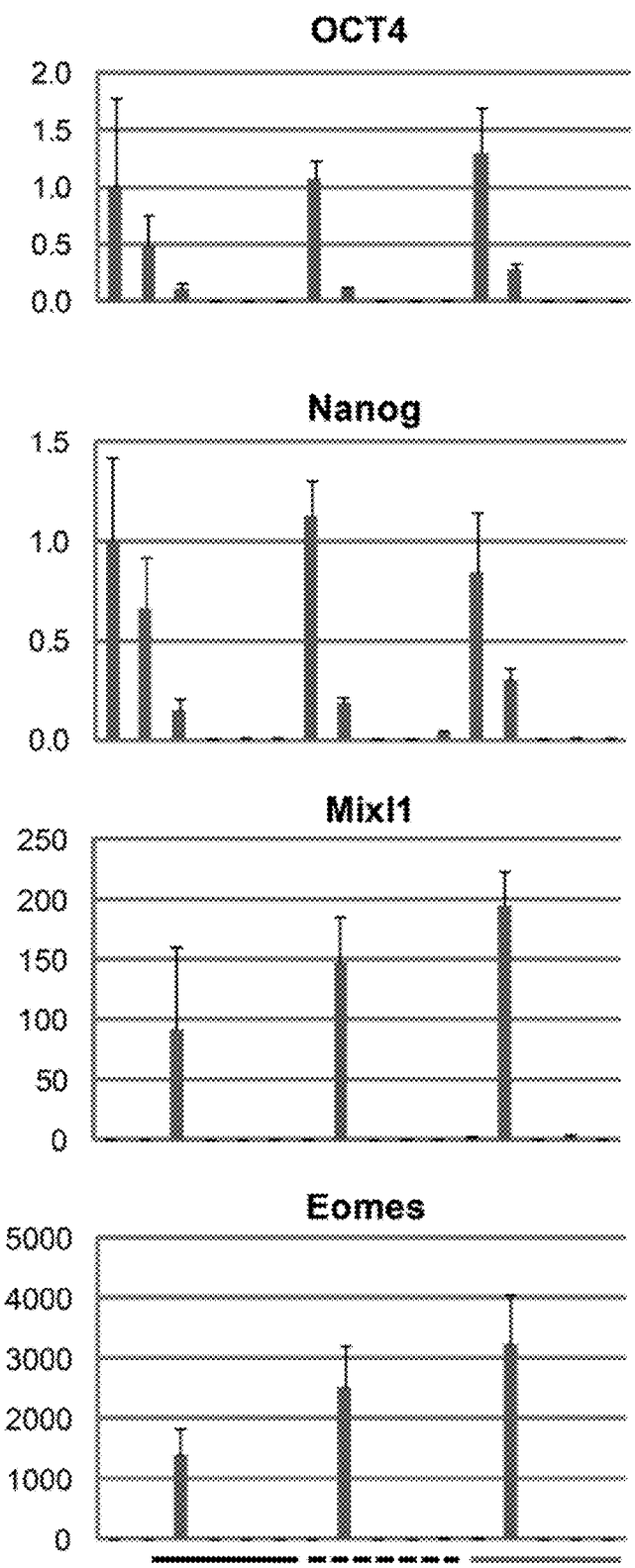
FIGS. 26A-D are bar charts showing the expression patterns of the various indicated marker genes in rolling bottle vessel format. The left sample of each chart represents day zero (d0) cell aggregates formed in 6-well trays (pluripotent cell marker control). The samples marked by bars represent (left to right): undifferentiated aggregates at day 0, and differentiating aggregates at days 2, 5, 8 and 12. Black bar, rolling bottles at $1\times10^6$ cells/mL; black dashed bar, rolling bottles at $2\times10^6$ cells/mL; grey bar, 6-well tray.
Figure 26B:
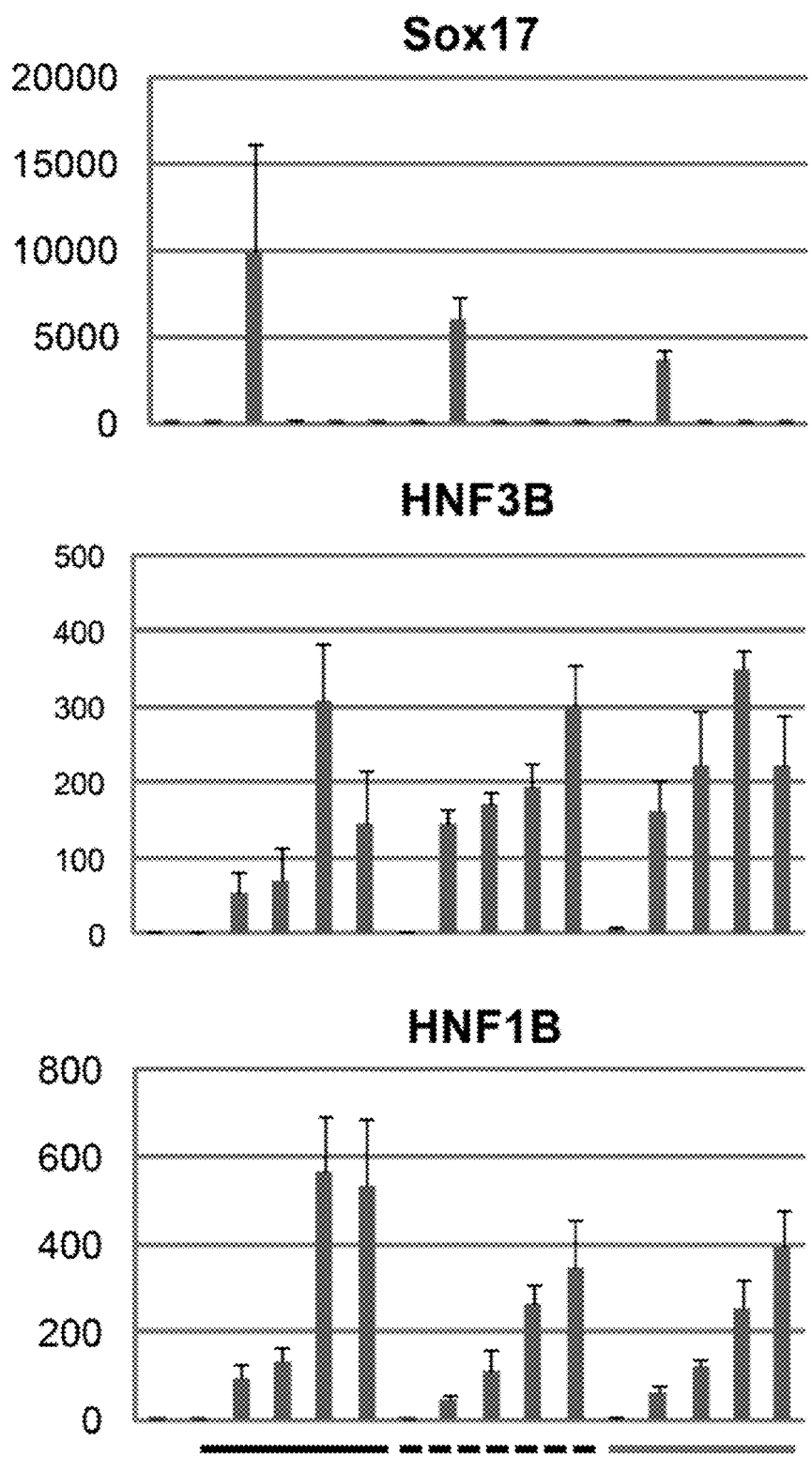
Figure 26C:
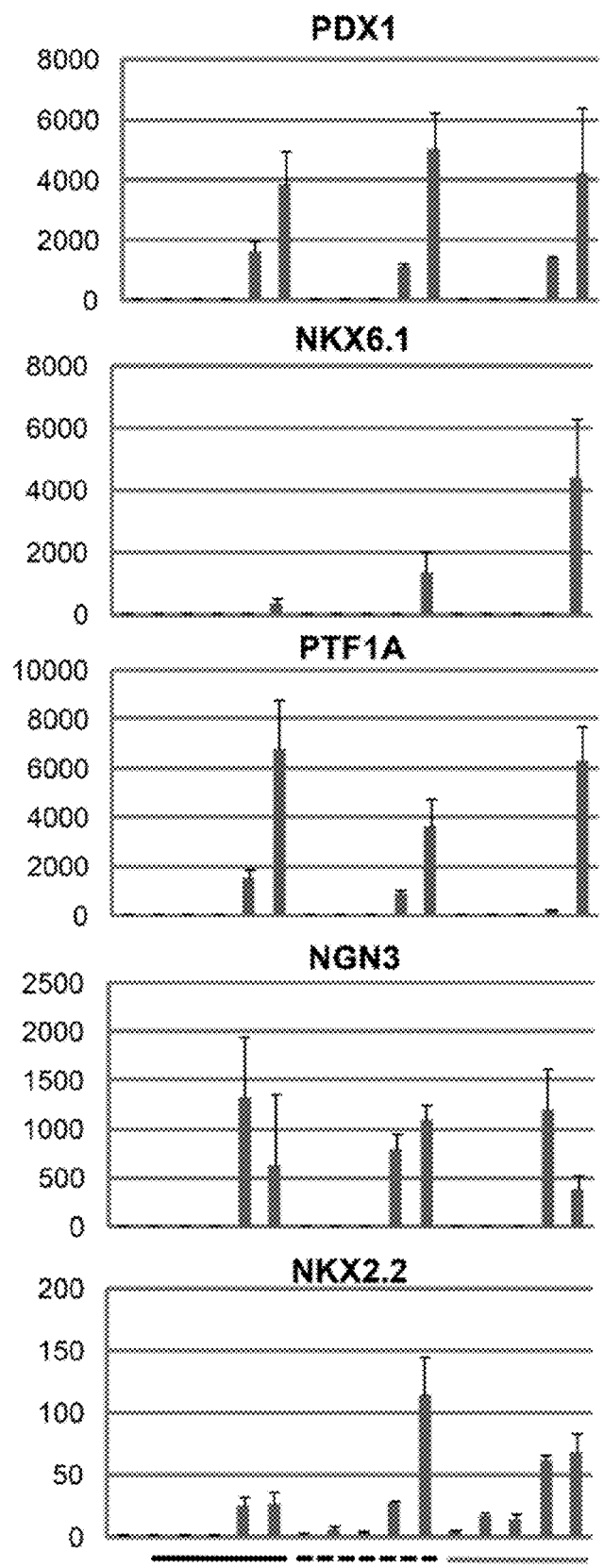
Figure 26D:
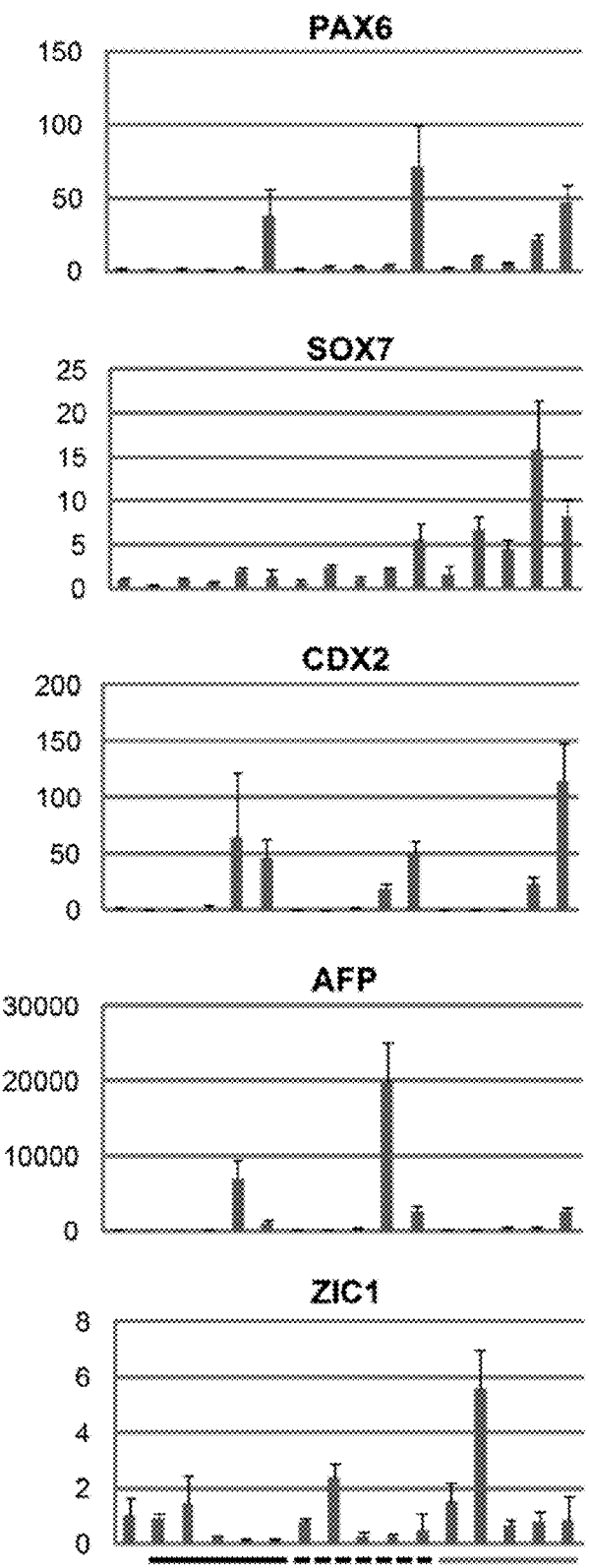

Human ES cells (Example 24) were aggregated in 150 mL bottles, and differentiated to pancreatic progenitors (or PEC) using Applicant's stages 1-4 differentiation protocol, as described above. 150 mL roller bottles were seeded with 120 mL cell suspension of either $1\times10^6$ cells/mL, or $2\times10^6$ cells/mL cell densities in StemPro® hESC SFM media or XF HA media; see Table 9. Stages 1-4 media conditions were substantially as that previously described (see Schulz et al. (2012) supra), which are summarized in Table 9. Rotation speeds of about 5 rpm, 8 rpm, 10 rpm or 12 rpm were tested throughout the hESC aggregation and Stages 1-4 differentiation and gassing with $CO_2$ was not incorporated into the incubator. Gassing with $CO_2$ may depend on what caps are used with the roller bottles, e.g., plug caps, vented or unvented caps. FIG. 25 shows the average diameter size of the cell aggregates formed during roller bottle aggregation and differentiation. Each box plot shows the minimum, maximum, 2nd and 3rd quartile, and median of the initial undifferentiated (d0) and differentiating cell aggregates (d2, d5, d8 and d12). Cell aggregate diameters were measured for both conditions. The average diameter of the cell aggregates initially formed was larger when the cultures were seeded at about $1\times10^6$ cell/mL as compared $2\times10^6$ cell/mL. However, at later stages of differentiation (e.g. Stages 3-4) the diameter sizes were comparable and indistinguishable. FIG. 25 also shows that there were no substantial differences between the differentiated cell aggregates that formed in the roller bottles and those that formed during previous suspension differentiation experiments performed in 6-well trays. Differentiation in the roller bottles also showed the typical expansion and contraction of aggregate diameter as previously observed in cultures performed in 6-well trays, bioreactors and the like (FIG. 25). The aggregate diameter was independent of the initial cell density and independent of the initial hESC or undifferentiated cell growth media composition. Briefly, the cell aggregates expanded during stages 1 and 2 (FIG. 25, d0 and d2), contracted during stage 3 (FIG. 25, d5), and expanded again during stage 4 (FIG. 25, d8 and d15). Throughout the differentiation, the cell aggregates did not show overt agglomeration (e.g., large aggregates of 300 microns or more) or shear-destruction.

TABLE 9

Media Conditions for Stages 1-4 Differentiation in 6-Well Trays and Roller Bottle

| Time point (day) | Stage (1-4) | Media Condition | Roller Bottle Speed (rpm) | 6-well tray Speed (rpm) |
| --- | --- | --- | --- | --- |
| d(−1) | hESC Aggregation | XF HA, SP | 5, 8, 10 or 12 | 95 |
| d0 | 1 | r0.2FBS-ITS1:5000 A100 | 5, 8, 10 or 12 | 95 |
| d1 | | r0.2FBS-ITS1:5000 A100 | 5, 8, 10 or 12 | 95 |
| d2 | 2 | r0.2FBS-ITS1:1000 K25 | 5, 8, 10 or 12 | 95 |
| d3 | | r0.2FBS-ITS1:1000 K25 | 5, 8, 10 or 12 | 95 |
| d4 | | r0.2FBS-ITS1:1000 K25 | 5, 8, 10 or 12 | 105 |
| d5 | 3 | db-CTT3 N50 | 5, 8, 10 or 12 | 105 |
| d6 | | db-CTT3 N50 | 5, 8, 10 or 12 | 105 |
| d7 | | db-CTT3 N50 | 5, 8, 10 or 12 | 105 |
| d8 | 4 | db-N50 K50 E50 | 5, 8, 10 or 12 | 105 |
| d9 | | db-N50 K50 E50 | 5, 8, 10 or 12 | 95 |
| d10 | | db-N50 K50 E50 | 5, 8, 10 or 12 | 95 |

TABLE 9-continued

Media Conditions for Stages 1-4 Differentiation in 6-Well Trays and Roller Bottle

| Time point (day) | Stage (1-4) | Media Condition | Roller Bottle Speed (rpm) | 6-well tray Speed (rpm) |
|---|---|---|---|---|
| d11 | | db-N50 K50 E50 | 5, 8, 10 or 12 | 95 |
| d12 | | db-N50 K50 E50 | 5, 8, 10 or 12 | 95 |

XF HA, DMEM/F12 containing GlutaMAX, supplemented with 10% v/v of Xeno-free KnockOut Serum Replacement, 1% v/v non-essential amino acids, 0.1 mM 2-mercaptoethanol, 1% v/v penicillin/streptomycin (all from Life Technologies), 10 ng/mL heregulin-1β (Peprotech) and 10 ng/mL activin A (R&D Systems);
SP, StemPro® hESC SFM (Life Technologies);
r0.2FBS: RPMI 1640 (Mediatech); 0.2% FBS (HyClone), 1x GlutaMAX-1 (Life Technologies), 1% v/v penicillin/streptomycin;
ITS: Insulin-Transferrin-Selenium (Life Technologies) diluted 1:5000 or 1:1000;
A100: 100 ng/mL recombinant human Activin A (R&D Systems);
W50: 50 ng/mL recombinant mouse Wnt3A (R&D Systems);
K25: 25 ng/mL recombinant human KGF (R&D Systems);
IV: 2.5 μM TGF-β RI Kinase inhibitor IV (EMD Bioscience);
db: DMEM HI Glucose (HyClone) supplemented with 0.5x B-27 Supplement (Life Technologies), 1x GlutaMAX-1 and 1% v/v penicillin/streptomycin;
CTT3: 0.25 μM KAAD-Cyclopamine (Toronto Research Chemicals) and 3 nM TTNPB (Sigma-Aldrich); N50: 50 ng/mL recombinant human Noggin (R&D Systems);
K50: 50 ng/mL recombinant human KGF (R&D Systems);
E50: 50 ng/mL recombinant human EGF (R&D Systems); 5, 8, 10, 12 rpm rotation speed were performed at either the hESC aggregation, at stages 1-4 differentiation, or both.

To examine gene expression throughout stages 1-4, Q-PCR was used to analyze the differentiations performed with $1\times10^6$ cell/mL vs. $2\times10^6$ cell/mL starting cell densities (FIG. 26). Although only certain genes are shown in FIG. 26, Applicant has previously described expression and non-expression of many genes in each of stages 1-4 in extensive detail. See e.g., U.S. Pat. No. 8,211,699, METHODS FOR CULTURING PLURIPOTENT STEM CELLS IN SUSPENSION USING ERBB3 LIGANDS, issued Jul. 3, 2012; U.S. Pat. No. 7,958,585, PREPRIMITIVE STREAK AND MESENDODERM CELLS, issued Jul. 26, 2011; U.S. Pat. No. 7,510,876, DEFINITIVE ENDODERM (CYTHERA.045A), issued on Mar. 31, 2009; U.S. Pat. No. 7,541,185, METHODS FOR IDENTIFYING FACTORS FOR DIFFERENTIATING DEFINITIVE ENDODERM, issued Jun. 2, 2009; U.S. Pat. No. 7,625,753, EXPANSION OF DEFINITIVE ENDODERM, issued Dec. 1, 2009; U.S. Pat. No. 7,695,963, METHODS FOR INCREASING DEFINITIVE ENDODERM PRODUCTION, issued Apr. 13, 2010; U.S. Pat. No. 7,704,738, DEFINITIVE ENDODERM, issued Apr. 27, 2010; U.S. Pat. No. 7,993,916, METHODS FOR INCREASING DEFINITIVE ENDODERM PRODUCTION, issued Aug. 9, 2011; U.S. Pat. No. 8,008,075, STEM CELL AGGREGATE SUSPENSION COMPOSITIONS AND METHODS OF DIFFERENTIATION THEREOF, issued Aug. 30, 2011; U.S. Pat. No. 8,178,878, COMPOSITIONS AND METHODS FOR SELF-RENEWAL AND DIFFERENTIATION IN HUMAN EMBRYONIC STEM CELLS, issued May 29, 2012; U.S. Pat. No. 8,216,836, METHODS FOR IDENTIFYING FACTORS FOR DIFFERENTIATING DEFINITIVE ENDODERM, issued Jul. 10, 2012; U.S. Pat. No. 7,534,608, METHODS OF PRODUCING PANCREATIC HORMONES, issued May 19, 2009; U.S. Pat. No. 7,695,965, METHODS OF PRODUCING PANCREATIC HORMONES, issued Apr. 13, 2010; U.S. Pat. No. 7,993,920 METHODS OF PRODUCING PANCREATIC HORMONES, issued Aug. 9, 2011; U.S. Pat. No. 8,129,182, ENDOCRINE PRECURSOR CELLS, PANCREATIC HORMONE EXPRESSING CELLS AND METHODS OF PRODUCTION, issued Mar. 6, 2012; U.S. patent application Ser. Nos 11/875,057, METHODS AND COMPOSITIONS FOR FEEDER-FREE PLURIPOTENT STEM CELL MEDIA CONTAINING HUMAN SERUM, filed Oct. 19, 2007; Ser. No. 12/618,659, ENCAPSULATION OF PANCREATIC LINEAGE CELLS DERIVED FROM HUMAN PLURIPOTENT STEM CELLS, filed Nov. 13, 2009; which are all incorporated herein by reference in their entireties. Only after obtaining a high degree of confidence in the differentiation methods did Applicant select a smaller set of markers as the signature markers to indicate and identify the various stages 1-4 cell populations as shown in FIG. 26.

FIG. 26 shows that cell aggregates differentiated in rolling bottle formats expressed the typical signature markers expected at each stage of differentiation, in agreement with differentiation studies performed simultaneously in 6-well trays (control, FIG. 26). Similarly, absence of expression of signature markers was observed where expected. For example, pluripotent stem cell markers such as OCT4 and Nanog were present at d0 for all culture conditions (FIG. 26A). Similarly, there was transient up-regulation of the mesendodermal markers MIXL1 and Eomes in both the roller bottle differentiations and that the 6-well tray differentiationss (FIG. 26, compare the black bar, blacked hatched bar, grey bars, respectively). Stage 2 cells produced definitive endoderm, which expresses SOX17 and HNF3β [FOXA2], similarly to that observed for stage 2 type cells differentiated in 6-well trays. Stage 4 type cells expressed PDX1 and NKX6.1 similarly to that observed for cultures differentiated in 6-well trays (FIG. 26, compare black bar, blacked hatched bar, grey bars, respectively). Lastly, expression of markers for off-target lineages was not substantially different in cultures differentiated in 6-well trays and 150 mL rolling bottles, indicating that control of differentiation remained tight in the rolling format. These markers included ZIC1 (ectoderm lineage), early expression PAX6 (neuronal lineage), SOX7 (extraembryonic endoderm), CDX2 (trophectoderm), and early expression of AFP (yolk sack).

TABLE 10a pPSC Differentiation in Large Roller Bottles

| Bottle Volume | Bottle Surface area | Aggregation Volume | Caps, Vented (V); Not-Vented (NV) | pellet volume d0 | % Incorporation d0 | Aggregate diameter (μm) |
|---|---|---|---|---|---|---|
| 1200 mL | 490 cm² | 275 mL | V | 1050 μL | 79.6 | 177 ± 23 |
| 1200 mL | 490 cm² | 275 mL | NV | 1090 μL | 78 | 167 ± 21 |

TABLE 10a-continued pPSC Differentiation in Large Roller Bottles

| Bottle Volume | Bottle Surface area | Aggregation Volume | Caps, Vented (V); Not-Vented (NV) | pellet volume d0 | % Incorporation d0 | Aggregate diameter (μm) |
|---|---|---|---|---|---|---|
| 2275 mL | 850 cm² | 580 mL | V | 2300 μL | 76 | 171 ± 26 |
| 6-well tray | — | 33 mL/tray | — | ~105 μL/tray | ~75 | 136 ± 15 |

Once it was demonstrated that pPSCs could be aggregated in a roller bottle format on a small scale (Example 25), larger cultures were prepared in order to demonstrate the practical scalability of aggregating and differentiating hESC to PEC in roller bottles. Experiments using CyT49 hESC were performed as indicated in Table 10. Human ESCs were aggregated in StemPro® hESC SFM medium, Other pluripotent stem cell media, for example XF HA media with and without human serum albumin (HAS), was used in other experiments (data not shown). Day 0 (d0) hESC aggregates formed effectively in each condition. The experimental cultures summarized in Table 10 were rotated at 8 rpm. In other experiments, aggregation at 5, 10 and 12 rpm was utilized and hESC aggregates formed with similar morphology and diameters as those observed in 6-well trays and roller bottles at 8 rpm (data not shown). In some instances where hESC aggregation was performed at the lower range of rotation speed, e.g. 5, 6, and 7 rpm or with StemPro® hESC SFM (Life Technologies) media, an increase in agglomeration of the cell aggregates was observed (i.e., structures greater than 300 μm; data not shown). Some experiments were performed using vented bottle caps (V) while others did not have vented bottle caps (NV). Vented did not make a substantial difference on the differentiation process, nor did it appear to affect the proper specification of hESCs as determined by qPCR gene expression analysis (FIG. 26). In summary, hESC aggregation in roller bottles can be accomplished over a range of rotation speeds, (e.g., between about 5 to 12 rpms), with various pluripotent stem cell culture media, and in vented or not vented bottle caps, and in $CO_2$ gassed or un-gassed incubators. These different factors do not appear to substantially change the morphology, shape and average diameter size of the aggregates.

Example 27

Scaled Differentiation of Stem Cell Aggregates in Roller Bottles

Human ESC aggregation was again performed using 1200 mL or 490 cm² roller bottles substantially as described above in Examples 25 and 26. Because the hESC aggregates in each roller bottle aggregation looked consistent and similar (e.g. morphology and diameter size), the aggregates were pooled, pelleted, and the pellet of aggregates distributed between 1200 mL or 490 cm² roller bottles for differentiation according to Table 11. The total volume of the hESC aggregate pellet was approximately 4400 μL and was redistributed to 4×1200 mL bottles (490 cm²) for differentiation according to Table 11. Differentiation was performed as described above in Table 9. The differentiating cultures exhibited similar morphologies, except minor amounts of agglomeration was observed in bottles, which were rotated at the lower rotation speeds (data not shown). However, aggregate pellet volumes by day 12 (Stage 4) were similar for all conditions tested, and all cell pellets recovered were about a 1:1 yield as compared to the starting pellet volume in each bottle (~1100 μL). See Table 11.

Aggregation of pPSC is not limited to hESCs. Human iPSC were tested in a substantially similar manner as that described above for hESCs, under conditions listed in Table 11. Human iPSC-482c7 (Cellular Dynamics International Inc. Madison, Wis., USA) were aggregated in a 490 cm² roller bottle. The total starting volume of the hiPSCs was only about 25 mL at $1 \times 10^6$ cells/mL. The aggregation platform is sufficiently robust to perform well over a range of cell volumes and even when there is a greater disparity between the starting volume and the larger 490 cm² roller bottle. The human iPSC cell aggregates appeared morphologically similar to hESCs aggregated in 6-well trays or roller bottles as described above, i.e., iPSC aggregate sizes ranges from about 100 to about 300 microns with no apparent agglomeration. Also, as described previously in U.S. patent application Ser. No. 12/765,714, entitled CELL COMPOSITIONS DERIVED FROM DEDIFFERENTIATED REPROGRAMMED CELLS, filed Apr. 22, 2010, which is incorporated herein in its entirety, the use of Rho kinase inhibitors improved pPSC aggregate differentiation; however, since the '714 application did not show hESC aggregation (only differentiation), that application did not show that use of for example 10 μM Y-27632 in the starting pPSC culture would also improve pPSC aggregation. Because hESC aggregation can be performed in a roller bottle, cell aggregate differentiation in roller bottles can be performed as well and substantially as described in detail in the '714 application or related application, or substantially as described herein and according to Table 9.

Additionally, to demonstrate the integrity of hESC aggregates, hESC aggregates were first formed in roller bottles and then subsequently differentiated in 6-well trays. This was performed using hESC aggregates first formed in roller bottles under a variety of conditions, e.g. at different rotation speeds and with different pluripotent stem cell media. Differentiation of roller bottle hESC aggregates in 6-well trays was comparable in aggregate shape and diameter, and cell morphology to that observed when hESC aggregates were first formed in 6-well trays (control; data not shown). Hence, the integrity of the hESC aggregates in roller bottles is substantially unchanged due to the format change.

To demonstrate that scaling using roller bottles does not compromise incorporation of cells into aggregates, cell counting of the live, unincorporated cells following aggregate formation was performed at d0 (i.e. 18-24 hours after the initiation of aggregations), confirming that about 75-80% of the input cells were incorporated into the undifferentiated hESC aggregates, which is comparable or better than that observed in 6-well trays (about 75%). See Schulz et al. 2012, supra, FIG. 54, S6. The percentage of incorporation may vary depending on the pluripotent stem culture media used since studies using XF HA media provided a range of incorporation from about 50% to about 77% (data not shown).

Figure 27A:
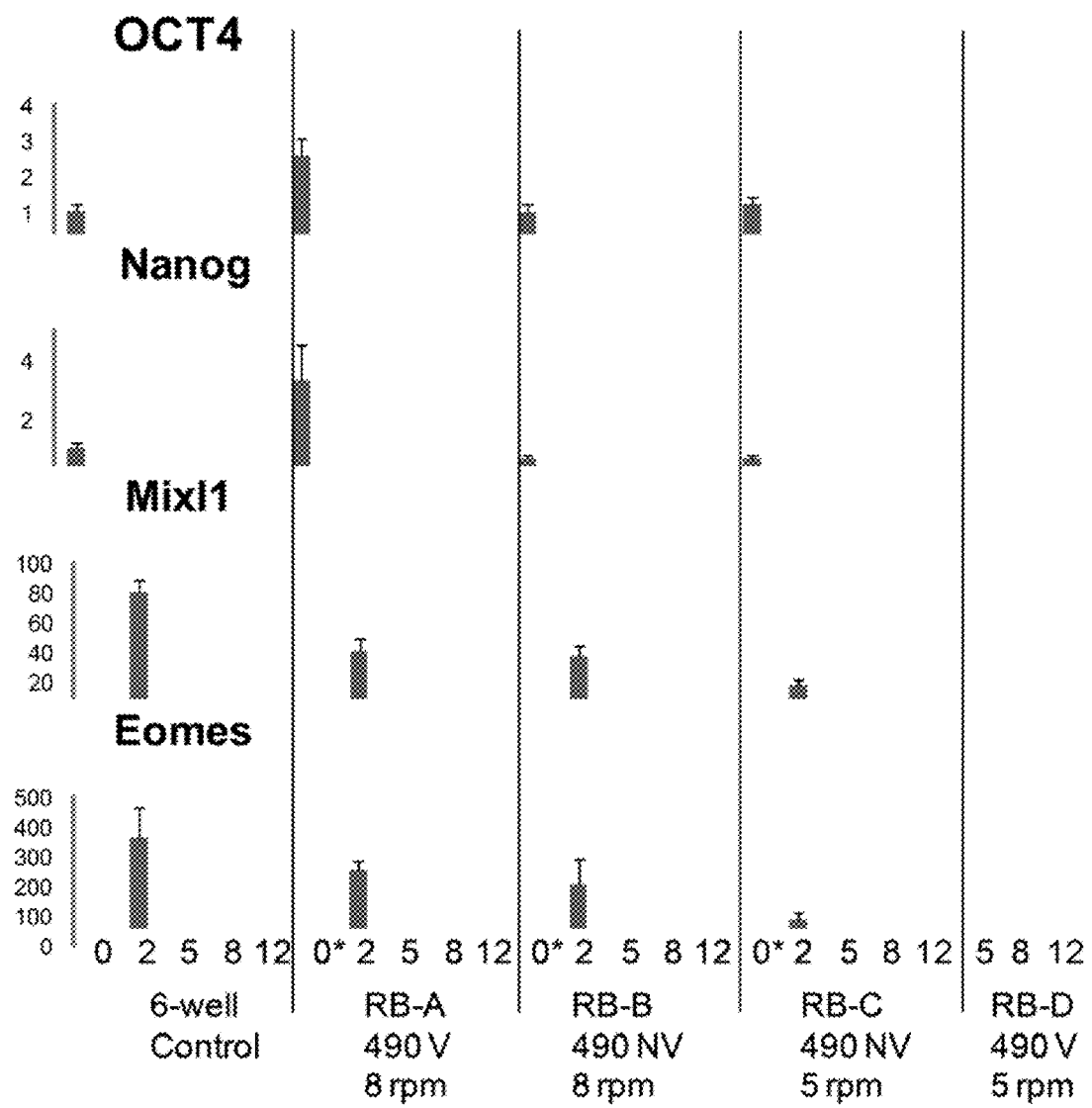
FIGS. 27A-D are bar charts showing the expression patterns of the various indicated marker genes in larger rolling bottle vessel formats as described in Table 11 and 12 in Example 27. The left sample represents a 6-well tray hESC aggregation and differentiation (control.
Figure 27B:
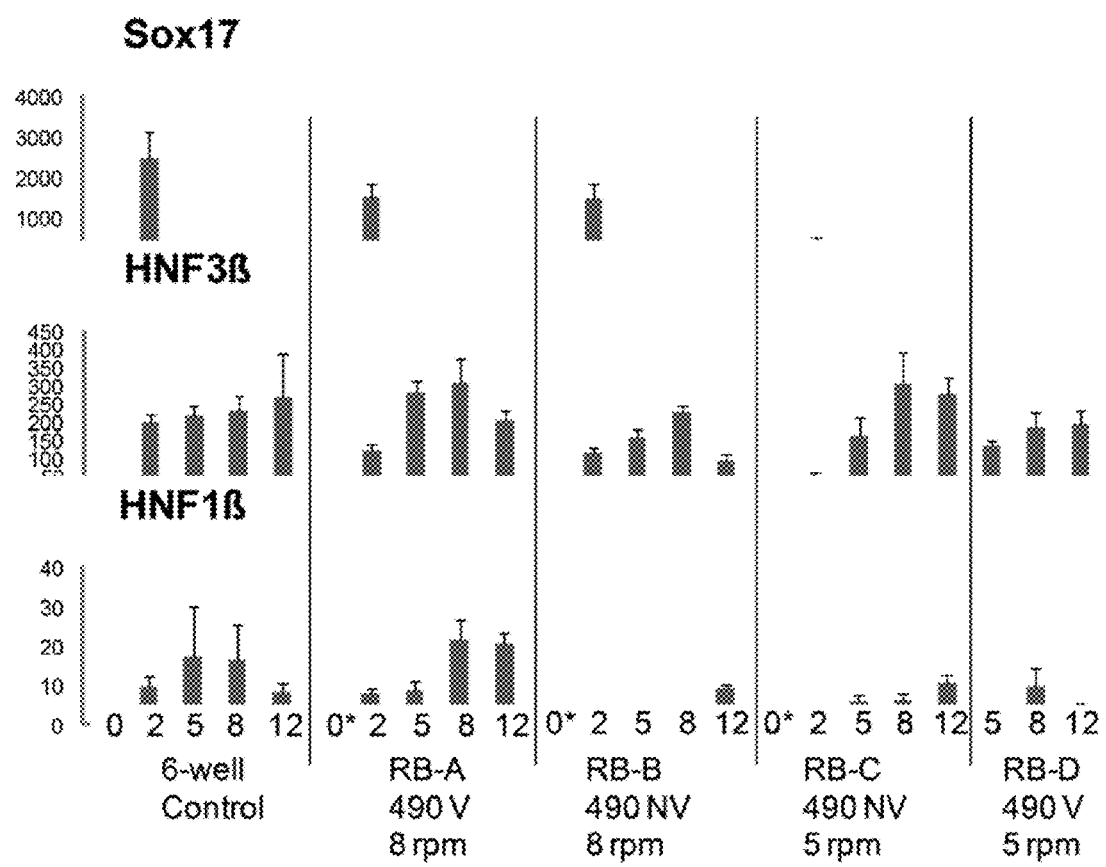
Figure 27C:
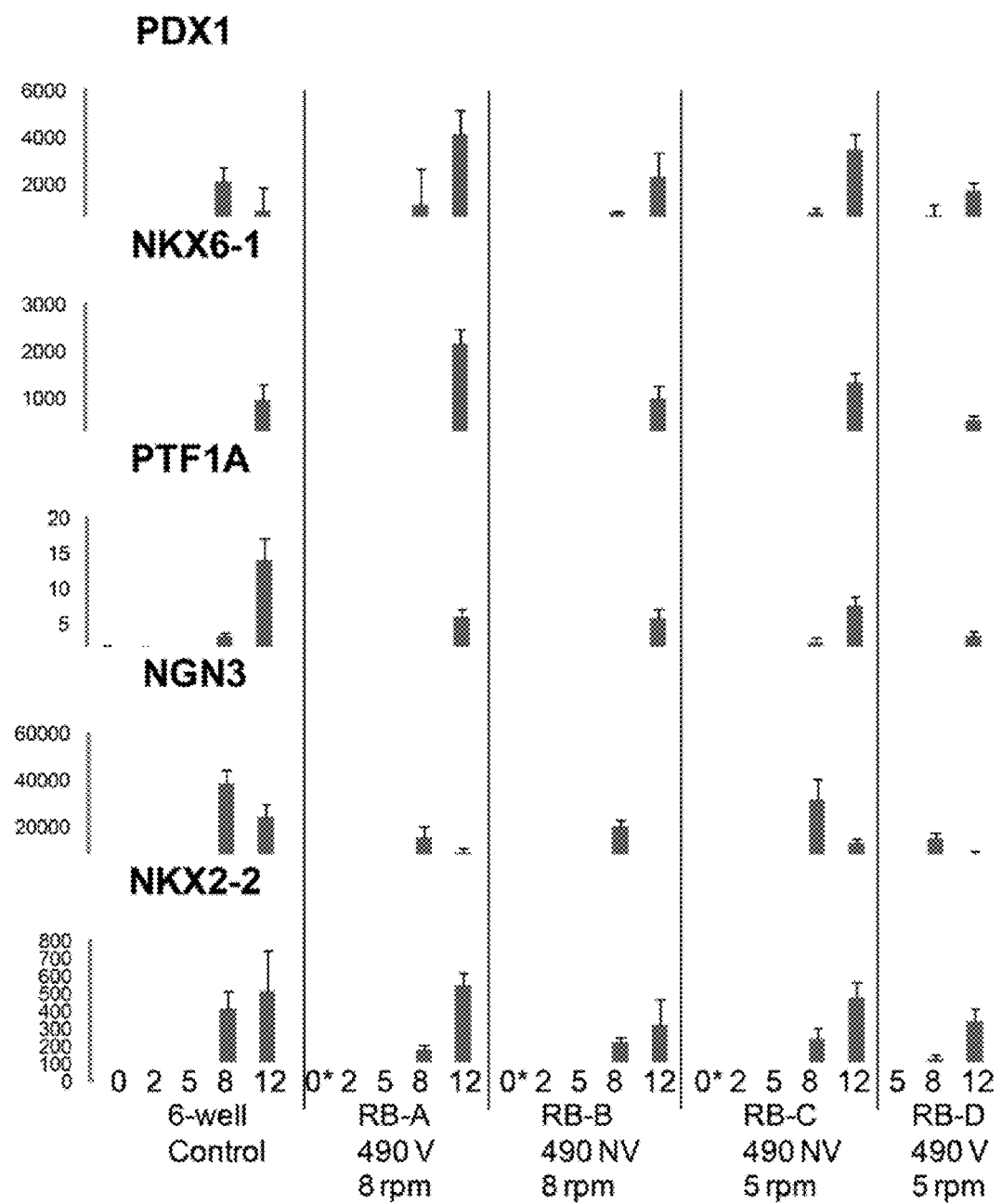
Figure 27D:
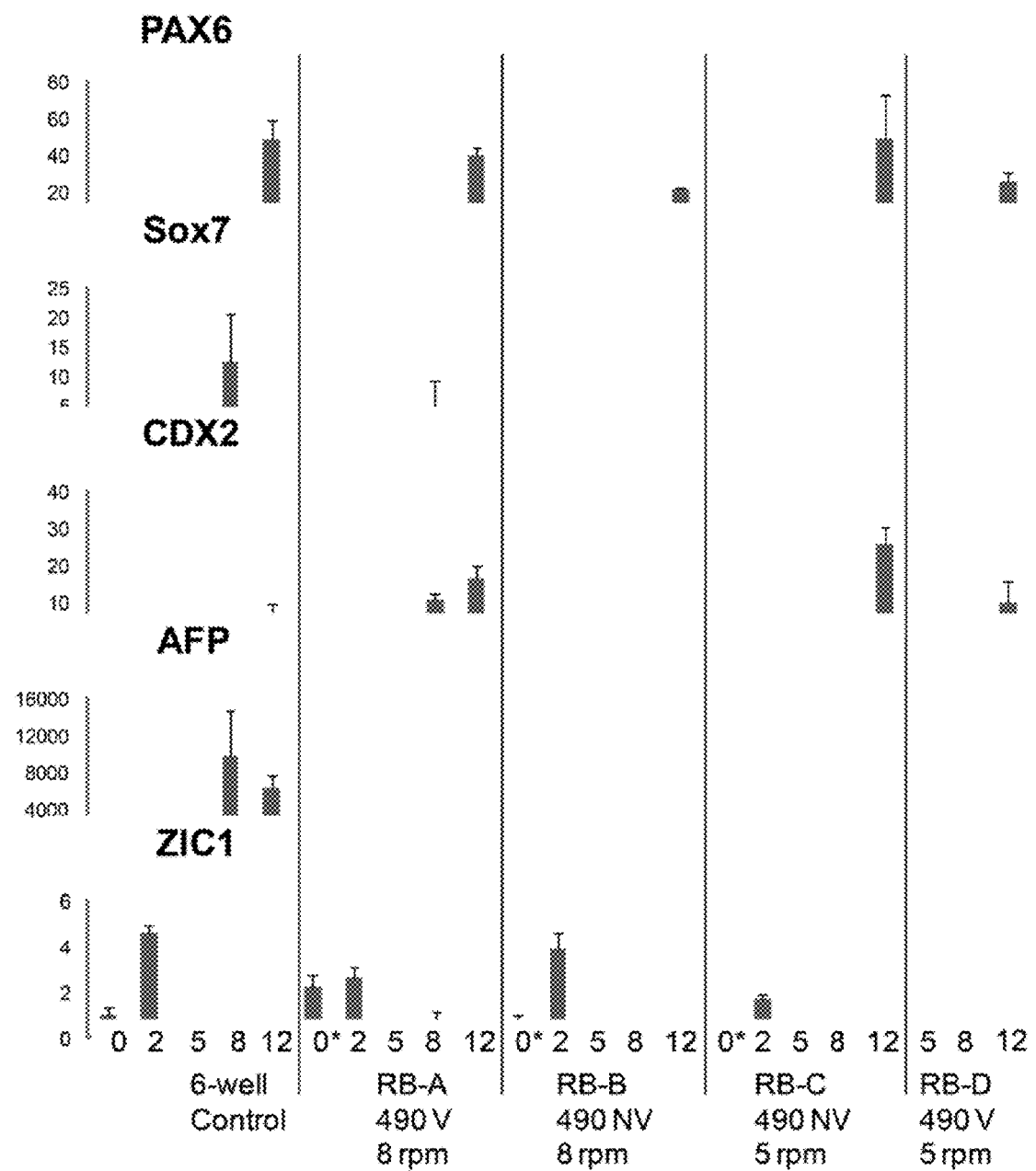

Q-PCR analysis of the differentiation process according to Tables 11 and 9, demonstrated that appropriate lineage specification occurred at each stage up to formation of PEC. See FIG. 27A-D. The four cultures as listed in Table 11 each exhibited down-regulation of markers of pluripotency (e.g., OCT4, Nanog) and transient up-regulation of markers of mesendoderm (e.g. MixL1, Eomes). See FIG. 27A. Markers of definitive endoderm (e.g., SOX17 and HNF313) were expressed from day 2 as expected, followed by other endodermal and pancreatic markers (e.g., HNF1β, PDX1, NKX6-1, PTF1A, NGN3, and NKX2-2). See FIG. 27B. Importantly, markers indicative of off-target lineages (non-endodermal or non-pancreatic lineages) were not elevated as compared to the 6-well tray control differentiation (e.g., PAX6, SOX7, CDX2, AFP and ZIC1), hence tight control of pancreatic specification was maintained in these scaled differentiation experiments. See FIG. 27C. For example, AFP expression, which typically indicates the presence of a minor off-target population that occurs sporadically in some differentiations, was low in the 6-well tray control. See FIG. 27D and Schulz et al. 2012, supra. AFP expression was even lower in the roller bottle cultures, potentially indicating a reduction in this minor population in the d12 aggregates. See FIG. 27D.

To assess the cellular compositions of pancreatic cell cultures differentiated from hESC with the multistep (Stages 1-4) protocol, flow cytometry analysis based on a combination of co-staining was used substantially as that previously described in Kelly et al. 2011, Nature Biotech 29:750-56; D'Amour et al. 2005, supra; Kroon et al. 2008 supra, Schulz et al. 2012, supra, which are herein incorporated by reference in their entireties. Schulz et al. 2012, supra for example showed extensive flow cytometry analysis and PEC cellular composition for at least 37 differentiation runs (FIG. 2). Schulz et al. described the cellular composition of PEC as consisting of: About 26-36% CHGA$^-$/NKX6-1$^+$/PDX1$^{+/-}$, about 46-56% CHGA$^+$/NKX6-1$^{+/-}$/PDX1$^{+/-}$ (poly-hormonal endocrine cells), about 10-15% CHGA$^-$/NKX6-1$^-$/PDX1$^+$ (PDX1-only endoderm cells) and less than 3% CHGA$^-$/NKX6-1$^-$/PDX1$^-$ (residual or triple negative cells). See Schulz et al. 2012, supra FIG. 2C.

Similarly, flow cytometry analysis was performed on stage 4 (day 12) PEC cultures differentiated in a roller bottles as indicated in Table 11. The PEC composition was consistent with that previously described in Schulz et al. above and the exact percentages as well as the average from the four roller bottle conditions is shown in Table 12. The PEC from these scaled roller bottle differentiations showed about 40% CHGA$^-$/NKX6-1$^+$/PDX1$^{+/-}$, about 43% CHGA$^+$/NKX6-1$^{+/-}$/PDX1$^{+/-}$ (or polyhormonal endocrine cells), about 10% CHGA$^-$/NKX6-1$^-$/PDX1$^+$ (or PDX1-only endoderm cells), and about 2% CHGA$^-$/NKX6-1$^-$/PDX1$^-$ (or residual cells; or triple negative cells). Flow cytometry analysis of the PEC composition also indicates that neither the different rotation speeds of 5 and 8 rpm nor the type of vented or not-vented bottle caps had an apparent effect on PEC cell composition. As described above and based on Q-PCE analysis, these conditions did not appear to effect the lineage specification of Stages 1-4 cells en route to PEC either (FIG. 26). Therefore, the above studies and analyses confirmed the effectiveness of hESC aggregation and differentiation to PEC in scalable rolling bottle format.

TABLE 11 pPSC Aggregation in Large Roller Bottles

| Bottle Surface area (1200 mL) | Aggregation Volume | Caps, Vented (V); Not-Vented (NV) | Speed | Stage 4, Day 12 pellet volume |
|---|---|---|---|---|
| 490 cm$^2$ | 275 mL | V | 5 rpm | 1000 µL |
| 490 cm$^2$ | 275 mL | NV | 5 rpm | 1100 µL |
| 490 cm$^2$ | 275 mL | V | 8 rpm | 800 µL |
| 490 cm$^2$ | 275 mL | NV | 8 rpm | 1200 µL |

TABLE 12

PEC Cell Composition from Roller Bottle after Stages 1-4 Differentiation

| | CHGA+ (Polyhormonal Endocrine) | CHGA– NKX6.1+ PDX1+ or – | CHGA– NKX6.1– PDX1+ (PDX only) | CHGA– NKX6.1– PDX1– (Residual-Triple Negative) |
|---|---|---|---|---|
| RB- A 490 cm$^2$ V 8 rpm | 40.2 | 41.0 | 16.8 | 1.92 |
| RB- B 490 cm$^2$ NV 8 rpm | 45.5 | 41.5 | 11.6 | 1.36 |
| RB- C 490 cm$^2$ V 5 rpm | 43.6 | 35.0 | 20.1 | 1.34 |
| RB- D 490 cm$^2$ NV 5 rpm | 43.8 | 42.9 | 9.71 | 3.65 |
| Average, RB A-D | 43.25 | 40.1 | 14.55 | 2.07 |

*V, vented; NV, not vented;

It will be appreciated that the methods and compositions described above relate to cells cultured in vitro. However, the above-described in vitro differentiated cell compositions may be used for in vivo applications. Use of the compositions described herein have been described detail in at least Applicant's U.S. Pat. Nos. 7,534,608; 7,695,965; and 7,993,920; entitled METHODS FOR PRODUCING PANCREATIC HORMONES, which issued May 19, 2009, Apr. 13, 2010 and Aug. 9, 2011, respectively; and 8,278,106, entitled ENCAPSULATION OF PANCREATIC CELLS DERIVED FROM PLURIPOTENT STEM CELLS, the disclosures of which are incorporated herein by reference in their entireties. Use and function of the compositions described herein have also been reported by Applicant in prior non-patent publications including Kroon et al. 2008 supra and Schulz et al. 2012, supra, which are also incorporated herein by reference in their entireties.

Accordingly, it will be apparent to one skilled in the art that varying substitutions, modifications or optimization, or combinations may be made to the embodiments disclosed herein without departing from the scope and spirit of the invention. As described above, roller bottles can be of varying size, shape and potentially even those containers not cylindrical in shape but which methods simulate the same motion as that of roller bottles can be used. Further, it is clear from the above description that use of different types of pPSC media, such as XF HA or StemPro® hESC SFM media and other types of media are wholly anticipated, e.g. mTeSR™ media, Essential™ 8 or any other pPSC media commonly employed in the industry for growth and culture of pPSC or like cells.

For example, whether aggregation and/or differentiation requires gassing (e.g. $CO_2$ and other gases) may in part depend on the type of roller bottle caps used (e.g. vented or not vented). $CO_2$ can be easily incorporated into the culture conditions in standard tissue culture incubators. However, aggregation and/or differentiation with no external $CO_2$ (ungassed) can bring certain advantages to manufacturing in scaling: more volume/bottle and therefore fewer bottles per large manufacturing run. Also, large arrays of bottles could be run in a walk-in hot room as compared to an incubator for example, greatly simplifying incorporation of robotics and automation in the scaling process.

Certain culture vessels have been described herein (e.g. 6 well trays, bioreactors, Erlenmeyer flasks, roller bottles and the like), however other similar culture vessels, for example, those with similar size, shape, dimension and function are contemplated. Commercial roller bottles, such as Corning's plastic and glass roller bottles, range in sizes: 490 cm$^2$ (hold 100 to 150 mL); 850 cm$^2$ (hold 170 to 255 mL); 1700 cm$^2$ (hold 340 to 510 mL); 1750 cm$^2$ (hold 350 to 525 mL); 670-680 cm$^2$ (hold 135 to 200 mL); 840 cm$^2$ (hold 170 to 255 mL); 1170 cm² (hold 235 to 350 mL); 1330 cm² (hold 265 to 400 mL); 1585 cm² (315 to 475 mL); and 1585 cm² (hold 315 to 475 mL).

Erlenmeyer flasks are conical shaped and have a tapered body and narrow neck. The shape, which is distinguished from a beaker, allows the contents to be swirled or stirred, with an external mechanical device or by hand, while the narrow neck keeps the contents from spilling out and reduces evaporative losses as compared to a beaker, while the flat bottom of the conical flask makes it stable. The invention described herein contemplates other containers that have similar shapes.

Still the invention described herein also contemplates use of bioreactors, or any manufactured or engineered device or system that supports a biologically active environment. Such bioreactors are commonly cylindrical, ranging in size from liters to cubic meters. There are many commercially available bioreactors and one skilled in the art can be guided to select the right vessel for their process given the detailed description provided herein.

Hence, the skilled artisan can easily choose the appropriate size roller bottle for their scale-up culture needs based on the present invention description and manufacture recommendations.

All publications and patents mentioned in this specification are herein incorporated in their entireties by reference.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

What is claimed is:

1. A roller bottle comprising primate pluripotent stem cell (pPSC) aggregates in suspension in a physiologically acceptable medium, wherein the pPSC aggregates are formed in the roller bottle.

2. The roller bottle of claim 1, wherein the pPSC aggregates have a diameter of about 100 to 300 microns.

3. The roller bottle of claim 1, substantially free of pPSC agglomerations having a diameter of more than 300 microns.

4. The roller bottle of claim 1, wherein the pPSC aggregates express at least one marker selected from the group consisting of OCT4, NANOG, SSEA-3, SSEA-4, Tra-1-80 and Tra-1-60.

5. The roller bottle of claim 1, wherein the pPSC aggregates are human cells.

6. The roller bottle of claim 5, wherein the pPSC aggregates are selected from the group consisting of human embryonic stem cells (hESC) and induced pluripotent stem cells (iPSC).

7. The roller bottle of claim 1, wherein the pPSC aggregates in suspension are generated by a method comprising:
   a. seeding a roller bottle with undifferentiated pPSCs in a culture medium that supports undifferentiated growth of the pPSCs; and
   b. agitating the pPSCs at low rotation speed to form pPSC aggregates, thereby generating a roller bottle comprising pPSC aggregates.

8. The roller bottle of claim 7, wherein the pPSC aggregates have a diameter of about 100 to 300 microns.

9. The roller bottle of claim 7, substantially free of pPSC agglomerations having a diameter of more than 300 microns.

10. The roller bottle of claim 7, wherein the pPSC aggregates express at least one marker selected from the group consisting of OCT4, NANOG, SSEA-3, SSEA-4, Tra-1-80 and Tra-1-60.

11. The roller bottle of claim 7, wherein the pPSC aggregates are human cells.

12. The roller bottle of claim 11, wherein the pPSC aggregates are cells selected from the group consisting of human embryonic stem cells (hESC) and induced pluripotent stem cells (iPSC).

13. The roller bottle of claim 7, wherein the rotation speed ranges from 3 to 20 rpm.

14. The roller bottle of claim 7, wherein the rotation speed ranges from 5 to 12 rpm.

15. The roller bottle of claim 7, wherein the undifferentiated pPSCs in step a is a suspension of single cell pPSCs.

16. A method for preparing the roller bottle of claim 1, comprising:
   a. seeding a roller bottle with a single cell suspension of undifferentiated pPSCs in a culture medium that supports undifferentiated growth of the pPSCs; and
   b. agitating the single cell suspension at low rotation speed in a roller bottle to form pPSC cell aggregates,
   thereby preparing a roller bottle comprising pPSC aggregates in suspension in a physiologically acceptable medium.

17. The method of claim 16, wherein the undifferentiated pPSCs is a suspension of thawed pPSCs.

18. The method of claim 16, wherein the rotation speed is about 3 rpm to about 20 rpm.

19. The method of claim 16, wherein the rotation is about 5 rpm to about 20 rpm.

20. The method of claim 16, wherein the rotation speed is about 5 rpm to about 12 rpm.

21. The method of claim 16, wherein the pPSC is a human cell.

22. The method of claim 21, wherein the pPSC is selected from the group consisting of hESC and iPSC.

* * * * *

UNITED STATES PATENT AND TRADEMARK OFFICE
CERTIFICATE OF CORRECTION

PATENT NO. : 8,895,300 B2
APPLICATION NO. : 13/672688
DATED : November 25, 2014
INVENTOR(S) : Thomas C Schulz Page 1 of 1

It is certified that error appears in the above-identified patent and that said Letters Patent is hereby corrected as shown below:

In the Specification

At Column 7, Line 32, "TRA-1-80" should read --TRA-1-81--.

In the Claims

At Column 99, Line 48, Claim 4, "TRA-1-80" should read --TRA-1-81--.

At Column 100, Line 16, Claim 10, "TRA-1-80" should read --TRA-1-81--.

Signed and Sealed this
Fifteenth Day of August, 2023

Katherine Kelly Vidal
*Director of the United States Patent and Trademark Office*